United States Patent
Kaplan et al.

(10) Patent No.: US 9,624,200 B2
(45) Date of Patent: *Apr. 18, 2017

(54) THERAPEUTIC PIPERAZINES

(71) Applicant: DART NEUROSCIENCE (CAYMAN) LTD., Grand Cayman (KY)

(72) Inventors: Alan P. Kaplan, San Diego, CA (US); Terence P. Keenan, San Diego, CA (US); Michael I. Weinhouse, Escondido, CA (US); Mark E. Wilson, Ramona, CA (US); Andrew K. Lindstrom, San Diego, CA (US); William C. Ripka, San Diego, CA (US); Mi Chen, San Diego, CA (US)

(73) Assignee: Dart NeuroScience (Cayman) Ltd. (KY)

( * ) Notice: Subject to any disclaimer, the term of this patent is extended or adjusted under 35 U.S.C. 154(b) by 18 days.

This patent is subject to a terminal disclaimer.

(21) Appl. No.: 14/508,970

(22) Filed: Oct. 7, 2014

(65) Prior Publication Data
US 2015/0087645 A1    Mar. 26, 2015

Related U.S. Application Data

(60) Division of application No. 12/887,920, filed on Sep. 22, 2010, now Pat. No. 8,927,546, which is a (Continued)

(51) Int. Cl.
| | |
|---|---|
| A61K 31/551 | (2006.01) |
| A61K 31/495 | (2006.01) |
| A61K 31/496 | (2006.01) |
| C07D 403/04 | (2006.01) |
| C07D 401/04 | (2006.01) |
| C07D 417/14 | (2006.01) |
| C07D 409/06 | (2006.01) |
| C07D 243/08 | (2006.01) |
| C07D 241/04 | (2006.01) |
| C07D 413/14 | (2006.01) |
| C07D 417/06 | (2006.01) |
| C07D 403/06 | (2006.01) |
| A61K 31/5377 | (2006.01) |
| A61K 45/06 | (2006.01) |
| C07D 401/06 | (2006.01) |
| C07D 413/06 | (2006.01) |
| C07D 401/14 | (2006.01) |
| C07D 403/14 | (2006.01) |

(52) U.S. Cl.
CPC .......... *C07D 403/06* (2013.01); *A61K 31/495* (2013.01); *A61K 31/496* (2013.01); *A61K 31/5377* (2013.01); *A61K 31/551* (2013.01); *A61K 45/06* (2013.01); *C07D 241/04* (2013.01); *C07D 243/08* (2013.01); *C07D 401/04* (2013.01); *C07D 401/06* (2013.01); *C07D 401/14* (2013.01); *C07D 403/04* (2013.01); *C07D 403/14* (2013.01); *C07D 409/06* (2013.01); *C07D 413/06* (2013.01); *C07D 413/14* (2013.01); *C07D 417/06* (2013.01); *C07D 417/14* (2013.01)

(58) Field of Classification Search
CPC .. A61K 31/551; A61K 31/495; A61K 31/496; A61K 31/5377; A61K 45/06; C07D 403/06; C07D 401/04; C07D 401/14; C07D 417/14; C07D 409/06; C07D 403/04; C07D 403/14; C07D 401/06; C07D 243/08; C07D 241/04; C07D 413/06; C07D 413/14; C07D 417/06
See application file for complete search history.

(56) References Cited

U.S. PATENT DOCUMENTS

| | | |
|---|---|---|
| 2,996,507 A | 8/1961 | Sommers |
| 3,306,903 A | 2/1967 | Nitya |

(Continued)

FOREIGN PATENT DOCUMENTS

| | | |
|---|---|---|
| DE | 23 45 422 A1 | 3/1975 |
| EP | 0 185 909 A1 | 7/1986 |

(Continued)

OTHER PUBLICATIONS http://onlinelibrary.wiley.com/doi/10.1002/iub.1104/pdf.*

(Continued)

*Primary Examiner* — Alexander R Pagano
*Assistant Examiner* — Ebenezer O Sackey
(74) *Attorney, Agent, or Firm* — Knobbe Martens Olson & Bear LLP

(57) ABSTRACT

The invention includes a compound of formula I:

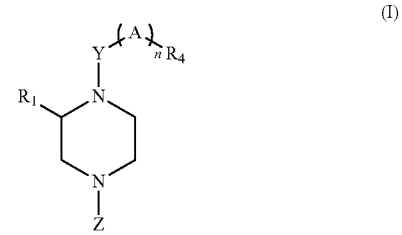

(I)

wherein $R_1$, Y, A, n, $R_4$ and Z have any of the values described herein, as well as salts of such compounds, compositions comprising such compounds, and therapeutic methods that comprise the administration of such compounds. The compounds are inhibitors of PDE4 function and are useful for improving cognitive function and/or treating cognitive disorders or impairment, traumatic and/or ischemic injuries of the central and peripheral nervous system and/or psychiatric disorders in animals, especially humans.

21 Claims, 2 Drawing Sheets

Related U.S. Application Data continuation-in-part of application No. 11/679,782, filed on Feb. 27, 2007, now Pat. No. 7,829,713.

(60) Provisional application No. 60/777,291, filed on Feb. 28, 2006.

(51) Int. Cl.

(56) References Cited

U.S. PATENT DOCUMENTS

| | | | |
|---|---|---|---|
| 3,857,945 | A | 12/1974 | Fernand et al. |
| 4,093,726 | A | 6/1978 | Winn et al. |
| 5,086,055 | A | 2/1992 | Walsh |
| 5,308,844 | A | 5/1994 | Rieu |
| 6,555,572 | B2 | 4/2003 | Lauener et al. |
| 6,953,801 | B2 | 10/2005 | Hutchison et al. |
| 7,429,666 | B2 | 9/2008 | Lachance et al. |
| 7,439,243 | B2 | 10/2008 | Johnson et al. |
| 7,589,199 | B2 | 9/2009 | Pennell et al. |
| 7,625,889 | B2 | 12/2009 | Eastwood et al. |
| 7,829,713 | B2 | 11/2010 | Keenan et al. |
| 8,338,405 | B2 * | 12/2012 | Keenan ............... C07D 241/04 514/218 |
| 2003/0073885 | A1 | 4/2003 | Theodoracopulos et al. |
| 2003/0144277 | A1 | 7/2003 | DeLucca |
| 2003/0220352 | A1 | 11/2003 | Lauener et al. |

FOREIGN PATENT DOCUMENTS

| | | |
|---|---|---|
| EP | 0 202 760 A2 | 11/1986 |
| EP | 0 277 725 A2 | 8/1988 |
| EP | 0 511 879 A1 | 11/1992 |
| EP | 0 527 081 A1 | 2/1993 |
| FR | 2 551 753 A2 | 3/1985 |
| GB | 1 446 791 | 8/1976 |
| GB | 1 575 904 A | 10/1980 |
| GB | 2 101 580 A | 1/1983 |
| WO | WO 01/54559 A2 | 8/2001 |
| WO | WO 01/54650 A2 | 8/2001 |
| WO | WO 01/68600 A2 | 9/2001 |
| WO | WO 01/72217 A1 | 10/2001 |
| WO | WO 2004/024728 A2 | 3/2004 |
| WO | WO 2004/103998 A1 | 12/2004 |
| WO | WO 2006/111549 A1 | 10/2006 |
| WO | WO 2007/100852 A1 | 9/2007 |

OTHER PUBLICATIONS

Abel et al., "Genetic Demonstration of a Role for PKA in the Late Phase of LTP and in Hippocampus-Based Long-Term Memory," Cell, 88(5): 615-626 (1997).

Barad et al., "Rolipram, a type IV-specific phosphodiesterase inhibitor, facilitates the establishment of long-lasting long-term potentiation and improves memory," Proc. Natl. Acad. Sci., 95(25): 15020-15025 (1998).

Bose et al., "Synthesis and antidepressant activity of 5-(1-aryl-4-piperazino)methyl-2-amino-2-oxazolines," Eur. J. Med. Chem., 27(5): 437-442 (1992).

Bourtchouladze et al., Deficient long-term memory in mice with a targeted mutation of the cAMP-responsive element-binding protein, Cell, 79(1): 59-68 (1994).

Bourtchouladze et al., "Different Training Procedures Recruit Either One or Two Critical Periods for Contextual Memory Consolidation, Each of Which Requires Protein Synthesis and PKA," Learn. Mem., 5(4): 365-374 (1998).

Bourtchouladze et al., "A mouse model of Rubinstein-Taybi syndrome: Defective long-term memory is ameliorated by inhibitors of phosphodiesterase 4," Proc. Natl. Acad. Sci., 100(8): 10518-10522 (2003).

D'Arrigo et al., "Chemo-enzymatic synthesis of the active enantiomer of the anorressant 2-benzylmorpholine," Tetrahedron: Asymmetry, 9(22): 4021-402 (1998).

Ennaceur, "The effects of neurotoxic lesions of the perirhinal cortex combined to fornix transection on object recognition memory in the rat," Behav. Brain Res., 88: 181-193 (1997).

Erlanger et al., "Development and Validation of a Web-Based Screening Tool for Monitoring Cognitive Status," J. Head Trauma Rehabil., 17: 458-476 (2002).

Ferrand et al., "Synthesis of new 1,2,3-triazin-4-ones as potential anti-depressants," Eur. J. Med. Chem., 22(4): 337-345 (1987).

Giese et al., "Autophosphorylation at $Thr^{286}$ of the $\alpha$ Calcium-Calmodulin Kinase II in LTP and Learning," Science, 279(5352): 870-873 (1998).

Heinrich et al., "Indolebutylamines as Selective $5-HT_{1A}$ Agonists," J. Med. Chem., 47(19): 4677-4683 (2004).

Kim et al., "Effects of Amygdala, Hippocampus, and Periaqueductal Gray Lesions on Short- and Long-Term Contextual Fear," Behav. Neurosci., 107(6): 1093-1098 (1993).

Kogan et al., "Spaced training induces normal long-term memory in CREB mutant mice," Curr. Biol., 7(1): 1-11 (1997).

Logue et al., "Hippocampal lesions cause learning deficits in inbred mice in the Morris water maze and conditioned-fear task," Behav. Neurosci., 111(1): 104-113 (1997).

Mitchell, "The medial frontal cortex and temporal memory: tests using spontaneous exploratory behaviour in the rat," Behav. Brain Res., 97(1-2): 107-113 (1998).

Mumby, "Perspectives on object-recognition memory following hippocampal damage: lessons from studies in rats," Brain Res., 127(1-2): 159-181 (2001).

Nguyen et al., "Strain-dependent Differences in LTP and Hippocampus-dependent Memory in Inbred Mice," Learn. Mem., 7: 170-179 (2000).

Phillips, "Differential contribution of amygdala and hippocampus to cued and contextual fear conditioning," Behav. Neurosci., 106: 274-285 (1992).

Pittenger et al., "Reversible Inhibition of CREB/ATF Transcription Factors in Region CA1 of the Dorsal Hippocampus Disrupts Hippocampus-Dependent Spatial Memory," Neuron, 34(3): 447-462 (2002).

Silva et al. "Impaired learning in mice with abnormal short-lived plasticity," Curr. Biol., 6(11): 1509-1518 (1996).

T.J. Torphy, et al., "Stimulation of beta adrenoceptors in a human monocyte cell line (U937) up-regulates cyclic AMP-specific phosphodiesterase activity," J. Pharmacol. Exp. Ther., 263(3): 1195-1205 (1992).

Tang et al., "Contrasting Effects on Discrimination Learning after Hippocampal Lesions and Conjoint Hippocampal-Caudate Lesions in Monkeys" J. Neurosci., 20(10): 3853-3863 (2000).

Tully et al., "Targeting the CREB pathway for memory enhancers," Nature Reviews Drug Discovery, 2: 267-277 (2003).

Van der Mey et al., "Novel Selective PDE4 Inhibitors. 2. Synthesis and Structure—Activity Relationships of 4-Aryl-Substituted cis-Tetra- and cis-Hexahydrophthalazinones," J. Med. Chem., 44: 2523-2535 (2001).

\* cited by examiner

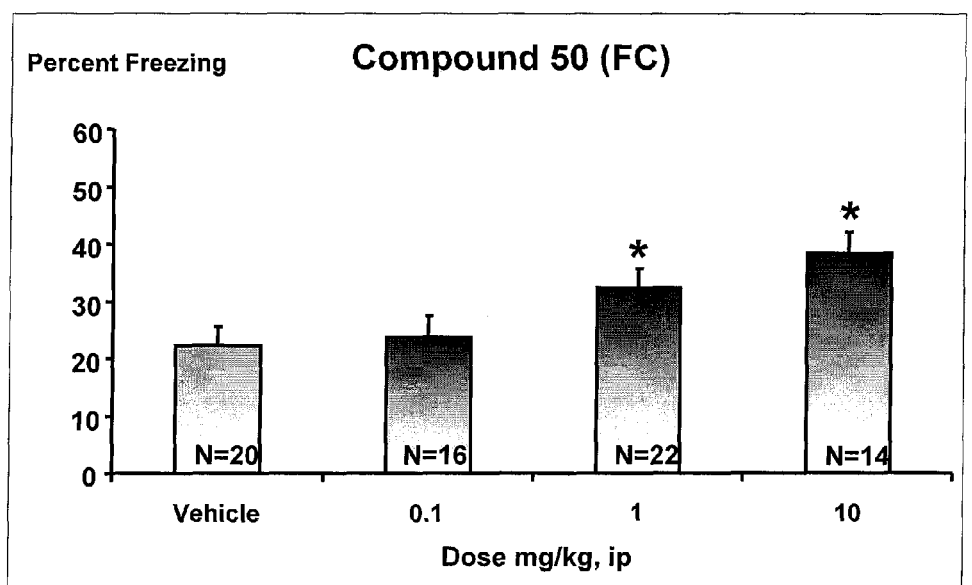
Figure 1. Effects of Compound 50 on contextual memory (fear conditioning, FC) in mice. 1 and 10 mg/kg Compound 50 injected 20 minutes before training significantly enhanced contextual memory in mice.

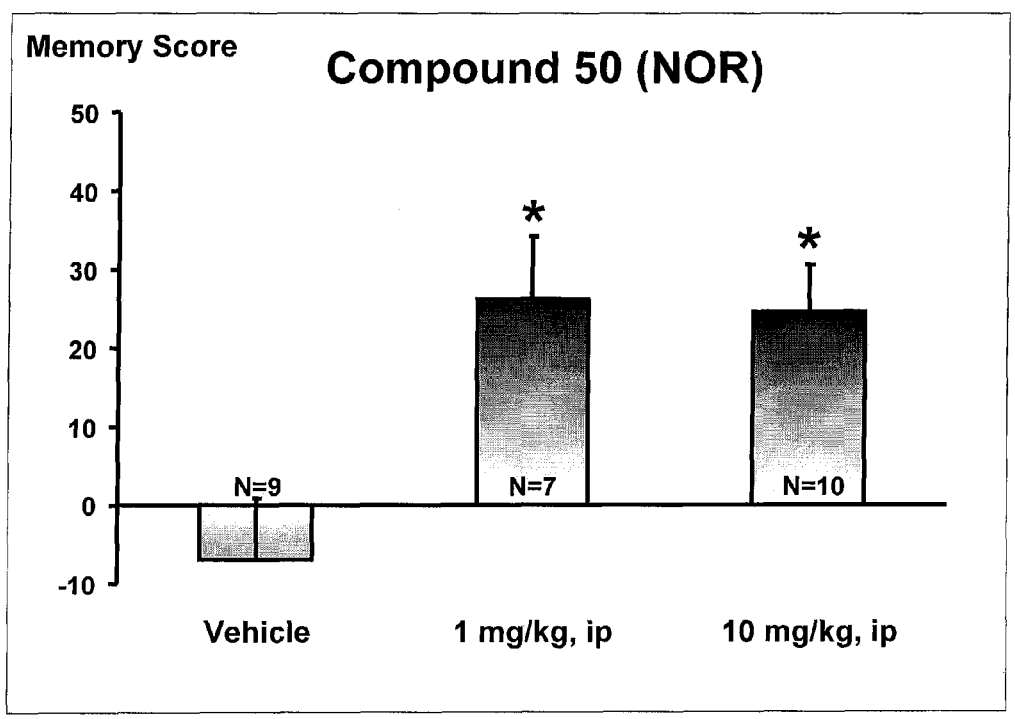
Figure 2. Effects of Compound 50 on novel object recognition (NOR) in C57Bl/6 mice. 24 hour memory in object recognition is deficient in C57BL/6 mice. Injections of 1 and 10 mg/kg Compound 50 20 min before training ameliorate long-term memory deficit in C57Bl/6 mice.

THERAPEUTIC PIPERAZINES

CROSS-REFERENCE TO RELATED APPLICATIONS

This application, which claims the benefit of priority under 35 U.S.C. §§120 and 119(e), is a divisional of U.S. application Ser. No. 12/887,920, filed Sep. 22, 2010, which is a continuation-in-part of U.S. application Ser. No. 11/679,782, filed Feb. 27, 2007, now U.S. Pat. No. 7,829,713, which claims priority to U.S. Provisional Application No. 60/777,291, filed Feb. 28, 2006, the entire disclosures of which are incorporated herein by reference.

BACKGROUND OF INVENTION

An estimated 4 to 5 million Americans (about 2% of all ages and 15% of those older than 65) have some form and degree of cognitive failure. Cognitive failure (dysfunction or loss of cognitive functions, the process by which knowledge is acquired, retained and used) commonly occurs in association with central nervous system (CNS) disorders or conditions, including age-associated memory impairment, delirium (sometimes called acute confusional state), dementia (sometimes classified as Alzheimer's or non-Alzheimer's type), Alzheimer's disease, Parkinson's disease, Huntington's disease (chorea), mental retardation (e.g. Rubenstein-Taybi Syndrome), cerebrovascular disease (e.g. stroke, ischemia), affective disorders (e.g. depression), psychotic disorders (e.g., schizophrenia, autism (Kanner's Syndrome)), neurotic disorders (e.g., anxiety, obsessive-compulsive disorder), attention deficit disorder (ADD), subdural hematoma, normal-pressure hydrocephalus, brain tumor, head or brain trauma.

Cognitive dysfunction is typically manifested by one or more cognitive deficits, which include memory impairment (inability to learn new information or to recall previously learned information), aphasia (language/speech disturbance), apraxia (impaired ability to carry out motor activities despite intact motor function), agnosia (failure to recognize or identify objects despite intact sensory function), disturbance in executive functioning (e.g., planning, organizing, sequencing, abstracting).

Cognitive dysfunction causes significant impairment of social and/or occupational functioning, which can interfere with the ability of an individual to perform activities of daily living and greatly impact the autonomy and quality of life of the individual. Thus, there is currently a need for compounds and methods that are useful for improving cognitive function in animals.

Phosphodiesterases (E.C. 3.1.4.17) are a class of enzymes that catalyze the hydrolysis of the 3'-phosphodiester bond of 3',5'-cyclic nucleotides. The phosphodiesterase 4 (PDE4) isoform specifically hydrolyzes adenonsine 3',5' cyclic monophosphate (cAMP) to form 5'-adenosine monophosphate (5'-AMP). cAMP is a well studied intracellular second messenger that is known to be responsible for regulating a number of cellular processes including transcriptional regulation. One signaling pathway known to be regulated by intracellular levels of cAMP is the CREB pathway. The CREB pathway is responsible for regulating transcriptional activity in the brain (including the hippocampus) that leads to protein syntheses required for learning and memory, especially the consolidation of short-term to long-term memory. It is known that inhibition of PDE4 improves cognitive function in mammals, including contextual memory and object recognition (Tully et. al., *Nature Reviews Drug Discovery* 2003 (2) 267-277; and Barad et al., *Proc Natl Acad Sci* 1998 (95) 15020-15025). It has also been shown to improve memory in animals with impaired CREB function (see Bourtchouladze et al., *Proc Natl Acad Sci* 2003 (100) 10518-10522).

Numerous companies have invested in the development of specific PDE4 inhibitors to treat a variety of diseases, most notably in the anti-inflammatory field (e.g., Rolipram™ and Ariflo™). A common side-effect of these treatments has been the induction of emesis. Accordingly, there is a particular need for PDE4 inhibiting compounds that cause little or no emesis.

SUMMARY OF THE INVENTION

The compounds are inhibitors of PDE4 function and are useful for improving cognitive function and/or treating cognitive disorders or impairment, traumatic and/or ischemic injuries of the central and peripheral nervous system and/or psychiatric disorders in animals, especially humans. Accordingly, in one embodiment the invention provides a compound of formula I:

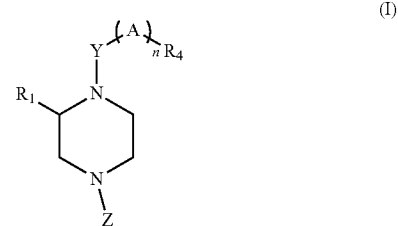

wherein:

$R_1$ is H, $(C_1-C_6)$alkyl, halo$(C_1-C_6)$alkyl, $R_aR_bN(C_1-C_6)$alkyl, hydroxy$(C_1-C_6)$alkyl, alkoxy$(C_1-C_6)$alkyl, het$(C_1-C_6)$alkyl, het$(C_1-C_6)$haloalkyl, aryl$(C_1-C_6)$alkyl, aryl$(C_1-C_6)$haloalkyl, aryl-(C=O)—, or het-(C=O)—;

Y is a direct bond, —$CH_2$—, —(C=O)—, or —[C=N—CN]—;

n is an integer from 0 to 6 inclusive;

each of the n instances of A is independently a direct bond, —(C=O)—, —($CR_cR_d$)—, —O—, —(S=O)—, —($SO_2$)— or [N(X)]—;

X is absent, H, O, OH, $(C_1-C_4)$alkyl, phenyl or benzyl;

$R_4$ is OH, $(C_1-C_6)$alkyl, aryl, het, $CO_2R_e$, $CONR_eR_f$, CN, or $NR_eC(O)NR_eR_f$;

Z is het, a phenyl ring substituted with one or more substituents independently selected from halogen, $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkoxy, $(C_3-C_8)$cycloalkyloxy, and $(C_3-C_8)$cycloalkyl$(C_1-C_6)$alkoxy; piperidnyloxy, piperidnyloxy$(C_1-C_6)$alkyl or Z is a phenyl ring that is fused to a saturated, partially unsaturated, or aromatic, mono- or bicyclic ring system comprising from about 3 to about 8 atoms selected from carbon, oxygen, and $NR_b$, wherein the mono- or bicyclic ring system of Z is optionally substituted with one or more $R_c$, and wherein the phenyl ring that is fused to the mono- or bicyclic ring system is optionally substituted with one or more substituents independently selected from $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_2-C_6)$alkoxy, $(C_3-C_8)$cycloalkyloxy, and $(C_3-C_8)$cycloalkyl$(C_1-C_6)$alkoxy, CN and halogen;

each $R_a$ and $R_b$ is independently H, $(C_1-C_6)$alkyl, aryl, aryl$(C_1-C_6)$alkyl, het, or het$(C_1-C_6)$alkyl;

each $R_c$ and $R_d$ is independently H, OH, $NH_2$, $(C_1-C_6)$alkyl, or $R_c$ and $R_d$ taken together may join to form a 3- to 5-member ring comprising C atoms and optionally one or more O atom(s) and/or N(X);

each $R_e$ and $R_f$ is independently H, $(C_1-C_6)$alkyl, $(C_1-C_6)$alkoxy, $NH_2$, NHOH or $NH(C_1-C_6)$alkyl, wherein any phenyl, aryl, het or heteroaryl of Z, $R_1$ and/or $R_4$ is optionally substituted at any position with one or more substitutents independently selected from $(C_1-C_6)$alkyl, hydroxy, hydroxy$(C_1-C_6)$alkyl, phenyl, $(C_1-C_6)$alkoxy, $(C_1-C_6)$alkanoyl, $(C_1-C_6)$alkoxycarbonyl, $(C_1-C_6)$alkanoyloxy, $(C_3-C_8)$cycloalkyl, $(C_3-C_8)$cycloalkyl$(C_1-C_6)$alkyl, halo$(C_1-C_6)$alkyl, $(C_3-C_8)$cycloalkyloxy, $(C_3-C_8)$cycloalkyl$(C_1-C_6)$alkoxy, halo$(C_1-C_6)$alkoxy, cyano, nitro, halo, $(C_1-C_6)$carboxy or $NR_cR_d$; and wherein the piperazine core ring of compound (I) is optionally substituted at one or more carbon atom(s) with one or more substituents independently selected from oxo, halogen, $(C_1-C_6)$alkyl or $(C_1-C_6)$alkoxy;

and when $R_1$ is H or $C_1$alkyl, $Y-(A)_n-R_4$ taken together is not aryl$(C_1-C_6)$alkyl or hydroxy$(C_1-C_6)$alkyl;

or a pharmaceutically acceptable salt thereof.

In another aspect, the present invention provides pharmaceutical compositions comprising a compound of formula I, or a pharmaceutically acceptable salt thereof, and a pharmaceutically acceptable diluent or carrier.

In another aspect, the present invention provides pharmaceutical compositions comprising a compound of formula I, or a pharmaceutically acceptable salt thereof, one or more therapeutic agents that are effective to treat central and/or peripheral nervous system dysfunction, damage and/or disorders, improve cognitive function and/or treat a psychiatric disorder, and a pharmaceutically acceptable diluent or carrier.

In another aspect, the present invention provides methods for preparing a compound of formula I, or a pharmaceutically acceptable salt thereof.

In another aspect, the present invention provides a method for improving cognitive function in an animal by administering to the animal an effective amount of a compound of formula I, or a pharmaceutically acceptable salt thereof.

In another aspect, the present invention provides a method for inhibiting one or more PDE4 receptors in vitro and/or in vivo by contacting said PDE4 receptors with an effective inhibitory amount of a compound of formula I, or a pharmaceutically acceptable salt thereof.

In another aspect, the present invention provides a method for activating the CREB pathway in an animal by administering to the animal an effective CREB pathway activating amount of a compound of formula I, or a pharmaceutically acceptable salt thereof.

In another aspect, the present invention provides a method for preventing central and/or peripheral nervous system dysfunction, damage and/or disorders in an animal by administering to the animal an effective amount of a compound of formula I, or a pharmaceutically acceptable salt thereof.

In another aspect, the present invention provides a method of treating central and/or peripheral nervous system dysfunction, damage and/or disorders in an animal by administering to the animal an effective amount of a compound of formula I, or a pharmaceutically acceptable salt thereof.

In another aspect, the present invention provides a method for promoting neuronal plasticity in an animal by administering to the animal an effective amount of a compound of formula I, or a pharmaceutically acceptable salt thereof.

In another aspect, the present invention provides a method for promoting neuronal function in an animal by administering to the animal an effective amount of a compound of formula I, or a pharmaceutically acceptable salt thereof.

In another aspect, the present invention provides a method for promoting neuronal growth in an animal by administering to the animal an effective amount of a compound of formula I, or a pharmaceutically acceptable salt thereof.

In another aspect, the present invention provides a method of modulating neuronal cell differentiation in an animal by administering to the animal an effective amount of a compound of formula I, or a pharmaceutically acceptable salt thereof.

In another aspect, the present invention provides a method for modulating neuronal cell differentiation in an animal by administering to the animal an effective amount of a compound of formula I, or a pharmaceutically acceptable salt thereof.

In another aspect, the present invention provides a method for enhancing neural progenitor cell proliferation in an animal by administering to the animal an effective amount of of a compound of formula I, or a pharmaceutically acceptable salt thereof.

In another aspect, the present invention provides a method for modulating stem cell self-renewal in an animal by administering to the animal an effective amount of a compound of formula I, or a pharmaceutically acceptable salt thereof.

In another aspect, the present invention provides a method of modulating neuronal cell programming in an animal by administering to the animal an effective amount of a compound of formula I, or a pharmaceutically acceptable salt thereof.

In another aspect, the present invention provides a method for stimulating neurite growth in an animal by administering to the animal an effective amount of a compound of formula I, or a pharmaceutically acceptable salt thereof.

In another aspect, the present invention provides a method for inhibiting neuronal damage in an animal by administering to the animal an effective amount of a compound of formula I, or a pharmaceutically acceptable salt thereof.

In another aspect, the present invention provides a method for treating a disease or condition in an animal wherein the activity of PDE4 receptors is implicated and inhibition of PDE4 receptor activity is desired by administering to the animal an effective PDE4 inhibiting amount of a compound of formula I, or a pharmaceutically acceptable salt thereof.

In another aspect, the present invention provides a method for treating a disease or condition in an animal wherein the activity of PDE4 receptors is implicated and inhibition of PDE4 receptor activity is desired by co-administering an effective PDE4 inhibiting amount of a compound of formula I, or a pharmaceutically acceptable salt thereof with one or more therapeutic agents that are effective to treat central and/or peripheral nervous system dysfunction, damage and/or disorders, improve cognitive function and/or treat a psychiatric disorder.

The invention also provides a method for activating the CREB pathway in vitro comprising contacting a sample comprising SK-N-MC cells stably expressing a CRE-luciferase construct with an effective CREB pathway activating amount of a compound of formula I, or a pharmaceutically acceptable salt thereof.

The invention also provides a therapeutic method for treating a psychiatric disorder in an animal comprising administering to an animal in need thereof an effective amount of a compound of formula I, or a pharmaceutically acceptable salt thereof.

The invention provides a compound of formula I, or a pharmaceutically acceptable salt thereof for use in medical therapy (e.g. for use in improving cognitive function or for use in treating a disease or condition wherein inhibition of PDE4 receptor function is indicated or for treating a psychiatric disorder), as well as the use of a compound of formula I for the manufacture of a medicament useful for improving cognitive function in an animal.

The invention also provides the use of a compound of formula I, or a pharmaceutically acceptable salt thereof for the manufacture of a medicament useful for inhibiting PDE4 receptors in an animal.

The invention also provides the use of a compound of formula I, or a pharmaceutically acceptable salt thereof for the manufacture of a medicament useful for activating the CREB pathway in an animal.

The invention also provides the use of a compound of formula I, or a pharmaceutically acceptable salt thereof for the manufacture of a medicament useful for treating a psychiatric disorder in an animal.

The invention also provides synthetic processes and intermediates disclosed herein that are useful for preparing compounds of formula (I) or pharmaceutically acceptable salts thereof. Some compounds of formula I may be useful as intermediates for preparing other compounds of formula I.

Representative compounds of formula I have also been tested and found to produce little or no emesis.

BRIEF DESCRIPTION OF THE FIGURES

FIG. 1 shows data for a representative compound 126 of the invention in the Contextual Memory Assay (fear conditioning) described herein.

FIG. 2 shows data for a representative compound 126 of the invention in the novel object recognition (NOR) assay described herein.

DETAILED DESCRIPTION

The following definitions are used, unless otherwise described: halogen and grammatical variations thereof is fluoro, chloro, bromo, or iodo, and also includes pseudohalogens such as triflate, mesylate, tosylate, etc. Alkyl, alkoxy, etc. denote both straight and branched groups; but reference to an individual radical such as propyl embraces only the straight chain radical, a branched chain isomer such as isopropyl being specifically referred to. Haloalkoxy denotes a straight chain or branched alkoxy group substituted with one or more halogen atoms which may be at any carbon(s) of the haloalkoxy group. Aryl denotes a phenyl radical or an ortho-fused bicyclic carbocyclic radical having about nine to ten ring atoms in which at least one ring is aromatic; Het encompasses a radical of a monocyclic, bicyclic, or tricyclic ring system containing a total of 3-20 atoms, including one or more (e.g., 1, 2, 3, 4, 5, or 6) carbon atoms, and one or more (e.g., 1, 2, 3, or 4) heteroatoms selected from oxygen, sulfur, and N(X) wherein X is absent or is H, O, ($C_1$-$C_4$)alkyl, phenyl or benzyl, wherein one or more ring carbons of Het can optionally be substituted with oxo (=O); heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. The term Het encompasses Heteroaryl. Het and Heteroaryl may be connected to the core piperazine structure of compound I via any atom of the Het or Heteroaryl group. Het or heteroaryl may optionally substituted at any position with one or more substitutents independently selected from ($C_1$-$C_6$)alkyl, hydroxy, hydroxy($C_1$-$C_6$)alkyl, phenyl, ($C_1$-$C_6$)alkoxy, ($C_1$-$C_6$)alkanoyl, ($C_1$-$C_6$)alkoxycarbonyl, ($C_1$-$C_6$)alkanoyloxy, ($C_3$-$C_8$)cycloalkyl, ($C_3$-$C_8$)cycloalkyl($C_1$-$C_6$)alkyl, halo($C_1$-$C_6$)alkyl, ($C_3$-$C_8$)cycloalkyloxy, ($C_3$-$C_8$)cycloalkyl($C_1$-$C_6$)alkoxy, halo($C_1$-$C_6$)alkoxy, cyano, nitro, halo, ($C_1$-$C_6$)carboxy or $NR_cR_d$. Aryl($C_1$-$C_6$)alkyl is an alkyl group substituted with one or more aryl groups; Het($C_1$-$C_6$)alkyl is an alkyl group substituted with one or more Het groups; and Heteroaryl($C_1$-$C_6$)alkyl is an alkyl group substituted with one or more Heteroaryl groups.

The term "animal" as used herein includes birds, reptiles, and mammals (e.g., domesticated mammals and humans).

The term "psychiatric disorder" as used herein includes psychotic disorders, neurological disorders and neurotic disorders. The term includes schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); and includes subdural hematoma; normal-pressure hydrocephalus; brain tumor; head trauma (postconcussional disorder) or brain trauma.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine PDE4 inhibiting activity using the standard tests described herein, or using other similar tests which are well known in the art.

Specific values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_8$)cycloalkyl can be cyclopropyl, cyclobutyl, cyclopentyl, or cyclohexyl; ($C_3$-$C_8$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$) alkoxy can be methoxy, ethoxy, propoxy, isopropoxy, butoxy, isobutoxy, sec-butoxy, tert-butoxy, pentoxy, 3-pentoxy, or hexyloxy; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; halo($C_1$-$C_6$)alkoxy can be fluoromethoxy, difluoromethoxy, trifluoromethoxy, chloromethoxy, dichloromethoxy, trichloromethoxy, ethoxy, fluoroethoxy, difluoroethoxy, trifluoroethoxy, tetrafluoroethoxy, pentafluoroethoxy, chloroethoxy, dichloroethoxy, trichloroethoxy, tetrachloroethoxy, pentachloroethoxy, etc. ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$-$C_6$)alkanoyloxy can be acetoxy, propanoyloxy, butanoyloxy, isobutanoyloxy, pentanoyloxy, or hexanoyloxy; ($C_3$-$C_8$)cycloalkyloxy can be cyclopropyloxy, cyclobutyloxy, cyclopropyloxy, cyclohexyloxy, or cyclohexyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Z is a phenyl ring substituted with one or more substituents independently selected from ($C_1$-$C_6$) alkyl, halo($C_1$-$C_6$)alkyl, ($C_3$-$C_8$)cycloalkyl, ($C_3$-$C_8$)cycloalkyl($C_1$-$C_6$)alkyl, ($C_1$-$C_6$)alkoxy, halo($C_1$-$C_6$)alkoxy, ($C_3$-$C_8$)cycloalkyloxy, ($C_3$-$C_8$)cycloalkyl($C_1$-$C_6$)alkoxy, piperidnyloxy, and piperidnyloxy($C_1$-$C_6$)alkyl.

A specific value for Z is:

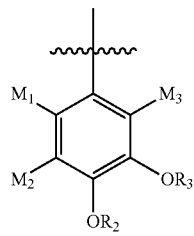

wherein:

$R_2$ and $R_3$ are each independently H, ($C_1$-$C_6$)alkyl, ($C_3$-$C_8$)cycloalkyl or halo($C_1$-$C_6$)alkyl; and $M_1$, $M_2$ and $M_3$ are each independently H, CN, halogen or ($C_1$-$C_2$)alkyl.

A specific value for $R_2$ is methyl, ethyl or difluoromethyl.

A specific value for $R_3$ is cyclopropyl, methylcyclopropyl, cyclobutyl, cyclopentyl, isopropyl, difluoromethyl, 1,3-difluoroisopropyl, N-methyl pyrrolidnyl or N-methylpiperidnyl.

A specific value for Z is a phenyl ring that is fused to a saturated, partially unsaturated, or aromatic, mono- or bicyclic ring system comprising from about 3 to about 8 atoms selected from carbon, oxygen, and $NR_b$; and Z is optionally substituted with one or more substituents independently selected from ($C_1$-$C_6$)alkyl, phenyl, ($C_1$-$C_6$)alkoxy, ($C_1$-$C_6$) alkanoyl, ($C_1$-$C_6$)alkoxycarbonyl, ($C_1$-$C_6$)alkanoyloxy, ($C_3$-$C_8$)cycloalkyl, ($C_3$-$C_8$)cycloalkyl($C_1$-$C_6$)alkyl, halo($C_1$-$C_6$) alkyl, ($C_3$-$C_8$)cycloalkyloxy, ($C_3$-$C_8$)cycloalkyl($C_1$-$C_6$) alkoxy, halo($C_1$-$C_6$)alkoxy, cyano, nitro, halo, carboxy or $NR_dR_e$.

A specific value for Z is:

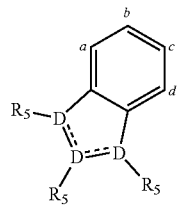 or 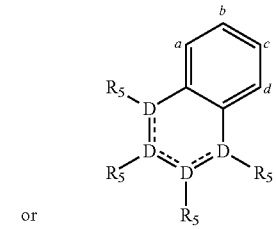

wherein:

===== is a single bond or a double bond,
each instance of D is independently C, N or O;
each $R_5$ is independently absent, H, ($C_1$-$C_6$)alkyl, phenyl, ($C_1$-$C_6$)alkoxy, ($C_1$-$C_6$)alkanoyl, ($C_1$-$C_6$)alkoxycarbonyl, ($C_1$-$C_6$)alkanoyloxy, ($C_3$-$C_8$)cycloalkyl, ($C_3$-$C_8$)cycloalkyl ($C_1$-$C_6$)alkyl, halo($C_1$-$C_6$)alkyl, ($C_3$-$C_8$)cycloalkyloxy, ($C_3$-$C_8$)cycloalkyl($C_1$-$C_6$)alkoxy, halo($C_1$-$C_6$)alkoxy, cyano, nitro, halo, carboxy or $NR_cR_d$;

and the attachment point of Z to the piperazine core ring of compound I may be at carbon a, b, c or d or at any $R_5$ when $R_5$ is absent.

A specific value for $R_1$ is ($C_2$-$C_6$)alkyl, aryl, aryl($C_1$-$C_6$) alkyl, het or het($C_1$-$C_6$)alkyl.

A specific value for $R_1$ is ethyl, n-propyl, isopropyl, n-butyl, sec-butyl, isobutyl, tert-butyl, benzyl, indolyl, indolylmethyl, phenyl, 2-methylpropyl, 2-, 3- or 4-methylbenzyl, benzhydryl, phenethyl, phenylpropyl, 1-naphthylmethyl, 2-naphthylmethyl, bipyridyl, 2-, 3- or 4-phenylbenzyl, 2-, 3- or 4-methoxybenzyl, 2-, 3- or 4-ethoxybenzyl, cyclohexylmethyl, morpholinomethyl, N-methyl-N-benzylmethyl, pyrrolidinylmethyl, pyrrolylmethyl, tetrahydroisoquinolinylmethyl, isoindolinylmethyl, pryazolylmethyl or fluorobenzyl.

A specific value for $R_4$ is H, OH, $NR_cR_d$, $CONR_cR_d$ ($C_1$-$C_6$)alkyl, ($C_1$-$C_6$)alkoxy, ($C_1$-$C_6$)alkanoyl, hydroxy($C_1$-$C_6$)alkyl, ($C_1$-$C_6$)alkoxycarbonyl, carboxy, aryl, aryl($C_1$-$C_6$) alkyl, het, or het($C_1$-$C_6$)alkyl.

A specific value for $Y$-$(A)_n$-$R_4$ is H, amido, methylamido, ethylamido, formylmethyl, methyl, ethyl, propyl, benzyl, ethylaminocarbonyl, methylsulfonyl, ethylsulfonyl, benzylsulfonyl, sulfonamido, hydroxyethyl, hydroxypropyl, hydroxybutyl, acetyl, hydroxyacetyl, aminoacetyl, N-methylaminoacetyl, acetamido, N-methylacetamido, N-ethylacetamido, cyanomethyl, cyanoethyl, cyanopropyl, methylaminoethanoyl, methylaminopropanoyl, ethylaminoethanoyl, methoxycarbonylmethyl, methoxyaminocarbonylmethyl, ethoxyaminocarbonylmethyl, propoxyaminocarbonyl, isobutoxyaminocarbonylmethyl, phenoxyaminocarbonylmethyl, benzyloxyaminocarbonylmethyl, prop-2-eneyloxyaminocarbonylmethyl, hydroxyaminocarbonylmethyl, hydrazocarbonylmethyl, 2-methylhydrazocarbonylmethyl, 2,2-dimethylhydrazocarbonylmethyl, amniopyridyl, pyridylmethyl, methoxycarbonyl, ethoxycarbonyl, propoxycarbonyl, tert-butoxycarbonyl, carboxymethyl, carboxyethyl, carboxypropyl, carboxybutyl, hydroxyethanoyl, hydroxypropanoyl, hydroxybutanoyl, amidomethanoyl, N-methylamidomethanoyl, amidoethanoyl, amidopropanoyl, N-methylamidoethanoyl, methylhydroxypropanoyl methylhydroxybutanoyl, carboxymethanoyl, carboxyethanoyl, carboxypropanoyl, carboxybutanoyl, aminohydroxymethylbutanoyl, hydrazocarbonylethanoyl, carboxycyclopropylmethanoyl, carboxycyclobutylmethanoyl, carboxycyclopentylmethanoyl, amidocyclopropylmethanoyl, amidocyclobutylmethanoyl, amidocyclopentylmethanoyl, thienylethanedionyl, thienylethanoyl, furanylethanoyl, imidazolylmethanoyl, imidazolylethanoyl, imidazolylpropanoyl, imidazolylmethyl, imidazolylethyl, methylpropanoyl, methoxyethanoyl, cyclopropoxymethanoyl, dimethylbutanoyl, methyltriazoylethanoyl, amidomethyl, amidoethyl, aminopropanoyl, hydroxypyrrolidnylmethanoyl, hydroxypyrrolidnylethanoyl, dimethylthiazolylmethanoyl, imidazolinonylmethanoyl, hydroxycyclopropylmethanoyl, ethanoyloxyethanoyl, pyrrolidinonylmethanoyl, hydroxyphenylmethanoyl, dihydroxyphenylmethanoyl, methylimidazolylethanoyl, thiazolylethanoyl, triazolonylethanoyl, tetrazolylethanoyl, dihydrofuranonylmethanoyl, hydroxycyclobutylmethanoyl, furanylethanedionyl, pyrazolylmethanoyl, methylpyrazolylethanoyl, pyrrolylethanoyl, pyrrolidnylethanoyl, carboxycyclobutylmethanoyl, methoxycarbonylcyclobutylmethanoyl, ethoxycarbonylcyclobutylmethanoyl, hydroxymethylcyclobutylmethanoyl, hydroxymethylpyrrolidnylethanoyl, methylpyrazolylethanolyl, hydroxymethylpyrrolidnylethanoyl, methylimidazolylethanoyl, nitrotriazolylethanoyl, methyltriazolylethanoyl, aminotriazolylethanoyl, pyrimidnylethanoyl, pryidylethanoyl, dimethylthiazolylmethyl, hydroxymethylphenylmethanoyl, hydroxyphenylmethyl, ethoxycarbonylethanoyl, fluorophenylethanoyl, difluorophenylethaonyl, methyloxadiazolylethanoyl, oxazolylethanoyl, methyloxazolylethanoyl, ethyltriazolylethanoyl, trifluoromethyltriazolylethanoyl, isopropyltriazolylethanoyl, ethylpyrazolylethanoyl, isopropylpyrazolylethanoyl, morpholinylethanoyl, pyrazinyl, thiazolyl, isoproprylimidazolylethanoyl, hydroxypyrrolidinylmethanoyl, hydroxymethylpyrrolidinylmethanoyl, hydroxyphenylamido, hydroxymethylphenylamido, methoxycarbonylpyrrolidinylmethanoyl or carboxypyrrolidinylmethanoyl.

A specific value for Z is a structure of formula III, IV, or V:

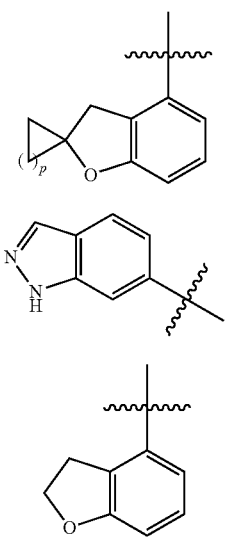

that is optionally substituted with one or more substituents selected from $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_2-C_6)$alkoxy, $(C_3-C_8)$cycloalkyloxy, and $(C_3-C_8)$cycloalkyl$(C_1-C_6)$alkoxy; and p is an integer from 1 to 6 inclusive.

A specific value for Z is a structure of formula VI, VII, and VIII:

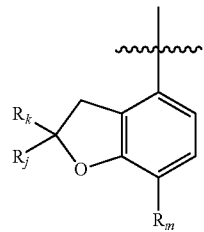

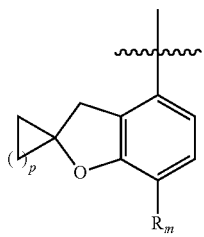

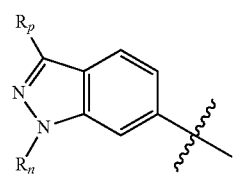

wherein:

$R_j$, $R_k$, $R_m$, $R_n$ and Rp are each independently selected from H, $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkoxy, $(C_3-C_8)$cycloalkyloxy and $(C_3-C_8)$cycloalkyl$(C_1-C_6)$alkoxy; and p is and integer from 1 to 6 inclusive.

A specific value for $R_j$ and $R_k$ is H and methyl.

A specific value for $R_m$ is methoxy.

A specific value for $R_n$ is cyclopentyl.

A specific value for $R_p$ is ethyl.

A specific value for p is 3.

Specific compounds of formula I are presented in the Examples below (e.g., compounds 1-513).

Processes for preparing compounds of formula I are provided as further embodiments of the invention and are illustrated by the following Preparative Examples, in which the meanings of any generic substituents are as given above unless otherwise qualified. Certain procedures or reactions known to those skilled in the art may be omitted so as to not unnecessarily obscure the present invention.

In one embodiment, the present invention provides a method for preparing a compound of formula 1 or a pharmaceutically acceptable salt thereof, comprising:

a) deprotecting a compound comprising one or more protecting groups to provide a compound of claim 1; and b) optionally forming said pharmaceutically acceptable salt of said compound of claim 1.

In another embodiment, the present invention provides A method for preparing a compound of claim 1 wherein Y-(A)$_n$-R$_4$ is other than H or a pharmaceutically acceptable salt thereof, comprising:

a) deprotecting a compound comprising one or more protecting groups to provide a compound of claim 1 wherein Y-(A)$_n$-R$_4$ taken together is H;

b) converting said compound of claim 1 wherein Y-(A)$_n$-R$_4$ taken together is H to a corresponding compound of claim 1 wherein Y-(A)$_n$-R$_4$ is other than H; and c) optionally forming said pharmaceutically acceptable salt of said compound of claim 1 wherein Y-(A)$_n$-R$_4$ is other than H.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient, in a variety of forms adapted to the chosen route of administration, e.g., orally or parenterally, by intravenous, intramuscular, topical or subcutaneous routes.

Furthermore, the present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with various of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 100 mg/kg, e.g., from about 10 to about 75 mg/kg of body weight per day, such as 3 to about 50 mg per kilogram body weight of the recipient per day, 0.5 to 90 mg/kg/day, or 1 to 60 mg/kg/day (or any other value or range of values therein). The compound is conveniently administered in unit dosage form; for example, containing 1 to 1000 mg, conveniently 10 to 750 mg, most conveniently, 50 to 500 mg of active ingredient per unit dosage form. Ideally, the active ingredient should be administered to achieve peak plasma concentrations of the active compound of from about 0.5 to about 75 $\mu$M, preferably, about 1 to 50 $\mu$M most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s). The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Compounds described in this invention are inhibitors of PDE4. The ability of the compounds described in the present disclosure to inhibit PDE4 makes them useful for preventing or reversing undesirable symptoms caused by PDE4 action, especially in human subjects. The inhibition of PDE4 indicates that the present compounds, pharmaceutically acceptable salts thereof, prodrugs of the present compounds, and pharmaceutical compositions containing the same are useful to treat, prevent, or ameliorate in mammals, and especially in humans, central nervous system or peripheral nervous system dysfunction, damage and/or disorders, cognitive disorders and/or psychiatric disorders.

Central or peripheral nervous system dysfunction, damage and/or disorders, cognitive disorders and/or psychiatric disorders may associated with lack of neuronal plasticity or attenuated neuronal function. The present PDE4 inhibitors may promote neuronal plasticity and/or neuronal recovery, e.g., after traumatic or ischemic injury to the central or peripheral nervous system. The present PDE4 inhibitors may also promote neurogenesis by modulating neuronal cell differentiation, by enhancing neural progenitor cell proliferation, by modulating stem cell self-renewal, by modulating cell reprogramming, by stimulating neurite growth, by elevating cAMP level to induce such neurite growth and by modulation and/or enhancement of neurotrophin levels and/or production (e.g., BDNF, GDNF, NGF). Further, the present PDE4 inhibitors may inhibit neuronal damage by inhibiting central nervous system gliosis, inhibiting microglial proliferation, inhibiting formation of reactive astrocytes, inhibiting neuronal excitotoxicity and/or inhibiting apoptosis.

Thus, in one aspect, the present invention provides a method for treating and/or ameliorating central or peripheral nervous system dysfunction, damage and/or disorders by administering the present PDE4 inhibitors. Such central or peripheral nervous system dysfunction, damage and/or disorders may include, but are not limited to: cerebrovascular disease, subdural hematoma, normal-pressure hydrocephalus, brain tumor, or head or brain trauma.

Another aspect of the invention provides a method of treating or preventing a PDE4 related disease comprising administering to a mammalian patient in need of such treatment a compound described in this invention in an amount which is effective for treating or preventing said PDE4 related disease. Such PDE4-related diseases include, but are not limited to: inflammation or autoimmune diseases, psychiatric disorders, psychotic disorders (e.g., schizophrenia), neurological disorders and neurotic disorders, disorders of the central nervous system including age-associated memory impairment, mild cognitive impairment, Alzheimer's disease, Parkinson's disease, Pick's Disease, vascular dementia, attention deficit disorder, affective disorder, depression and anxiety disorder.

Accordingly, another aspect of the invention provides a method of treating or preventing a PDE4 related disease comprising administering to a mammalian patient in need of such treatment a compound described in this invention in an amount which is effective for treating or preventing said PFE4 related disease. The present invention also provides a method for improving cognitive function in a healthy animal, especially a human.

The compounds of the invention can also optionally be administered in combination with one or more other therapeutic agents that are effective to improve cognition or treat a psychiatric disorder and/or one or more therapeutic agents that are effective to treat age associated memory impairment (AAMI); mild cognitive impairment (MCI), delirium (acute confusional state); dementia (sometimes further classified as Alzheimer's or non-Alzheimer's type dementia); Alzheimer's disease; Parkinson's disease; Pick's Disease, multiple sclerosis, Huntington's disease (chorea); mental retardation; (e.g., Rubenstein-Taybi, Fragile X, Angelman Syndrome, Coffin-Lowry Syndrome and Downs Syndrome); Wilson's Disease, Creutzfeldt-Jacob Disease, Neurofibromatosis type 1, Wernicke-Korsakoff Syndrome, cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) and brain trauma (see Diagnostic and Statistical Manual of Mental Disorders-IV, American Psychiatric Association, 1994).

The ability of a compound to inhibit PDE 4 activity can be determined using assays that are known, or it can be determined using the following assay.

PDE4 Inhibition Assay

PDE4 from human U-937 cells was used (see T. J. Torphy, et al., J. Pharmacol. Exp. Ther., 1992, 263, 1195-1205). Test compound at various concentration and/or vehicle was pre-incubated with 2 µg/ml enzyme in Tris-HCl buffer pH 7.5 for 15 minutes at 25° C. The reaction was initiated by addition of 1 1 µM cAMP and 0.01 1 µM [$^3$H]-cAMP for another 20 minute incubation period and terminated at 100° C. The resulting [$^3$H]-AMP was converted to [$^3$H]-adenosine by addition of snake venom nucleotidase and separated by AG1-X2 resin. An aliquot was removed and counted to determine the amount of [$^3$H]-adenosine formed. Results were converted to percent inhibition and IC so determined using XLfit from IDBS (ID Business Solutions Ltd., 2 Occam Court, Surrey Research Park, Guildford, Surrey, GU2 7QB UK).

Representative compounds of the present invention were tested and found to have significant PDE4 inhibition in this assay. Compounds described herein were found to have potencies in the described PDE4 assay according to the following classification:

| Potency Class | Inhibitory Concentration |
| --- | --- |
| A | <200 nm |
| B | 200 nm to 1 µm |
| C | >1 µm |
| ND | Not determined |

The ability of a compound to activate CREB can be determined using the following assay.

CREB Activation Assay

The following CRE-Luci assay is a high throughput, well-based method for identifying compounds that enhance cognition by increasing CREB pathway function. The assay enables the identification of cognitive enhancers that do not affect CREB pathway function alone, but act to increase (enhance) CREB pathway function in combination with a CREB function stimulating agent.

The assay is carried out by (a) contacting host cells (particularly cells of neural origin (e.g. human neuroblastoma SK-N-MC cells) having a luciferase gene operably linked to a CRE promoter with a test compound and a suboptimal dose of a CREB function stimulating agent (e.g., forskolin); (b) determining luciferase activity in the host cells which have been contacted with the test compound and with the CREB function stimulating agent; and (c) comparing the luciferase activity determined in step (b) with the luciferase activity in control cells which have been contacted with the CREB function stimulating agent and which have not been contacted with the test compound (i.e., control cells which have been contacted with the CREB function stimulating agent alone).

Host cells comprising luciferase gene operably linked to a CRE-promoter can be manufactured by introducing into cells a DNA construct comprising a luciferase gene operably linked to a CRE promoter. DNA constructs can be introduced into cells according to methods known in the art (e.g., transformation, direct uptake, calcium phosphate precipitation, electroporation, projectile bombardment, using liposomes). Such methods are described in more detail, for example, in Sambrooke et al., Molecular Cloning: A Laboratory Manual, 2nd edition (New York: Cold Spring Harbor University Press, 1989); and Ausubel et al., Current Protocols in Molecular Biology (New York: John Wiley & Sons, 1998).

SK-N-MC cells stably transfected with CRE-luc construct are seeded in 96-well, white assay plates (PerkinElmer) at a concentration of 20,000 cells/well in 100 pi, MEM complete media. These cells are incubated in a $CO_2$ incubator under standard cell culture condition. After 18 to 24 hours of incubation, cells are treated with either a vehicle control (DMSO, Sigma), the test compounds (5 µM final concentration), or a positive control (HT0712, 5 µM final concentration) (16 wells for each treatment) for 2 hours. Forskolin (5 µM final concentration, Sigma) is then added to 8 wells of each treatment group and an equivalent amount of DMSO is added to the other 8 wells. Six hours after forskolin addition, luciferase activity is measured by adding 25 µl, of assay reagent (BriteLite kit, PerkinElmer) to each well. After incubation at room temperature for 3 minutes, luminescence is detected using a Wallac Victor5 plate reader (PerkinElmer). The transcription induction ratio is derived by normalizing the luciferase activity of the compound or positive control in the presence of forskolin over forskolin treatment alone. The compound treatment alone serves as control to determine whether compound can activate CRE promoter by itself.

Representative compounds of the invention were found to increase CREB pathway function using this assay.

The ability of a compound to modulate cognitive behavior can be evaluated using the following Contextual Memory Assay.

Contextual Memory Assay: Fear Conditioning

Contextual memory is a form of Pavlovian fear conditioning in which a naive mouse is placed into a novel chamber (context) containing distinct visual, olfactory and tactile cues. After several minutes of acclimation, the mouse receives a brief, mild electric shock to its feet. From this negative experience, the mouse will remember for months that that chamber is dangerous. When placed back into the same context at some later time after training, the mouse's natural response to danger is to "freeze," sitting stone still for many seconds. This is similar to what happens to humans when they experience fear. The percent of time during an observation period that the mouse spends frozen represents a quantitative measure (memory score) of its memory of the context.

Contextual conditioning has been extensively used to investigate the neural substrates mediating fear-motivated learning (Phillips, LeDoux, Behav Neurosci 1992 (106), 274-285; Kim et al., Behav Neurosci 1993 (107) 1093-1098; Bourtchouladze et al., Learn Mem 1998 (5) 365-374; and Bourtchouladze et al., Cell 1994 (79) 59-68). Contextual conditioning has been also used to study the impact of various mutations on hippocampusdependent memory (Bourtchouladze et al., Learn Mem 1998 (5) 365-374; Bourtchouladze et al., Cell 1994 (79) 59-68; Silva et al., Curr Biol 1996 (6) 1509-1518; Kogan et al., Curr Biol 1997 (7) 1-11; Abel et al., Cell 1997 (88) 615-626; and Giese et al., Science 1998 (279), 870-873); and strain and genetic background differences in mice (Logue et al., Behav Neurosci 1997 (111), 104-113; and Nguyen et al., Learn Mem 2000 (7) 170-179). Because robust memory can be triggered with a few minutes training session, contextual conditioning has been especially useful to study biology of temporally distinct processes of short- and longterm memory (Kim et al., *Behav Neurosci* 1993 (107) 1093-1098; Bourtchouladze et al., *Learn Mem* 1998 (5) 365-374; Bourtchouladze et al., *Cell* 1994 (79), 59-68; and Abel, et al., *Cell,* 1997 (88), 615-626). As such, contextual conditioning is an excellent model to evaluate the role of various novel drug-compounds in hippocampus-dependent memory.

Young-adult (10-12 weeks old) C57BL/6 male mice and Sprague Dawley male rats of 250-300 g (Taconic, N.Y.) were used. Mice were group-housed (5 mice) in standard laboratory cages while rats were housed in pairs and maintained on a 12:12 light-dark cycle. The experiments were always conducted during the light phase of the cycle. With the exception of testing times, the mice had ad lib access to food and water. The experiments were conducted according with the Animal Welfare assurance #A3280-01 and animals were maintained in accordance with the animal Welfare Act and Department of Health and Human Services guide.

To assess contextual memory, a modified contextual fear conditioning task originally developed for evaluation of memory in CREB knock-out mice was used (Bourtchouladze, et. aL, Cell, 1994, 79, 59-68). On the training day, the mouse was placed into the conditioning chamber (Med Associates, Inc., VA) for 2 minutes before the onset of unconditioned stimulus (US), 0.5 mA, of 2 sec foot shock. The US was repeated two times with a 1 min inter-trial interval between shocks. Training was performed by automated software package (Med Associates, Inc., VA). After the last training trial, the mice were left in the conditioning chamber for another 30 sec and were then placed back in their home cages. 24 hours after training, the mouse was placed into the same training chamber and contextual memory was assessed by scoring freezing behavior ('freezing' serves as memory score). Freezing was defined as the complete lack of movement in intervals of 5 seconds (Kim et al., *Behav Neurosci* 1993 (107) 1093-1098; Phillips, LeDoux, *Behav Neurosci* 1992 (106) 274-285; Bourtchouladze et al., *Learn Mem* 1998 (5) 365-374; and Bourtchouladze et al., *Cell* 1994 (79) 59-68; Abel et al., *Cell* 1997 (88), 615-626). Total testing time lasted 3 minutes. After each experimental subject, the experimental apparatus was thoroughly cleaned with 75% ethanol, water, dried, and ventilated for a few minutes.

All experiments were designed and performed in a balanced fashion, meaning that (i) for each experimental condition (e.g. a specific dose-effect) an equal number of experimental and control mice was used; (ii) each experimental condition was replicated 2-3 independent times, and replicate days were added to generate final number of subjects. The proceeding of each experiment was filmed. In each experiment, the experimenter was unaware (blind) to the treatment of the subjects during training and testing. Data were analyzed by Student's unpaired t test using a software package (Statview 5.0.1; SAS Institute, Inc). All values in the text and figures are expressed as mean+SEM.

Compounds were dissolved in 1% DMSO/PBS and administered intraperitonially (I.P.) in a volume of 8 mL/kg 20 min before training. Control animals received vehicle alone (1% DMSO/PBS). For oral administration the compounds were dissolved in 30% DMSO/1.4% CMC. Consequently, control animals received 30% DMSO/1.4% CMC. For each training and drug-injecting procedure, an experimentally naive group of animals was used.

To evaluate the effects of representative Compound 126 on contextual memory, mice were injected with Compound 126 or vehicle 20 minutes before training and trained with 2 training trials (US). Mice were than tested in the same context 24 hours after training (FIG. 1). 1 mg/kg Compound 126-injected mice froze significantly more than vehicle injected mice (32.5+3.2% vs. 22.3+3.2%; n=22 and n=20 for Compound 126 and controls, respectively; p<0.05, Student's unpaired t test). Similarly, 10 mg Compound 126-injected mice showed significantly more memory than vehicle injected mice (38.3% vs. 22.3+3.2%; n=22 and n=20, for Compound 126 and controls, respectively; p<0.005, Student's unpaired t test), while 0.1 mg/kg Compound 126 had no significant effect on contextual memory.

The ability of a compound to modulate cognitive behavior can also be evaluated using the following Object Recognition Assay.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, et. al., Proc Natl Acad Sci USA, 2003, 100, 10518-10522). Recent neuroimaging studies in humans demonstrated that memory in object recognition depends on prefrontal cortex (PFC) (Deibert et al., *Neurology* 1999 (52) 1413-1417). Consistent with these findings, rats with the PFC lesions show poor working memory when they are required to discriminate between familiar and novel objects (Mitchell, Laiacona, *Behav Brain Res* 1998 (97) 107-113). Other studies on monkeys and rodents suggest that the hippocampus is important for novel object recognition (Teng et al., *J. Neurosci* 2000 (20) 3853-3863; Mumby, *Brain Res* 2001 (127) 159-181). Hence, object recognition provides an excellent behavioral model to evaluate drug-compound effects on cognitive task associated with function of hippocampus and cortex.

Prior to initiation of training, animals were handled for 3-5 minutes for 5 days. Training and testing were performed identically for mice and rats with an exception of training apparatus dimensions (for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see Pittenger et al., *Neuron* 2002 (34) 447-462; and Bourtchouladze et al., *Proc Natl Acad Sci USA* 2003 (100) 10518-10522). Training was initiated 24 h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To insure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, Aggleton, *Behav Brain Res* 1997 (88) 181-193; and Bourtchouladze et al., *Proc Natl Acad Sci USA* 2003 (100) 10518-10522). These data were analyzed by Student's unpaired t test using a software package (Statview 5.0.1; SAS Institute, Inc). All values in the text and figures are expressed as mean±SEM.

Memory Improvement in Humans

A randomized, double-blind, placebo-controlled clinical study of a PDE4 inhibitor of the present invention of formula I will be conducted in normal healthy adult male and female subjects. The study will identify the maximum tolerated dose (MTD) and dose-limiting side effects, assess the effects thereof on quantitative memory scores, assess the perceived central nervous system (CNS) effects following administration, assess the effects of a PDE4 inhibitor of the present invention of formula I on the cardiovascular system, explore the relationship between dose, tolerability, safety and pharmacological effects of a PDE4 inhibitor of the present invention, and define the pharmacokinetics (PK) thereof.

There are five (5) treatment periods in each trial. Each treatment period is one (1) week in duration and consists of two (2) consecutive days of treatment ("treatment period") with a PDE4 inhibitor of the present invention (at doses of, e.g., 5 mg, 15 mg, 30 mg, 45 mg, etc.) or placebo, followed by five (5) consecutive days without a PDE4 inhibitor of the present invention or placebo ("washout period"). The design is an ascending dose safety design with a placebo dose randomly inserted into the sequence. Each subject is randomly administered a single dose of a PDE4 inhibitor of the present invention (e.g., 5 mg, 15 mg, 30 mg, or 45 mg, etc.) or a randomly assigned dose of placebo during each treatment period on the two consecutive treatment days. Each subsequent treatment group includes whatever dose of a PDE4 inhibitor of the present invention (or placebo) has not previously been administered, until the patient has received each of the screened doses (e.g., 5 mg, 15 mg, 30 mg, 45 mg, etc.) or single placebo treatment to conclude the five week treatment period. Safety data are reviewed after each dose prior to advancement to the next dose level.

The Rey Auditory Visual Learning Test (RAVLT, Rey, A. (1941). *L'examen psychologique dans les cas d'encephalopathie traumatique*. Archives de Psychologie, 28, 21, Lezak, M. D. (1995). Neuropsychological Assessment (3rd ed.). New York: Oxford University Press) is conducted during each of the two consecutive days when the patent receives a PDE4 inhibitor of the present invention or placebo. RAVLT is not conducted during the washout period.

The RAVLT assessment for word recall is made at two (2) different times following treatment (a PDE4 inhibitor of the present invention or placebo) during each of the five treatment periods. The first RAVLT assessment is made on the first day of treatment in each treatment period and consists of two parts. Fifteen (15) nouns are read aloud to the patient by an Examiner, followed by an interference or distraction trial, which is then followed by a free-recall test of the 15 nouns. After an additional 30-minute delay period, the subject is again required to recall the first set of 15 nouns and also complete a 50-word recognition test. The second RAVLT assessment is made on the second day of treatment in each treatment period and consists of a repeat of the Recall test and the 50-word Recognition test given on the previous day. The second RAVLT assessment evaluates word recall 24 hours (±2 hours) after the first RAVLT assessment and does not consist of another exposure to nouns by an Examiner, but rather a recall of the nouns given to the subject 24 hours earlier.

Safety and tolerability assessments are changes in vital signs, ECGs, Holter monitoring, laboratory tests, physical examination and adverse events. Serial blood and urine samples are collected up to 24 hours after dosing for determination of plasma concentrations of a PDE4 inhibitor of the present invention and calculation of pharmacokinetic parameters.

For each patient, RAVLT data will demonstrate that all dose groups have mean values higher than the placebo at 30 minutes. Two exemplary higher doses (e.g., 30 mg and 45 mg) exhibit the greatest improvement (highest values) compared to placebo testing. The benefit observed at 30 minutes is maintained at 24 hours, with the recalled number of words slightly lower at 24 hours for each dose compared to the corresponding results at 30 minutes. The recall scores are approximately 10 words following administration of e.g., a 45 mg dose a PDE4 inhibitor of the present invention, compared to approximately 7-8 words recalled when the placebo dose is administered.

A pooled statistical analysis of the 30-minute and 24-hour RAVLT memory scores is performed. The scores show an overall statistically significant ($p<0.05$) improvement in RAVLT score with respect to a dose of a PDE4 inhibitor of the present invention at both 30 minutes and 24 hours post-treatment. In addition, improvements in RAVLT scores observed with the 30 mg and 45 mg doses of a PDE4 inhibitor of the present invention are statistically significant ($p<0.05$), based on the Wilcoxon signed rank test, when compared to placebo at both 30 minutes and 24 hours post-dose. The difference is also significant ($p=<0.05$) at the 5 mg dose for the 24-hour recall scores. A comparison of each individual subject's placebo score to their best score on any dose of a PDE4 inhibitor of the present invention shows that RAVLT memory performance for all subjects improves following treatment with a PDE4 inhibitor of the present invention.

These data demonstrate that a PDE4 inhibitor of the present invention enhances memory, in particular memory consolidation.

Improvement in Cognitive Processes

A computerized cognitive screening tool (HeadMinder, Inc. (New York, N.Y.)) will be employed for the assessment and longitudinal tracking of cognitive functioning (Erlanger, D. M., et al., J. Head Trauma Rehabil. 17:458-476 (2002); US2003/0073885A1 (2003); WO 01/54650 (2001); WO 01/72217 (2001); WO 01/54559 (2001), the relevant portions of each of which are hereby incorporated by reference).

Mild cognitive impairment in subjects is diagnosed based on conventional neuropsychiatric testing parameters—scoring below the age- and educational-adjusted cutoff on the Logical Memory II subscale from the Wechsler Memory Scale. A single test score is used to define subjects with mild cognitive impairment. In addition, the subjects used in this study will not score higher than 0.5 on the Clinical Dementia Rating scale. Some subjects with a Clinical Dementia Rating of 0.5 can have early Alzheimer's disease. Some subjects enrolled in this study may score in the Alzheimer's disease range of some cognitive assessments. Thus, some subjects classified as having mild cognitive impairment may actually have early Alzheimer's disease. In populations of humans with mild cognitive impairment and early Alzheimer's disease, neuropsychiatric tests typically measure a continuum (bell-shaped curve) and the definitions are relatively arbitrary cut points for the abnormal population—typically 1 or 1.5 standard deviations below the norm adjusted for age and education.

The battery of nine (9) tests to be completed by the subjects includes two (2) "warm-up" tasks. The remaining seven (7) subtests are included to evaluate cognitive abilities, such as learning and memory, attention, reaction time, and executive function.

Test Factors and Subtest Descriptions

Keyboard Proficiency 1
A green ball appears on the screen. The subject presses the space bar as quickly as possible until the ball turns red.
Keyboard Proficiency 2
Numbers from 0-9 appear. The subject presses the number that appears on the screen on the keyboard as quickly as possible.
Learning and Memory
  Memory Cabinet 1
  Subjects learn the placement of nine (9) household objects placed in a cabinet over three (3) learning trials.
  Memory Cabinet 2—Delayed Memory
  Following intervening tasks, one (1) recall trial of the Memory Cabinet is administered to the subject.
Attention and Executive Function
  Response Direction 1—Simple Attention (a Low Demand Task)
  Numbers are presented. The subject presses the "1" key when a 1 is presented and presses the "0" key when a 0 is presented.
  Response Direction 2—Response Reversal (a High Demand Task)
  Numbers are presented one at a time. The subject presses the "1" key when a 0 is presented and presses the "0" key when a 1 is presented.
Supplemental Tests
  The subject places his or her fingers on 4 keys, each representing a box on the screen.
  Visuo-Motor Speed 1
  Boxes light up one at a time. The subject presses the corresponding key as quickly as possible.
  Visuo-Motor Speed 2
  Instructions appear in the center of the screen. The subject presses the corresponding key shown as quickly as possible.
  Visuo-Motor Speed 3
  Instructions are presented on the screen in the wrong location. The subject presses keys according to each instruction while ignoring the location of the instruction (e.g., "UPPER RIGHT" appears in the lower right of the screen).

Subjects

Subjects will be randomly assigned to receive either a PDE4 inhibitor of the present invention or a placebo. Subjects treated with a PDE4 inhibitor of the present invention receive 5 mg per day for the first seven (7) days of the study, following by 15 mg per day for the next seven (7) days of the study, followed by 30 mg per day for the next fourteen (14) days of the study. Subjects receiving placebo receive identical dosages of placebo pills for the duration of the study. Cognitive functions are assessed at baseline (day 0) and on days 1, 8, 15 and 28 of treatment or placebo.

Results

To demonstrate equivalent keyboard and general cognitive skills, an ANCOVA (Analysis of Co-Variance) exploring the treatment condition (treatment=administration of a PDE4 inhibitor of the present invention at 5 mg, 15 mg, 30 mg) is performed with Keyboard Proficiency 2 as the dependent variable and age as the covariate. PDE4 inhibitor of the present invention and placebo subjects do not differ in performance on this task at any test instance, indicating they are roughly equivalent. Higher scores in the keyboard proficiency indicate slower performance.

To determine whether the subjects receiving a PDE4 inhibitor of the present invention have improved memory function, two ANCOVAS exploring the treatment condition are performed with learning and memory as the dependent variables and age as the covariate. Learning and memory are improved in subjects receiving a PDE4 inhibitor of the present invention. Significant improvements ($p<0.05$) in the learning and memory at 30 mg doses (days 15 and 29) are observed in subjects receiving a PDE4 inhibitor of the present invention compared to subjects receiving placebo. Placebo treated subjects show no improvement in learning and memory.

Improvements in executive function following treatment with a PDE4 inhibitor of the present invention or placebo will be assessed by determining the difference between performance on Response Direction 1 (Low Demand Task) and Response Direction 2 (High Demand Task). Maintained learning efficiency is associated with a stable difference score across repeated assessments. Decreased learning efficiency, which is expected in a subject with mild cognitive impairment, is associated with increased differences across repeated assessments since inefficient subjects make greater improvements due to practice effects on the low demand task than on the high demand task, while efficient subjects improve on both tasks at a similar rate.

An ANCOVA will show significant differences between subjects treated with a PDE4 inhibitor of the present invention (30 mg, day 15) and placebo. A linear contrast of difference scores between the low and high demand tasks across repeated assessments will not be significant for participants in the PDE4 inhibitor of the present invention group and will be significant for participants in the placebo group. This indicates that those in the a PDE4 inhibitor of the present invention group maintain learning efficiency and that those in the placebo group do not. The placebo group's performance improves on the low demand task, but not on the high demand task, causing the differences to increase in a linear manner. In contrast, the a PDE4 inhibitor of the present invention group improves equally on both the low and high demand tasks, so that the differences remain roughly the same. In the a PDE4 inhibitor of the present invention group, a large decrease in learning efficiency at the final assessment—when the medication is no long active—is observed.

Prior to treatment with a PDE4 inhibitor of the present invention, mild cognitive impairment and early Alzheimer's disease subjects will exhibit cognitive impairments. Treatment of subjects with placebo will not improve cognitive function. In contrast, subjects treated with a PDE4 inhibitor of the present invention will exhibit improved performance on tests for learning, memory and executive function to the extent (one standard deviation or more) such that subjects treated with a PDE4 inhibitor of the present invention score within the normal range on tests assessing learning, memory and executive function. The magnitude of improvement in learning, memory and executive function following compound treatment will be clinically significant and efficaciously statistically significant (p<0.05) for each of the learning, memory and executive function assessments.

Improvements in memory, learning and executive function by treatment with a PDE4 inhibitor of the present invention can have profound implications for improvement in the clinical symptoms of mild cognitive impairment, early Alzheimer's disease and in performances of everyday tasks ranging from managing medications to grocery shopping and operating a vehicle.

Improvement in Memory in Humans

Randomized, double-blind, placebo-controlled clinical studies will be conducted in healthy adult male and female subjects who will be administered a PDE4 inhibitor of the present invention. The first Phase I clinical trial is conducted with healthy subjects who do not have memory or cognitive impairments (also referred to herein as "normal subjects"), ranging in age from 20-60 years and 61-80 years who are administered placebo or 1 mg, 4 mg, 16 mg or 32 mg of a PDE4 inhibitor of the present invention. A second Phase I clinical trial will be conducted with normal subjects with an age range of 50-64 years. In the second clinical trial, subjects will receive either 25 mg, 50 mg, 100 mg of a PDE4 inhibitor of the present invention, some of whom will also receive placebo (0 mg of compound), or 150 mg of a PDE4 inhibitor of the present invention.

The studies are designed to identify a maximum tolerated dose and dose-limiting side effects of a PDE4 inhibitor of the present invention; to assess the effects of a PDE4 inhibitor of the present invention on quantitative memory scores for example, by the California Verbal Learning Test (CVLTII) or RAVLT; to assess the perceived CNS effects following the administration of a PDE4 inhibitor of the present invention on the cardiovascular system; to explore the relationship between dose, tolerability, safety and pharmacological effects of a PDE4 inhibitor of the present invention; and to define the pharmacokinetics of a PDE4 inhibitor of the present invention.

There will be six (6) treatment periods in the first Phase I clinical trial. There will be four (4) treatment periods in the second Phase I clinical trial. Each treatment period is one (1) week in duration and consists of two (2) consecutive days of treatment with a PDE4 inhibitor of the present invention (1, 4, 16 or 32 mg for the first Phase I study and 25, 50 or 100 mg for the second Phase I study) or a placebo, followed by five (5) consecutive days without a PDE4 inhibitor of the present invention or a placebo. Each subject is randomly administered a single dose of one of the PDE4 inhibitor of the present invention doses or randomly assigned a dose of placebo during each treatment period. Each subsequent treatment group includes whatever dose of a PDE4 inhibitor of the present invention has not previously been administered, until the patient has received each of the PDE4 inhibitor of the present invention doses or a single placebo treatment to conclude the treatment period. Safety data will be reviewed after each dose prior to advancement to the next dose level. The RAVLT assessment for word recall is performed as described above and made at two different times following the administration of a PDE4 inhibitor of the present invention or a placebo during each of the treatment periods. The initial RAVLT training is conducted approximately two and a half hours after administration of the PDE4 inhibitor of the present invention or a placebo. After a 30-minute delay period, the subject is required to recall a first set of 15 nouns. The second RAVLT assessment is made approximately 24-hours following treatment with a PDE4 inhibitor of the present invention.

Safety and tolerability assessments are as described for treatment with Phase I clinical study with a PDE4 inhibitor of the present invention and consist of assessments in vital signs, ECGs, physical examination and the noting of any adverse events.

Data from the second Phase I study will show that all dose groups have mean values greater than placebo at 30 minutes and 24 hours. Thus, the benefit in improving memory following the administration of a PDE4 inhibitor of the present invention observed at 30 minutes is maintained at 24 hours. No difference in memory scores is observed in subjects in the first Phase I study. These data show that administration of a PDE4 inhibitor of the present invention enhances memory in subjects who do not have any known impairment in memory or cognition.

Improvement in Cognitive Processes Following Administration of a PDE4 Inhibitor of the Present Invention A randomized, double-blind, placebo-controlled, dose escalation study in human subjects, who were not suffering from an impairment in a memory or cognitive process ("normal subjects"), will be conducted to assess the safety, tolerability and pharmacokinetics and improvement in cognitive processes, including memory, following the administration of a PDE4 inhibitor of the present invention (25 mg, 50 mg, 100 mg, 150 mg).

Eight (8) subjects will receive 25 mg, 50 mg, 100 mg of a PDE4 inhibitor of the present invention; of these eight (8) subjects, five (5) subjects also receive placebo and three (3) subjects receive 150 mg of a PDE4 inhibitor of the present invention. The studies are conducted employing a battery of cognitive tests developed by Cognitive Drug Research (CDR) in the United States.

A selection of tasks from the CDR computerized cognitive assessment system is administered and parallel forms of the tests are presented on each testing session. The CDR tasks are well-established assessments of cognition and known to one of skill in the art. All tasks are computer-controlled, the information is presented on high resolution screens, and the responses are recorded via a response module containing two buttons, one marked 'NO' and the other 'YES'. The tracking task additionally involves the use of a joystick. The test battery takes about 20-25 minutes to perform. The tests are administered in the following order:

Picture Presentation

A series of 20 pictures is presented on the screen at the rate of 1 every 3 seconds for the subject to remember. No data are recorded from this task.

Simple Reaction Time

The subject is instructed to press the 'YES' response button as quickly as possible every time the word 'YES' is presented on the screen. Fifty stimuli are presented with a varying inter-stimulus interval.

Digit Vigilance

A target digit is randomly selected and constantly displayed to the right of the screen. A series of digits is then presented in the center of the screen at the rate of 150 per minute and the subject is required to press the 'YES' button as quickly as possible every time the digit in the series matches the target digit. There are 45 targets in the series. The task lasts for 3 minutes.

Choice Reaction Time

Either the word 'NO' or the word 'YES' is presented on the screen and the subject is instructed to press the corresponding button as quickly as possible. There are 50 trials for which each stimulus word is chosen randomly with equal probability and there is a varying inter-stimulus interval.

Rapid Visual Information Processing

A series of digits is presented on the screen at the rate of 100 per minute. The subject has to detect targets consisting of consecutive sequences of either three odd digits or three even digits, and to report them by pressing the 'YES' button as quickly as possible. There are 32 targets. The task lasts for 4 minutes.

Tracking

The subject uses a joystick to track a randomly moving target on the screen for one minute. The distance off-target per second is recorded.

Spatial Working Memory

A picture of a house is presented on the screen with four of its nine windows lit. The subject has to memorize the position of the lit windows. For each of the 36 subsequent presentations of the house, the subject is required to decide whether or not the one window that was lit was also lit in the original presentation. The subject responds by pressing the 'YES' or 'NO' buttons as appropriate, as quickly as possible.

Numeric Working Memory

A series of five digits is presented for the subject to hold in memory. This is followed by a series of 30 probe digits for each of which the subject has to decide whether or not it was in the original series and press the 'YES' or 'NO' response button as appropriate, as quickly as possible. This procedure is repeated twice more, using two different series and probes.

Picture Recognition

The original pictures plus 20 distracter pictures are presented one at a time in a randomized order. For each picture the subject has to indicate whether or not the subject recognized it as being from the original series by pressing the 'YES' or 'NO' button as appropriate, as quickly as possible.

Summary statistics are calculated for the unadjusted scores, and the difference from baseline (pre-dose) data collected. Repeated measures analysis of variance (ANOVA) are conducted on the difference from baseline data fitting terms for dose, time, period and the dose-time interaction. A random effect of subjects is fitted to the model.

A PDE4 inhibitor of the present invention will generally exhibit a dose-dependent effect on speed of response. This dose dependent pattern indicates a post-dose decline with placebo treatment, and increasing post-dose improvements in response speed with active dosing using a combined Total Speed score, which combines the reaction time measures from all the CDR tasks, except the Tracking task. Subjects receiving placebo will take a longer time to respond with a dose-response reduction in the total response time. A dose dependent pattern will be evident in the mean difference from baseline. A pattern for dose dependent benefit will be evident on several of the reaction time measures. Total speed tasks assess cognitive functions.

Administration of a PDE4 inhibitor of the present invention (25 mg, 150 mg) will improve the Picture Recognition—Sensitivity Index, a task that assesses memory. A significant effect of treatment will be seen from the ANOVA ($p \leq 0.05$). The mean comparisons will show significant benefits for 25 mg and 150 mg over placebo.

In summary, these data will show a dose dependent effect of a PDE4 inhibitor of the present invention on reaction time (speed of response) on the CDR task measures. A dose of 25 mg and 150 mg of a PDE4 inhibitor of the present invention will show an improved Picture Recognition—Sensitivity Index (accuracy), an assessment of memory. A dose dependent benefit of a PDE4 inhibitor of the present invention on Information Processing Targets Detected (accuracy) will also observed, which is an assessment of cognition. This benefit is also associated with increased False Alarms on the task, which may indicate a change in response strategy (increased responding), rather than a direct benefit to accuracy. However, when the False Alarms measures is used as a covariate in the analysis of the Targets Detected (accuracy) measure, the benefits following administration of a PDE4 inhibitor of the present invention remain, indicating a benefit to accuracy following administration. Therefore, a PDE4 inhibitor of the present invention will exhibit dose dependent effects benefiting response speed, and beneficial effects, on memory and information processing accuracy. These beneficial effects observed in normal healthy subjects support the beneficial effects for use of a PDE4 inhibitor of the present invention of the invention in subjects having cognitive impairments.

The invention will now be illustrated by the following non-limiting examples.

LC/MS Protocol

Equipment: Waters 2695 Separations Unit, 2487 Dual Absorbance Detector, Micromass ZQ fitted with ESI Probe.
Sample Preparation:
Materials dissolved in acetonitrile and diluted with equal volume water.
LC Protocol:
Observed, 254 nm. Solvent system, acetonitrile (0.1% formic acid) and water (0.1% formic acid). Column, XTerra MS C-18 3.5 uM (2.1×50 mm), 30° C. oven temperature.
Inlet Method A:

| Time (min) | Flow (mL/min) | % acetonitrile (0.1% formic acid) | % water (0.1% formic acid) |
|---|---|---|---|
| 0 | 0.3 | 10 | 90 |
| 5 | 0.3 | 90 | 10 |

-continued

| Time (min) | Flow (mL/min) | % acetonitrile (0.1% formic acid) | % water (0.1% formic acid) |
|---|---|---|---|
| 7 | 0.3 | 90 | 10 |
| 7.5 | 0.3 | 10 | 90 |

Inlet Method B:

| Time (min) | Flow (mL/min) | % acetonitrile (0.1% formic acid) | % water (0.1% formic acid) |
|---|---|---|---|
| 0 | 1.0 | 10 | 90 |
| 0.1 | 1.0 | 10 | 90 |
| 4 | 1.0 | 90 | 10 |
| 4.5 | 1.0 | 90 | 10 |
| 4.6 | 1.0 | 10 | 90 |
| 5.5 | 1.0 | 10 | 90 |

NMR Protocol:

Analysis was carried out on a Varian 400 MHz NMR. Samples were analyzed in either chloroform-D (CDCl$_3$), methanol-d$_4$ (MeOH-d$_4$), or dimethyl sulfoxide-d$_6$ (DMSO-d$_6$) For chloroform-D samples, tetramethylsilane (TMS) was used as an internal standard with the TMS resonance set to a chemical shift of 0.00 ppm for $^1$H NMR spectra. The 100 MHz $^{13}$C NMR spectra were set to the internal residual chloroform resonance at 77.23 ppm. For methanol-d$_4$ the residual central resonance peak at 3.31 ppm for $^1$H and 49.00 ppm for $^{13}$C was used for chemical shift assignment. For dimethyl sulfoxide-d$_6$, the residual central resonance peak at 2.54 ppm for $^1$H and 39.51 for $^{13}$C was used as reference for chemical shift assignment. DEPT experiments are expressed in the $^{13}$C NMR listings by notation of their respective multiplicity: CH, CH$_2$, and CH$_3$.

PREPARATIVE EXAMPLES 1-22

Intermediate nitrogen containing heterocyclic diones were prepared as illustrated below.

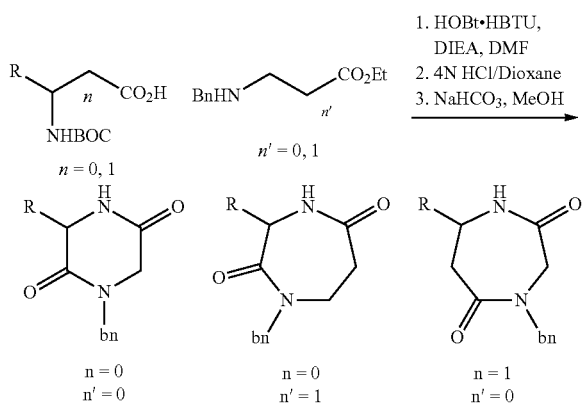

Preparative Example 1

1-Benzyl-3(S)-(2'-methylbenzyl)-piperazine-2,5-dione

A solution of Boc-2-methyl-L-phenylalanine (2.79 g, 10 mmol) in DMF (25 mL) was treated sequentially with HOBt (2.03 g, 15 mmol), diisopropylethylamine (4.35 mL, 25 mmol), N-benzylglycine ethyl ester (2.03 mL, 11 mmol), and HBTU (5.69 g, 15 mmol). The resulting solution was allowed to stir for 16 h after which time the mixture was poured onto a mixture of a 1 N aqueous HCl (50 mL) solution and EtOAc (50 mL). The organic portion was separated and further extracted with a saturated aqueous NaHCO$_3$ solution (50 mL) follow by brine (50 mL). The organic phase was dried over MgSO$_4$, filtered and evaporated to an oil, which was purified by silica gel flash chromatography with 20% then 30% EtOAc/hexanes as eluant to afford titled compound as a solid (4.31 g, 95%). LC/MS (Method A) 7.43 min, [M+1]$^+$ 455.

The coupled product was dissolved in 4 N solution of hydrogen chloride in 1,4-dioxane and stirred for 3 h at room temperature then evaporated to dryness and placed on a vacuum pump for 24 h. The crude deprotected material was then dissolved in MeOH (10 mL) and treated with a saturated aqueous solution of NaHCO$_3$ (~10 mL). The solution rapidly solidified and the resulting paste filtered with the aid of water and air dried to provide solid titled compound (2.83 g, 97%). $^1$H NMR (DMSO-d$_6$) 8.35 (br d, J=2.6, 1 H), 7.41-7.33 (m, 3 H), 7.22-7.19 (m, 2 H), 7.14-7.11 (m, 2 H), 7.01 (d, J=7.3, 1 H), 6.93-6.88 (m, 1 H), 4.49 (d, J=14.5, 1 H), 4.39 (d, J=14.5, 1 H), 4.25-4.21 (m, 1 H), 3.46 (d, J=17.1, 1 H), 3.05 (dd, J=13.8, 5.1, 1 H), 2.83 (d, J=17.1, 1 H), 2.28 (s, 3 H), 2.55-2.53 (m, 1 H). $^{13}$C NMR 166.0, 164.9, 136.9, 135.8, 134.1, 130.5 (CH), 130.2 (CH), 128.5 (CH), 128.2 (CH), 127.5 (CH), 126.8 (CH), 125.5 (CH), 55.7 (CH), 48.5 (CH$_2$), 48.3 (CH$_2$), 36.2 (CH$_2$), 19.3 (CH$_3$). LC/MS (Method A) 3.78 min, [M+1]$^+$ 309.

Preparative Example 2

1-Benzyl-3 (R)-(benzyl)-piperazine-2,5-dione

Colorless solid (88%); $^1$H NMR (DMSO-d$_6$) 8.39 (s, 1 H), 7.38-7.32 (m, 3 H), 7.25-7.11 (m, 7 H), 4.63 (d, J=14.5, 1 H), 4.31 (m, 1 H), 4.22 (d, J=14.5, 1 H), 3.49 (d, J=17.1, 1 H), 3.20 (dd, J=13.6, 4.2, 1 H), 2.93 (dd, J=13.6, 4.8, 1 H), 2.69 (d, J=17.1, 1 H). LC/MS (Method A) 4.98 min, [M+1]$^+$ 295

Preparative Example 3

1-Benzyl-3(S)-(3'-methylbenzyl)-piperazine-2,5-dione

Colorless solid (100%); $^1$H NMR (DMSO-d$_6$) 8.35 (br s, 1 H), 7.37-7.30 (m, 3 H), 7.16-7.12 (m, 2 H), 7.06-7.05 (m, 2 H), 7.01 (br s, 1 H), 6.92-6.89 (m, 1 H), 4.59 (d, J=14.5, 1 H), 4.29-4.24 (m, 2 H), 3.50 (d, J=17.4, 1 H), 3.15 (dd, J=13.4, 4.0, 1 H), 2.91 (dd, J=13.4, 4.8, 1 H), 2.78 (d, J=17.1, 1 H), 2.55-2.53 (m, 1 H), 2.23 (s, 1 H). $^{13}$C NMR 165.4, 164.9, 137.0, 135.7, 135.5, 130.7, 128.5, 128.0, 127.9, 127.4, 127.3, 127.0, 55.5, 48.3, 20.9. LC/MS (Method A) 4.53 min, [M+1]$^+$ 309.

Preparative Example 4

1-Benzyl-3(S)-(4'-methylbenzyl)-piperazine-2,5-dione

Colorless solid (94%); $^1$H NMR (DMSO-d$_6$) 8.35 (br s, 1 H), 7.36-7.33 (m, 3 H), 7.17-7.14 (m, 2 H), 6.97 (m, 4 H), 4.64 (d, J=14.5, 1 H), 4.28 (br t, J=4.0, 1 H), 4.20 (d, J=14.3, 1 H), 3.49 (d, J=17.1, 1 H), 3.15 (dd, J=13.4, 4.0, 1 H), 2.89 (dd, J=13.4, 4.6, 1 H), 2.69 (d, J=17.4, 1 H), 2.55-2.53 (m, 1 H), 2.25 (s, 3 H). $^{13}$C NMR 165.4, 164.9, 135.7, 135.7, 132.3, 129.9, 128.6, 128.4, 128.3, 127.4, 55.6, 48.3, 48.2, 38.8, 20.6. LC/MS (Method A) 4.01 min, [M+1]$^+$ 309.

Preparative Example 5

1-Benzyl-3(S)-(2'-methoxylbenzyl)-piperazine-2,5-dione

Colorless solid (78%); $^1$H NMR (DMSO-d$_6$) 8.12 (d, J=2.2, 1 H), 7.42-7.36 (m, 3 H), 7.28-7.22 (m, 3 H), 7.03 (dd, J=7.3, 1.5, 1 H), 6.97 (d, J=8.1, 1 H), 6.75 (t, J=7.5, 1 H), 4.47 (s, 2 H), 4.20-4.15 (m, 1 H), 3.78 (s, 3 H), 3.51 (d, J=17.1, 1 H), 3.19 (obs d, J=17.1, 1 H), 3.14 (obs dd, J=13.4, 5.3, 1 H), 2.99 (dd, J=13.4, 5.9, 1 H). LC/MS (Method A) 5.02 min, [M+1]$^+$ 325.

Preparative Example 6

1-Benzyl-3(S)-(3'-methoxylbenzyl)-piperazine-2,5-dione

Colorless solid (60%); $^1$H NMR (DMSO-d$_6$) 8.39 (s, 1 H), 7.36-7.30 (m, 3 H), 7.14-7.11 (m, 3 H), 7.07 (d, J=7.9, 1 H), 6.83 (dd, J=8.1, 2.4, 1 H), 6.75 (m, 1 H), 6.69 (d, J=7.5, 1 H), 4.60 (d, J=14.5, 1 H), 4.32 (m, 1 H), 4.27 (d, J=14.7, 1 H), 3.72 (s, 3 H), 3.52 (d, J=17.4, 1 H), 3.17 (dd, J=13.4, 4.2, 1 H), 2.92 (obs dd, J=13.4, 4.6, 1 H), 2.86 (d, J=17.6, 1 H). LC/MS (Method A) 4.95 min, [M+1]$^+$ 325.

Preparative Example 7

1-Benzyl-3(S)-(4'-methoxylbenzyl)-piperazine-2,5-dione

Colorless solid (83%); $^1$H NMR (DMSO-d$_6$) 8.34 (d, J=2.3, 1 H), 7.37-7.35 (m, 3 H), 7.19-7.16 (m, 2 H), 6.97 (d, J=8.8, 2 H), 6.67 (d, J=8.8, 2 H), 4.69 (d, J=14.5, 1 H), 4.25 (m, 1 H), 4.15 (d, J=14.5, 1 H), 3.71 (s, 3 H), 3.49 (d, J=17.4, 1 H), 3.13 (dd, J=13.6, 3.7, 1 H), 2.84 (dd, J=13.6, 4.6, 1 H), 2.64 (d, J=17.4, 1 H). LC/MS (Method A) 4.93 min, [M+1]$^+$ 325.

Preparative Example 8

1-Benzyl-3(S)-(4'-ethoxylbenzyl)-piperazine-2,5-dione

Colorless solid (90%); $^1$H NMR (DMSO-d$_6$) 8.35 (br s, 1 H), 7.37-7.34 (m, 3 H), 7.19-7.16 (m, 2 H), 6.96 (d, J=8.8, 2 H), 6.66 (d, J=8.6, 2 H), 4.67 (d, J=14.5, 1 H), 4.24 (br s, 1 H), 4.17 (d, J=14.5, 1 H), 3.91-3.99 (m, 2 H), 3.48 (d, J=17.1, 1 H), 3.12 (dd, J=13.6, 3.7, 1 H), 1.33 (t, J=7.0, 1 H), 2.64 (d, J=17.4, 1 H), 2.84 (dd, J=13.6, 4.8, 1 H). LC/MS (Method A) 4.33 min, [M+1]$^+$ 339.

Preparative Example 9

1-Benzyl-3(S)-(2-phenethyl)-piperazine-2,5-dione

Colorless solid (92%); $^1$H NMR (DMSO-d$_6$) 8.55 (br d, J=1.8, 1 H), 7.42-7.19 (m, 10H), 4.63 (d, J=14.7, 1 H), 4.52 (d, J=14.7, 1 H), 4.01-4.00 (m, 1 H), 3.95 (d, J=17.4, 1 H), 3.83 (d, J=17.1, 1 H), 2.71-2.64 (m, 2 H), 2.11-2.02 (m, 2 H). $^{13}$C NMR 166.3, 165.5, 141.2, 136.4, 128.6, 128.4, 127.8, 127.5, 125.9, 54.0, 49.1, 48.5, 35.0, 30.3. LC/MS (Method A) 4.72 min, [M+1]$^+$ 309.

Preparative Example 10

1-Benzyl-3(R)-(2-phenethyl)-piperazine-2,5-dione

Colorless solid (92%). LC/MS (Method A) 5.32 min, [M+1]$^+$ 309.

Preparative Example 11

1-Benzyl-3(S)-(3-phenylpropyl)-piperazine-2,5-dione

Colorless solid (91%); $^1$H NMR (DMSO-d$_6$) 1.60-1.68 (m, 2 H), 1.75-1.84 (m, 2 H), 2.61 (t, J=7.6), 3.77 (d, J=17.3, 1 H), 3.87 (d, J=17.3, 1 H), 4.47 (d, J=14.9, 1 H), 4.62 (d, J=14.6, 1 H), 7.20-7.23 (m, 3 H), 7.27-7.41 (m, 7 H), 8.42 (d, J=2.3, 1 H). LC/MS (Method A) 5.59 min, [M+1]$^+$ 323.

Preparative Example 12

1-Benzyl-3(S)-(1'-naphthylmethyl)-piperazine-2,5-dione

Colorless solid (89%); $^1$H NMR (DMSO-d$_6$) 8.37 (d, J=2.9, 1 H), 8.18 (d, J=7.5, 1 H), 7.97 (dd, J=7.3, 2.4, 1 H), 7.87-7.84 (m, 1 H), 7.63-7.53 (m, 2 H), 7.38-7.29 (m, 5 H), 7.09-7.06 (m, 2 H), 4.35 (m, 3 H), 3.64-3.50 (m, 2 H), 3.41 (d, J=17.1, 1 H), 2.96 (d, J=17.1, 1 H). $^{13}$C NMR 165.9, 164.9, 135.8, 133.4, 132.2, 131.9, 128.5, 127.9, 127.4, 126.1, 125.6, 125.2, 124.0, 55.8, 48.4, 48.3, 36.0. LC/MS (Method A) 4.72 min, [M+1]$^+$ 345.

Preparative Example 13

1-Benzyl-3(S)-(2'-naphthylmethyl)-piperazine-2,5-dione

Colorless solid (92%); $^1$H NMR (DMSO-d$_6$) 8.50 (s, 1 H), 7.91-7.88 (m, 1 H), 7.84-7.82 (m, 1 H), 7.74 (d, J=8.4, 1 H), 7.70 (s, 1 H), 7.51-7.56 (m, 2 H), 7.31 (dd, J=8.6, 1.5, 1 H), 7.23 (d, J=7.3, 1 H), 7.17-7.13 (m, 2 H), 7.03-7.01 (m, 2 H), 4.68 (d, J=14.5, H), 4.19 (d, J=14.7, 1H), 3.52 (d, J=17.4, 1 H), 3.39 (dd, J=13.4, 4.4, 1 H), 3.14 (dd, J=13.6, 4.8, 1 H), 2.81 (d, J=17.1, 1 H). $^{13}$C NMR 165.3, 164.7, 135.6, 133.5, 132.8, 131.9, 128.7, 128.3, 128.2, 127.9, 127.5, 127.3, 126.0, 125.7, 55.6, 48.3, 48.3, 39.2. LC/MS (Method A) 4.72 min, [M+1]$^+$ 345.

Preparative Example 14

1-Benzyl-3(S)-(4'-biphenylmethyl)-piperazine-2,5-dione

Colorless solid (99%); $^1$H NMR (DMSO-d$_6$) 8.42 (s, 1 H), 7.65-7.62 (m, 2 H), 7.39-7.53 (m, 4 H), 7.35-7.32 (m, 2 H), 7.20-7.17 (m, 4 H), 4.73 (d, J=14.2, H), 4.18 (d, J=14.5, 1 H), 3.55 (d, J=17.4, 1 H), 3.23 (dd, J=13.2, 3.9, 1 H), 2.97 (dd, J=13.4, 4.8, 1 H), 2.78 (d, J=17.4, 1 H). $^{13}$C NMR 165.4, 164.9, 139.6, 138.4, 135.7, 134.8, 130.6, 128.4, 128.4, 127.5, 127.3, 126.4, 126.2, 55.5, 48.4, 48.3, 40.3 (methylene resonance obscured by solvent, visible in DEPT experiment), 38.7. LC/MS (Method A) 5.39 min, [M+1]$^+$ 371.

Preparative Example 15

1-Benzyl-3(S)-(diphenylmethyl)-piperazine-2,5-dione

Colorless solid (99%); $^1$H NMR (DMSO-$d_6$) 7.38-7.22 (m, 12 H), 7.16-7.12 (m, 3 H), 4.83-4.80 (m, 1 H), 4.61 (d, J=4.6, 1 H), 4.60 (s, 1 H), 4.20 (d, J=14.5, 1 H), 3.51 (dd, J=17.4, 4.8, 1 H), 3.02 (d, J=17.1, 1 H), $^{13}$C NMR 166.6, 166.0, 141.1, 140.4, 136.6, 130.1, 129.3, 129.2, 128.9, 128.9, 128.2, 127.5, 127.3, 59.0, 55.4, 49.4, 49.3. LC/MS (Method A) 5.28 min, [M+1]$^+$ 371.

Preparative Example 16

1-Benzyl-3(S)-(cyclohexylmethyl)-piperazine-2,5-dione

Colorless solid (93%); $^1$H NMR (DMSO-$d_6$) 8.46 (s, 1 H), 7.42-7.27 (m, 5 H), 4.60 (d, J=14.7, 1 H), 4.49 (d, J=14.7, 1 H), 3.94 (d, J=17.1, 1 H), 3.93 (obs m, 1 H), 3.75 (d, J=17.1, 1 H), 1.80-1.46 (m, 8 H), 1.24-1.12 (m, 3 H), 0.99-0.84 (m, 2 H). $^{13}$C NMR 167.0, 165.4, 136.4, 128.6, 127.8, 127.4, 52.5, 49.0, 48.4, 40.9, 33.2, 32.8, 31.9, 26.0, 25.8, 25.6. LC/MS (Method A) 4.84 min, [M+1]$^+$ 301.

Preparative Example 17

Tetrahydro-1,3-bis(phenylmethyl)-(3S)-1H-1,4-Diazepine-2,5-dione, CAS [612844-06-1]

Colorless solid (64%); $^1$H NMR (DMSO-$d_6$) 7.43-7.16 (m, 10 H), 4.82-4.77 (m, 1 H), 4.58 (d, J=14.7, 1 H), 4.50 (d, J=14.9, 1 H), 4.10-4.00 (m, 1 H), 3.21-3.11 (m, 2 H), 2.84 (dd, J=14.3, 7.7, 1 H), 2.51-2.43 (m, 1 H), 2.27-2.15 (m, 1 H). $^{13}$C NMR 170.9, 170.7, 138.2, 137.9, 129.4, 128.5, 128.1, 127.7, 127.2, 126.2, 52.8, 49.4, 42.1, 35.3, 34.8. LC/MS (Method A) 5.30 min, [M+1]$^+$ 309.

Preparative Example 18

Tetrahydro-1,3-bis(phenylmethyl)-(3R)-1H-1,4-Diazepine-2,5-dione

Colorless solid (57%). LC/MS (Method A) 5.30 min, [M+1]$^+$ 309.

Preparative Example 19

Tetrahydro-1,5-bis(phenylmethyl)-(5S)-1H-1,4-Diazepine-3,7-dione

Colorless solid (31%); $^1$H NMR (DMSO-$d_6$) 7.78 (d, J=2.2, 1 H), 7.40-7.27 (m, 10H), 4.59 (s, 2 H), 4.06 (s, 2 H), 3.71-3.78 (m, 1 H), 2.94 (dd, J=13.2, 4.4, 1 H), 2.81-2.64 (m, 3H). $^{13}$C NMR 171.2, 168.8, 138.3, 137.9, 130.3, 129.2, 129.1, 128.2, 127.9, 127.2, 53.3, 52.7, 50.9, 42.7, 37.4. LC/MS (Method A) 5.14 min, [M+1]$^+$ 309.

Preparative Example 20

Tetrahydro-1,5-bis(phenylmethyl)-(5R)-1H-1,4-Diazepine-3,7-dione Colorless solid (32%)

LC/MS (Method A) 5.14 min, [M+1]$^+$ 309.

Preparative Example 21

(3S)-1-benzyl-3-(1H-pyrazol-1-ylmethyl)piperazine-2,5-dione

Oil (63%). LC/MS (Method B) 3.50 min, [M+1]$^+$ 431.

Preparative Example 22

(3S)-1-benzyl-3-(4-fluorobenzyl)piperazine-2,5-dione

Colorless solid (94%). $^1$H NMR (DMSO-$d_6$) 8.41-8.26 (m, 1 H), 7.37-7.22 (m, 3 H), 7.18-7.00 (m, 3 H), 6.98-6.84 (m, 2 H), 4.70-4.52 (m, 1 H), 4.32-4.04 (m, 2 H), 3.12 (dd, J=13.7, 4.1, 1 H), 2.86 (dd, J=13.6, 4.8, 1 H), 2.76 (d, J=17.4, 1 H), 2.52-2.45 (m, 1 H). LC/MS (Method B) 2.82 min, [M+1]$^+$ 313.

Preparative Examples 23-46

As illustrated below, the dione heterocycles were reduced to provide the nitrogen containing heterocycles.

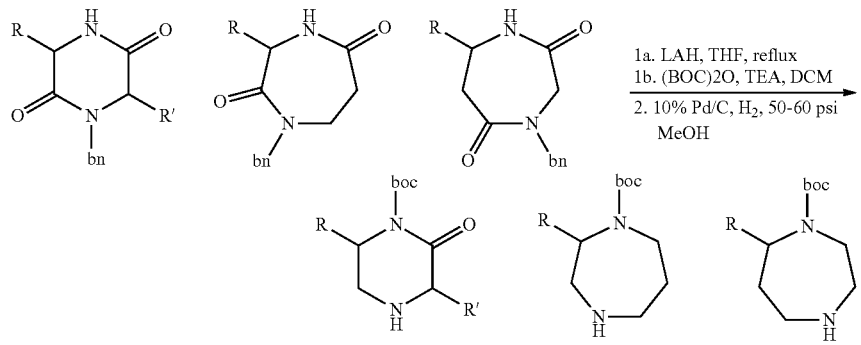

Preparative Example 23

2(S)—N1 BOC-2-(2'-methylbenzyl)piperazine

1-Benzyl-3(S)-(2-methylbenzyl)-piperazine-2,5-dione (617 mg, 2 mmol) in THF (10 mL) was treated with a 1 N THF solution of lithium aluminum hydride and heated at reflux for 6 h. The reaction was then cooled to room temperature and quenched dropwise with a 15% aqueous NaOH solution (0.5 mL) followed by water (1 mL). The resulting mixture was treated with a small amount of MgSO$_4$ and filtered through a pad of Celite® with the aid of EtOAc. The organic filtrate was then evaporated to an oil, dissolved in CH$_2$Cl$_2$ (5 mL), and treated with TEA (560 uL, 4 mmol) and di-tert-butyl dicarbonate (640 mg, 3 mmol). The reaction was stirred for 3 h after which time and additional portion of CH$_2$Cl$_2$ (10 mL) was added and the solution washed with a saturated aqueous solution of NH$_4$Cl (15 mL) followed by brine (2×10 mL). The organic portion was dried over MgSO$_4$, filtered and evaporated to an oil which was purified by silica gel flash chromatography with 15% EtOAc/hexanes as eluant to afford the N1-BOC N-4-benzylated intermediate as a colorless waxy solid (615 mg, 81%). LC/MS (Method A) 5.44 min, [M+1]$^+$ 381.

The N1-BOC N-4-benzylated solid (1.2 g, 3.15 mmol) was dissolved in MeOH (60 mL) and purged with nitrogen for 3 min followed by addition of 10% palladium-on-carbon (50% water content, 500 mg). The reaction mixture was hydrogenated at ~50-60 psi hydrogen for 6 h after which time the mixture was filtered through a pad of Celite®. The organic filtrate was evaporated and dissolved in MeOH (10 mL) and filtered through a nylon syringe filter (0.45 micron, 13 mm) to remove traces of palladium-on-carbon. The organic filtrate was again evaporated to afford titled compound as a clear colorless oil (875 mg, 96%). $^1$H NMR (CDCl$_3$) 7.16-7.09 (m, 4 H), 4.21 (br t, 1 H), 3.95 (br d, J=12.5, 1 H), 3.22-2.93 (m, 3 H), 2.91-2.67 (m, 4 H), 2.39 (s, 3 H), 1.33 (s, 9 H). $^{13}$C NMR 137.5, 136.9, 130.5 (CH), 130.4 (CH), 126.9, 126.6 (CH), 126.1 (CH), 79.7, 51.5 (CH), 47.6 (CH$_2$), 46.3 (CH$_2$), 33.2 (CH$_2$), 32.7 (CH$_2$), 28.5 (CH$_3$), 19.7 (CH$_3$). LC/MS (Method A) 4.09 min, [M+1]$^+$ 291.

Preparative Example 24

2(R)—N1 BOC-2-(benzyl)-piperazine

Colorless waxy solid (intermediate 89%, 96%). LC/MS (Method A) 3.90 min, [M+1]$^+$ 277.

Preparative Example 25

2(S)—N1 BOC-2-(3'-methylbenzyl)-piperazine

Colorless oil (intermediate 84%, 92%). LC/MS (Method A) 4.14 min, [M+1]$^+$ 291.

Preparative Example 26

2(S)—N1 BOC-2-(4'-methylbenzyl)-piperazine

Colorless oil (intermediate 86%, 94%). LC/MS (Method A) 4.10 min, [M+1]$^+$ 291.

Preparative Example 27

2(S)—N1 BOC-2-(2'-methoxylbenzyl)-piperazine

Colorless oil (intermediate 83%, 94%). LC/MS (Method A) 3.92 min, [M+1]$^+$ 307.

Preparative Example 28

2(S)—N1 BOC-2-(3'-methoxylbenzyl)-piperazine

Colorless oil (intermediate 47%, 83%). LC/MS (Method A) 3.84 min, [M+1]$^+$ 307.

Preparative Example 29

2(S)—N1 BOC-2-(4'-methoxylbenzyl)-piperazine

Colorless oil (intermediate 85%, 88%). LC/MS 3.74 min, [M+1]$^+$ 307.

Preparative Example 30

2(S)—N1 BOC-2-(4'-ethoxylbenzyl)-piperazine

Colorless oil (intermediate 82%, 86%). LC/MS (Method A) 4.41 min, [M+1]$^+$ 321.

Preparative Example 31

2(S)—N1 BOC-2-(2-phenethyl)-piperazine

Colorless oil (intermediate 83%, 96%). LC/MS (Method A) 4.13 min, [M+1]$^+$ 291.

Preparative Example 32

2(R)—N1 BOC-2-(2-phenethyl)-piperazine

Colorless oil (intermediate 85%, 96%). LC/MS (Method A) 4.14 min, [M+1]$^+$ 291.

Preparative Example 33

2(S)—N1 BOC-2-(3-phenylpropyl)-piperazine

Colorless oil (intermediate 97%, 89%). LC/MS (Method A) 4.32 min, [M+1]$^+$ 305.

Preparative Example 34

2(S)—N1 BOC-2-(1'-naphthylmethyl)-piperazine

Colorless waxy solid (intermediate 84%, 90%). LC/MS (Method A) 4.35 min, [M+1]$^+$ 327.

Preparative Example 35

2(S)—N1 BOC-2-(2'-naphthylmethyl)-piperazine

Colorless oil (intermediate 73%, 98%). LC/MS (Method A) 4.39 min, [M+1]$^+$ 327.

Preparative Example 36

2(S)—N1 BOC-2-(4'-biphenylmethyl)-piperazine

Colorless waxy solid (intermediate 66%, 99%). LC/MS (Method A) 4.68 min, [M+1]$^+$ 353.

Preparative Example 37

2(S)—N1 BOC-2-(diphenylmethyl)-piperazine

Colorless oil (intermediate 35%, 92%). LC/MS (Method A) 4.40 min, [M+1]$^+$ 353.

Preparative Example 38

2(S)—N1 BOC-2-(cyclohexylmethyl)-piperazine

Colorless oil (intermediate 87%, 89%). LC/MS (Method A) 4.43 min, [M+1]$^+$ 283.

Preparative Example 39

(S)-2-Benzyl-[1,4]diazepane-1-carboxylic acid tert-butyl ester

Colorless oil (intermediate 75%, 93%). LC/MS (Method A) 3.98 min, [M+1]$^+$ 291.

Preparative Example 40

(R)-2-Benzyl-[1,4]diazepane-1-carboxylic acid tert-butyl ester

Colorless oil (intermediate 65%, 92%). LC/MS (Method A) 3.95 min, [M+1]$^+$ 291.

Preparative Example 41

(5)-7-Benzyl-[1,4]diazepane-1-carboxylic acid tert-butyl ester

Colorless oil (intermediate 73%, 88%). LC/MS (Method A) 4.57 min, [M+1]$^+$ 291.

Preparative Example 42

(R)-7-Benzyl-[1,4]diazepane-1-carboxylic acid tert-butyl ester

Colorless oil (intermediate 71%, 88%). LC/MS (Method A) 4.57 min, [M+1]$^+$ 291.

Preparative Example 43

(2S,5S)-2-Benzyl-5-methyl-piperazine-1-carboxylic acid tert-butyl ester

Prepared from (3S,6S)-6-methyl-, 1,3-bis(phenylmethyl)-2,5-piperazinedione (CAS [561303-33-1]) Colorless oil (intermediate 66%, 92%). LC/MS (Method A) 4.26 min, [M+1]$^+$ 291.

Preparative Example 44

(2S,5R)-2-Benzyl-5-methyl-piperazine-1-carboxylic acid tert-butyl ester

Prepared from (3S,6R)-6-methyl-, 1,3-bis(phenylmethyl)-2,5-piperazinedione (CAS [850036-85-0]) Colorless oil (intermediate 84%, 89%). LC/MS (Method A) 4.46 min, [M+1]$^+$ 291.

Preparative Example 45 tert-butyl (2R)-2-(1H-pyrazol-1-ylmethyl)piperazine-1-carboxylate

Prepared from (3S)-1-benzyl-3-(1H-pyrazol-1-ylmethyl) piperazine-2,5-dione. Colorless oil (intermediate 77%, 95%). $^1$H NMR (CDCl$_3$) 7.50 (s, 1 H), 7.42 (br s, 1 H), 6.24 (s, 1 H), 4.53-4.36 (br m, 3 H), 4.00 (br s, 1 H), 3.37 (br s, 1 H), 3.20-3.03 (m, 2 H), 2.88-2.81 (m, 2 H), 2.73 (td, J=3.4, 12.0, 1 H), 1.38 (br s, 9 H). LC/MS 1.14 min, [M+1]$^+$ 267.

Preparative Example 46

2(S)-[(4-fluorophenyl)methyl]-1-piperazinecarboxylic acid, 1,1-dimethylethyl ester Prepared from (3S)-1-benzyl-3-(4-fluorobenzyl)piperazine-2,5-dione. Colorless oil (100%); $^1$H NMR (MeOH-d$_4$) 7.25-7.19 (m, 2 H), 7.03-6.96 (m, 2 H), 4.25-4.15 (m, 1 H), 3.84 (d, J=13.5, 1 H), 3.15-2.70 (m, 6 H), 2.61 (dt, J=12.5, 3.7, 1 H), 1.28 (s, 9 H). LC/MS (method B) 2.82 min, [M+1]$^+$ 295.

Preparative Examples 47-50

Preparative Example 47

(S)-2-benzylmorpholine

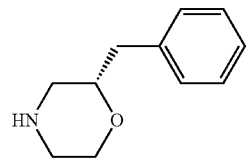

The title compound was prepared from (S)-(2,3-epoxypropyl)benzene by the method of D'Arrigo, Lattanzio, Fantoni and Servi in *Tetrahedron: Asymmetry*, 1998, 9, 4021-4026.

Preparative Example 48

6R and 6S-(phenylmethyl)piperazinone

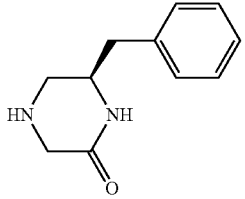 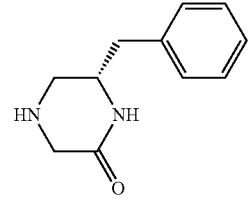

The title compound (6R)-isomer was prepared from N-Cbz-D-phenylalinal by the method of DeLucca in US2003/0144277 A1 describing the preparation of 6S-(phenylmethyl) piperazinone (CAS [503186-95-6]) from N-Cbz-L-phenylalinal. LC/MS (Method A) 5.40 and 5.34 min, [M+1]$^+$ 191 and 191, respectively.

Preparative Example 49

4-bromo-7-methoxy-spiro[benzofuran-2(3H),1'-cyclopentane], CAS [185244-55-7]

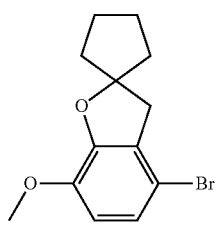 [SMILES: COc1ccc(Br)c2c1OC1(CCCC1)C2]

The title compound was prepared from 5-bromo-2-methoxybenzaldehyde by the method of Van der Mey, Margaretha; et. al., *Journal of Medicinal Chemistry* 2001, 44, 2523-2535.

Preparative Example 50

2(S)—N1 BOC-2-(benzyl)-piperazine CAS [169447-86-3], 2(R)—N1 BOC-2-(phenyl)-piperazine CAS [859518-32-4], 2(S)—N1 BOC-2-(isobutyl)-piperazine, 2(R)—N1 BOC-2-(isopropyl)-piperazine, and 2(R)—N1 BOC-2-(3-indolylmethyl)-piperazine were purchased from CNH Technologies, Inc (Woburn, Mass., USA).

Preparative Examples 51-62

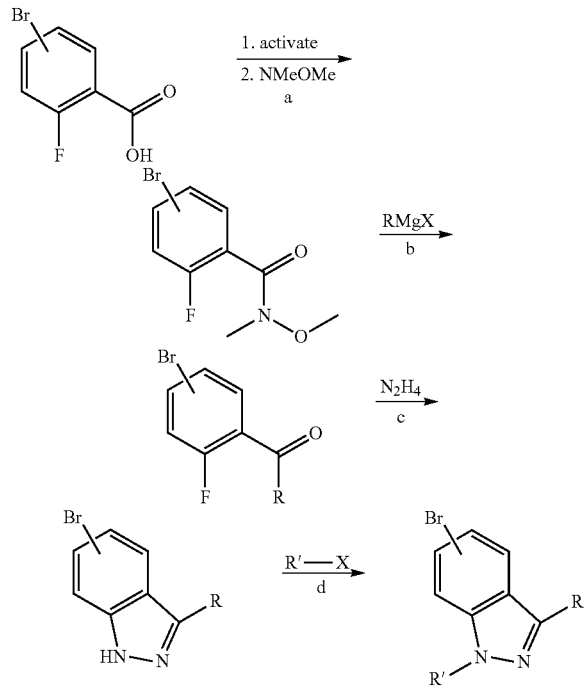

Preparative Example 51

6-Bromo-1-cyclopentyl-3methyl-1H-indazole

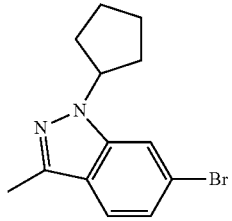 [SMILES: Cc1nn(C2CCCC2)c2cc(Br)ccc12]

A solution of 4-bromo-2-fluoro-N-methoxy-N-methyl-benzamide (CAS [801303-33-3]) (13.1 g, 50.0 mmol) in THF (50 mL) at −78° C. was treated with a 3 N solution of methyl magnesium bromide in diethyl ether (16.7 mL, 50 mmol) and allowed to warm with stirring to 0° C. over a 2-3 h period, after which time the reaction mixture was quenched with a half saturated aqueous solution of $NH_4Cl$ (100 mL) and EtOAc (200 mL). The mixture was separated and the organic component, washed with brine (2×50 mL), dried over $MgSO_4$, filtered, and evaporated to an oil which was purified by silica gel flash chromatography with 5% EtOAc/hexanes as eluant to afford 1-(4-bromo-2-fluorophenyl)-ethanone as a liquid (9.25 g, 85%). The ethanone (2.17 g, 10 mmol) was then dissolved in ethanol (25 mL), treated with hydrazine hydrate (535 uL, 11 mmol), and heated at reflux for 8 h. The reaction mixture was then evaporated and purified by silica gel flash chromatography with 30% then 60% EtOAc/hexanes as eluant to afford the hydrazone as a solid (2.29 g, 99%). The hydrazone (3.69 g, 16 mmol) was then treated with ethylene glycol (25 mL) and heated at 165° C. for 6 h after which time the cooled reaction mixture was poured onto water (100 mL). The aqueous mixture was neutralized, with rapid stirring, using a small amount of an aqueous saturated solution of $NaHCO_3$ to afford a pale yellow precipitate. The solids were filtered, washed with water, and air dried to afford cyclized indazole product (2.62 g, 78%). The indazole (2.32 g, 11 mmol) was then dissolved in anhydrous DMF (50 mL) and treated with a 60% dispersion of sodium hydride in mineral oil (420 mg, 10.5 mmol). After 30 min of stirring, cyclopentyl bromide (1.53 mL, 14.3 mmol) was added and the reaction stirred for 24 h. The reaction mixture was quenched by pouring onto water (500 mL) which was neutralized with a small portion of a 1 N aqueous HCl solution and extracted with EtOAc (2×200 mL, then 100 mL). The combined organic extracts were dried over $MgSO_4$, filtered, and evaporated to an oil, which was purified by silica gel flash chromatography with 25% then 80% EtOAc/hexanes as eluant to afford titled compound as a clear yellow tinted oil (1.65 g, 54%). $^1$H NMR ($CDCl_3$) 7.55 (d, J=1.5, 1 H), 7.32 (dd, J=8.4, 0.7, 1 H), 7.18 (dd, J=8.4, 1.5, 1 H), 4.87-4.77 (m, 1 H), 2.54 (s, 3 H), 2.16-2.08 (m, 4 H), 2.01-1.93 (m, 2 H), 1.78-1.68 (m, 2 H). $^{13}$C NMR 141.4, 141.1, 123.2 (CH), 122.5, 121.8 (CH), 120.5, 112.2 (CH), 59.5 (CH), 32.2 ($CH_2$), 24.7 ($CH_2$), 12.1 ($CH_3$). LC/MS (Method A) 7.71 min, [M+1]$^+$ 280/282.

Preparative Example 52

6-Bromo-1-cyclopentyl-3-ethyl-1H-indazole, CAS [199172-02-6]

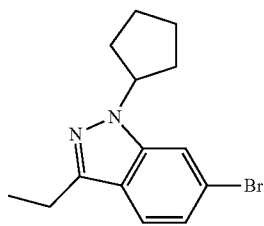 [SMILES: CCc1nn(C2CCCC2)c2cc(Br)ccc12]

The titled compound was prepared by the method outlined for Preparative Example 51 using a 25% wt THF solution of ethyl magnesium bromide and stirring the resulting solution for 24 h at 0° C. in lieu of methyl magnesium bromide and a 2-3 h period at 0° C. LC/MS (Method A) 8.14 min, [M+1]$^+$ 293/295.

Preparative Example 53

6-Bromo-1-cyclobutyl-3-ethyl-1H-indazole

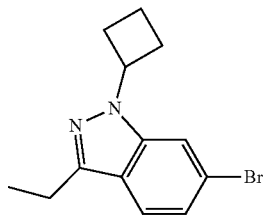 [SMILES: CCc1nn(C2CCC2)c2cc(Br)ccc12]

A solution of 4-bromo-2-fluoro-N-methoxy-N-methyl-benzamide (CAS [801303-33-3]) (24.9 g, 95.0 mmol) in THF (100 mL) at −78° C. was treated with a 3 N solution of ethyl magnesium bromide in diethyl ether (33.25 mL, 115 mmol) and allowed to warm to 0 C and stir for a 6 h period, after which time the reaction mixture was quenched with a half saturated aqueous solution of NH$_4$Cl (200 mL) and EtOAc (100 mL). The mixture was separated and the organic component, washed with brine (2×50 mL), dried over MgSO$_4$, filtered, and evaporated to an oil which was purified by silica gel flash chromatography with 20% EtOAc/hexanes as eluant to afford 1-(4-bromo-2-fluorophenyl)-propanone as a pale yellow solid (16.25 g, 74%). The propanone (21.15 g, 91.6 mmol) was then dissolved in ethanol (100 mL), treated with hydrazine hydrate (4.9 mL, 100.7 mmol), and heated at reflux for 4 h. The reaction mixture was then evaporated and dissolved in ethylene glycol (100 mL) and heated at 160-165° C. for 8 h after which time the cooled reaction mixture was poured onto water (500 mL) with stirring. The aqueous mixture was neutralized, with rapid stirring, using a small amount of an aqueous saturated solution of NaHCO$_3$ to afford a pale yellow precipitate. The solids were filtered, washed with water, and air dried to afford cyclized indazole product (16.1 g, 78%).

The indazole (6.75 g, 30.0 mmol) was then dissolved in anhydrous DMF (30 mL), cooled to 0-5° C. and treated with a 60% dispersion of sodium hydride in mineral oil (1.44 g, 36.0 mmol). After 10 min of stirring, cyclobutylbromide (4.86 g, 36.0 mmol) was added and the reaction heated at 80° C. for 8 h. The reaction mixture was then cooled and quenched by addition of a saturated aqueous solution of NH$_4$Cl (200 mL) then extracted with EtOAc (2×100 mL). The combined organic extracts were dried over MgSO$_4$, filtered, and evaporated to an oil, which was purified by silica gel flash chromatography with 5% EtOAc/hexanes as eluant to afford titled compound as a clear liquid (5.2 g, 62%). $^1$H NMR (CDCl$_3$) 7.56 (d, J=1.2, 1H), 7.52 (dd, J=8.7, 0.6, 1H), 7.18 (dd, J=8.6, 1.5, 1H), 4.88-4.97 (m, 1 H), 2.98 (q, J=7.6, 2 H), 2.83-2.72 (m, 2 H), 2.52-2.44 (m, 2 H), 2.00-1.85 (m, 2 H), 1.38 (t, J=7.7, 3 H). $^{13}$C NMR 147.1, 140.6, 123.1, 121.6, 121.5, 120.3, 112.1, 52.3, 29.9, 20.5, 15.0, 13.9. LC/MS (Method B) 4.45 min, [M+1]$^+$ 279/281.

Preparative Example 54

6-Bromo-3-ethyl-1-isopropyl-1H-indazole

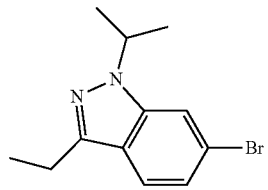

The title compound was prepared by the method outlined for Preparative Example 52 using 2-bromopropane as alkyl halide. Titled compound was obtained as a clear liquid (8.1 g, 61%). $^1$H NMR (CDCl$_3$) 7.55 (d, J=1.6, 1H), 7.53 (dd, J=8.4, 1.4, 1 H), 7.17 (dd, J=8.5, 1.6, 1 H), 4.73-4.66 (m, 1 H), 2.97 (q, J=7.6, 2 H), 1.55 (d, J=6.8, 6 H), 1.37 (t, J=7.6, 3 H). $^{13}$C NMR 146.7, 140.3, 122.9, 121.7, 121.4, 120.1, 112.0, 50.3, 22.0, 20.5, 14.0. LC/MS (Method B) 4.18 min, [M+1]$^+$ 267/269.

Preparative Example 55

6-Bromo-1,3-diethyl-1H-indazole

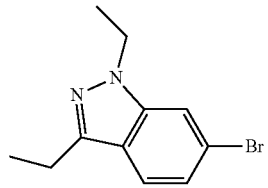

The title compound was prepared by the method outlined for Preparative Example 52 using 2-iodoethane as alkyl halide. Titled compound was obtained as a clear liquid (185 mg, 37%). $^1$H NMR (CDCl$_3$) 7.50 (s, 1 H), 7.48 (dd, J=7.6, 0.7, 1 H), 7.15 (dd, J=7.3, 1.5, 1 H), 4.28 (q, J=7.2, 2 H), 2.95 (q, J=7.6, 2 H), 1.44 (t, J=7.2, 3 H), 1.37 (t, J=7.4, 3 H). $^{13}$C NMR 147.0, 140.7, 123.0 (CH), 121.7 (CH), 121.5, 120.5, 111.8 (CH), 43.5 (CH$_2$), 20.4 (CH$_2$), 15.0 (CH$_3$), 13.8 (CH$_3$). LC/MS (Method A) 6.89 min, [M+1]$^+$ 253/255.

Preparative Example 56

6-Bromo-3-ethyl-1-propyl-1H-indazole

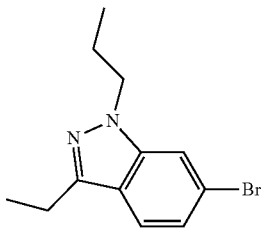

The title compound was prepared by the method outlined for Preparative Example 52 using 2-bromopropane as alkyl halide. Titled compound was obtained as a clear liquid (257 mg, 48%). $^1$H NMR (CDCl$_3$) 7.51 (s, 1 H), 7.49 (dd, J=6.3, 0.4, 1 H), 7.15 (dd, J=8.8, 1.6, 1 H), 4.19 (t, J=7.3, 2 H), 2.95 (q, J=7.7, 2 H), 1.86 (m, 2 H), 1.37 (t, J=7.4, 3 H), 0.90 (t, J=7.3, 3H). $^{13}$C NMR 147.0, 141.3, 123.0 (CH), 121.7 (CH), 121.4, 120.5, 111.9 (CH), 50.4 (CH$_2$), 23.3 (CH$_2$), 20.4 (CH$_2$), 13.9 (CH$_3$), 11.5 (CH$_3$). LC/MS (Method A) 7.27 min, [M+1]$^+$ 267/269.

Preparative Example 57

6-Bromo-1-cyclobutyl-3-ethyl-1H-indazole

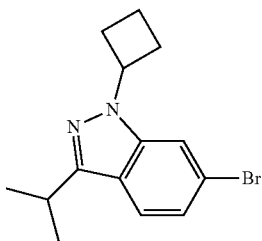 [SMILES: CC(C)c1nn(C2CCC2)c2cc(Br)ccc12]

A solution of 4-bromo-2-fluoro-N-methoxy-N-methyl-benzamide (CAS [801303-33-3]) (7.86 g, 30.0 mmol) in THF (10 mL) at −78° C. was treated with a 2 N solution of isopropyl magnesium bromide in diethyl ether (26.25 mL, 62.5 mmol) and allowed to warm to 0° C. and stir for a 3 h period, after which time the reaction mixture was quenched with a half saturated aqueous solution of NH$_4$Cl (50 mL) and diethyl ether (50 mL). The mixture was separated and the organic component, washed with brine (2×10 mL), dried over MgSO$_4$, filtered, and evaporated to an oil which was purified by silica gel flash chromatography with 100% hexanes then 10% EtOAc/hexanes as eluant to afford product as a highly volatile pale yellow liquid (970 mg, 13%). $^1$H NMR (CDCl$_3$) 7.60 (t, J=7.8, 1 H), 7.29 (dd, J=8.4, 1.8, 1 H), 7.24 (dd, J=10.4, 1.7, 1 H), 3.31-3.23 (m, 1 H), 1.10 (d, J=6.9, 6 H). $^{19}$F NMR 108.7.

The 2-methylpropanone (1.4 g, 5.71 mmol) was placed in a sealed tube, treated with ethylene glycol (5 mL) and hydrazine hydrate (333 uL, 6.86 mmol), then heated at 160-165° C. for 8 h after which time the cooled reaction mixture was poured onto water (20 mL) and extracted with EtOAc (2×20 mL). The organic extract was then washed with brine (10 mL), dried over MgSO$_4$, filtered, and evaporated to afford a solid which was purified by silica gel flash chromatography with 20% then 30% EtOAc/hexanes as eluant to afford indazole intermediate as a pale yellow solid (1.04 g, 76%). $^1$H NMR (CDCl$_3$) 7.59 (d, J=8.6, 1H), 7.55 (d, J=1.0, 1H), 7.19 (dd, J=8.4, 1.6, 1 H), 3.43-3.36 (m, 1 H), 1.43 (d, J=6.9, 6 H). $^{13}$C NMR 152.6, 142.1, 123.6, 121.8, 120.9, 120.0, 112.8, 27.6, 22.1. LC/MS (Method B) 3.45 min, [M+1]$^+$ 239/241.

The 5-bromo-3-isopropyl-1H-indazole intermediate (1.00 g, 4.18 mmol) was then dissolved in anhydrous DMF (5 mL), cooled to 0-5° C. and treated with a 60% dispersion of sodium hydride in mineral oil (209 mg, 5.23 mmol). After 10 min of stirring, cyclobutylbromide (4.94 uL, 5.23 mmol) was added and the reaction heated at 80° C. for 8 h. The reaction mixture was then cooled and quenched by addition of a saturated aqueous solution of NH$_4$Cl (10 mL) then extracted with EtOAc (20 mL). The organic extract was dried over MgSO$_4$, filtered, and evaporated to an oil, which was purified by silica gel flash chromatography with 2% then 5% EtOAc/hexanes as eluant to afford titled compound as a clear copper-tinged liquid (986 mg, 80%). $^1$H NMR (CDCl$_3$) 7.56-7.59 (m, 2 H), 7.16 (dd, J=8.4, 1.6, 1 H), 4.95-4.89 (m, 1 H), 3.41-3.34 (m, 1 H), 2.84-2.73 (m, 2 H), 2.51-2.43 (m, 2 H), 1.97-1.85 (m, 2 H), 1.44 (d, J=7.1, 6 H). $^{13}$C NMR 150.7, 140.8, 122.8, 122.0, 120.7, 120.0, 112.2, 52.4, 29.8, 28.1, 22.3, 15.0. LC/MS (Method B) 4.77 min, [M+1]$^+$ 293/295.

Preparative Example 58

6-Bromo-1-ethyl-3-isopropyl-1H-indazole

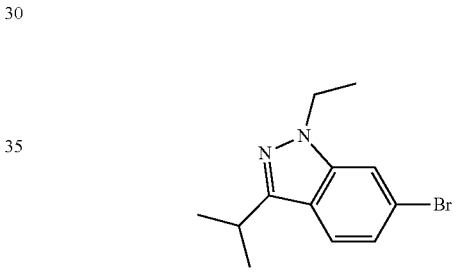

The title compound was prepared by the method outlined for Preparative Example 57 using indazole intermediate 5-bromo-3-isopropyl-1H-indazole (151.1 mg, 0.632 mmol), NaH (37.6 mg, 0.94 mmol), and ethyl iodide (120 mg, 0.769 mmol) to afford 109.1 mg (65%) of the titled compound as a colorless oil. $^1$H NMR (CDCl$_3$) 7.89 (s, 1H), 7.45 (d, J=9.2, 1 H), 7.26 (d, J=9.2, 1 H), 4.41 (q, J=7.2, 2 H), 3.38 (pent, J=6.8, 1 H), 2.41-1.49 (m, 9 H). LC/MS (Method B) 4.17 min, [M+1]$^+$ 267/269.

Preparative Example 59

5-Bromo-3-cyclobutyl-1-ethyl-1H-indazole

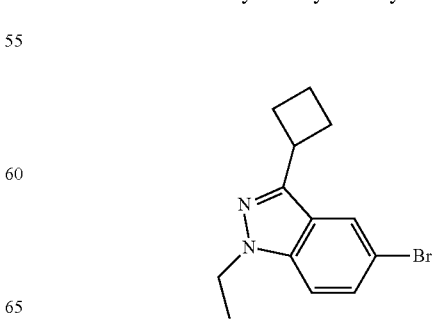

Into a 250 mL flame-dried flask were added magnesium turnings (2.81 g, 115 mmol), diethyl ether (20 mL), and iodine (1 small crystal 5 mg). The suspension was heated to reflux under nitrogen and a solution of bromocyclobutane (10.35 g, 76.67 mmol) in 10 mL diethyl ether was added over 15 min. The suspension was refluxed an additional 1 h after which time all Mg solids had dissolved. The solution was cooled to 0° C., and a solution of 5-bromo-2-fluoro-N-methoxy-N-methyl-benzamide (CAS [910912-20-8]) (10.07 g, 38.16 mmol) in THF (20 mL) was added drop-wise over 15 min. The solution was allowed to warm to room temperature and stirred an additional 8 h. The reaction mixture was cooled to 0 C and 1N HCl was added to achieve a pH ~6. EtOAc was added and the mixture was separated and the organic component was washed with brine, dried over $MgSO_4$, filtered, and evaporated to an oil which was purified by silica gel flash chromatography (220 g column) with a 0 to 25% EtOAc/hexanes gradient to afford product as a yellow oil (6.43 g, 66%). $^1$H NMR (DMSO-$d_6$) 7.87 (dd, 6.2, 2.4, 1 H), 7.83-7.79 (m, 1 H), 7.33 (dd, J=10.4, 8.8, 1 H), 3.93-3.88 (m, 1 H), 2.21-2.15 (m, 4 H), 1.98-1.92 (m, 1 H), 1.78-1.72 (m, 1 H).

The (5-bromo-2-fluoro-phenyl)-cyclobutyl-methanone intermediate (5.88 g, 22.89 mmol) was placed in a 40 mL screw-cap vial along with ethylene glycol (20 mL) and hydrazine hydrate (0.938 g, 29.26 mmol). The reaction was heated at 165° C. for 8 h after which time the cooled reaction mixture was diluted with water and extracted 3× with EtOAc. The organic extract was then washed with brine (10 mL), dried over $MgSO_4$, filtered, and evaporated to afford a solid which was crystallized from EtOH. The mother liquor was purified by silica gel flash chromatography 0-30% EtOAc/hexanes gradient. The combined purified and crystallized indazole intermediate afforded a tan solid (3.55 g, 62%). $^1$H NMR (DMSO-$d_6$) 12.84 (br s, 1H), 7.89 (s, 1 H), 7.44-7.37 (m, 2 H), 3.86 (m, 1 H), 2.38-2.31 (m, 4 H), 2.05-1.88 (m, 2 H). LC/MS (Method B) 3.67 min, [M+1]$^+$ 253.

The 5-bromo-3-cyclobutyl-1H-indazole intermediate (1.501 g, 5.97 mmol) was dissolved in anhydrous DMF (25 mL), cooled to 0° C. and treated with a 60% dispersion of sodium hydride in mineral oil (330 mg, 8.26 mmol). The cold bath was removed and the reaction mixture was stirred at room temperature for 2 h after which time iodoethane (1.034 g, 6.62 mmol) was added and the reaction mixture was stirred 8 h. The reaction mixture was then cooled and quenched by addition of a saturated aqueous solution of $NH_4Cl$ (10 mL) then extracted with EtOAc (20 mL). The organic extract was dried over $MgSO_4$, filtered, and evaporated to an oil, which was purified by silica gel flash chromatography with a 0-10% EtOAc/hexanes gradient to afford titled compound as a light yellow oil (1.14 g, 68%). $^1$H NMR (DMSO-$d_6$) 7.90 (s, 1 H), 7.58 (d, J=8.5, 1 H), 7.44 (d, J=8.5, 1 H), 4.35 (q, J=7.2, 2 H), 3.85 (pent, J=7.6, 1 H), 2.35-2.31 (m, 4 H), 2.31-2.02 (m, 1H), 1.99 (m, 1H), 1.35 (t, J=7.6, 3 H). LC/MS (Method B) 4.27 min, [M+1]$^+$ 279/281.

Preparative Example 60

5-Bromo-3-cyclobutyl-1-methyl-1H-indazole

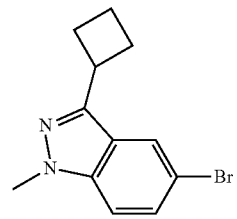

The title compound was prepared by the method outlined for Preparative Example 59 using the 5-bromo-3-cyclobutyl-1H-indazole intermediate (427 mg, 1.70 mmol), NaH (97.5 mg, 2.25 mmol), and methyl iodide (294 mg, 2.06 mmol) to afford titled compound as a colorless oil (317 mg, 71%). $^1$H NMR (CDCl$_3$) 7.82 (s, 1 H), 7.41 (d, J=8.8, 1 H), 7.21 (d, J=8.8, 1 H), 3.90 (s, 3 H), 3.88 (pent, J=9.2, 1 H), 2.51-2.43 (m, 4 H), 2.18-2.13 (m, 1 H), 2.01 (m, 1 H). LC/MS (Method B) 4.05 min, [M+1]$^+$ 265/267.

Preparative Example 61

5-Bromo-3-cyclobutyl-1-isopropyl-1H-indazole

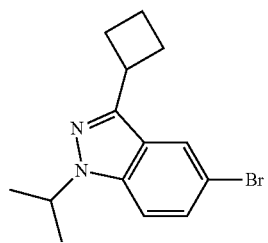 [SMILES: CC(C)n1nc(C2CCC2)c2cc(Br)ccc21]

The title compound was prepared by the method outlined for Preparative Example 59 using 5-bromo-3-cyclobutyl-1H-indazole intermediate (1.05 g, 4.16 mmol), NaH (211 mg, 5.26 mmol), and 2-bromopropane (667 mg, 5.42 mmol) to afford titled compound as a light yellow oil (850 mg, 70%). $^1$H NMR (CDCl$_3$) 7.86 (s, 1 H), 7.37 (d, J=8.8, 1 H), 7.27 (d, J=8.8, 1 H), 4.75 (m, 1 H), 3.88 (pent, J=8.4, 1 H), 2.55-2.43 (m, 4 H), 2.15-2.05 (m, 1H), 2.01 (m, 1H), 1.57 (d, J=6.8, 6 H). LC/MS (Method B) 4.72 min, [M+1]$^1$293/295.

Preparative Example 62

(5-Bromo-3-cyclobutyl-1H-indazol-1-yl)acetonitrile

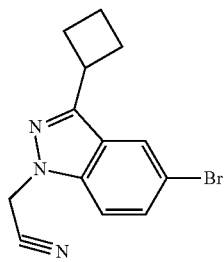 [SMILES: N#CCn1nc(C2CCC2)c2cc(Br)ccc21]

The title compound was prepared by the method outlined for Preparative Example 59 using 5-bromo-3-cyclobutyl-1H-indazole intermediate (225 mg, 0.898 mmol), NaH (41 mg, 1.02 mmol), and chloroacetonitrile (78 mg, 1.03 mmol) to afford titled compound as an off-white solid (160 mg, 62%). $^1$H NMR (DMSO-d$_6$) 7.99 (s, 1 H), 7.72 (d, J=8.8, 1 H), 7.62 (d, J=8.8, 1 H), 5.74 (s, 2 H), 3.91 (pent, J=8.8, 1 H), 2.38-2.32 (m, 4 H), 2.08-2.06 (m, 1 H), 1.95 (m, 1 H). LC/MS (Method B) 3.99 min, [M+1]$^+$ 290/292].

Preparative Examples 63-79

Preparative Example 63

4-(5-Bromo-2-methoxyphenoxy)-1-methylpiperidine

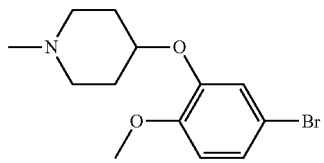 [SMILES: COc1ccc(Br)cc1OC1CCN(C)CC1]

Into a 40 mL screw-cap vial were added triphenylphosphine (1.55 g, 5.91 mmol) and toluene. The solution was stirred a 0° C. for 5 min then a diisopropylazodicarboxylate (1.18 mL, 5.99 mmol) was added drop-wise over 2 min. The solution was allowed to warm to room temperature over 1 h, then a solution of 5-bromo-2-methoxy-phenol (1.01 g, 4.98 mmol) and 1-methyl-piperidin-4-ol (701 mg, 6.08 mmol) in 4 mL of toluene was added. The reaction mixture was stirred at room temperature for 3 h. The reaction mixture was adsorbed onto silica gel and purified by silica gel flash chromatography with a 0-20% MeOH/CH$_2$Cl$_2$ gradient to afford titled compound as a light yellow oil that solidified upon standing (906 mg, 61%). $^1$H NMR (MeOH-d$_4$) 7.10 (d. J=8.8, 1 H), 7.08 (dd. J=8.8, 2.4, 1 H), 6.89 (d, J=8.8, 1 H), 4.34 (m, 1 H), 3.80 (s, 3 H), 2.73 (m, 2 H), 2.34 (m, 2 H), 2.29 (s, 3 H), 1.95 (m, 2H), 1.81 (m, 2 H). LC/MS (Method B) 1.85 min, [M+1]$^+$ 300/302.

Preparative Example 64

(3R)-3-(5-Bromo-2-methoxyphenoxy)-1-methylpyrrolidine

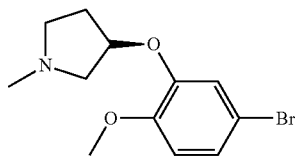

The title compound was prepared by the method outlined for Preparative Example 63 using 5-bromo-2-methoxy-phenol (1.00 g, 4.926 mmol) and (S)-1-methyl-pyrrolidin-3-ol (601 mg, 5.94 mmol) to afford titled compound as a colorless solid (823 mg, 58%). LC/MS (Method B) 1.18 min, [M+1]$^+$ 286/288.

Preparative Example 65

(3S)-3-(5-Bromo-2-methoxyphenoxy)-1-methylpyrrolidine

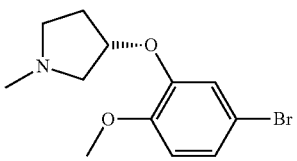

The title compound was prepared by the method outlined for Preparative Example 63 using 5-bromo-2-methoxy-phenol (1.00 g, 4.93 mmol) and (S)-1-methyl-pyrrolidin-3-ol (593 mg, 5.86 mmol) to afford titled compound as a colorless solid (430 mg, 30%). LC/MS (Method B) 1.17 min, [M+1]$^+$ 286/288.

Preparative Example 66

4-Bromo-2-[2-fluoro-1-(fluoromethyl)ethoxy]-1-methoxybenzene

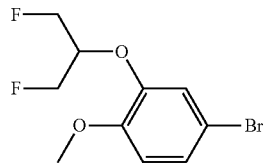

The title compound was prepared by the method outlined for Preparative Example 63 using 5-bromo-2-methoxy-phenol (765 uL, 9.87 mmol) and 1,3-difluoro-2-propanol (765 uL, 9.87 mmol) to afford titled compound as a colorless solid (1.58 g, 55%). $^1$H NMR (DMSO-d$_6$) 7.28 (d, J=2.4, 1 H), 7.14 (dd, J=8.8, 2.4, 1 H), 6.97 (d, J=8.8, 1 H), 4.55-4.35 (m, 5 H), 3.75 (s, 3 H). LC/MS (Method B) 3.50 min, [M+1]$^+$ 281/283.

Preparative Example 67

4-Bromo-2-cyclopropoxy-1-methoxy-benzene

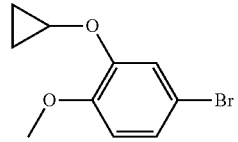

Into a flame-dried 250 mL round-bottomed flask were added 5-bromo-2-methoxy-phenol (10.01 g, 49.3 mmol), 2-chloroethyl p-toluenesulfonate (25.32 g, 107.9 mmol), CsCO$_3$ (20.43 g, 62.7 mmol), Triton X-405 (0.57 g, 1 mmol), and THF (55 mL). The slurry was heated at 65° C. for 7 h, then cooled to room temperature. The reaction solution was cooled to 0° C., and a solution of potassium tert-butoxide (18.11 g, 1.48 mol) in 100 mL THF was added dropwise over 30 min. The reaction mixture was allowed to warm to room temperature and stirred an additional 2.5 h. The reaction was quenched by addition of a saturated aqeuous NH₄Cl solution, and extracted 3× with EtOAc. The combined organic phase was treated with brine, dried over MgSO₄, filtered, concentrated, and then co-evaporated 3× with toluene. The intermediate 4-bromo-1-methoxy-2-vinyloxy-benzene was obtained as an orange-tinted oil (12.2 g). $^1$H NMR (DMSO-d$_6$) 7.26 (dd, J=8.8, 2.4, 1 H), 7.20 (d, J=2.4 Hz, 1 H), 6.77 (dd, J=13.6, 6.0, 1 H), 4.63 (d, J=13.6, 1 H), 4.42 (d, J=6.0, 1 H), 3.76 (s, 3 H).

Into a 25 mL flame-dried flask were added diethylzinc (8.75 mL, 1N solution in hexanes). The solution was cooled to −20° C. and a solution of trichloroacetic acid (1.43 g, 8.75 mmol, dissolved in 2 mL of CH₂Cl₂ was added dropwise over 10 min, then the solution was stirred an additional 20 min. A solution of diiodomethane (2.38 g, 8.89 mmol) in 1 mL CH₂Cl₂ was then added dropwise and the solution was stirred an additional 20 minutes. A solution of 4-bromo-1-methoxy-2-vinyloxy-benzene (1.029 g, 4.365 mmol, dissolved in 900 uL CH₂Cl₂) was then added and the reaction mixture was stirred for 8 h at room temperature. The reaction mixture was poured onto a 100 mL 1 N aqueous HCl solution containing some ice, then extracted 3× with EtOAc. The combined organic phase was washed with 1 N aqueous NaHCO₃, brine, then dried (MgSO4), filtered and concentrated. Purification by flash column on silica gel (0-100% Hexanes/EtOAc gradient) to afford titled compound as a colorless crystalline solid (738 mg, 67%). $^1$H NMR (DMSO-d$_6$) 7.33 (s, 1 H), 7.06 (d, J=8.4, 1 H), 6.90 (d, J=8.4, 1 H), 3.84 (m, 1 H), 3.70 (s, 3 H), 0.75 (m, 2 H), 0.64 (m, 2H). LC/MS (Method B) 3.64 min, [M+1]⁺ 243/245.

Preparative Example 68

4-Bromo-2-(cyclopentyloxy)-1-methoxybenzene CAS [138509-45-2]

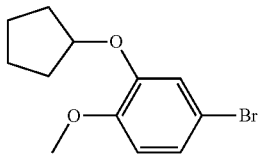

5-Bromo-2-methoxy-phenol was synthesized by dissolving 5-bromo-2-methoxybenzaldehyde (50 g, 233 mmol), in CH₂Cl₂ (150 mL) was cooled with an ice bath to 0° C., and subsequently, 3-chloroperoxybenzoic acid (70-75% purity) (68.1 g, 276 mmol) in CH₂Cl₂ (500 mL) was added. The reaction mixture was allowed to warm slowly to room temperature and stirred for 72 h. The colorless solid was filtered off, and the filtrate was stirred for 2 h with a 2 N Na₂SO₃ solution (200 mL). The organic layer was evaporated and the remainder dissolved in diethyl ether and washed with 1 N Na₂SO₃ and a half saturated NaHCO₃ solution. The organic phase was extracted with a 2 N aqueous NaOH solution. The combined basic extract was acidified (pH∼3-4) with concentrated HCl and then extracted with diethyl ether. The combined organic extracts were dried over MgSO4, filtered, and the solvent evaporated to afford intermediate 5-bromo-2-methoxy-phenol (43.5 g, 90%). $^1$H NMR (CDCl₃) 7.06 (d, J=2.3, 1 H), 6.96 (dd, J=8.6, 2.3, 1 H), 6.70 (d, J=8.6, 1 H), 5.67 (s, 1 H), 3.86 (s, 3 H).

The 5-bromo-2-methoxy-phenol intermediate (15 g, 73.9 mmol) was dissolved in DMF (100 mL) and treated with anhydrous K₂CO₃ (20.4 g, 148 mmol), followed by the addition of cyclopentyl bromide (19.1 g, 128 mmol). The reaction was heated at 65° C. for 12 h after which time the reaction was cooled to room temperature and the reaction mixture diluted with diethyl ether, and the solution washed with a 1 N aqueous NaOH solution followed by water. The organic layer was dried over MgSO₄, filtered, and concentrated to afford titled compound as an oil (19.5 g, 90%). $^1$H NMR (CDCl₃) 7.07-6.93 (m, 2 H), 6.73 (d, J=8.2, 1 H), 4.80-4.68 (m, 1 H), 3.83 (s, 3 H), 2.03-1.50 (m, 8 H).

Preparative Example 69

4-bromo-2-cyclobutoxy-1-methoxybenzene CAS [944334-02-5]

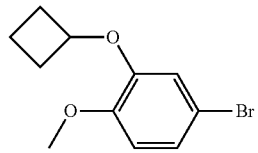

Prepared by the method outlined for Example 68 using 5-bromo-2-methoxy-phenol and bromocyclobutane as starting materials. Titled compound as an oil (7.5 g, 83%). LC/MS (Method B) 4.05 min, [M+1]⁺ 257/259.

Preparative Example 70

4-bromo-2-isopropoxy-1-methoxybenzene CAS [462092-23-5]

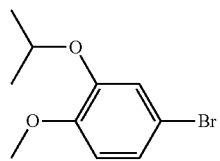

Prepared by the method outlined for Example 68 using 5-bromo-2-methoxy-phenol and 2-bromo-propane as starting materials. Titled compound as an oil (8 g, 88%). LC/MS (Method B) 4.05 min, [M+1]⁺ 245/247.

Preparative Example 71

4-bromo-2-(cyclobutyloxy)-1-ethoxybenzene

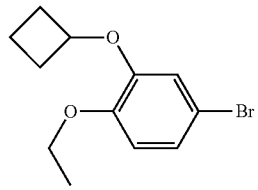

A solution of 5-bromo-2-ethoxy-benzaldehyde (50 g, 233 mmol), in $CH_2Cl_2$ (150 mL) at 0-5° C., was treated with a solution of 3-chloroperoxybenzoic acid (70-75% purity) (68.1 g, 276 mmol) in $CH_2Cl_2$ (500 mL) and the reaction mixture allowed to warm slowly to room temperature and stirred for 72 h. The resulting precipitate was filtered and the filtrate then stirred for 2 h with a 2 N aqueous $Na_2SO_2O_3$ solution (200 mL). The organic layer was then concentrated, dissolved in diethyl ether, and washed with an aqueous 1 N $Na_2SO_3$ followed by a half saturated $NaHCO_3$ solution. The organic phase was extracted with a 2 N aqueous NaOH solution and the combined basic extract acidified (pH~3-4) with concentrated HCl. The acidified mixture was extracted with diethyl ether, dried over MgSO4, filtered, and evaporated to afford intermediate 5-bromo-2-methoxy-phenol (43.5 g, 90%). $^1$H NMR ($CDCl_3$) 7.06 (br s, 1 H), 6.96 (dd, J=8.6, 2.3, 1 H), 6.70 (d, J=8.6, 1 H), 5.67 (s, 1 H), 4.05 (q, J=7.1, 2 H), 1.44 (t, J=7.1, 3 H).

The intermediate 5-bromo-2-ethoxy-phenol (15 g, 73.9 mmol) was dissolved in DMF (100 mL) then treated with anhydrous $K_2CO_3$ (20.4 g, 148 mmol) followed by the addition of bromocyclobutane (19.1 g, 128 mmol). The reaction was heated at 65° C. for 12 h, then cooled to room temperature, diluted with diethyl ether, and the solution washed with a 1 N aqeuous NaOH solution followed by water. The organic layer was then dried over MgSO4, filtered, and concentrated to afford titled compound as an oil (19.5 g, 90%). $^1$H NMR ($CDCl_3$) 6.98 (dd, J=8.4, 2.1, 1 H), 6.83 (d, J=2.4, 1 H), 6.73 (d, J=8.7, 1 H), 4.65-4.57 (m, 1 H), 4.05 (q, J=7.1, 2 H), 2.50-2.42 (m, 2 H), 2.30-2.18 (m, 2 H), 1.90-1.81 (m, 1 H), 1.73-1.63 (m, 1 H), 1.44 (t, J=7.1, 3 H). $^{13}$C NMR 148.2, 147.8, 123.4 (CH), 117.0 (CH), 114.7 (CH), 112.7, 72.5 (CH), 64.8 ($CH_2$), 30.6 ($CH_2$), 14.7 ($CH_3$), 13.1 ($CH_2$). LC/MS (Method B) 4.18 min, $[M+1]^+$ 271/273.

Preparative Example 72

4-bromo-2-(cyclopentyloxy)-1-ethoxybenzene

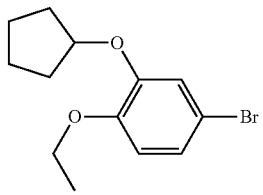 [SMILES: CCOc1ccc(Br)cc1OC1CCCC1]

Prepared by the method outlined for Preparative Example 71 using bromocyclopentane as alkyl halide. Titled compound as an oil (6.8 g, 85%). $^1$H NMR ($CDCl_3$) 6.99-6.96 (obs s and obs dd, 2 H), 6.73 (d, J=8.4, 1 H), 4.74-4.71 (m, 1 H), 4.01 (q, J=6.0, 2 H), 1.91-1.79 (m, 6 H), 1.64-1.59 (m, 2 H), 1.40 (t, J=7.0, 3 H). $^{13}$C NMR 149.1, 148.8, 123.5 (CH), 118.9 (CH), 115.6 (CH), 112.9, 76.7 (CH), 65.0 ($CH_2$), 32.8 ($CH_2$), 24.0 ($CH_2$), 14.9 ($CH_3$). LC/MS (Method B) 4.43 min, $[M+1]^+$ 285/287.

Preparative Example 73

4-bromo-1,2-bis(difluoromethoxy)benzene, CAS [330475-65-5]

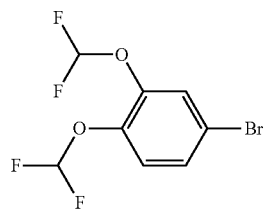 [SMILES: FC(F)Oc1ccc(Br)cc1OC(F)F]

A solution of 5-bromo-2-hydroxybenzaldehyde (10 g, 50 mmol) was dissolved in a 1 N aqeuious NaOH solution (55 mL). To this yellow solution was added hydrogen peroxide (36%, 12 mL) dropwise via addition funnel at room temperature. After stirring for 2 h, the reaction was quenched by adding saturated solution of $Na_2S_2O_3$, and extracted with EtOAc. The organic extract was washed with 1N HCl, water, brine, and passed through a short pad of silica gel to obtain 4-bromobenzene-1,2-diol (7.0 g, 74%) as a brown solid. $^1$H NMR (300 MHz, $CDCl_3$) 7.02 (d, J=2.1, 1H), 6.91 (dd, J=8.8, 2.1, 1H), 6.73 (d, J=8.8, 1H).

A slurry of the 4-bromobenzene-1,2-diol intermediate (3.0 g, 15.9 mmol), $CF_2ClCO_2Na$ (9.7 g, 63.5 mmol, 4 equiv), and $K_2CO_3$ (5.3 g, 38.1 mmol, 2.4 equiv) in DMF (30 mL)/water (3.5 mL) was degassed for 15 min by using a nitrogen sparge. The reaction was then heated to 100° C. for 2 h after which time the reaction mixture was cooled to room temperature and treated with concentrated HCl (12 N, 5 mL) and water (12 mL). The reaction mixture was allowed to stir for 12 h then basified to pH~10 by addition of an aqeuous NaOH solution (5N) and the mixture extracted with EtOAc. The organic extract was washed with water, buffer (pH=7), brine, and dried over $Na_2SO_4$. Filtration followed by evaporation afforded a residue which was purified using an ISCO system (0-5% EtOAc in Hexanes) to afford titled compound (1.6 g, 35%) as a colorless oil. $^1$H NMR: (300 MHz, $CDCl_3$) 7.43 (d, J=2.1, 1 H), 7.37 (dd, J=8.4, 2.1, 1 H), 7.15 (d, J=8.8, 1 H), 6.50 (t, J=73, 2 H, $CHF_2$). $^{19}$F NMR (282 MHz, DMSO) −82.6, −82.9, −83.0, −83.3.

Preparative Example 74

4-bromo-2-(cyclopentyloxy)-1-(difluoromethoxy) benzene

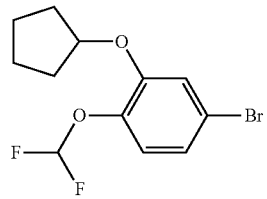 [SMILES: FC(F)Oc1ccc(Br)cc1OC1CCCC1]

A mixture of catechol (11.0 g, 100 mmol) and solid NaOH (4.0 g, 100 mmol) in EtOH (20 mL) were stirred for 1 h. To the resulting brown solution was added dropwise bromocyclopentane (17.4 g, 117 mmol, 1.17 equiv) via addition funnel over 30 min. After heating at reflux for 24 h, the reaction mixture was cooled to room temperature and concentrated. The resulting crude material was dissolved in CH₂Cl₂, washed with water, and concentrated. The resulting residue was suspended in hexanes and extracted with an aqueous 1 N NaOH solution (3×30 mL). The combined aqueous extracts were washed with EtOAc, acidified with an aqueous 3 N HCl solution, and extracted with EtOAc (3×). The combined organic extracts were washed with water, brine, and dried over Na₂SO₄. Filtration followed by evaporation afforded a residue which was purified by ISCO (0-25% EtOAc in hexanes) to provide the 2-(cyclopentyloxy)phenol intermediate (6.0 g, 33%) as colorless oil. ¹H NMR (300 MHz, CDCl₃) 6.94-6.90 (m, 2 H), 6.87-6.79 (m, 2 H), 5.63 (s, 1 H), 4.83 (m, 1 H), 1.94-1.62 (m, 8 H).

A solution of 2-(cyclopentyloxy)phenol intermediate (5.6 g, 31 mmol) in CH₂Cl₂ (40 mL) at −78° C. was treated dropwise with a solution of bromine (4.9 g, 31 mmol) in CH₂Cl₂ (10 mL) via addition funnel over a 1 h period. After warming up to room temperature gradually over 3 h, the reaction was quenched by addition of a saturated aqueous solution of Na₂S₂O₄. The isolated organic layer was washed with water, brine, dried over Na₂SO₄, filtered, and concentrated. The crude mixture was then purified by ISCO (0-10% EtOAc in hexanes) to afford intermediate 4-bromo-2-(cyclopentyloxy)phenol (2.6 g, 32%) as colorless oil. ¹H NMR (300 MHz, CDCl₃) 6.97-6.93 (m, 2 H), 6.78 (d, J=9.3, 1 H), 5.54 (s, 1 H), 4.78 (m, 1 H), 1.95-1.63 (m, 8 H).

A solution of 4-bromo-2-(cyclopenyloxy)phenol (1.06 g, 4.12 mmol) in acetonitrile (16 mL) in a sealed screwcap vial was treated with 2-chloro-2,2-difluoro-1-phenylethanone (1.7 g, 8.24 mmol), followed by an aqueous 30% KOH solution (16 mL, 21 equiv). After heating at 80° C. for 8 h, the reaction mixture was extracted with EtOAc, the combined extracts dried over Na₂SO₄, filtered and concentrated to afford a residue which was purified by ISCO (hexanes) to obtain the product (400 mg, 33%) as colorless oil. In parallel, 10 reactions were carried out for the scale up. The final pure titled compound was obtained by Kugelrohr distillation (130° C./1 mmHg). ¹H NMR (300 MHz, CDCl₃) 7.07 (s, 1 H), 7.01 (s, 2 H), 6.48 (t, J=75, 1 H, CHF2), 4.77 (m, 1 H), 1.93-1.62 (m, 8 H). ¹⁹F NMR (282 MHz, CDCl3) −81.9, −82.2. LC/MS, 95% pure.

Preparative Example 75

4-bromo-2-cyclobutoxy-1-difluoromethoxy-benzene, CAS [944333-97-5]

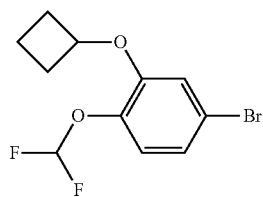 [SMILES: FC(F)Oc1ccc(Br)cc1OC1CCC1]

Prepared by the method outlined for Example 74 using bromocyclobutane and catechol as starting materials. Titled compound as an oil (100 mg, 55%). LC/MS (Method A) 3.55 min, [M+1]⁺ 293/295.

Preparative Example 76

4-bromo-2-(cyclopropylmethoxy)-1-(difluoromethoxy)benzene CAS [680184-55-8]

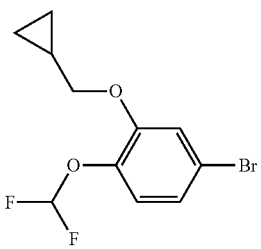 [SMILES: FC(F)Oc1ccc(Br)cc1OCC1CC1]

Prepared by the method outlined for Example 74 using bromomethylcyclopropane and catechol as starting materials. Titled compound as an oil (100 mg, 65%). LC/MS (Method A) 3.55 min, [M+1]⁺ 293/295.

Preparative Examples 77-79

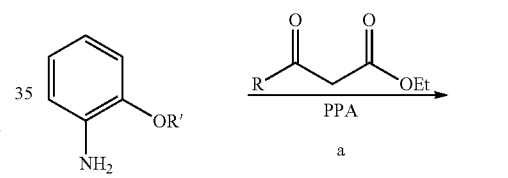

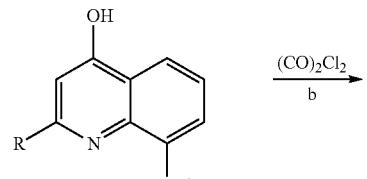

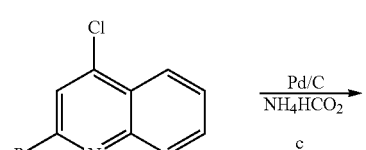

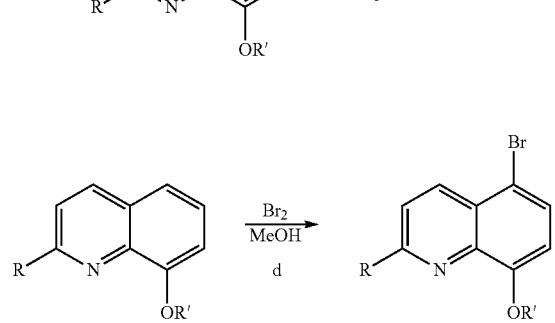

Preparative Example 77

5-Bromo-2-chloro-8-methoxyquinoline

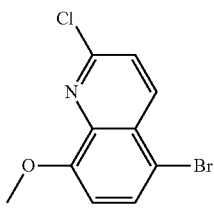

A solution of 8-methoxy-2-(chloro)quinoline CAS [74668-74-9] (1.0 g, 4.4 mmol) in MeOH (6.25 mL) was treated with a 1.5 N solution of bromine in MeOH (3.53 mL, 5.3 mmol) over 15 min period. The reaction mixture was stirred 2 h, treated with a 1 N aqueous $Na_2S_2O_3$ solution (20 mL) followed by EtOAc (100 mL). The organic portion was washed with brine followed by a saturated aqueous solution of $NaHCO_3$ followed by brine. The organic phase was dried over $Na_2SO_4$, filtered, evaporated, and purified by silica gel chromatography eluting with $CH_2Cl_2$ to afford titled compound as a colorless solid (49%). $^1$H NMR ($CDCl_3$) 8.44 (dd, J=8.8, 1.2, 1 H), 7.73 (dd, J=8.4, 1.2, 1 H), 7.51 (dd, J=8.8, 1.2, 1 H), 6.97 (d, J=8.4, 1 H), 4.06 (s, 3 H). LC/MS 3.45 min, [M+1]$^+$ 271/273.

Preparative Example 78

5-Bromo-8-methoxy-2-(trifluoromethyl)quinoline [199872-02-1]

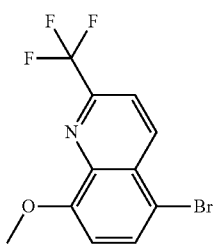 [SMILES: COc1ccc(Br)c2ccc(C(F)(F)F)nc12]

A solution of 4-chloro-8-methoxy-2-(trifluoromethyl)quinoline CAS [41192-89-6] (5.89 g, 22.5 mmol) in EtOH (55 mL) was treated with ammonium formate (4.26 g, 67.5 mmol) followed by palladium (10%, dry) on carbon (0.33 g) and the mixture was stirred at 80° C. for 2 h. The mixture was then cooled and filtered through a pad of Celite® with the aid of EtOH and evaporated. Purification by silica gel chromatography eluting with 25% EtOAc in hexanes afforded intermediate 8-methoxy-2-(trifluoromethyl)quinoline (2.53 g, 50%) as a colorless solid. $^1$H NMR (MeOH-d$_4$) 8.51 (d, J=18.6, 1 H), 7.85 (d, J=18.4, 1 H), 7.66 (t, J=18.0, 1 H), 7.56 (dd, J=8.4, 1.2, 1 H), 7.30 (dd, J=7.8, 1.2, 1 H), 4.08 (s, 3 H). LC/MS (Method B) 3.20 min, [M+1]$^+$ 228.

The intermediate 8-methoxy-2-(trifluoromethyl)quinoline (2.21 g, 9.7 mmol) in MeOH (15 mL) was treated with a 1.5 N solution of bromine in MeOH (7.8 mL, 11.7 mmol) over a 15 min period. This mixture was stirred 2 h then treated with a 1 N aqueous solution of $Na_2S_2O_3$ (30 mL) and EtOAc (300 mL). The phases where separated and the organic portion washed with brine, a saturated aqueous solution of $NaHCO_3$, and again with brine. The organic phase was dried with $Na_2SO_4$, filtered, and evaporated to afford titled compound as a light brown solid. $^1$H NMR ($CDCl_3$) 8.70 (dd, J=8.8, 0.6, 1 H), 7.86 (d, J=8.8, 1 H), 7.85 (d, J=8.4, 1 H), 7.02 (d, J=8.4, 1 H), 4.10 (s, 3 H). LC/MS (Method B) 3.82 min, [M+1]$^+$ 305/307.

Preparative Example 79

5-Bromo-8-methoxy-2-methyl-quinoline

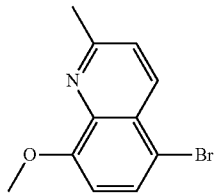

Prepared using the same procedure described in Example 78 from 8-methoxy-2-methyl-quinoline [CAS 3033-80-5] (1.21 g, 6.96 mmol) and bromine (1.35 g, 8.42 mmol) to afford titled compound as a yellow solid (1.52 g, 86%). $^1$H NMR (DMSO-d$_6$) 8.30 (d. J=8.4, 1H), 7.76 (d. J=8.4, 1 H), 7.57 (d. J=8.4, 1 H), 7.10 (d. J=8.4, 1 H), 3.93 (s, 3 H), 2.66 (s, 3 H). LC/MS (Method B) 2.07 min, [M+1]$^+$ 252/254.

PREPARATIVE EXAMPLE 80

Preparative Example 80

(R)-1-(3-Cyclopentyloxy-4-methoxy-phenyl)-3-(2-formayl)-piperazine

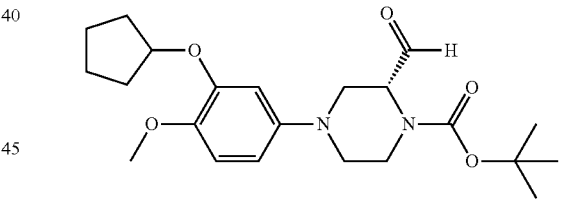

The title compound was prepared by the method outlined for Example 1 using (2R)-[(phenylmethoxy)methyl]-1-Piperazinecarboxylic acid, 1,1-dimethylethyl ester CAS [740806-54-6] as amine component. The coupled product was purified by silica gel flash chromatography with 15% EtOAc/hexanes as eluant to afford coupled intermediate as an oil (4.1 g, 83%). $^1$H NMR ($CDCl_3$) 7.33-7.25 (m, 5 H), 6.78 (d, J=8.6, 1 H), 6.52 (s, 1 H), 6.38-6.41 (m, 1 H), 4.70-4.65 (m, 1 H), 4.60-4.56 (m, 2 H), 4.35 (br, 1 H), 3.96 (br, 1 H), 3.89-3.84 (m, 1 H), 3.79 (s, 3H), 3.66 (br d, J=11.3, 1 H), 3.58 (br, 1 H), 3.30 (br d, 1 H), 3.10 (br t, 1 H), 2.77-2.64 (m, 2 H), 1.86-1.80 (m, 6 H), 1.60-1.50 (m, 2 H), 1.46 (s, 9 H). LC/MS (Method B) 4.92 min, [M+1]$^+$ 497.

The intermediate coupled product (5.6 g, 11.3 mmol) was dissolved in ethanol (100 mL) and treated with Pearlman's catalyst (5.0 g) and hydrogenated at ~75 psi $H_2$ pressure for 36 h. The reaction mixture was purged with nitrogen and filtered through a pad of Celite with the addition of additional ethanol and the filtrate evaporated to afford a crude residue. The O-benzyl deprotected intermediate was purified by silica gel flash chromatography with 30% EtOAc/hexanes followed by 100% EtOAc as eluant to afford intermediate as an oil (2.75 g, 60%). $^1$H NMR (CDCl$_3$) 6.80 (dd, J=8.6, 2.8, 1 H), 6.60 (br s, 1 H), 6.49 (br d, J=8.2, 1 H), 4.77-4.74 (m, 1 H), 4.25 (br s, 1 H), 4.10-3.95 (m, 3 H), 3.80 (s, 3 H), 3.52 (d, J=11.5, 1 H), 3.49-3.32 (m, 2 H), 2.88 (br dd, J=11.9, 3.3, 1 H), 2.73 (br t, J=11.8, 1 H), 1.93-1.78 (m, 6 H), 1.65-1.57 (m, 2 H), 1.49 (s, 9 H). LC/MS (Method B) 3.69 min, [M+1]$^+$ 407.

The intermediate carbinol (2.74 g, 6.74 mmol) was dissolved in DMSO (10 mL) and CH$_2$Cl$_2$ (10 mL) followed by cooling to 0-5° C. and treatment with diisopropylethylamine (3.52 mL, 20.2 mmol) and solid sulfur trioxide-pyridine complex (3.22 g, 20.2 mmol). The reaction mixture was allowed to stir for 3 h and then warmed to room temperature and partitioned between EtOAc (50 mL) and water (50 mL). The organic portion was washed with brine (2×25 mL), dried over MgSO$_4$, filtered, and evaporated to an oil, which was purified by silica gel flash chromatography with 20% then 30% EtOAc/hexanes as eluant to afford titled compound as a clear colorless oil (2.0 g, 73%). $^1$H NMR (CDCl$_3$) 9.70 (s, 1 H), 6.79 (d, J=8.6, 1 H), 6.55 (d, J=2.3, 1 H), 6.45 (dd, J=8.6, 2.7, 1 H), 4.78-4.73 (m, 1 H), rotomers 4.51 and 4.70 (br s, 1 H), 4.11-3.91 (m, 2 H), 3.80 (s, 3 H), 3.49-3.21 (m, 2 H), 2.92 (br d, J=11.5, 1 H), 2.75-2.69 (m, 1H), 2.05-1.79 (m, 6 H), 1.63-1.56 (m, 2 H), rotomers 1.47 and 1.51 (br s, 9 H),. LC/MS (Method B) 3.69 min, [M+1]$^+$ 405.

Preparative Examples 81-88

Preparative Example 81

Methyl (5-ethyl-1H-1,2,4-triazol-3-yl)acetate, CAS [893762-31-7]

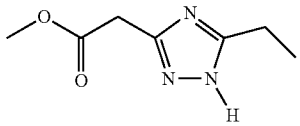

A mixture of propionylhydrazide (42.8 g, 534 mmol), ethyl 3-ethoxy-3-iminopropionate (85 g, 534 mmol), and TsOH (5.0 g, 27 mmol) in anhydrous toluene (2 L) was allowed to reflux overnight. The mixture was then concentrated and purified by silica gel chromatography to afford product as the ethyl ester CAS [100187-11-9] (7.1 g, 7.3%).

The intermediate ethyl ester (7.1 g, 38.8 mmol) was dissolved in dry MeOH (150 mL), cooled to 0° C. and treated with NaOMe (2.3 g, 42.7 mmol). The mixture was allowed to reflux overnight after which time the solvent was removed and the residue acidified with a 5% aqueous solution of hydrochloric acid to pH=3 and extracted with ethyl acetate. The organic layer was washed with brine, dried over Na$_2$SO$_4$ and concentrated to afford the titled compound (2.7 g, 41%). $^1$H NMR (CDCl$_3$) 12.1 (br s, 1 H), 3.86 (s, 2 H), 3.73 (s, 3 H), 2.78 (q, J=7.6, 2 H), 1.31 (t, J=5.2, 3 H). MS [M+1] 170.

Preparative Example 82

Methyl (5-isopropyl-1H-1,2,4-triazol-3-yl)acetate

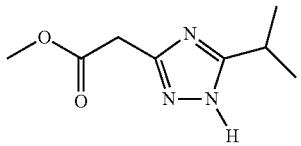

A mixture of isobutyrylhydrazine (65 g, 630 mmol), ethyl 3-ethoxy-3-iminopropionate (105 g, 630 mmol), and TsOH (5.7 g, 30 mmol) in anhydrous toluene (2 L) was allowed to reflux overnight. The mixture was then concentrated and purified by silica gel chromatography to afford product as the ethyl ester CAS [929339-32-2] (3.0 g, 8%).

The intermediate ethyl ester (3.0 g, 15.0 mmol) was dissolved in dry MeOH (50 mL), cooled to 0° C. and treated with NaOMe (1.6 g, 30.0 mmol). The mixture was allowed to reflux overnight after which time the solvent was removed and the residue acidified with a 5% aqueous solution of hydrochloric acid to pH=3 and extracted with ethyl acetate. The organic layer was washed with brine, dried over Na$_2$SO$_4$ and concentrated to afford the titled compound (1.0 g, 36%). $^1$H NMR (CDCl$_3$) 10.6 (br s, 1 H), 3.88 (s, 2 H), 3.75 (s, 3 H), 3.17-3.06 (m, 1 H), 1.35 (d, J=7.2, 6 H). $^{13}$C NMR 170.0, 164.5, 154.6, 52.4, 33.6, 27.1, 21.2. MS [M+1] 184.

Preparative Example 83

Methyl [5-(trifluoromethyl)-1H-1,2,4-triazol-3-yl]acetate

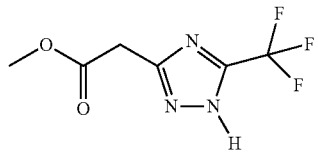

A mixture of trifluoroacetic acid hydrazide (100 g, 0.78 mol) in ethyl cyanoacetate (200 mL) was heated at 200° C. for 3 h after which time dichloromethane was added and the reaction filtered The filtrate was then concentrated and purified by column chromatography using 10% EtOAc/petroleum ether as eluant to afford crude product. Residual cyanoacetate was removed by distillation under reduced pressure to afford the ethyl ester intermediate (12 g, 7%) as brown solid.

The intermediate ethyl ester (12.0 g, 54.0 mmol) was dissolved in dry MeOH (150 mL), cooled to 0° C. and treated with NaOMe (8.7 g, 160 mmol). The mixture was allowed to reflux overnight after which time the solvent was removed and the residue acidified with a 5% aqueous solution of hydrochloric acid to pH=3 and extracted with ethyl acetate. The organic layer was washed with brine, dried over sodium sulfate, concentrated, and purified by preparative HPLC to afford the titled compound (3.0 g, 27%). $^1$H NMR (DMSO-d$_6$) 4.05 (s, 2 H), 3.67 (s, 3 H). $^{13}$C NMR 168.6, 152.69, 120.0 (q, J=268), 52.8, 32.4. MS [M+1]$^+$ 210.

Preparative Example 84 tert-Butyl 5-amino-3-(2-methoxy-2-oxoethyl)-1H-1,2,4-triazole-1-carboxylate

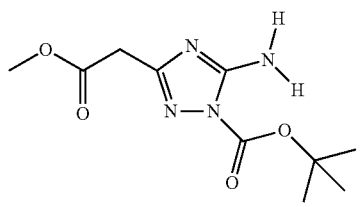 [SMILES: COC(=O)Cc1nc(N)n(C(=O)OC(C)(C)C)n1]

To a solution of 1H-1,2,4-triazole-3-acetic acid, 5-amino-, methyl ester CAS [875764-86-6] (2.0 g, 12.8 mmol) in MeOH (5 mL) was treated with triethylamine (2 mL) followed by di-tert-butyl dicarbonate (4.0 g, 18.3 mmol) and the reaction mixture stirred for 24 h. The reaction mixture was then evaporated and the residue purified by chromatography on silica gel using 65% EtOAc/petroleum ether as eluant to afford titled compound (2.0 g, 61%). $^1$H NMR (CDCl$_3$) 6.44 (br s, 2 H), 3.74 (s, 2 H), 3.66 (s, 3 H), 1.65 (s, 9 H). MS [M+1]$^+$ 535.

Preparative Example 85

Methyl (3-methyl-1,2,4-oxadiazol-5-yl)acetate, CAS [55152-01-7]

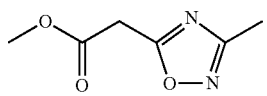

A suspension of N-hydroxyacetamidine (37 g, 0.50 mol) in DME (500 mL) was treated dropwise with pyridine (118.5 g, 1.50 mol) at room temperature under N$_2$ gas atmosphere. The mixture was then cooled to 0° C. and ethyl malonyl chloride (113 g, 0.75 mol) added drop-wise. After stirring at 0° C. for 30 min, then the mixture was warmed to room temperature, quenched with water, separated, the aqueous phase was extracted with EtOAc. The combined organic extracts were washed with brine, dried, concentrated to dryness. The intermediate was purified by the flash chromatography on silica gel to afford ethyl 3-({[(1Z)-1-aminoethylidene]amino}oxy)-3-oxopropanoate as a colorless solid (20 g, 21%). $^1$H NMR (CDCl$_3$) 5.00 (br s, 2 H), 4.23 (q, J=7.2, 2 H), 3.52 (s, 2H), 2.01 (s, 3 H), 1.31 (t, J=7.2, 3 H).

The O-acylated intermediate (12 g, 64.0 mmol) was dissolved in pyridine (100 mL) and stirred at reflux overnight. After this time the reaction was cooled and evaporated to a residue which was partitioned between CH$_2$Cl$_2$ (100 mL) and water (30 mL). The aqueous phase was further extracted with CH$_2$Cl$_2$ (3×50 mL) and the combined organic layers washed with brine, dried, and concentrated to a crude residue which was purified by purified by the flash chromatography on silica gel to afford ethyl ester product as an oil (9.0 g, 83%). $^1$H NMR (CDCl$_3$) 4.25 (q, J=7.2, 2 H), 3.92 (s, 2 H), 2.40 (s, 3 H), 1.27 (t, J=7.2, 3 H).

The intermediate ethyl ester (2.86 g, 53.0 mmol) was dissolved in dry MeOH (100 mL), cooled to 0° C. and treated with NaOMe (8.7 g, 160 mmol). The mixture was allowed to reflux overnight after which time the solvent was removed and the residue acidified with a 5% aqueous solution of hydrochloric acid to pH=3 and extracted with ethyl acetate. The organic layer was washed with brine, dried over sodium sulfate, concentrated, and purified by flash chromatography on silica gel to afford titled compound as an oil (7.0 g, 85%). $^1$H NMR (CDCl$_3$) 3.93 (2 H), 3.75 (s, 3 H), 2.38 (s, 3 H). MS [M+1]$^+$ 157.

Preparative Example 86

Methyl (2-methyl-1H-imidazol-4-yl)acetate, hydrochloride

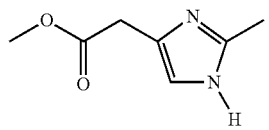

1H-Imidazole-5-acetic acid, 2-methyl-, ethyl ester CAS [812675-83-5] (2.8 g, 17.0 mmol) was dissolved in dry MeOH (20 mL), cooled to 0° C. and treated with NaOMe (1.9 g, 34.0 mmol). The mixture was then filtered and the filtrate concentrated (temperature <30° C.) to afford crude product as yellow oil. The residue was purified by pre-HPLC and salification with 2 N HCl/methyl tert-butyl ether to afford titled compound (1.8 g, 61%) as colorless oil. $^1$H NMR (MeOH-d$_4$) 3.83 (s, 2 H), 3.70 (s, 3 H), 2.62 (s, 3 H). MS [M+1]$^+$ 155.

Preparative Example 87

(2-Methyl-1,3-oxazol-5-yl)acetic acid

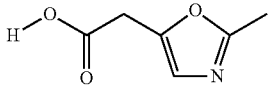

A solution of 5-(bromomethyl)-2-methyl-oxazole CAS [82190-68-9] (15 g, 85 mmol) in DMF (150 mL) was treated with NaCN (10.4 g, 213 mmol) at room temperature and the mixture stirred at 70° C. for 1 h. After this time the mixture was poured onto ice-cooled water (300 mL) and extracted with CH$_2$Cl$_2$ (5×200 mL). The combined organic extracts were then washed with brine, dried with Na$_2$SO$_4$ for 30 min, and the mixture concentrated to afford crude 2-methyl-5-oxazoleacetonitrile product CAS [1159511-94-0] (10 g).

The intermediate crude nitrile (10.3 g, crude) was dissolved a 2 N methanolic HCl solution (180 mL) and heated under reflux for 12 h. The cooled reaction mixture was then concentrated under reduce pressure remove solvent, basified with saturated NaHCO$_3$ to pH~9-10, extracted with CH$_2$Cl$_2$, dried over NaSO$_4$, and concentrated to afford the methyl ester of desired product (10.3 g, crude) which was used for the next step without further purification. $^1$H NMR (CDCl$_3$) 6.79 (s, 1 H), 3.71 (s, 3 H), 3.66 (s, 2 H), 2.41 (s, 3 H).

A solution of crude ethyl ester (10.3 g, crude) in MeOH (80 mL) was treated with a solution of NaOH (7.9 g 0.19 mol) in water (80 mL) and stirred at room temperature for 2 h. After this time volatile solvents were removed and the remaining solution acidified with a 1M HCl solution. The mixture was concentrated and salts removed by the addition of $CH_2Cl_2$. The surplus solution was concentrated to afford titled compound (2.5 g). $^1$H NMR (MeOH-$d_4$) 6.85 (s, 1 H), 3.72 (s, 3 H), 2.42 (s, 3 H). MS [M+1]$^+$ 142.

Preparative Example 88

Methyl 1H-pyrazol-4-ylacetate

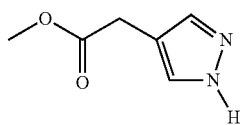

A solution of 1-(tetrahydro-2H-pyran-2-yl)-1H-pyrazole-4-methanol CAS [1038392-13-0] (13.0 g, 71 mmol) in anhydrous $CH_2Cl_2$ (100 mL) at −10° C. was treated with triethylamine (28.7 g, 284 mmol) followed by dropwise addition of a solution of methanesulfonyl chloride (10.5 g, 93 mmol) in $CH_2Cl_2$ (30 mL). The reaction mixture was stirred at this temperature until the reaction was completed then washed with water and brine. The organic phase was then dried over anhydrous $Na_2SO_4$, filtered, and concentrated to afford the O-mesylate (11.0 g, 60%) as yellow oil. The crude mesylate (11.0 g, 43 mmol) was then dissolved in DMF (150 mL) then treated with NaCN (4.2 g, 85 mmol) and the mixture stirred at 50° C. for 3 h. The reaction was then treated with water and extracted with $CH_2Cl_2$. The combined organic extracts were washed with water, dried over anhydrous $Na_2SO_4$, filtered, and concentrated to afford crude residue which was purified by chromatography on silica gel to afford desired nitrile intermediate (3.6 g, 44.2%) as yellow oil. $^1$H NMR (CDCl$_3$) 7.64 (s, 1 H), 7.49 (s, 1 H), 5.37-5.33 (m, 1 H), 4.07-4.03 (m, 1 H), 3.72-3.67 (m, 1 H), 3.59 (s, 2 H), 2.07-2.03 (m, 3 H), 1.70-1.62 (m, 3 H).

The nitrile intermediate (7.0 g, 37 mmol) was then dissolved in a saturated methanolic hydrogen chloride solution (70 mL) and the mixture stirred at 50° C. for 2 h. After this time the reaction mixture was evaporated, the residue dissolved in water, and the pH adjusted with a saturated aqueous $NaHCO_3$ solution to pH~8-9. The aqueous solution was extracted with EtOAc, dried over anhydrous $Na_2SO_4$, filtered, and concentrated to afford crude product which was purified by chromatography on silica gel to afford titled compound (3.6 g, 70%) as a yellow solid. $^1$H NMR (CDCl$_3$) 7.58 (s, 2 H), 3.72 (s, 3 H), 3.56 (s, 2 H). MS [M+1]$^+$ 141.

EXAMPLES 1-74

The following compounds of the invention were prepared as illustrated below.

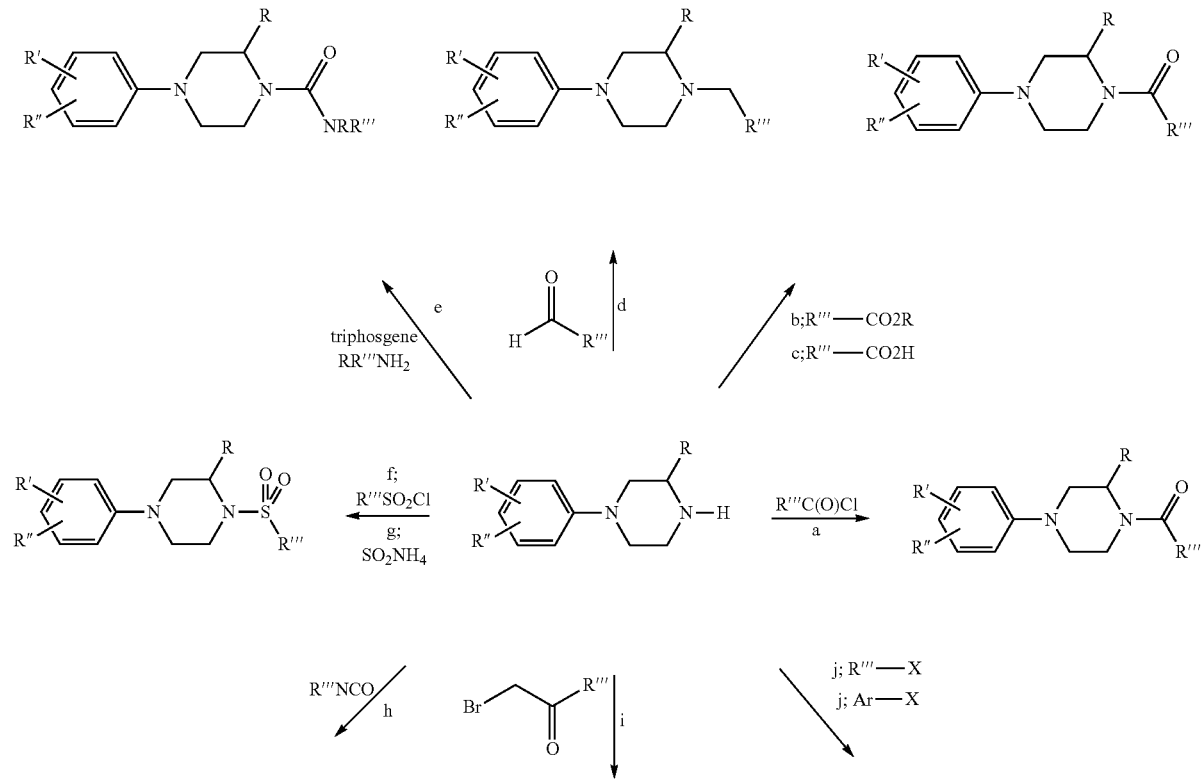

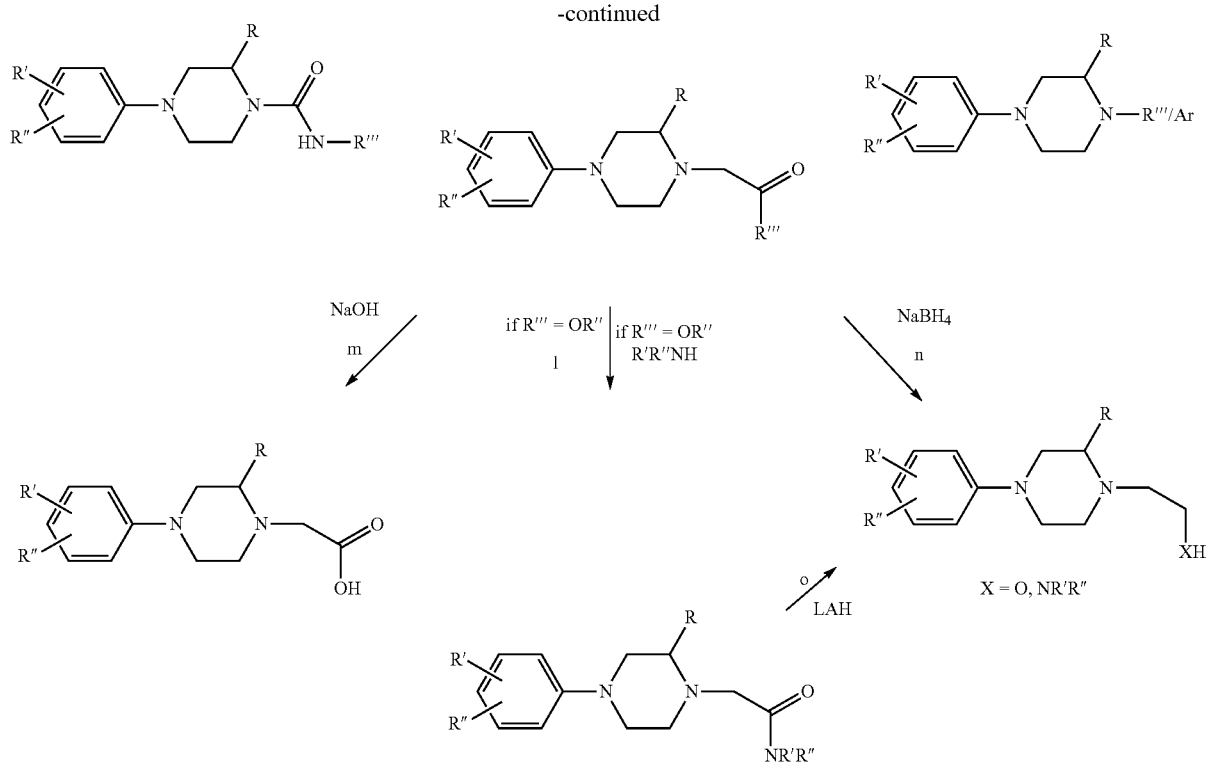

Example 1

Preparation of Compound 89, (S)-1-(3-Cyclopentyloxy-4-methoxy-phenyl)-3-(2-methyl-benzyl)-piperazine

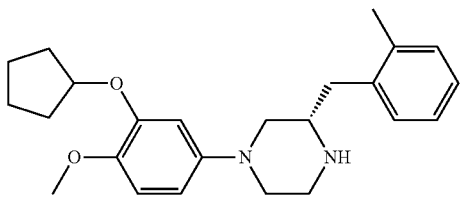 [SMILES: COc1ccc(N2CCN[C@@H](Cc3ccccc3C)C2)cc1OC1CCCC1]

A solution of 2(S)—N1 BOC-2-(2'-methylbenzyl)piperazine (290 mg, 1.0 mmol) in anhydrous toluene (2 mL) was treated with 3-(cyclopentoxy)-4-methoxy-bromobenzene (271 mg, 1.0 mmol), sodium tert-butoxide (96 mg, 1.0 mmol), 2-dicyclohexylphosphino-2'-(N,N-dimethylamino)biphenyl (56 mg, 0.06 mmol), and tris(dibenzylideneacetone) dipalladium (14 mg, 0.015 mol). The resulting mixture was heated under nitrogen atmosphere at 100-105° C. for 5 h. The crude reaction mixture was then diluted with EtOAc (10 mL), washed with water (10 mL) followed by a saturated aqueous NaHCO₃ solution (10 mL), and brine (10 mL). The organic portion was then dried over MgSO₄, filtered and evaporated to an oil, which was purified by silica gel flash chromatography with 15% EtOAc/hexanes as eluant to afford intermediate (S)-4-(3-Cyclopentyloxy-4-methoxy-phenyl)-2-(2-methyl-benzyl)-piperazine-1-carboxylic acid tert-butyl ester as an oil (215 mg, 45%). LC/MS (Method A) 8.63 min, [M+1]⁺ 481.

A solution of intermediate (S)-4-(3-Cyclopentyloxy-4-methoxy-phenyl)-2-(2-methyl-benzyl)-piperazine-1-carboxylic acid tert-butyl ester (215 mg, 0.447 mmol) in 1,4-dioxane (2 mL) was then treated with a 4 N solution of hydrogen chloride (4 mL) and stirred for 2 h. The reaction was then evaporated to a colorless solid, suspended in EtOAc (10 mL), and washed with a saturated aqueous K₂CO₃ solution (3 mL) followed by brine (3 mL). The organic portion was then dried over MgSO₄, filtered, and evaporated to afford the title compound as a burgundy colored oil (127 mg, 75%). ¹H NMR (CDCl₃) 7.26-7.11 (m, 4 H), 6.78 (d, J=8.8, 1 H), 6.53 (d, J=2.9, 1 H), 6.43 (dd, 8.7, 2.6, 1 H), 4.74-4.71 (m, 1 H), 3.78 (s, 3 H), 3.39-3.35 (m, 2 H), 3.16-3.08 (m, 2 H), 2.96 (td, J=11.2, 2.9, 1 H), 2.87-2.70 (m, 2 H), 2.56-2.49 (m, 1 H), 2.36 (s, 3 H), 1.92-1.72 (m, 6 H), 1.61-1.57 (m, 2 H). ¹³C NMR 148.4, 146.5, 144.8, 136.7, 136.4, 130.7 (CH), 130.2 (CH), 126.8 (CH), 126.1 (CH), 113.3 (CH), 108.6 (CH), 106.8 (CH), 80.6, (CH), 56.8 (CH₂), 56.8 (CH₃), 55.3 (CH), 51.3 (CH₂), 46.0 (CH₂), 37.9 (CH₂), 32.97 (CH₂), 24.2 (CH₂), 19.8 (CH₃). LC/MS (Method A) 5.03 min, [M+1]⁺ 381.

Example 2

Preparation of Compound 90, (S)-3-Benzyl-1-(3-cyclopentyloxy-4-methoxy-phenyl)-piperazine

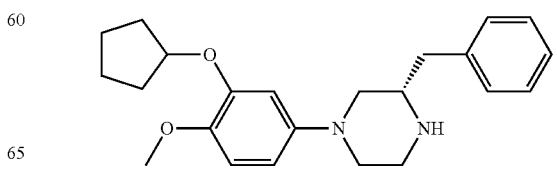

The title compound was prepared by the method outlined for Example 1 using 2(S)—N1 BOC-2-(benzyl)-piperazine CAS [169447-86-3] as the amine component. Both intermediate and title compound were isolated as oils (68 and 90%). LC/MS (Method A) 8.46 and 5.05 min, [M+1]+ 467 and 367.

Example 3

Preparation of Compound 91, (S)-1-(3-Cyclopentyloxy-4-difluoromethoxy-phenyl)-3-phenyl-piperazine

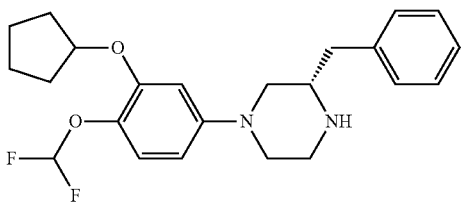 [SMILES: FC(F)Oc1ccc(N2CCN[C@@H](Cc3ccccc3)C2)cc1OC1CCCC1]

The title compound was prepared by the method outlined for Example 1 using 4-bromo-2-(cyclopentyloxy)-1-methoxy-benzene CAS [138509-45-2] as the aryl halide and 2(S)—N1 BOC-2-(benzyl)-piperazine CAS [169447-86-3] as the amine component. The title compound was isolated as an oil (3.8 g, 81%). $^1$H NMR (CDCl$_3$) 7.30-7.27 (m, 2 H), 7.23-7.18 (m, 3 H), 6.75 (d, J=8.6, 1 H), 6.53 (d, J=2.9, 1 H), 6.42 (dd, J=8.6, 2.8, 1 H), 4.53 (m, 2 H), 3.42-3.34 (m, 2 H), 3.13-3.04 (m, 2 H), 2.94 (td, J=11.3, 2.9, 1 H), 2.83-2.64 (m, 3 H), 2.48 (t, J=10.2, 1 H), 2.21 (br, 1 H), 1.90-1.80 (m, 6 H), 1.62-1.56 (m, 2 H). LC/MS (Method B) 2.50 min, [M+1]+ 403.

Example 4

Preparation of Compound 92, (S)-1-(3-Cyclobutyloxy-4-difluoromethoxy-phenyl)-3-phenyl-piperazine

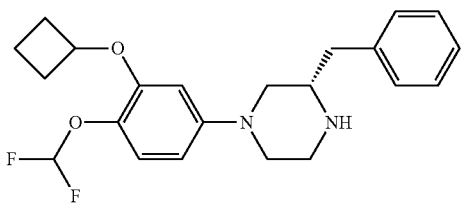 [SMILES: FC(F)Oc1ccc(N2CCN[C@@H](Cc3ccccc3)C2)cc1OC1CCC1]

The title compound was prepared by the method outlined for Example 1 using 4-bromo-2-(cyclobutyloxy)-1-(difluoromethoxy)-benzene CAS [944333-97-5] as the aryl halide and 2(S)—N1 BOC-2-(benzyl)-piperazine CAS [169447-86-3] as the amine component. The title compound was isolated as an oil (3.8 g, 81%). $^1$H NMR (CDCl$_3$) 7.30-7.27 (m, 2 H), 7.23-7.18 (m, 3 H), 6.75 (d, J=8.6, 1 H), 6.28-6.24 (m, 2 H), 4.53 (m, 2 H), 3.32-3.17 (m, 3 H), 2.93-2.85 (m, 2 H), 2.71 (td, J=11.3, 2.9, 1 H), 2.67-2.62 (m, 2 H), 2.49-2.44 (m, 2 H), 2.31-2.17 (m, 3 H), 2.02-1.93 (m, 1 H), 1.73-1.70 (m, 1 H), 1.61-1.50 (m, 1 H). LC/MS (Method B) 2.50 min, [M+1]+ 389.

Example 5

Preparation of Compound 93, (S)-1-(3-Cyclopropylmethoxy-4-difluoromethoxy-phenyl)-3 phenyl piperazine

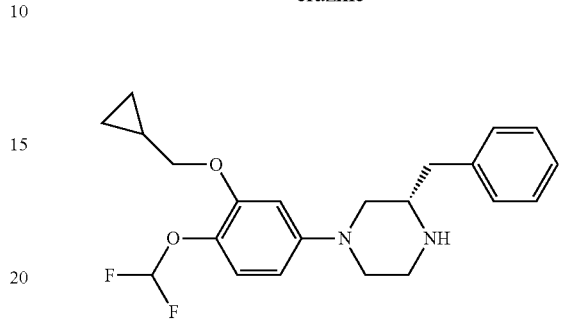

The title compound was prepared by the method outlined for Example 1 using 4-bromo-2-(cyclopropylmethoxy)-1-(difluoromethoxy)-benzene CAS [680184-55-8] as the aryl halide and 2(S)—N1 BOC-2-(benzyl)-piperazine CAS [169447-86-3] as the amine component. The title compound was isolated as an orange oil (0.56 g, 85%). $^1$H NMR (MeOH-d$_4$) 7.34-7.30 (m, 3 H), 7.26-7.23 (m, 3 H), 6.96 (d, J=8.8, 1 H), 6.51 (d, J=2.8, 1 H), 6.40 (dd, J=8.8, 2.8, 1 H), 3.81 (d, J=7.2 Hz, 2 H), 3.44 (m, 2 H), 3.03 (m, 2 H), 2.87 (td, J=11.3, 2.9, 1 H), 2.75 (m, 3 H), 2.44 (dd, J=11.3, 10.0, 1 H), 2.22 (m, 1 H), 0.60 (m, 2 H), 0.33 (m, 2 H). LC/MS (Method B) 2.47 min, [M+1]+ 389.

Example 6

Preparation of Compound 94, (3S)-3-benzyl-1-[3,4-bis(difluoromethoxy)phenyl]-piperazine

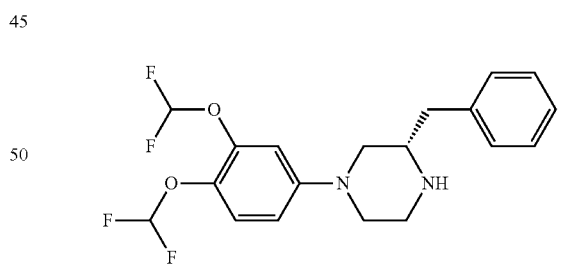

The title compound was prepared by the method outlined for Example 1 using 4-bromo-1,2-bis(difluoromethoxy)-benzene CAS [330475-65-5] as the aryl halide and 2(S)—N1 BOC-2-(benzyl)-piperazine CAS [169447-86-3] as the amine component. The title compound was isolated as an oil (4.2 g, 79%). $^1$H NMR (CDCl$_3$) 7.36-7.32 (m, 2 H), 7.28-7.24 (m, 3 H), 7.12 (d, J=8.6, 1 H), 6.73-6.68 (m, 2 H), 3.52-3.45 (m, 2 H), 3.13-3.05 (m, 2 H), 2.95-2.81 (m, 3 H), 2.74-2.68 (m, 2 H), 2.61-2.58 (m, 2 H), 2.39 (br, 1 H). LC/MS (Method B) 2.25 min, [M+1]+ 385.

Example 7

Preparation of Compound 95, (S)-3-Benzyl-1-(3-cyclobutoxy-4-methoxy-phenyl)-piperazine

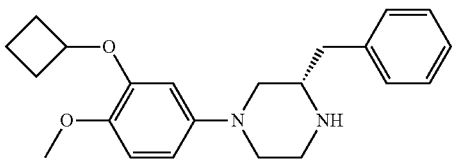 [SMILES: COc1ccc(N2CCN[C@@H](Cc3ccccc3)C2)cc1OC1CCC1]

The title compound was prepared by the method outlined for Example 1 using 4-bromo-2-(cyclobutyloxy)-1-methoxy-benzene CAS [944334-02-5] as the aryl halide and 2(S)—N1 BOC-2-(benzyl)-piperazine CAS [169447-86-3] as the amine component. The title compound was isolated as an oil (3.8 g, 81%). $^1$H NMR (CDCl$_3$) 7.30-7.27 (m, 2 H), 7.23-7.18 (m, 3 H), 6.75 (d, J=8.6, 1 H), 6.28-6.24 (m, 2 H), 4.53 (q, J=6.9, 1 H), 3.62 (s, 3 H), 3.32-3.17 (m, 3 H), 2.93-2.85 (m, 2 H), 2.71 (td, J=11.3, 2.9, 1 H), 2.67-2.62 (m, 2 H), 2.49-2.44 (m, 2 H), 2.31-2.17 (m, 3 H), 2.02-1.93 (m, 1 H), 1.73-1.70 (m, 1 H), 1.61-1.50 (m, 1 H). LC/MS (Method B) 3.10 min, [M+1]$^+$ 353.

Example 8

Preparation of Compound 96, (S)-1-(3-cyclobutoxy-4-methoxyphenyl)-3-(4-fluorobenzyl)piperazine

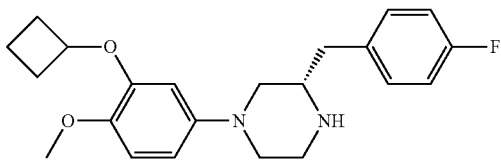 [SMILES: COc1ccc(N2CCN[C@@H](Cc3ccc(F)cc3)C2)cc1OC1CCC1]

The title compound was prepared by the method outlined for Example 1 using 4-bromo-2-(cyclobutyloxy)-1-methoxy-benzene CAS [944334-02-5] as the aryl halide and 2(S)—N1 BOC-2-(4-fluorobenzyl)-piperazine CAS [169447-86-3] as the amine component. The title compound was isolated as a yellow solid (59%). $^1$H NMR (MeOH-d$_4$) 9.69 (d, J=8.4, 1 H), 9.35 (d, J=9.0, 1 H), 7.39-7.34 (m, 2 H), 7.23-7.16 (m, 2 H), 6.81 (d, J=8.6, 1 H), 6.43-6.38 (m, 1 H), 6.34 (s, 1 H), 4.58-4.50 (m, 1 H), 3.66 (s, 3 H), 3.58-3.50 (m, 2 H), 3.33 (d, J=12.5, 2 H), 3.17-3.01 (m, 3H), 2.99-2.86 (m, 2 H), 2.33-2.24 (m, 2 H), 2.03-1.91 (m, 2 H), 1.79-1.69 (m, 1H), 1.65-1.51 (m, 1 H). LC/MS 2.50 min, [M+1]$^+$ 371.

Example 9

Preparation of Compound 97, (S)-3-Benzyl-1-(3-(1-methylethoxy)-4-methoxy-phenyl)-piperazine

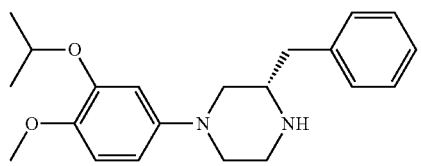 [SMILES: COc1ccc(N2CCN[C@@H](Cc3ccccc3)C2)cc1OC(C)C]

The title compound was prepared by the method outlined for Example 1 using 4-bromo-1-methoxy-2-(1-methylethoxy)-benzene CAS [462092-23-5] as the aryl halide and 2(S)—N1 BOC-2-(benzyl)-piperazine CAS [169447-86-3] as the amine component. The title compound was isolated as an oil (3.8 g, 81%). $^1$H NMR (CDCl$_3$) 7.30-7.26 (m, 2 H), 7.23-7.16 (m, 3 H), 6.73 (d, J=8.6, 1 H), 6.45 (d, J=2.9, 1 H), 6.30 (dd, J=8.6, 2.8, 1 H), 4.43 (q, J=6.9, 1 H), 3.63 (s, 3 H), 3.31-3.21 (m, 2 H), 2.92-2.86 (m, 2 H), 2.73-2.56 (m, 1 H), 2.51-2.43 (m, 2H), 2.12 (t, J=10.2, 1 H), 1.99 (s, 1 H), 1.18 (d, J=6.4, 1 H). LC/MS (Method B) 2.50 min, [M+1]$^+$ 341.

Example 10

Preparation of Compound 98, (S)-3-Benzyl-1-(3-cycloproyloxy-4-methoxy-phenyl)-piperazine

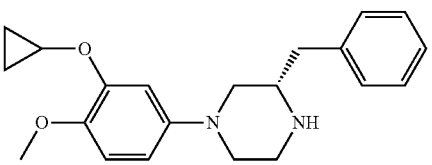 [SMILES: COc1ccc(N2CCN[C@@H](Cc3ccccc3)C2)cc1OC1CC1]

The title compound was prepared by the method outlined for Example 1 using 4-bromo-2-(cyclopropyloxy)-1-methoxy-benzene CAS [944333-99-7] as the aryl halide and 2(S)-N1 BOC-2-(benzyl)-piperazine CAS [169447-86-3] as the amine component. The title compound was isolated as a colorless oil. $^1$H NMR (MeOH-d$_4$) 7.32-7.29 (m, 2 H), 7.23-7.21 (m, 3 H), 5.10-5.03 (m, 3 H), 4.30 (m, 1 H), 3.81 (s. 3 H), 3.48-3.41 (m, 2 H), 3.00 (m, 2 H), 2.82 (td, J=11.6, 3.2, 1 H), 2.72 (m, 3 H), 2.63-2.54 (m, 2 H), 2.43-2.38 (m, 1 H), 2.43-2.40 (m, 2 H). LC/MS (Method B) 2.32 min, [M+1]$^+$ 339.

Example 11

Preparation of Compound 99, (S)-3-Benzyl-1-(3-cyclopentyloxy-4-ethoxy-phenyl)-piperazine

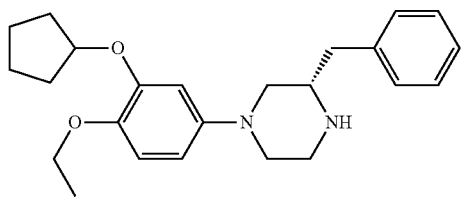 [SMILES: CCOc1ccc(N2CCN[C@@H](Cc3ccccc3)C2)cc1OC1CCCC1]

The title compound was prepared by the method outlined for Example 1 using 4-bromo-2-(cyclopentyloxy)-1-ethoxy-benzene and 2(S)—N1 BOC-2-(benzyl)-piperazine CAS [169447-86-3] as the amine component. The title compound was isolated as an oil (3.1 g, 75%). $^1$H NMR (CDCl$_3$) 7.33 (m, 2 H), 7.26-7.21 (m, 3 H), 6.80 (d, J=8.6, 1 H), 6.53 (d, J=2.9, 1 H), 6.42 (dd, J=8.6, 2.8, 1 H), 4.75 (m, 1H), 3.98 (q, J=6.9, 2 H), 3.42-3.34 (m, 2 H), 3.13-3.04 (m, 2 H), 2.94 (td, J=11.3, 2.9, 1 H), 2.83-2.64 (m, 3 H), 2.48 (t, J=10.2, 3

H), 2.21 (br, 1 H), 1.90-1.80 (m, 6 H), 1.62-1.56 (m, 2 H), 1.37 (t, J=7.0, 3 H). $^{13}$C NMR 149.0, 146.8, 143.9, 138.2, 129.9 (CH), 128.6 (CH), 126.6 (CH), 116.2 (CH), 108.8 (CH), 107.2 (CH), 80.8 (CH), 65.7 (CH$_2$), 56.7 (CH$_2$), 56.5 (CH), 50.9 (CH$_2$), 45.9 (CH$_2$), 40.7 (CH$_2$), 32.8 (CH$_2$), 24.0 (CH$_2$), 15.1 (CH$_3$). LC/MS (Method B) 3.10 and 3.09 min, [M+1]$^+$ 245 and 381.

Example 12

Preparation of Compound 100, (S)-3-Benzyl-1-(3-cyclobutyloxy-4-ethoxy-phenyl)-piperazine

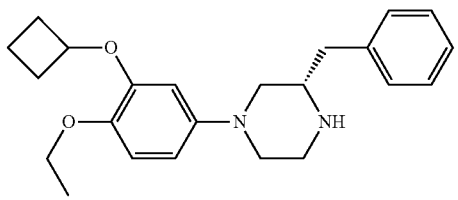 [SMILES: CCOc1ccc(N2CCN[C@@H](Cc3ccccc3)C2)cc1OC1CCC1]

The title compound was prepared by the method outlined for Example 1 using 4-bromo-2-(cyclobutoxy)-1-ethoxy-benzene and 2(S)—N1 BOC-2-(benzyl)-piperazine CAS [169447-86-3] as the amine component. The title compound was isolated as an oil (3.1 g and 75%). $^1$H NMR (CDCl$_3$) 7.33 (m, 2 H), 7.26-7.21 (m, 3 H), 6.80 (d, J=8.6, 1 H), 6.53 (d, J=2.9, 1 H), 6.42 (dd, J=8.6, 2.8, 1 H), 4.75 (m, 1H), 3.98 (q, J=6.9, 2 H), 3.42-3.34 (m, 2 H), 3.13-3.04 (m, 2 H), 2.94 (td, J=11.3, 2.9, 1 H), 2.83-2.64 (m, 3 H), 2.48 (t, J=10.2, 1 H), 2.21 (br, 1 H), 1.90-1.80 (m, 4 H), 1.62-1.56 (m, 2 H), 1.37 (t, J=7.0, 3 H). LC/MS (Method A) 3.10 min, [M+1]$^+$ 367.

Example 13

Preparation of Compound 101, (2S,5S)-5-Benzyl-1-(3-cyclopentyloxy-4-methoxy-phenyl)-2-methyl-piperazine

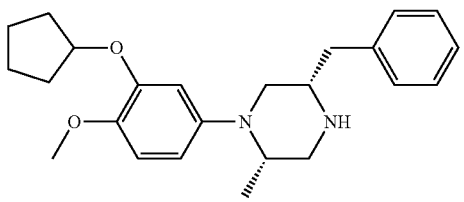 [SMILES: COc1ccc(N2C[C@H](Cc3ccccc3)NC[C@@H]2C)cc1OC1CCCC1]

The title compound was prepared by the method outlined for Example 1 using (2S,5S)-2-Benzyl-5-methyl-piperazine-1-carboxylic acid tert-butyl ester as the amine component. The intermediate was isolated as a foam and the title compound was isolated as an oil (33 and 96%). LC/MS (Method A) 8.48 and 5.06 min, [M+1]$^+$ 481 and 381.

Example 14

Preparation of Compound 102, (2R,5S)-5-Benzyl-1-(3-cyclopentyloxy-4-methoxy-phenyl)-2-methyl-piperazine

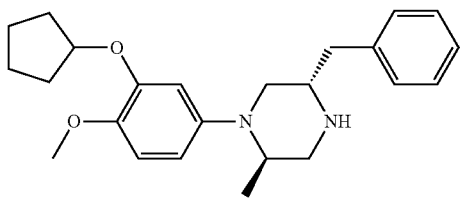 [SMILES: COc1ccc(N2C[C@H](Cc3ccccc3)NC[C@H]2C)cc1OC1CCCC1]

The title compound was prepared by the method outlined for Example 1 using (2S,5R)-2-Benzyl-5-methyl-piperazine-1-carboxylic acid tert-butyl ester as the amine component. The intermediate was isolated as a foam and the title compound was isolated as an oil (61 and 86%). LC/MS (Method A) 8.57 and 5.03 min, [M+1]$^+$ 481 and 381.

Example 15

Preparation of Compound 103, (R)-6-Benzyl-4-(3-cyclopentyloxy-4-methoxy-phenyl)-piperazin-2-one

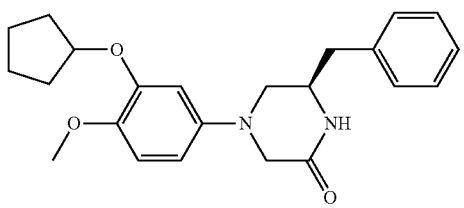 [SMILES: COc1ccc(N2CC(=O)N[C@H](Cc3ccccc3)C2)cc1OC1CCCC1]

The title compound was prepared by the method outlined for Example 1 using 6R-(phenylmethyl) piperazinone as the amine component. The title compound was isolated as a colorless solid (10%). $^1$H NMR (CDCl$_3$) 7.38-7.20 (m, 5 H), 6.80 (d, J=8.8, 1 H), 6.48 (d, J=2.6, 1 H), 6.39 (dd, 8.6, 2.6, 1 H), 6.25 (br s, 1 H), 4.74-4.70 (m, 1 H), 3.80 (s, 3 H), 3.77 (obs dd, 1 H), 3.44 (dd, J=12.5, 3.7, 1 H), 3.07 (dd, J=12.5, 7.0, 1 H), 2.98 (dd, J=13.6, 6.4, 1 H), 2.82 (dd, J=13.4, 8.1, 1 H), 1.90-1.77 (m, 6 H), 1.62-1.59 (m, 2 H). LC/MS (Method A) 6.26 min, [M+1]$^+$ 381.

Example 16

Preparation of Compound 104, (S)-6-Benzyl-4-(3-cyclopentyloxy-4-methoxy-phenyl)-piperazin-2-one

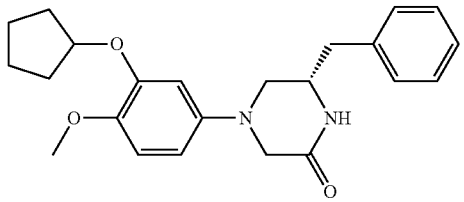 [SMILES: COc1ccc(N2CC(=O)N[C@@H](Cc3ccccc3)C2)cc1OC1CCCC1]

The title compound was prepared by the coupling method outlined in Example 1, using 6S-(phenylmethyl) piperazinone CAS [503186-95-6] as the amine component. The title compound was isolated as a colorless solid (11%). LC/MS (Method A) 6.39 min, [M+1]+ 381.

Example 17

Preparation of Compound 105, (R)-3-Benzyl-1-(3-cyclopentyloxy-4-methoxy-phenyl)-piperazine

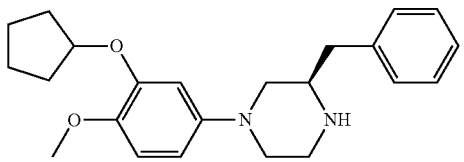 [SMILES: COc1ccc(N2CCN[C@H](Cc3ccccc3)C2)cc1OC1CCCC1]

(R)-6-Benzyl-4-(3-cyclopentyloxy-4-methoxy-phenyl)-piperazin-2-one (365 mg, 0.96 mmol) was dissolved in THF (10 mL), cooled to 0° C., and treated with solid lithium aluminum hydride (73 mg, 1.92 mmol). The reaction mixture was heated at 60° C. for 3 hr then cooled to 0° C. and quenched with EtOAc (2 mL) and a 1 N aqueous solution of NaOH (2 mL). The reaction was filtered with the aid of EtOAc, dried over MgSO$_4$, filtered, and evaporated to an oil, which was purified by silica gel flash chromatography with 5% MeOH/CH$_2$Cl$_2$ as eluant to afford the title compound as a brown oil (228 mg, 65%). LC/MS (Method A) 5.12 min, [M+1]+ 367.

Example 18

Preparation of Compound 106, (S)-1-(3-Cyclopentyloxy-4-methoxy-phenyl)-3-(3-methyl-benzyl)-piperazine

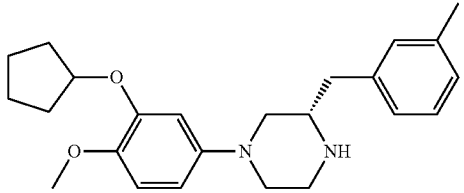 [SMILES: COc1ccc(N2CCN[C@@H](Cc3cccc(C)c3)C2)cc1OC1CCCC1]

The title compound was prepared by the method outlined for Example 1 using 2(S)—N1 BOC-2-(3'-methylbenzyl)-piperazine as the amine component. The intermediate and title compound were isolated as oils (38 and 92%). LC/MS (Method A) 8.67 and 5.18 min, [M+1]+ 481 and 381.

Example 19

Preparation of Compound 107, (S)-1-(3-Cyclopentyloxy-4-methoxy-phenyl)-3-(4-methyl-benzyl)-piperazine

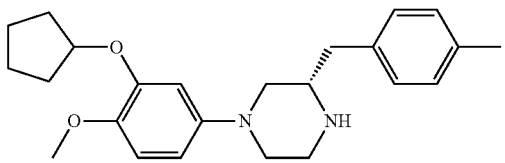 [SMILES: COc1ccc(N2CCN[C@@H](Cc3ccc(C)cc3)C2)cc1OC1CCCC1]

The title compound was prepared by the method outlined for Example 1 using 2(S)—N1 BOC-2-(4'-methylbenzyl)-piperazine as the amine component. The intermediate and title compound were isolated as oils (34 and 88%). LC/MS (Method A) 8.68 and 5.07 min, [M+1]+ 481 and 381.

Example 20

Preparation of Compound 108, (S)-1-(3-Cyclopentyloxy-4-methoxy-phenyl)-3-(2-methoxy-benzyl)-piperazine

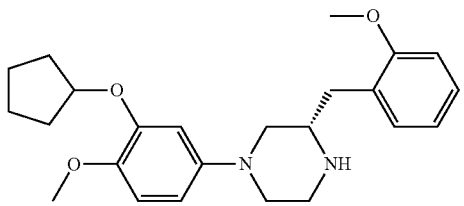 [SMILES: COc1ccccc1C[C@H]1CN(c2ccc(OC)c(OC3CCCC3)c2)CCN1]

The title compound was prepared by the method outlined for Example 1 using 2(S)—N1 BOC-2-(2'-methoxybenzyl)-piperazine as the amine component. The intermediate and title compound were isolated as oils (56 and 80%). LC/MS (Method A) 8.29 and 5.03 min, [M+1]+ 497 and 397.

Example 21

Preparation of Compound 109, (S)-1-(3-Cyclopentyloxy-4-methoxy-phenyl)-3-(3-methoxy-benzyl)-piperazine

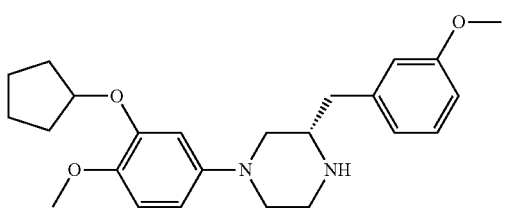 [SMILES: COc1cccc(C[C@H]2CN(c3ccc(OC)c(OC4CCCC4)c3)CCN2)c1]

The title compound was prepared by the method outlined for Example 1 using (S)—N1 BOC-2-(3'-methoxybenzyl)-piperazine as the amine component. The intermediate and title compound were isolated as oils (42 and 92%). LC/MS (Method A) 8.19 and 4.83 min, [M+1]+ 497 and 397.

Example 22

Preparation of Compound 110, (S)-1-(3-Cyclopentyloxy-4-methoxy-phenyl)-3-(4-methoxy-benzyl)-piperazine

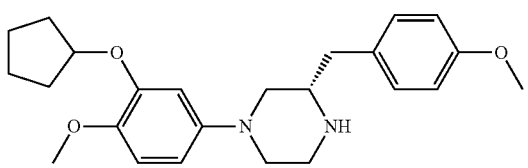 [SMILES: COc1ccc(C[C@H]2CN(c3ccc(OC)c(OC4CCCC4)c3)CCN2)cc1]

The title compound was prepared by the method outlined for Example 1 using (S)—N1 BOC-2-(4'-methoxybenzyl)- piperazine as the amine component. The intermediate and title compound were isolated as oils (64 and 85%). LC/MS (Method A) 8.15 and 4.81 min, [M+1]+ 497 and 397.

Example 23

Preparation of Compound 111, (S)-1-(3-Cyclopentyloxy-4-methoxy-phenyl)-3-(4-ethoxy-benzyl)-piperazine

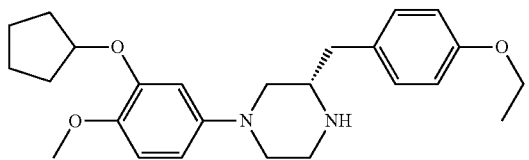 [SMILES: CCOc1ccc(C[C@H]2CN(c3ccc(OC)c(OC4CCCC4)c3)CCN2)cc1]

The title compound was prepared by the method outlined for Example 1 using (S)—N1 BOC-2-(4'-ethoxybenzyl)-piperazine as the amine component. The intermediate and title compound were isolated as oils (67 and 75%). LC/MS (method A) 8.44 and 4.96 min, [M+1]+ 511 and 411.

Example 24

Preparation of Compound 112, (S)-1-(3-Cyclopentyloxy-4-methoxy-phenyl)-3-phenethyl-piperazine

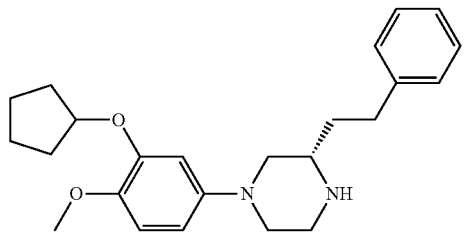 [SMILES: COc1ccc(N2CCN[C@@H](CCc3ccccc3)C2)cc1OC1CCCC1]

The title compound was prepared by the method outlined for Example 1 using 2(S)—N1 BOC-2-(2-phenethyl)-piperazine as the amine component. The intermediate and title compound were isolated as oils (44 and 91%). LC/MS (Method A) 8.49 and 4.91 min, [M+1]+ 481 and 381.

Example 25

Preparation of Compound 113, (R)-1-(3-Cyclopentyloxy-4-methoxy-phenyl)-3-phenethyl-piperazine

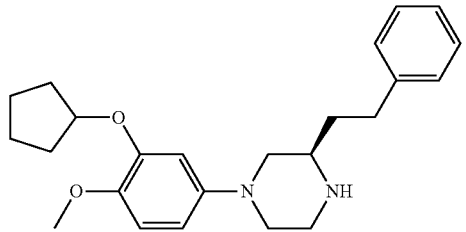 [SMILES: COc1ccc(N2CCN[C@H](CCc3ccccc3)C2)cc1OC1CCCC1]

The title compound was prepared by the method outlined for Example 1 using 2(R)—N1 BOC-2-(2-phenethyl)-piperazine as the amine component. The intermediate and title compound were isolated as oils (51 and 86%). LC/MS (Method A) 8.49 and 4.96 min, [M+1]+ 481 and 381.

Example 26

Preparation of Compound 114, (S)-1-(3-Cyclopentyloxy-4-methoxy-phenyl)-3-(3-phenyl-propyl)-piperazine

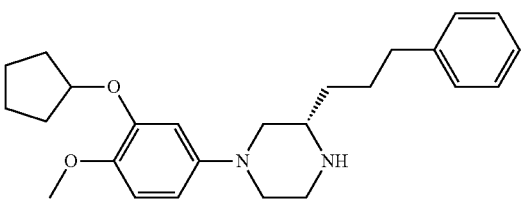 [SMILES: COc1ccc(N2CCN[C@@H](CCCc3ccccc3)C2)cc1OC1CCCC1]

The title compound was prepared by the method outlined for Example 1 using 2(S)—N1 BOC-2-(3-phenylpropyl)-piperazine as the amine component. The intermediate and title compound were isolated as oils (38 and 91%). LC/MS (Method A) 8.71 and 5.22 min, [M+1]+ 495 and 395.

Example 27

Preparation of Compound 115, (S)-1-(3-Cyclopentyloxy-4-methoxy-phenyl)-3-naphthalen-1-ylmethyl-piperazine

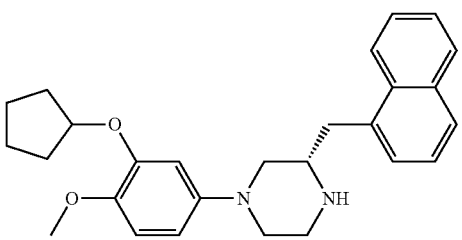 [SMILES: COc1ccc(N2CCN[C@@H](Cc3cccc4ccccc34)C2)cc1OC1CCCC1]

The title compound was prepared by the method outlined for Example 1 using 2(S)—N1 BOC-2-(1'-naphthylmethyl)-piperazine as the amine component. The intermediate and title compound were isolated as oils (42 and 96%). LC/MS (Method A) 8.81 and 5.30 min, [M+1]+ 517 and 417.

Example 28

Preparation of Compound 116, (S)-1-(3-Cyclopentyloxy-4-methoxy-phenyl)-3-naphthalen-2-ylmethyl-piperazine

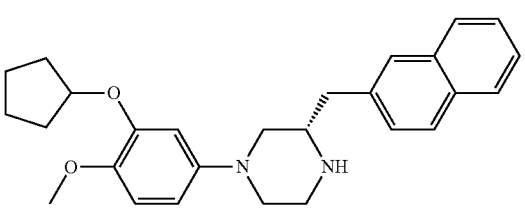 [SMILES: COc1ccc(N2CCN[C@@H](Cc3ccc4ccccc4c3)C2)cc1OC1CCCC1]

The title compound was prepared by the method outlined for Example 1 using 2(S)—N1 BOC-2-(2'-naphthylmethyl)-piperazine as the amine component. The intermediate and title compound were isolated as oils (43 and 89%). LC/MS (Method A) 8.78 and 5.29 min, [M+1]+ 517 and 417.

Example 29

Preparation of Compound 117, (S)-3-Biphenyl-4-ylmethyl-1-(3-cyclopentyloxy-4-methoxy-phenyl)-piperazine

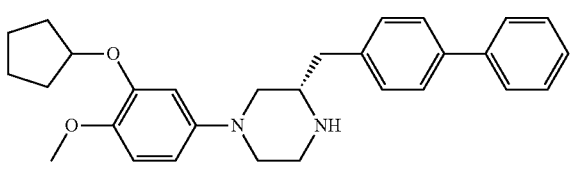 [SMILES: COc1ccc(N2CCN[C@@H](Cc3ccc(-c4ccccc4)cc3)C2)cc1OC1CCCC1]

The title compound was prepared by the method outlined for Example 1 using 2(S)—N1 BOC-2-(4'-biphenylmethyl)-piperazine as the amine component. The intermediate and title compound were isolated as oils (59 and 94%). LC/MS (Method A) 9.03 and 5.52 min, [M+1]+ 543 and 443.

Example 30

Preparation of Compound 118, (S)-3-Benzhydryl-1-(3-cyclopentyloxy-4-methoxy-phenyl)-piperazine

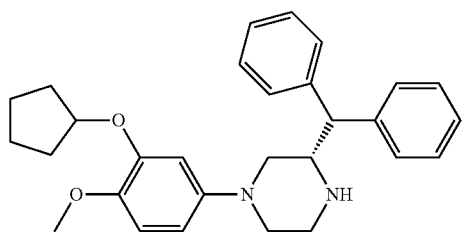 [SMILES: COc1ccc(N2CCN[C@@H](C(c3ccccc3)c3ccccc3)C2)cc1OC1CCCC1]

The title compound was prepared by the method outlined for Example 1 using 2(S)—N1 BOC-2-(diphenylmethyl)-piperazine as the amine component. The intermediate and title compound were isolated as oils (28 and 100%). LC/MS (Method A) 8.58 and 5.39 min, [M+1]+ 543 and 443.

Example 31

Preparation of Compound 119, (R)-1-(3-Cyclopentyloxy-4-methoxy-phenyl)-3-phenyl-piperazine

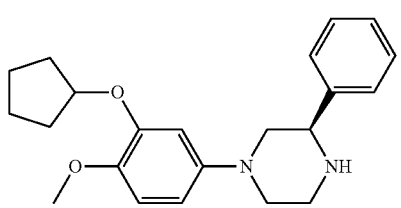 [SMILES: COc1ccc(N2CCN[C@H](c3ccccc3)C2)cc1OC1CCCC1]

The title compound was prepared by the method outlined for Example 1 using 2(R)—N1 BOC-2-(phenyl)-piperazine as the amine component. The intermediate was isolated as a foam and the title compound was isolated as an oil (66 and 86%). LC/MS (Method A) 8.09 and 4.78 min, [M+1]+ 453 and 353.

Example 32

Preparation of Compound 120, (S)-1-(3-Cyclopentyloxy-4-methoxy-phenyl)-3-isopropyl-piperazine

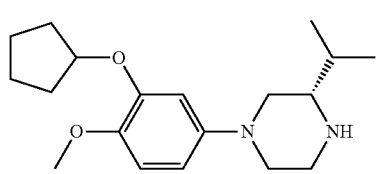 [SMILES: COc1ccc(N2CCN[C@@H](C(C)C)C2)cc1OC1CCCC1]

The title compound was prepared by the method outlined for Example 1 using 2(R)—N1 BOC-2-(isopropyl)-piperazine as the amine component. The intermediate and title compound were isolated as oils (54 and 71%). LC/MS (Method A) 8.32 and 4.62 min, [M+1]+ 419 and 319.

Example 33

Preparation of Compound 121, (S)-1-(3-Cyclopentyloxy-4-methoxy-phenyl)-3-isobutyl-piperazine

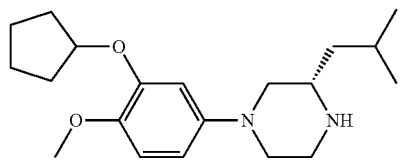 [SMILES: COc1ccc(N2CCN[C@@H](CC(C)C)C2)cc1OC1CCCC1]

The title compound was prepared by the method outlined for Example 1 using 2(R)—N1 BOC-2-(isobutyl)-piperazine as the amine component. The intermediate and title compound were isolated as oils (63 and 94%). LC/MS (Method A) 8.41 and 4.58 min, [M+1]+ 433 and 333.

Example 34

Preparation of Compound 122, (S)-1-(3-Cyclobutyloxy-4-methoxy-phenyl)-3-isobutyl-piperazine

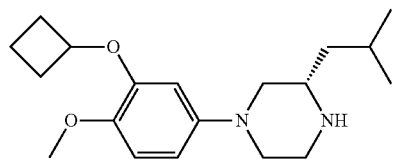 [SMILES: COc1ccc(N2CCN[C@@H](CC(C)C)C2)cc1OC1CCC1]

The title compound was prepared by the method outlined for Example 1 using 4-bromo-2-(cyclobutyloxy)-1-methoxy-benzene CAS [944334-02-5] as the aryl halide and 2(R)—N1 BOC-2-(isobutyl)-piperazine CAS [674792-06-4] as the amine component. The title compound was isolated as an oil (90%). $^1$H NMR (CDCl$_3$) 6.78 (d, J=8.4, 1 H), 6.57 (dd, 2.4, 2.4, 1 H), 6.42 (d, 2.8, 1 H), 4.70-4.60 (m, 1 H), 3.82 (s, 3 H); 3.42-3.35 (d, J=12.4, 2H), 3.30-3.20 (m, 1 H), 3.17-3.05 (m, 2 H), 2.9 (t, 1 H), 2.55 (t, 1 H), 2.50-2.40 (m, 2 H), 2.35-2.20 (m, 2 H), 1.94-1.70 (m, 3 H), 1.60-1.40 (m, 2 H), 0.96 (d, J=3.5, 3 H), 0.94 (d, J=3.5, 3 H). LC/MS (Method B) 2.27 min, [M+1]$^+$ 319.

Example 35

Preparation of Compound 123, (S)-1-(3-isopropoxy-4-methoxy-phenyl)-3-isobutyl-piperazine

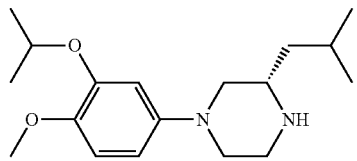 [SMILES: COc1ccc(N2CCN[C@@H](CC(C)C)C2)cc1OC(C)C]

The title compound was prepared by the method outlined for Example 1 using 4-bromo-1-methoxy-2-(1-methylethoxy)-benzene CAS [462092-23-5] as the aryl halide and 2(R)—N1 BOC-2-(isobutyl)-piperazine CAS [674792-06-4] as the amine component. The title compound was isolated as an oil (92%). $^1$H NMR (CDCl$_3$) 6.78 (d, J=8.8, 1 H), 6.57 (d, J=2.4, 1 H), 6.48 (dd, 2.8, 1 H), 4.56-4.42 (m, 1 H), 3.80 (s, 3 H), 3.82-3.60 (m, 2 H), 3.45-3.20 (m, 2 H), 3.15-3.05 (m, 2 H), 3.00-2.90 (m, 1 H), 2.65-2.55 (m, 1 H), 1.85-1.70 (m, 1 H), 1.60-1.40 (m, 2 H), 1.35 (d, J=6.4, 6 H), 0.95 (d, J=6, 6 H). LC/MS (Method B) 2.22 min, [M+1]$^+$ 307.

Example 36

Preparation of Compound 124, (S)-1-(3-Cyclopentyloxy-4-difluoromethoxy-phenyl)-3-isobutyl-piperazine

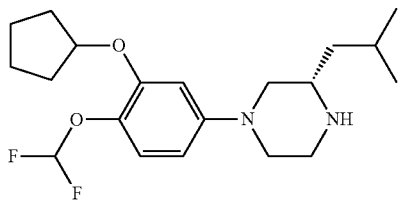 [SMILES: CC(C)C[C@H]1CN(c2ccc(OC(F)F)c(OC3CCCC3)c2)CCN1]

The title compound was prepared by the method outlined for Example 1 using 4-bromo-2-(cyclopentyloxy)-1-(difluoromethoxy)benzene as the aryl halide and 2(R)—N1 BOC-2-(isobutyl)-piperazine CAS [674792-06-4] as the amine component. LC/MS (Method A) 2.87 min, [M+1]$^+$ 369.

Example 37

Preparation of Compound 125, (S)-1-(3-Cyclopropylmethoxy-4-difluoromethoxy-phenyl)-3-isobutyl-piperazine

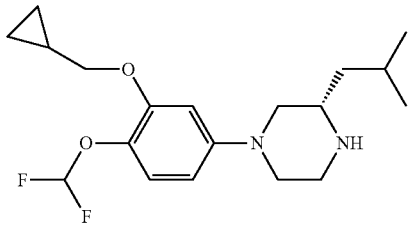 [SMILES: CC(C)C[C@H]1CN(c2ccc(OC(F)F)c(OCC3CC3)c2)CCN1]

The title compound was prepared by the method outlined for Example 1 using 4-bromo-2-(cyclopropylmethoxy)-1-(difluoromethoxy)-benzene CAS [680184-55-8] as the aryl halide and 2(R)—N1 BOC-2-(isobutyl)-piperazine CAS [674792-06-4] as the amine component. LC/MS (Method A) 2.70 min, [M+1]$^+$ 355.

Example 38

Preparation of Compound 126, (S)-3-Cyclohexylmethyl-1-(3-cyclopentyloxy-4-methoxy-phenyl)-piperazine

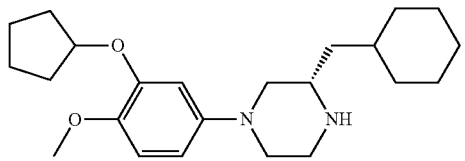 [SMILES: COc1ccc(N2CCN[C@@H](CC3CCCCC3)C2)cc1OC1CCCC1]

The title compound was prepared by the method outlined for Example 1 using 2(S)—N1 BOC-2-(cyclohexylmethyl)-piperazine as the amine component. The intermediate and title compound were isolated as oils (49 and 88%). LC/MS (Method A) 9.36 and 5.30 min, [M+1]$^+$ 473 and 373.

Example 39

Preparation of Compound 127, (S)-3-((4-(3-(cyclopentyloxy)-4-methoxyphenyl)piperazin-2-yl)methyl)-1H-indole

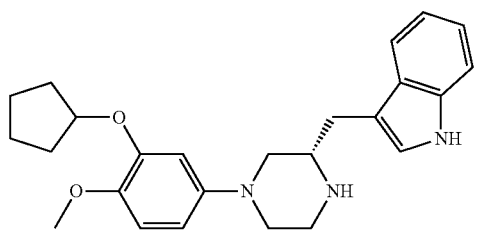 [SMILES: COc1ccc(N2CCN[C@@H](Cc3c[nH]c4ccccc34)C2)cc1OC1CCCC1]

The title compound was prepared by the method outlined for Example 1 using 2(R)—N1 BOC-2-(3-indolylmethyl)-piperazine as the amine component. The BOC-protected intermediate was chromatographically purified with a 2.5% then 7.5% MeOH/CH$_2$Cl$_2$ solvent system. The intermediate and title compound were isolated as oils (25 and 92%). LC/MS (Method A) 5.72 and 4.55 min, [M+1]$^+$ 506 and 406.

Example 40

Preparation of Compound 128, (S)-1-(3-(cyclopentyloxy)-4-methoxyphenyl)-3-(pyrrolidin-1-ylmethyl) piperazine, dihydrochloride

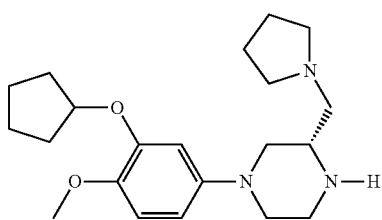 [SMILES: COc1ccc(N2CCN[C@@H](CN3CCCC3)C2)cc1OC1CCCC1]

A solution of (R)-1-(3-cyclopentyloxy-4-methoxy-phenyl)-3-(2-formayl)-piperazine (280 mg, 0.69 mmol) was dissolved in CH$_2$Cl$_2$ (5 mL) and treated with pyrrolidine (48 μL, 0.69 mmol). The reaction mixture was allowed to stir for 10 min after which time sodium triacetoxyborohydride was added (220 mg, 1.0 mmol). The reaction mixture was stirred for 3 h then treated with a half saturated aqueous NaHCO$_3$ solution (3 mL) and stirred for 30 min. An additional portion of CH$_2$Cl$_2$ (10 mL) was added and the organic portion separated, dried over MgSO$_4$, filtered, and evaporated to afford the intermediate (S)-4-(3-Cyclopentyloxy-4-methoxy-phenyl)-2-pyrrolidin-1-ylmethyl-piperazine-1-carboxylic acid tert-butyl ester as an oil (304 mg, 95%). LC/MS (Method B) 2.80 min, [M+1]$^+$ 460.

The intermediate (S)-4-(3-Cyclopentyloxy-4-methoxy-phenyl)-2-pyrrolidin-1-ylmethyl-piperazine-1-carboxylic acid tert-butyl ester (300 mg, 0.65 mmol) was then dissolved in 1,4-dioxane (2 mL) and treated with a 4 N solution of hydrogen chloride in 1,4-dioxane (4 mL) and stirred for 3 h. The reaction was then evaporated to afford the title compound as a colorless solid. (280 mg, 99%). LC/MS (Method B) 1.05 min, [M+1]$^+$ 360.

Example 41

Preparation of Compound 129, (S)-4-((4-(3-(cyclopentyloxy)-4-methoxyphenyl)piperazin-2-yl)methyl) morpholine, dihydrochloride

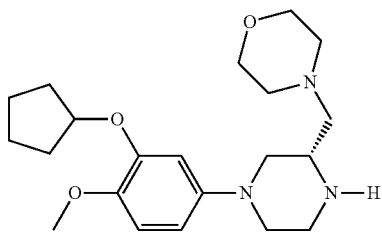 [SMILES: COc1ccc(N2CCN[C@@H](CN3CCOCC3)C2)cc1OC1CCCC1]

The title compound was prepared by the method outlined for Example 40 using morpholine as the amine component. The intermediate was isolated as an oil and the title compound as a solid (260 mg, 64%, 304 mg, 99%). LC/MS (Method B) 2.72 and 2.02 min, [M+1]$^+$ 476 and 376.

Example 42

Preparation of Compound 130, (S)—N-benzyl-1-(4-(3-(cyclopentyloxy)-4-methoxyphenyl)piperazin-2-yl)-N-methylmethanamine, dihydrochloride

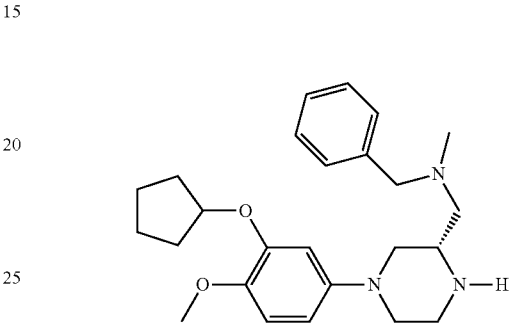

A solution of (R)-1-(3-cyclopentyloxy-4-methoxy-phenyl)-3-(2-formayl)-piperazine (203 mg, 0.50 mmol) was dissolved in dichloroethane (5 mL) and treated with N-methylbenzylamine (65 μL, 0.50 mmol). The reaction mixture was allowed to stir for 10 min after which time sodium triacetoxyborohydride was added (159 mg, 0.75 mmol). The reaction mixture was stirred for 6 h then treated with a half saturated aqueous NaHCO$_3$ solution (3 mL) and stirred for 30 min. The reaction mixture was then diluted with CH$_2$Cl$_2$ (10 mL) and the organic portion separated, dried over MgSO$_4$, filtered, and evaporated to afford an oil. Crude material was purified by silica gel flash chromatography with 20% EtOAc/hexanes as eluant to afford the intermediate (S)-2-[(Benzyl-methyl-amino)-methyl]-4-(3-cyclopentyloxy-4-methoxy-phenyl)-piperazine-1-carboxylic acid tert-butyl ester as an oil (216 mg, 85%). $^1$H NMR (CDCl$_3$) 7.31-7.28 (m, 5 H), 6.78 (d, J=8.6, 1 H), 6.53 (d, J=2.8, 1 H), 6.39 (dd, J=8.8, 2.8, 1 H), 4.73-4.68 (m, 1 H), 4.20 (br, 1 H), 3.95 (br, 1 H), 3.80 (s, 3 H), 3.75 (d, J=11.8, 1 H), 3.66 (d, J=13.5, 1 H), 3.51 (d, J=13.5, 1 H), 3.28 (br d, J=8.3, 1 H), 3.02 (br, 1 H), 2.72 (dd, J=11.9, 3.7, 1 H), 2.64 (td, J=12.0, 3.5, 1 H), 2.43 (br, 1 H), 2.27 (s, 3 H), 1.91-1.77 (m, 6 H), 1.56-1.51 (m, 2 H), 1.49 (s, 9 H). LC/MS (Method B) 3.15 min, [M+1]$^+$ 510.

The intermediate (S)-2-[(Benzyl-methyl-amino)-methyl]-4-(3-cyclopentyloxy-4-methoxy-phenyl)-piperazine-1-carboxylic acid tert-butyl ester (300 mg, 0.65 mmol) was then dissolved in 1,4-dioxane (2 mL) and treated with a 4 N solution of hydrogen chloride in 1,4-dioxane (4 mL) and stirred for 6 h. The reaction was then evaporated to afford the title compound as a colorless solid. (180 mg, 99%). LC/MS (Method B) 2.32 min, [M+1]$^+$ 410.

Example 43

Preparation of Compound 131, (S)-24(4-(3-(cyclopentyloxy)-4-methoxyphenyl)piperazin-2-yl)methyl)isoindoline, dihydrochloride

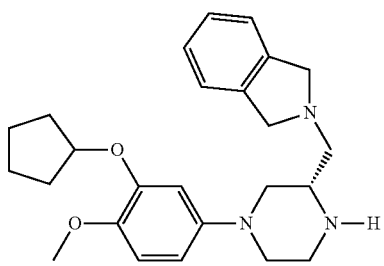 [SMILES: COc1ccc(N2CCN[C@@H](CN3Cc4ccccc4C3)C2)cc1OC1CCCC1]

The title compound was prepared by the method outlined for Example 40 using isoindoline as the amine component. The intermediate was isolated as an oil (228 mg, 90%). $^1$H NMR (CDCl$_3$) 7.20 (s, 5 H), 6.76 (d, J=8.8, 1H), 6.59 (d, J=2.8, 1 H), 6.40 (dd, J=8.7, 2.6, 1 H), 4.64-4.62 (m, 1 H), 4.09-3.99 (m, 4 H), 3.82 (d, J=11.8, 1 H), 3.78 (s, 3 H), 3.34-3.04 (m, 2 H), 3.19-3.13 (m, 1 H), 2.76-2.67 (m, 3 H), 1.87-1.65 (m, 6 H), 1.50 (s, 9 H), 1.55-1.37 (m, 2 H). LC/MS (Method B) 3.00 min, [M+1]$^+$ 508. The title compound was isolated as a colorless solid (186 mg, 99%). LC/MS (Method B) 2.27 min, [M+1]$^+$ 408.

Example 44

Preparation of Compound 132, (S)-2-((4-(3-(cyclopentyloxy)-4-methoxyphenyl)piperazin-2-yl)methyl)-1,2,3,4-tetrahydroisoquinoline, dihydrochloride

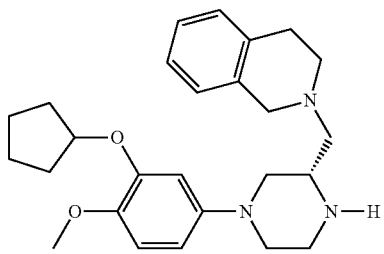 [SMILES: COc1ccc(N2CCN[C@@H](CN3CCc4ccccc4C3)C2)cc1OC1CCCC1]

The title compound was prepared by the method outlined for Example 40 using 1,2,3,4-tetrahydroisoquinoline as the amine component. The intermediate was isolated as an oil (260 mg, 100%). $^1$H NMR (CDCl$_3$) 7.15-7.11 (m, 3 H), 7.10-6.99 (m, 1 H), 6.75 (d, J=8.8, 1 H), 6.53 (d, J=2.5, 1 H), 6.37 (dd, J=8.6, 2.6, 1 H), 4.59-4.56 (m, 1 H), 4.33 (br, 1 H), 3.95 (br, 1 H), 3.78 (s, 3 H), 3.83-3.69 (m, 3 H), 3.33 (br, 1 H), 3.14 (br, 1 H), 3.00-2.89 (m, 3 H), 2.73-2.64 (m, 3 H), 2.46 (br, 1 H), 1.87-1.65 (m, 6 H), 1.50 (s, 9 H), 1.50-1.43 (m, 2 H). LC/MS (Method B) 3.09 min, [M+1]$^+$ 522. The title compound was isolated as a colorless solid (221 mg, 99%). LC/MS (Method B) 2.46 min, [M+1]$^+$ 422.

Example 45

Preparation of Compound 133, (R)-3-((1 H-pyrazol-1-yl)methyl)-1-(3-(cyclopentyloxy)-4-ethoxyphenyl)piperazine

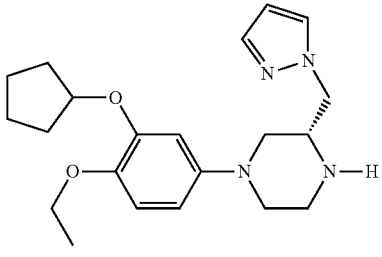 [SMILES: CCOc1ccc(N2CCN[C@@H](Cn3cccn3)C2)cc1OC1CCCC1]

The title compound was prepared by the method outlined for Example 1 using 4-bromo-2-(cyclopentyloxy)-1-ethoxybenzene as the aryl halide and tert-butyl (2R)-2-(1 H-pyrazol-1-ylmethyl)piperazine-1-carboxylate as amine component. The intermediate and title compound were isolated as oils (76 and 77%). $^1$H NMR (CDCl$_3$) 7.55 (d, J=1.6, 1 H), 7.43 (d, J=1.9, 1 H), 6.80 (d, J=8.6, 1 H), 6.53 (d, J=2.8, 1 H), 6.42 (dd, J=8.6, 2.7, 1 H), 6.26 (t, J=2.2, 1 H), 4.76-4.73 (m, 1 H), 4.23 (dd, J=13.7, 4.9, 1 H), 4.14 (dd, J=13.5, 7.6, 1 H), 3.98 (q, J=7.1, 2 H), 3.42-3.27 (m, 3 H), 3.09 (dt, J=11.8, 3.0, 1 H), 2.96 (td, J=10.8, 3.0, 1 H), 2.75 (td, J=11.1, 3.1, 1 H), 2.49 (t, J=9.6, 1 H), 1.89-1.81 (m, 6 H), 1.62-1.59 (m, 2 H), 1.37 (t, J=6.8, 3 H). $^{13}$C NMR 149.0, 146.7, 144.0, 139.9 (CH), 130.1 (CH), 116.1 (CH), 108.9 (CH), 107.3 (CH), 105.6 (CH), 80.8, (CH), 65.7 (CH$_2$), 55.1 (CH), 55.0 (CH), 54.4 (CH$_2$), 51.0 (CH$_2$), 45.1 (CH$_2$), 32.8 (CH$_2$), 23.9 (CH$_2$), 15.1 (CH$_3$). LC/MS (Method B) 4.40 and 2.55 min, [M+1]$^+$ 471 and 371.

Example 46

Preparation of Preparation of Compound 134, (S)-3-Benzyl-1-(3-cyclopentyloxy-4-methoxy-phenyl)-[1,4]diazepane

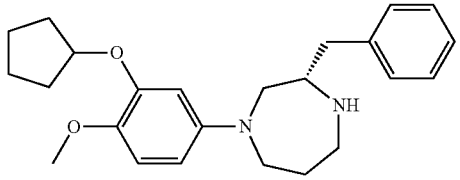 [SMILES: COc1ccc(N2CCCN[C@@H](Cc3ccccc3)C2)cc1OC1CCCC1]

The title compound was prepared by the method outlined for Example 1 using (S)-2-Benzyl-[1,4]diazepane-1-carboxylic acid tert-butyl ester as piperazine component. The intermediate and title compound were isolated as oils (42 and 92%). LC/MS (Method A) 7.99 and 5.07 min, [M+1]$^+$ 481 and 381.

Example 47

Preparation of Compound 135, (R)-3-Benzyl-1-(3-cyclopentyloxy-4-methoxy-phenyl)-[1,4]diazepane

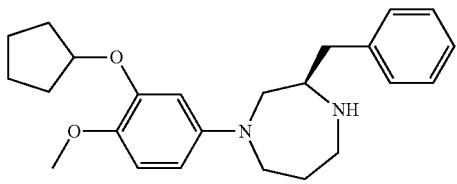 [SMILES: COc1ccc(N2CCCN[C@H](Cc3ccccc3)C2)cc1OC1CCCC1]

The title compound was prepared by the method outlined for Example 1 using (R)-2-Benzyl-[1,4]diazepane-1-carboxylic acid tert-butyl ester as piperazine component. The intermediate and title compound were isolated as oils (29 and 93%). LC/MS (Method A) 7.96 and 5.03 min, [M+1]$^+$ 481 and 381.

Example 48

Preparation of Preparation of Compound 136, (S)-5-Benzyl-1-(3-cyclopentyloxy-4-methoxy-phenyl)-[1,4]diazepane

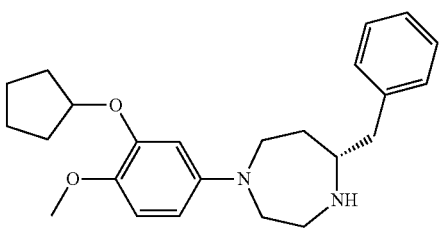 [SMILES: COc1ccc(N2CCN[C@@H](Cc3ccccc3)CC2)cc1OC1CCCC1]

The title compound was prepared by the method outlined for Example 1 using (S)-7-Benzyl-[1,4]diazepane-1-carboxylic acid tert-butyl ester as piperazine component. The intermediate and title compound were isolated as oils (23 and 99%). LC/MS (Method A) 7.42 and 4.91 min, [M+1]$^+$ 481 and 381.

Example 49

Preparation of Compound 137, (R)-5-Benzyl-1-(3-cyclopentyloxy-4-methoxy-phenyl)-[1,4]diazepane

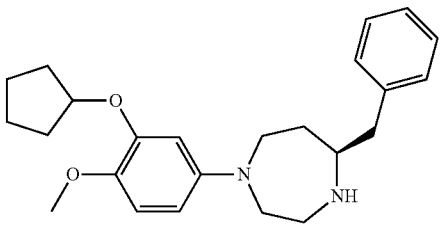 [SMILES: COc1ccc(N2CCN[C@H](Cc3ccccc3)CC2)cc1OC1CCCC1]

The title compound was prepared by the method outlined for Example 1 using (R)-7-Benzyl-[1,4]diazepane-1-carboxylic acid tert-butyl ester as piperazine component. The intermediate and title compound were isolated as oils (16 and 91%). LC/MS (Method A) 7.43 and 4.89 min, [M+1]$^+$ 481 and 381.

Example 50

Preparation of Compound 138, 1-(3-Cyclopentyloxy-4-methoxy-phenyl)-piperazine

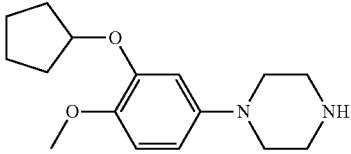 [SMILES: COc1ccc(N2CCNCC2)cc1OC1CCCC1]

The title compound was prepared by the method outlined for Example 1 using N-BOC-piperazine as piperazine component. The title compound was isolated as an oil (65% for two steps). LC/MS (Method A) 4.11 min, [M+1]$^+$ 277.

Example 51

Preparation of Compound 139, (S)-2-Benzyl-4-(3-cyclopentyloxy-4-methoxy-phenyl)-morpholine

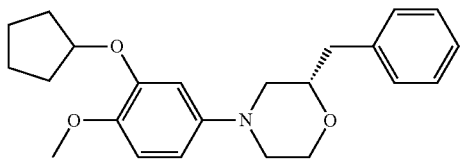 [SMILES: COc1ccc(N2CCO[C@@H](Cc3ccccc3)C2)cc1OC1CCCC1]

The title compound was prepared by the coupling method outlined for Example 1 using 2(S)-2-(benzyl)-morpholine as the amine component. The title compound was isolated as an oil (29%). LC/MS (Method A) 7.27 min, [M+1]$^+$ 368.

Example 52

Preparation of Compound 140, (S)-3-benzyl-1-(7-methoxy-3H-spiro[benzofuran-2,1'-cyclopentane]-4-yl)piperazine

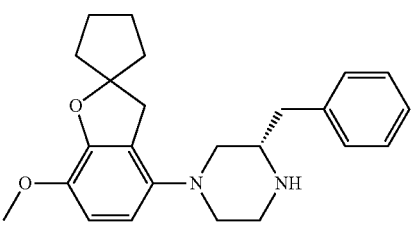 [SMILES: COc1ccc(N2CCN[C@@H](Cc3ccccc3)C2)c2c1OC1(CCCC1)C2]

The title compound was prepared by the method outlined for Example 1 using 4-bromo-7-methoxy-spiro[benzofuran-2(3H),1'-cyclopentane] CAS [185244-55-7] as the aryl halide and 2(S)—N1 BOC-2-(benzyl)-piperazine as the amine component. The title compound was isolated as an oil (79% for two steps). LC/MS (Method A) 5.02 min, [M+1]$^+$ 379.

Example 53

Preparation of Compound 141, (S)-6-(3-benzylpiperazin-1-yl)-1-cyclopentyl-3-methyl-1H-indazole

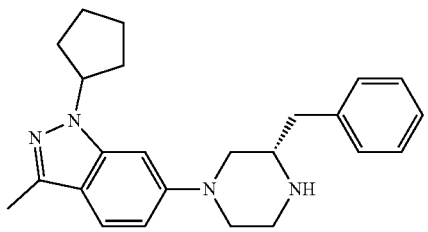 [SMILES: Cc1nn(C2CCCC2)c2cc(N3CCN[C@@H](Cc4ccccc4)C3)ccc12]

The title compound was prepared by the method outlined for Example 1 using 6-bromo-1-cyclopentyl-3-methyl-1H-indazole as the aryl halide and 2(S)—N1 BOC-2-(benzyl)-piperazine as the amine component. The intermediate and title compound were isolated as oils (81 and 76%). LC/MS (Method A) 5.13 min, [M+1]$^+$ 375.

Example 54

Preparation of Compound 142, 1-Cyclopentyl-3-ethyl-6-piperazin-1-yl-1H-indazole

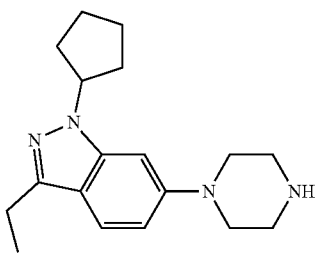 [SMILES: CCc1nn(C2CCCC2)c2cc(N3CCNCC3)ccc12]

The title compound was prepared by the method outlined for Example 1 using 6-bromo-1-cyclopentyl-3-ethyl-1H-indazole CAS [199172-02-6] as the aryl halide and N-BOC-piperazine as the amine component. The title compound was isolated as an oil (88% for two steps). LC/MS (Method A) 4.56 min, [M+1]$^+$ 299.

Example 55

Preparation of Compound 143, (S)-1-Cyclobutyl-3-ethyl-6-(3-isobutylpiperazin-1-yl)-1H-indazole

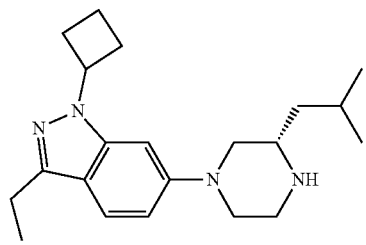 [SMILES: CCc1nn(C2CCC2)c2cc(N3CCN[C@@H](CC(C)C)C3)ccc12]

The title compound was prepared by the method outlined for Example 1 using 6-bromo-1-cyclobutyl-3-ethyl-1H-indazole as the aryl halide and 2(R)—N1 BOC-2-(isobutyl)-piperazine CAS [674792-06-4] as amine component. The title compound was isolated as an oil (89% for two steps). LC/MS (Method A) 5.22 min, [M+1]$^+$ 341.

Example 56

Preparation of Compound 144, 6-((S)-3-Benzyl-piperazin-1-yl)-1-cyclopentyl-3-ethyl-1H-indazole

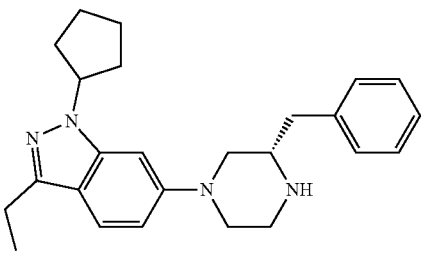 [SMILES: CCc1nn(C2CCCC2)c2cc(N3CCN[C@@H](Cc4ccccc4)C3)ccc12]

The title compound was prepared by the method outlined for Example 1 using 6-bromo-1-cyclopentyl-3-ethyl-1H-indazole CAS [199172-02-6] as the aryl halide and 2(S)—N1 BOC-2-(benzyl)-piperazine as the amine component. The intermediate and title compound were isolated as oils (86 and 90%). $^1$H NMR (300 MHz, CDCl$_3$) 7.52 (d, J=8.8, 1 H), 7.39-7.19 (m, 5 H), 6.83 (dd, J=9.2, 1.9, 1 H), 6.67 (d, J=1.8, 1 H), 4.87-4.76 (m, 1 H), 3.65-3.54 (m, 2 H), 3.17-3.08 (m, 2 H), 3.02-2.87 (m, 5 H), 2.73-2.57 (m, 2 H), 2.16-2.10 (m, 3 H), 1.98-1.93 (m, 2 H), 1.81-1.70 (m, 3 H), 1.35 (t, J=7.5, 3 H). $^{13}$C NMR 151.0, 146.4, 141.8, 138.4, 129.5, 128.9, 126.8, 121.0, 117.4, 113.2, 94.5, 59.2 (CH), 56.7 (CH), 56.6 (CH$_2$), 51.0 (CH$_2$), 46.1 (CH$_2$), 41.0 (CH$_2$), 31.9 (CH$_2$), 24.7 (CH$_2$), 20.9 (CH$_2$), 14.3 (CH$_3$). LC/MS (Method A) 5.28 min, [M+1]$^+$ 389.

Example 57

Preparation of Compound 145, (S)-6-(3-benzylpiperazin-1-yl)-1-cyclobutyl-3-ethyl-1H-indazole

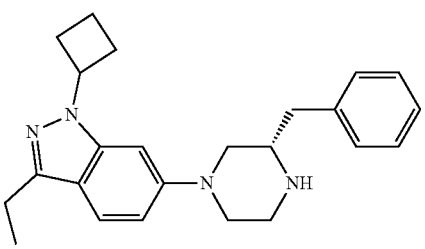 [SMILES: CCc1nn(C2CCC2)c2cc(N3CCN[C@@H](Cc4ccccc4)C3)ccc12]

The title compound was prepared by the method outlined for Example 1 using 6-bromo-1-cyclobutyl-3-ethyl-1H-indazole as the aryl halide and 2(S)—N1 BOC-2-(benzyl)-piperazine as the amine component. The intermediate and title compound were isolated as oils (82 and 90%). $^1$H NMR (CDCl$_3$) 7.51 (d, J=8.8, 1 H), 7.39-7.24 (m, 5 H), 7.14 (br, NH), 6.72 (dd, J=8.8, 1.9, 1 H), 6.63 (d, J=1.8, 1 H), 4.91-4.82 (m, 1 H), 3.59 (br t, J=9.4, 1 H), 3.48-3.40 (m, 1 H), 3.35-3.30 (m, 1 H), 3.20-3.11 (m, 2 H), 3.07-2.87 (m, 5

H), 2.82-2.70 (m, 2 H), 2.48-2.40 (m, 2 H), 1.95-1.83 (m, 2 H), 1.36 (t, J=7.6, 3 H). $^{13}$C NMR 149.7, 146.8, 141.0, 136.1, 129.2, 128.9, 127.2, 121.2, 117.7, 113.3, 95.2, 56.3, 54.0, 51.9, 48.9, 44.3, 38.5, 29.9, 20.7, 15.0, 14.1. LC/MS (Method B) 2.74 min, [M+1]$^+$ 375.

Example 58

Preparation of Compound 146, (S)-1-cyclobutyl-3-ethyl-6-(3-(4-fluorobenzyl)piperazin-1-yl)-1H-indazole

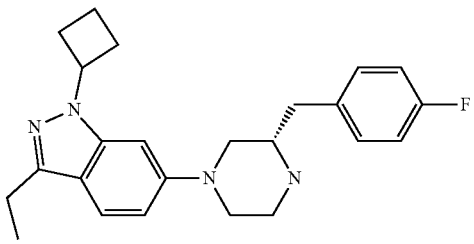 [SMILES: CCc1nn(C2CCC2)c2cc(N3CCN[C@@H](Cc4ccc(F)cc4)C3)ccc12]

The title compound was prepared by the method outlined for Example 1 using 6-bromo-1-cyclobutyl-3-ethyl-1H-indazole as the aryl halide and 2(S)—N1 BOC-2-(benzyl)-piperazine as the amine component. The title compound was isolated as a yellow solid (77%). $^1$H NMR (MeOH-d$_4$) 7.86 (d, J=9.2, 1 H), 7.44-7.40 (m, 2 H), 7.21-7.12 (m, 3 H), 6.99 (d, J=1.7, 1 H), 5.44-5.33 (m, 1 H), 4.14-4.00 (m, 2 H), 3.78-3.70 (m, 1H), 3.58-3.53 (m, 1H), 3.46-3.05 (m, 7 H), 2.78-2.56 (m, 4 H), 2.06-1.96 (m, 2 H), 1.44 (t, J=7.7, 3 H). LC/MS (Method B) 2.75 min, [M+1]$^+$ 393.

Example 59

Preparation of Compound 147, (S)-6-(3-benzylpiperazin-1-yl)-3-ethyl-1-isopropyl-1H-indazole

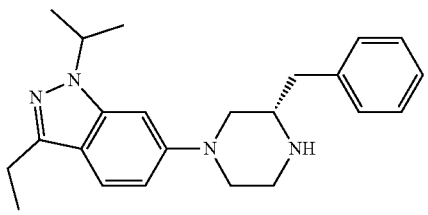 [SMILES: CCc1nn(C(C)C)c2cc(N3CCN[C@@H](Cc4ccccc4)C3)ccc12]

The title compound was prepared by the method outlined for Example 1 using 6-bromo-3-ethyl-1-isopropyl-1H-indazole as the aryl halide and 2(S)—N1 BOC-2-(benzyl)-piperazine as the amine component. The intermediate and title compound were isolated as oils (83 and 85%). $^1$H NMR (CDCl$_3$) 7.52 (d, J=8.8, 1 H), 7.35-7.23 (m, 5 H), 6.81 (dd, J=9.0, 2.0, 1 H), 6.60 (d, J=1.7, 1 H), 4.71-4.64 (m, 1 H), 3.64-3.55 (m, 2 H), 3.22-3.10 (m, 2 H), 3.02-2.84 (m, 5 H), 2.75-2.62 (m, 2 H), 1.55 (d, J=2.2, 3 H), 1.53 (d, J=2.1, 3 H), 1.36 (t, J=7.6, 3 H). $^{13}$C NMR 150.6, 146.4, 140.9, 137.9, 129.3, 128.7, 126.7, 121.0, 117.1, 113.0, 94.1, 56.4, 56.2, 50.5, 49.5, 45.7, 40.4, 22.0, 20.7, 14.2. LC/MS (Method B) 2.55 min, [M+1]$^+$ 363.

Example 60

Preparation of Compound 148, (S)-6-(3-benzylpiperazin-1-yl)-1,3-diethyl-1H-indazole

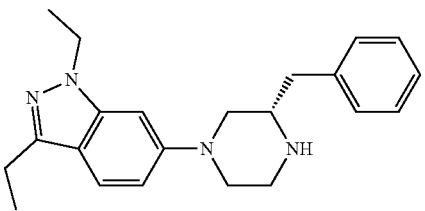 [SMILES: CCc1nn(CC)c2cc(N3CCN[C@@H](Cc4ccccc4)C3)ccc12]

The title compound was prepared by the method outlined for Example 1 using 6-bromo-1,3-diethyl-1H-indazole as the aryl halide and 2(S)—N1 BOC-2-(benzyl)-piperazine as the amine component. The intermediate and title compound were isolated as oils (79 and 86%). $^1$H NMR (300 MHz, CDCl$_3$) 7.52 (d, J=9.0, 1 H), 7.37-7.27 (m, 5 H), 6.79 (dd, J=8.8, 2.0, 1 H), 6.60 (d, J=1.8, 1 H), 4.71 (br, NH), 4.28 (q, J=7.0, 2 H), 3.64-3.56 (m, 2 H), 3.27-3.18 (m, 2 H), 3.08-2.69 (m, 7 H), 1.44 (t, J=7.2, 3 H), 1.37 (t, J=7.6, 3 H). $^{13}$C NMR 150.7, 146.4, 141.3, 137.6, 129.4, 128.9, 126.7, 121.2, 117.4, 113.2, 94.2, 56.5, 55.6, 50.1, 45.4, 43.2, 39.9, 20.7, 15.0, 14.1. LC/MS (Method A) 4.68 min, [M+1]$^+$ 349.

Example 61

Preparation of Compound 149, (S)-6-(3-benzylpiperazin-1-yl)-1-cyclobutyl-3-isopropyl-1H-indazole

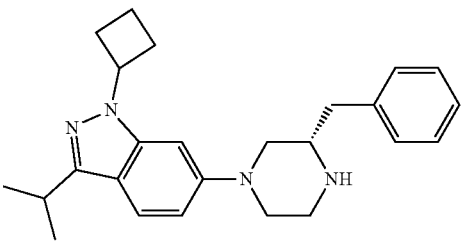 [SMILES: CC(C)c1nn(C2CCC2)c2cc(N3CCN[C@@H](Cc4ccccc4)C3)ccc12]

The title compound was prepared by the method outlined for Example 1 using 6-bromo-3-ethyl-1-propyl-1H-indazole as the aryl halide and 2(S)—N1 BOC-2-(benzyl)-piperazine as the amine component. The intermediate and title compound were isolated as oils (82 and 93%). $^1$H NMR (CDCl$_3$) 7.59 (d, J=8.8, 1 H), 7.37-7.26 (m, 5 H), 6.81 (dd, J=9.0, 2.0, 1 H), 6.68 (d, J=1.8, 1 H), 4.96-4.87 (m, 1 H), 3.64-3.54 (m, 2 H), 3.38-3.31 (m, 1 H), 3.17-3.08 (m, 2 H), 2.97 (td, J=11.2, 2.8, 1 H), 2.90-2.74 (m, 4 H), 2.71-2.58 (m, 2 H), 2.49-2.41 (m, 2 H), 1.95-1.83 (m, 2 H), 1.77 (br, NH), 1.43 (d, J=6.9, 6 H). $^{13}$C NMR 150.6, 150.4, 141.5, 138.2, 129.3 (CH), 128.7 (CH), 126.6 (CH), 121.3 (CH), 116.1, 112.9 (CH), 94.2 (CH), 67.1, 56.5 (CH), 56.4 (CH$_2$), 52.0 (CH), 50.6 (CH$_2$), 45.9 (CH$_2$), 40.8 (CH$_2$), 29.8 (CH$_2$), 28.4 (CH), 22.5 (CH$_3$), 15.1 (CH$_2$). LC/MS (Method B) 3.37 min, [M+1]$^+$ 389.

Example 62

Preparation of Compound 150, (S)-5-(3-benzylpiperazin-1-yl)-3-cyclobutyl-1-ethyl-1H-indazole

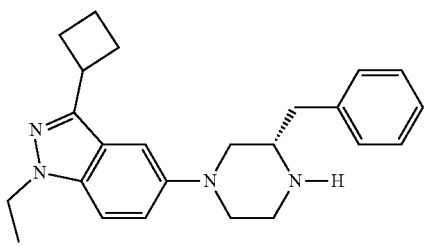 [SMILES: CCn1nc(C2CCC2)c2cc(N3CCN[C@@H](Cc4ccccc4)C3)ccc21]

The title compound was prepared by the method outlined for Example 1 using 5-Bromo-3-cyclobutyl-1-ethyl-1H-indazole as the aryl halide and 2(S)—N1 BOC-2-(benzyl)-piperazine as the amine component. The title compound was isolated as a brown oil (0.84 g, 78%). $^1$H NMR (MeOH-$d_4$) 7.36-7.23 (m, 6 H), 7.14 (dd, J=9.2, 2.0, 1 H), 7.07 (d, J=2.0, 1 H), 4.33 (q, J=7.2, 2 H), 3.87 (pent, J=8.5, 1 H), 3.40 (m, 2H), 3.11 (m, 2H), 2.97 (m, 1 H), 2.78 (m, 3H), 2.44 (m, 5H), 2.16 (m, 1H), 1.99 (m, 1H), 1.37 (t, J=7.2, 3 H), 1.23 (t, J=6.8, 1 H). LC/MS (Method B) 2.75 min, [M+1]$^+$ 375.

Example 63

Preparation of Compound 151, (S)-5-(3-benzylpiperazin-1-yl)-3-cyclobutyl-1-methyl-1H-indazole

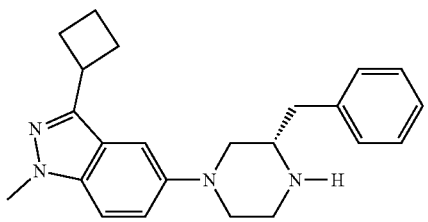 [SMILES: Cn1nc(C2CCC2)c2cc(N3CCN[C@@H](Cc4ccccc4)C3)ccc21]

The title compound was prepared by the method outlined for Example 1 using 5-Bromo-3-cyclobutyl-1-methyl-1H-indazole as the aryl halide and (S)-2-benzyl-piperazine-1-carboxylic acid tert-butyl ester as the amine component to afford the title compound as a brown oil (409 mg, 99%). $^1$H NMR (MeOH-$d_4$) 8.72 (d, J=8.7 Hz, 1 H), 7.79 (d, J=8.8 Hz, 1 H), 7.32-7.18 (m, 6 H), 4.08 (s, 3 H), 3.79-3.46 (m, 3 H), 3.35-3.34 (m, 1 H), 3.31-3.30 (m, 2 H), 3.15-3.07 (m, 4 H), 2.88-2.77 (m, 5 H), 2.69-2.61 (m, 1 H). LC/MS (Method B) 2.49 min, [M+1]$^+$ 361.

Example 64

Preparation of Compound 152, (S)-5-(3-benzylpiperazin-1-yl)-3-cyclobutyl-1-isopropyl-1H-indazole

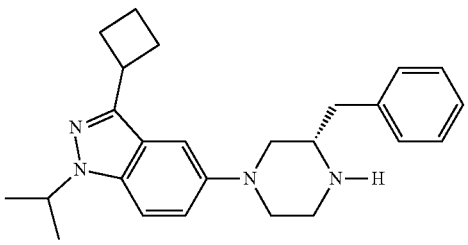 [SMILES: CC(C)n1nc(C2CCC2)c2cc(N3CCN[C@@H](Cc4ccccc4)C3)ccc21]

The title compound was prepared by the method outlined for Example 1 using 5-Bromo-3-cyclobutyl-1-isopropyl-1H-indazole as the aryl halide and (S)-2-benzyl-piperazine-1-carboxylic acid tert-butyl ester as the amine component to afford the title compound as a brown oil (780 mg, 55%). $^1$H NMR (MeOH-$d_4$) 7.44-7.20 (m, 5 H), 7.16-6.87 (m, 3 H), 4.78 (td, J=13.4, 6.7 Hz, 1 H), 3.95-3.83 (m, 1 H), 3.46-3.33 (m, 2 H), 3.20-3.05 (m, 2 H), 3.03-2.91 (m, 1 H), 2.82-2.75 (m, 3 H), 2.57-2.36 (m, 6 H), 2.24-2.09 (m, 1 H), 1.50 (d, J=6.7 Hz, 6 H). LC/MS (Method B) 2.79 min, [M+1]$^+$ 389.

Example 65

Preparation of Compound 153, (S)-5-(3-benzylpiperazin-1-yl)-8-methoxy-2-(trifluoromethyl)quinoline The title compound was prepared by the method outlined for Example 1 using 5-bromo-8-methoxy-2-(trifluoromethyl)quinoline CAS [199872-02-1] as the aryl halide and 2(S)—N1 BOC-2-(benzyl)-piperazine as the amine component. The intermediate and title compound were isolated as yellow oils (83 and 79%). $^1$H NMR (CDCl$_3$) 8.71 (d, J=8.7, 1 H), 7.74 (d, J=8.7, 1 H), 7.33-7.22 (m, 6 H), 7.05 (d, J=8.1, 1 H), 4.06 (s, 3 H), 3.32-3.22 (m, 1 H), 3.20-3.10 (m, 4 H), 2.91-2.66 (m, 4 H) 1.86 (s, 1 H). $^{19}$F NMR −67.00. LC/MS (Method B) 5.12 min, [M+1]$^+$ 402.

Example 66

Preparation of Compound 154, (S)-5-(3-(4-fluorobenzyl)piperazin-1-yl)-8-methoxy-2-(trifluoromethyl)quinoline

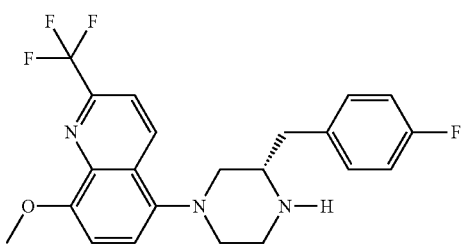 [SMILES: COc1ccc(N2CCN[C@@H](Cc3ccc(F)cc3)C2)c2ccc(C(F)(F)F)nc12]

The title compound was prepared by the method outlined for Example 1 using 5-bromo-8-methoxy-2-(trifluoromethyl)quinoline CAS [199872-02-1] as the aryl halide and 2(S)—N1 BOC-2-(4-fluorobenzyl)-piperazine as the amine component. The title compound was isolated as a yellow solid (48%). $^1$H NMR (MeOH-d$_4$) 8.81 (d, J=8.4, 1 H), 7.87 (d, J=8.8, 1 H), 7.44 (d, J=8.5, 1 H), 7.39-7.34 (m, 2 H), 7.25 (d, J=8.4, 1 H), 7.14-7.08 (m, 2 H), 4.07 (s, 3 H), 3.96-3.89 (m, 1 H), 3.60-3.50 (m, 2 H), 3.40-3.32 (m, 2 H), 3.26-3.14 (m, 2 H), 3.08-3.00 (m, 2H). LC/MS (Method B) 2.62 min, [M+1]$^+$ 420.

Example 67

Preparation of Compound 155, (S)-5-(3-benzylpiperazin-1-yl)-8-methoxy-2-methylquinoline

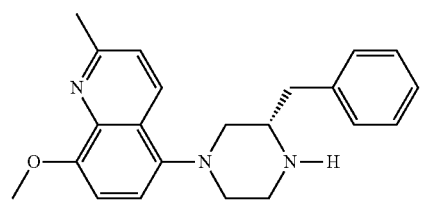 [SMILES: COc1ccc(N2CCN[C@@H](Cc3ccccc3)C2)c2ccc(C)nc12]

The title compound was prepared by the method outlined for Example 1 using 5-bromo-8-methoxy-2-methyl quinoline CAS [103862-55-1] as the aryl halide and 2(S)—N1 BOC-2-(benzyl)-piperazine as the amine component. The title compound was isolated as a brown oil (0.84 g, 78%). $^1$H NMR (MeOH-d$_4$) 8.36 (d, J=8.8, 1 H), 7.32-7.03 (m, 6 H), 7.06 (m, 2 H), 3.97 (s, 3 H), 3.27 (m, 1 H), 3.10-3.03 (m, 4 H), 2.79 (m, 3 H), 2.66 (s, 3 H), 2.55 (t, J=11.4, 1H). LC/MS (Method B) 0.84 min, [M+1]$^+$ 348.

Example 68

Preparation of Compound 156, (S)-5-(3-benzylpiperazin-1-yl)-2-chloro-8-methoxyquinoline

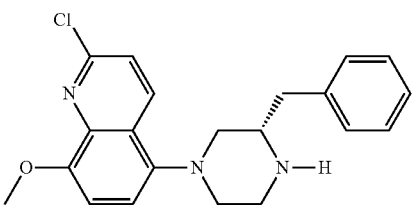 [SMILES: COc1ccc(N2CCN[C@@H](Cc3ccccc3)C2)c2ccc(Cl)nc12]

The title compound was prepared by the method outlined for Example 1 using 5-bromo-8-chloro-2-methyl quinoline as the aryl halide and 2(S)—N1 BOC-2-(benzyl)-piperazine as the amine component. The title compound was isolated as a yellow solid (22%); LC/MS (Method B) 2.34 min, [M+1]$^+$ 368.

Example 69

Preparation of Compound 157, (S)-3-benzyl-1-(3-(difluoromethoxy)-4-methoxyphenyl)piperazine

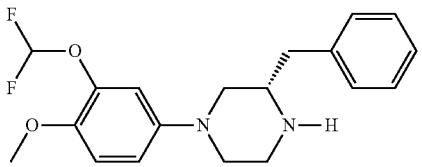 [SMILES: COc1ccc(N2CCN[C@@H](Cc3ccccc3)C2)cc1OC(F)F]

The title compound was prepared by the method outlined for Example 1 using 4-bromo-2-(difluoromethoxy)-1-methoxybenzene (prepared in analogous fashion to 4-bromo-2-(cyclopentyloxy)-1-(difluoromethoxy)benzene) as the aryl halide and 2(S)—N1 BOC-2-(benzyl)-piperazine as the amine component. The title compound was isolated as an oil. LC/MS (Method B) 2.50 min, [M+1]$^+$ 349.

Example 70

Preparation of Compound 158, (S)-5-(3-benzylpiperazin-1-yl)-8-methoxyquinoline

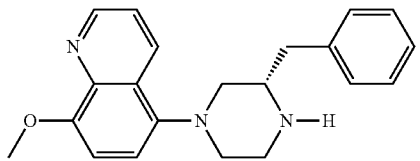

The title compound was prepared by the method outlined for Example 1 using 5-bromo-8-methoxy-quinoline as the aryl halide and 2(S)—N1 BOC-2-(benzyl)-piperazine as the amine component. The title compound was isolated as an oil (3.8 g, 81% for 2 steps). $^1$H NMR (CDCl$_3$) 8.78 (dd, J=4, 1.6, 1 H), 8.37 (dd, J=8.4, 1.6, 1 H), 7.46 (dd, J=8.6, 4, 1 H), 7.28-7.21 (m, 4 H). 7.19-7.11 (m, 1 H), 7.09-7.00 (m, 2 H), 3.88 (s, 3 H), 3.20-3.10 (m, 1 H), 3.09-2.89 (m, 4 H), 2.75-2.58 (m, 3 H), 2.50-2.40 (m, 2 H). LC/MS (Method B) 3.10 min, [M+1]+ 334.

Example 71

Preparation of Compound 159, (S)-3-benzyl-1-(4-methoxy-3-(1-methylpiperidin-4-yloxy)phenyl)piperazine

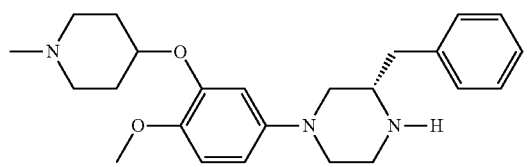

The title compound was prepared by the method outlined for Example 1 using 4-(5-bromo-2-methoxy-phenoxy)-1-methyl-piperidine as the aryl halide and 2(S)-benzyl-piperazine-1-carboxylic acid tert-butyl ester as the amine component. The title compound was isolated as an orange oil. $^1$H NMR (MeOH-$d_4$) 7.33-7.29 (m, 2 H), 7.25-7.22 (m, 3 H), 6.85 (d, J=8.8, 1 H), 6.55 (d, J=2.8, 1 H), 6.50 (dd, J=8.8, 2.8, 1 H), 4.24 (m, 1 H), 3.74 (s, 3 H), 3.35-3.27 (m, 2 H), 3.05-3.00 (m, 2 H), 2.91-2.85 (m, 1 H), 2.74-2.65 (m, 5H), 2.36 (m, 3H), 2.28 (s, 3 H), 1.90 (m, 2 H), 1.78 (m, 2 H). LC/MS (Method B) 0.97 min, [M+1]+ 396.

Example 72

Preparation of Compound 160, (S)-3-benzyl-1-(4-methoxy-3-((S)-1-methylpyrrolidin-3-yloxy)phenyl)piperazine

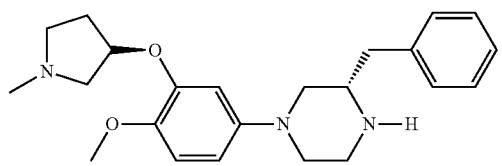

The title compound was prepared by the method outlined for Example 1 using (3S)-3-(5-Bromo-2-methoxyphenoxy)-1-methylpyrrolidine as the aryl halide and 2(S)-benzyl-piperazine-1-carboxylic acid tert-butyl ester as the amine component. The title compound was isolated as an orange oil. $^1$H NMR (MeOH-$d_4$) 7.33-7.30 (m, 2 H), 7.26-7.22 (m, 3 H), 6.83 (d, J=9.2, 1 H), 6.44 (m, 2 H), 4.81 (m, 1 H), 3.73 (s, 3 H), 3.36-3.28 (m, 2 H), 3.04 (m, 2 H), 2.93-2.66 (m, 8 H), 2.52-2.46 (m, 1 H), 2.36 (s, 3 H), 2.19 (m, 1 H), 1.95 (m, 1 H). LC/MS (Method B) 0.87 min, [M+1]+ 382.

Example 73

Preparation of Compound 161, (S)-3-benzyl-1-(4-methoxy-3-((R)-1-methylpyrrolidin-3-yloxy)phenyl)piperazine

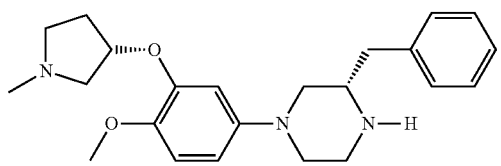

The title compound was prepared by the method outlined for Example 1 using (3R)-3-(5-Bromo-2-methoxyphenoxy)-1-methylpyrrolidine as the aryl halide and 2(S)-benzyl-piperazine-1-carboxylic acid tert-butyl ester as the amine component. The title compound was isolated as an orange oil. LC/MS (Method B) 0.87 min, [M+1]+ 382.

Example 74

Preparation of Compound 162, (S)-3-benzyl-1-(3-(1,3-difluoropropan-2-yloxy)-4-methoxyphenyl)piperazine

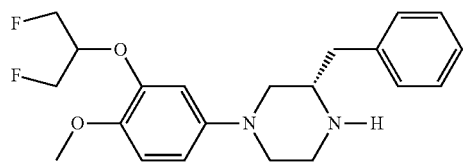 [SMILES: COc1ccc(N2CCN[C@@H](Cc3ccccc3)C2)cc1OC(CF)CF]

The title compound was prepared by the method outlined for Example 1 using 4-bromo-2-(2-fluoro-1-fluoromethyl-ethoxy)-1-methoxy-benzene as the aryl halide and 2(S)—N1 BOC-2-(benzyl)-piperazine as the amine component. The title compound was isolated as a pale brown oil (0.59 g, 42%). $^1$H NMR (MeOH-$d_4$) 7.34-7.23 (m, 5 H), 6.90 (d, J=8.8, 1 H), 6.66 (d, J=2.8, 1 H), 6.68 (dd, J=8.8, 2.8, 1 H), 4.69 (m, 2 H), 4.56 (m, 3 H), 3.77 (s, 3 H), 3.35 (m, 2 H), 3.08 (m, 2 H), 2.91 (m, 1 H), 2.77-2.69 (m, 3 H), 2.42 (dd, J=11.8, 10.4, 1 H). LC/MS (Method B) 2.27 min, [M+1]+ 377.

EXAMPLES 75-425

Example 75

Preparation of Compound 163, (S)-2-Benzyl-4-(3-cyclopentyloxy-4-methoxy-phenyl)-1-methyl-piperazine

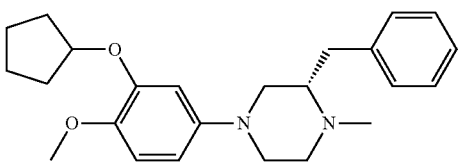 [SMILES: COc1ccc(N2CCN(C)[C@@H](Cc3ccccc3)C2)cc1OC1CCCC1]

A solution of (S)-3-Benzyl-1-(3-cyclopentyloxy-4-methoxy-phenyl)-piperazine (73 mg, 0.20 mmol) in $CH_2Cl_2$ (5 mL) was treated with a 37% aqueous formaldehyde solution (16 μL, 0.22 mmol) and stirred for 5 min after which time solid sodium triacetoxyborohydride (64 mg, 0.30 mmol) was added. The suspension was then stirred for 3 hr then quenched with a saturated aqueous $NaHCO_3$ solution (2 mL). The organic component was separated, dried over $MgSO_4$, filtered, and evaporated to an oil which was purified by silica gel flash chromatography with 5% $MeOH/CH_2Cl_2$ as eluant to afford the title compound as a burgundy oil (69 mg, 91%). $^1H$ NMR ($CDCl_3$) 7.33-7.20 (m, 5 H), 6.72 (d, J=8.6, 1H), 6.35 (d, J=2.9, 1 H), 6.30 (dd, J=8.6, 2.9, 1 H), 4.62-4.59 (m, 1 H), 3.76 (s, 3 H), 3.32-3.22 (m, 2 H), 3.13-3.02 (m, 3 H), 2.67-2.60 (m, 4 H), 2.57 (s, 3 H), 1.85-1.77 (m, 6 H), 1.61-1.54 (m, 2 H). $^{13}C$ NMR 148.4, 146.1, 144.5, 139.0 (CH), 129.5 (CH), 128.6, 126.4 (CH), 113.2 (CH), 107.8 (CH), 106.2 (CH), 80.4 (CH), 63.7 (CH), 56.8 ($CH_3$), 55.1 ($CH_2$), 55.0 ($CH_2$), 50.2 ($CH_2$), 42.9 ($CH_3$), 36.3 ($CH_2$), 33.0 ($CH_2$), 24.2 ($CH_2$). LC/MS (Method A) 5.10 min, $[M+1]^+$ 381.

Example 76

Preparation of Compound 164, (S)-2-Benzyl-4-(3-cyclopentyloxy-4-methoxy-phenyl)-1-ethyl-piperazine

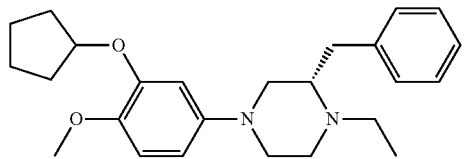 [SMILES: CCN1CCN(c2ccc(OC)c(OC3CCCC3)c2)C[C@@H]1Cc1ccccc1]

The title compound was prepared by the method outlined for Example 75 using acetaldehyde as the aldehyde component. The title compound was isolated as an oil (84%). LC/MS 4.73 min, $[M+1]^+$ 395.

Example 77

Preparation of Compound 165, (S)-2-Benzyl-4-(3-cyclopentyloxy-4-methoxy-phenyl)-1-propyl-piperazine

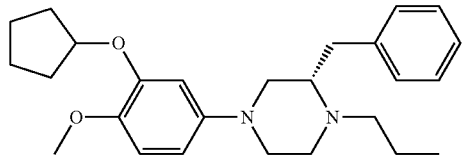 [SMILES: CCCN1CCN(c2ccc(OC)c(OC3CCCC3)c2)C[C@@H]1Cc1ccccc1]

The title compound was prepared by the method outlined for Example 75 using propionaldehyde as the aldehyde component. The title compound was isolated as an oil (95%). LC/MS (Method A) 4.80 min, $[M+1]^+$ 409.

Example 78

Preparation of Compound 166, (S)-2-Benzyl-4-(3-cyclopentyloxy-4-methoxy-phenyl)-1-benzyl-piperazine

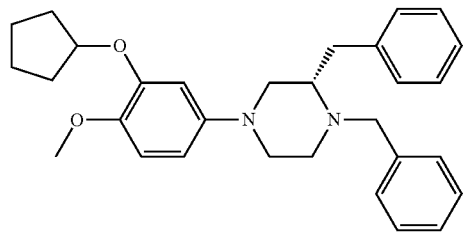 [SMILES: COc1ccc(N2CCN(Cc3ccccc3)[C@@H](Cc3ccccc3)C2)cc1OC1CCCC1]

The title compound was prepared by the method outlined for Example 75 using benzaldehyde as the aldehyde component. The title compound was isolated as an oil (50%). LC/MS (Method A) 5.43 min, $[M+1]^+$ 457.

Example 79

Preparation of Compound 167, (S)-2-Benzyl-4-(3-cyclopentyloxy-4-methoxy-phenyl)-1-pyridin-2-ylmethyl-piperazine

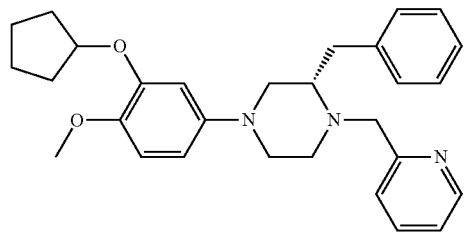 [SMILES: COc1ccc(N2CCN(Cc3ccccn3)[C@@H](Cc3ccccc3)C2)cc1OC1CCCC1]

The title compound was prepared by the method outlined for Example 75 using 2-pyridinecarboxaldehyde as the aldehyde component. The title compound was isolated as an oil (44%). LC/MS (Method A) 5.38 min, $[M+1]^+$ 458.

Example 80

Preparation of Compound 168, (S)-2-Benzyl-4-(3-cyclopentyloxy-4-methoxy-phenyl)-1-pyridin-3-ylmethyl-piperazine

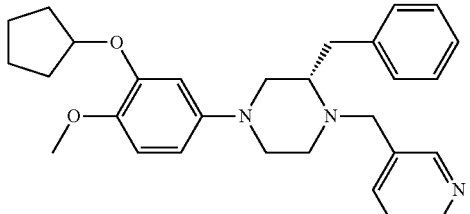

The title compound was prepared by the method outlined for Example 75 using 3-pyridinecarboxaldehyde as the aldehyde component. The title compound was isolated as an oil (57%). LC/MS (Method A) 5.07 min, [M+1]+ 458.

Example 81

Preparation of Compound 169, (S)-2-Benzyl-4-(3-cyclopentyloxy-4-methoxy-phenyl)-1-pyridin-4-ylmethyl-piperazine

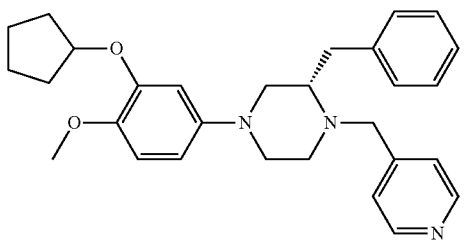 [SMILES: COc1ccc(N2CCN(Cc3ccncc3)[C@@H](Cc3ccccc3)C2)cc1OC1CCCC1]

The title compound was prepared by the method outlined for Example 75 using 4-pyridinecarboxaldehyde as the aldehyde component. Product as an oil (44%). LC/MS (Method A) 5.21 min, [M+1]+ 458.

Example 82

Preparation of Compound 170, (S)-2-Benzyl-4-(3-cyclopentyloxy-4-methoxy-phenyl)-1-(3H-imidazol-4-ylmethyl)-piperazine

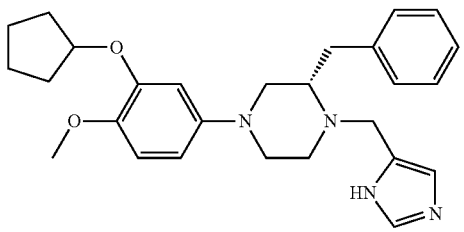 [SMILES: COc1ccc(N2CCN(Cc3cnc[nH]3)[C@@H](Cc3ccccc3)C2)cc1OC1CCCC1]

The title compound was prepared by the method outlined for Example 75 using 1-tritylimidazole-4-carboxaldehyde as the aldehyde component. The resulting intermediate (S)-2-Benzyl-4-(3-cyclopentyloxy-4-methoxy-phenyl)-1-(1-trityl-1H-imidazol-4-ylmethyl)-piperazine was isolated as an oil (69%). LC/MS 6.25 min, [M+1]+ 689.

The intermediate (S)-2-Benzyl-4-(3-cyclopentyloxy-4-methoxy-phenyl)-1-(1-trityl-1H-imidazol-4-ylmethyl)-piperazine (90 mg, 0.13 mmol) was dissolved in CH$_2$Cl$_2$ (0.5 mL) and was treated with triethylsilane (0.5 mL) followed by trifluoroacetic acid (1.0 mL). The reaction mixture was stirred for 2 h then evaporated to a residue which was triturated with a 10% EtOAc/hexane solution (4×1 mL). The residue was then partitioned between EtOAc (1 mL) and a saturated aqueous K$_2$CO$_3$ solution (0.5 mL). The organic component was separated, dried over MgSO$_4$, filtered, and evaporated to afford the title compound as a foam (50 mg, 83%). LC/MS (Method A) 4.50 min, [M+1]+ 447.

Example 83

Preparation of Compound 171, (S)-2-Benzyl-4-(3-cyclopentyloxy-4-methoxy-phenyl)-1-(1H-imidazol-2-ylmethyl)-piperazine

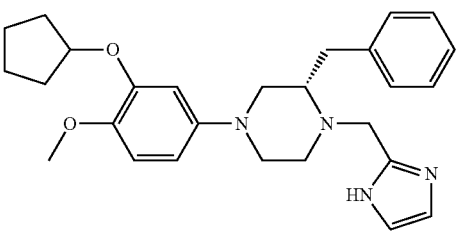

The title compound was prepared by the method outlined for Example 82 using 1-tritylimidazole-2-carboxaldehyde as the aldehyde component. The intermediate and title compound were isolated as oil and foam respectively (63 and 75%). LC/MS (Method A) 6.20 and 4.77 min, [M+1]+ 689 and 447.

Example 84

Preparation of Compound 172, (S)-2-Benzyl-4-(3-cyclopentyloxy-4-methoxy-phenyl)-1-methanesulfonyl-piperazine

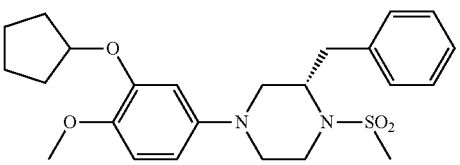

A solution of the bis-hydrochloride salt of (S)-3-Benzyl-1-(3-cyclopentyloxy-4-methoxy-phenyl)-piperazine (50 mg, 0.11 mmol) in pyridine (1 mL) was treated with methanesulfonyl chloride (26 µL, 0.34 mmol) and stirred at room temperature for 16 h. The reaction mixture was evaporated and partitioned between EtOAc (2 mL) and a saturated aqueous NaHCO$_3$ solution (2 mL). The organic component was separated, dried over MgSO$_4$, filtered, and evaporated to an oil which was purified by silica gel flash chromatography with 30% then 40% EtOAc/hexane as eluant to afford the title compound as an oil (46 mg, 91%). $^1$H NMR (CDCl$_3$) 7.36-7.23 (m, 5 H), 6.78 (d, J=8.6, 1 H), 6.48 (br s, 1 H), 6.42 (br d, J=8.1, 1 H), 4.71 (m, 1 H), 4.30 (br t, 1 H), 3.80 (s, 3 H), 3.77 (m, 1 H), 3.56-3.19 (m, 5H), 2.80-2.76 (m, 2H), 2.55 (s, 3 H), 2.04-1.90 (m, 2 H), 1.87-1.84 (m, 4 H), 1.62-1.60 (m, 2 H). LC/MS (Method A) 7.25 min, [M+1]+ 445.

Example 85

Preparation of Compound 173, (S)-2-Benzyl-4-(3-cyclopentyloxy-4-methoxy-phenyl)-1-ethanesulfonyl-piperazine

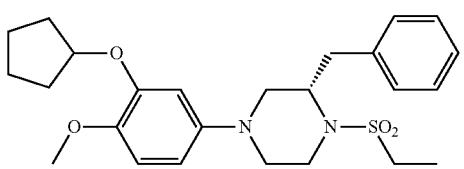 [SMILES: COc1ccc(N2CCN(S(C)(=O)=O)[C@@H](Cc3ccccc3)C2)cc1OC1CCCC1]

The title compound was prepared by the method outlined for Example 84 using ethanesulfonyl chloride as the sulfonyl chloride component. The title compound was isolated as an oil (17%). LC/MS (Method A) 7.41 min, [M+1]$^+$ 459.

Example 86

Preparation of Compound 174, (S)-2-Benzyl-4-(3-cyclopentyloxy-4-methoxy-phenyl)-1-benzylsulfonyl-piperazine

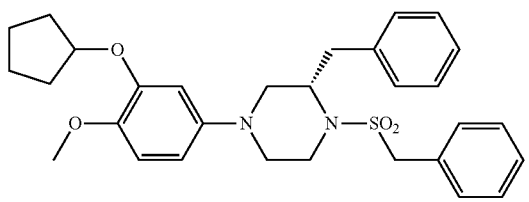 [SMILES: COc1ccc(N2CCN(S(=O)(=O)Cc3ccccc3)[C@@H](Cc3ccccc3)C2)cc1OC1CCCC1]

The title compound was prepared by the method outlined for Example 84 using benzylsulfonyl chloride as the sulfonyl chloride component. The title compound was isolated as an oil (6%). LC/MS (Method A) 7.82 min, [M+1]$^+$ 521.

Example 87

Preparation of Compound 175, (S)-1-(2-benzyl-4-(3-(cyclopentyloxy)-4-methoxyphenyl)piperazin-1-yl)ethanone

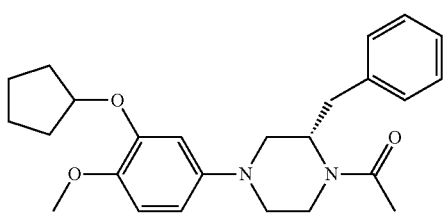 [SMILES: COc1ccc(N2CCN(C(C)=O)[C@@H](Cc3ccccc3)C2)cc1OC1CCCC1]

A solution of the bis-hydrochloride salt of (S)-3-Benzyl-1-(3-cyclopentyloxy-4-methoxy-phenyl)-piperazine in pyridine (1 mL) was treated with acetic anhydride (32 µL, 0.34 mmol) and stirred for 16 h. The reaction mixture was evaporated and partitioned between EtOAc (2 mL) and a saturated aqueous NaHCO$_3$ solution (2 mL). The organic component was separated, dried over MgSO$_4$, filtered, and evaporated to residue which was purified by silica gel flash chromatography with EtOAc as eluant to afford the title compound as an oil (45 mg, 97%). LC/MS (Method A) 6.88 min, [M+1]$^+$ 409.

Example 88

Preparation of Compound 176, (S)-2-Benzyl-4-(3-cyclopentyloxy-4-methoxy-phenyl)-piperazine-1-carboxylic acid ethylamide

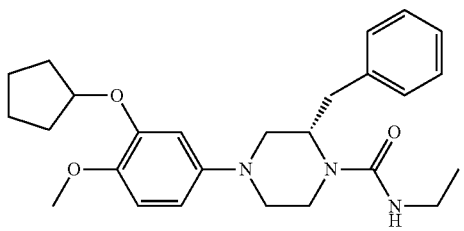 [SMILES: CCNC(=O)N1CCN(c2ccc(OC)c(OC3CCCC3)c2)C[C@@H]1Cc1ccccc1]

A solution of (S)-3-Benzyl-1-(3-cyclopentyloxy-4-methoxy-phenyl)-piperazine (73 mg, 0.2 mmol) in CH$_2$Cl$_2$ (0.5 mL) at 0° C. was treated with ethyl isocyanate (19 µL, 0.24 mmol) and stirred for 1 h, then evaporated and the residue purified by silica gel flash chromatography with 50% then 75% EtOAc/hexane as eluant to afford the title compound as a foam (60 mg, 69%) $^1$H NMR (CDCl$_3$) 7.35-7.22 (m, 5 H), 6.78 (d, J=8.8, 1 H), 6.49 (br s, 1 H), 6.40 (br d, J=7.5, 1 H), 4.73-4.70 (m, 1 H), 4.27-4.13 (m, 2 H), 3.93 (br d, J=12.5, 1 H), 3.79 (s, 3 H), 3.43-3.00 (m, 7 H), 2.75-2.67 (m, 2 H), 1.96-1.91 (m, 2 H), 1.90-1.79 (m, 3 H), 1.64-1.59 (m, 2 H), 1.04 (t, J=7., 3 H). LC/MS (Method A) 6.86 min, [M+1]$^+$ 438.

Example 89

Preparation of Compound 177, (S)-2-Benzyl-4-(3-cyclopentyloxy-4-methoxy-phenyl)-piperazine-1-carboxylic acid ethyl ester

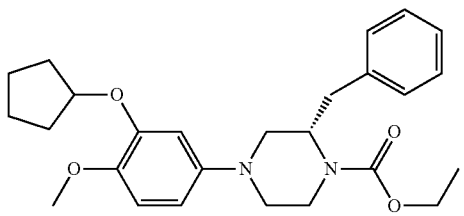 [SMILES: CCOC(=O)N1CCN(c2ccc(OC)c(OC3CCCC3)c2)C[C@@H]1Cc1ccccc1]

A solution of (S)-3-Benzyl-1-(3-cyclopentyloxy-4-methoxy-phenyl)-piperazine (73 mg, 0.2 mmol) in THF (0.5 mL) at room temperature was treated with triethylamine (28 µL, 0.2 mmol) followed by ethyl chloroformate (19 µL, 0.2 mmol). The reaction mixture was stirred for 2 h then diluted with EtOAc (2 mL) followed by a saturated aqueous NaHCO$_3$ solution (1 mL). The organic phase was isolated and further washed with an additional portion of a saturated aqueous NaHCO$_3$ solution (1 mL) followed by a brine solution (1 mL). The organic component was dried over MgSO$_4$, filtered, and evaporated to an oil which was purified by silica gel flash chromatography with 10% then 30% EtOAc/hexane as eluant to afford the title compound as an oil (30 mg, 34%). $^1$H NMR (CDCl$_3$) 7.34-7.22 (m, 5 H), 6.77 (d, J=8.6, 1 H), 6.47 (s, 1 H), 6.39 (dd, J=8.6, 2.4, 1 H), 4.72-4.69 (m, 1 H), 4.40 (br s, 1 H), 4.13-4.08 (m, 3 H), 3.79 (s, 3 H), 3.42-3.33 (m, 2 H), 3.28-3.20 (m, 2 H), 2.95 (dd, J=12.9, 4.8, 1 H), 2.72-2.60 (m, 2 H), 2.00-1.92 (m, 2 H), 1.89-1.79 (m, 3 H), 1.65-1.60 (m, 2 H), 1.25 (t, J=7.2, 3 H). LC/MS (Method A) 7.81 min, [M+1]$^+$ 439.

Example 90

Preparation of Compound 178, (S)-1-(2-benzyl-4-(3-(cyclopentyloxy)-4-methoxyphenyl)piperazin-1-yl)-2-hydroxyethanone

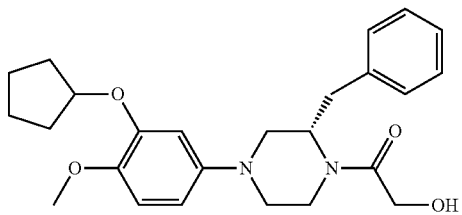 [SMILES: COc1ccc(N2CCN(C(=O)CO)[C@@H](Cc3ccccc3)C2)cc1OC1CCCC1]

A solution of (S)-3-Benzyl-1-(3-cyclopentyloxy-4-methoxy-phenyl)-piperazine (73 mg, 0.2 mmol) in THF (1.5 mL) at room temperature was treated with triethylamine (42 µL, 0.3 mmol) followed by benzyloxyacetyl chloride (19 µL, 0.2 mmol). The reaction mixture was stirred for 2 h then diluted with EtOAc (2 mL) and water (2 mL). The organic phase was isolated and further washed with an additional portion of a water (2 mL) followed by a brine solution (2 mL). The organic component was dried over MgSO$_4$, filtered, and evaporated to an oil which was purified by silica gel flash chromatography with 20% then 40% EtOAc/hexane as eluant to afford intermediate 1-[2-Benzyl-4-(3-cyclopentyloxy-4-methoxy-phenyl)-piperazin-1-yl]-2-benzyloxy-ethanone as an oil (69 mg, 67%). LC/MS 7.64 min, [M+1]$^+$ 515.

Intermediate 1-[2-Benzyl-4-(3-cyclopentyloxy-4-methoxy-phenyl)-piperazin-1-yl]-2-benzyloxy-ethanone (60 mg, 0.12 mmol) was dissolved in MeOH (20 mL), purged with a stream of nitrogen, treated with 20% Pd/C (140 mg, 50% water content) and hydrogenated under 40 psi pressure of hydrogen for 4 h. The crude reaction mixture was then purged with nitrogen, filtered, evaporated, and purified by silica gel flash chromatography with 40% then 75% EtOAc/hexane as eluant to afford the title compound as an oil (9 mg, 18%). LC/MS (Method A) 6.55 min, [M+1]$^+$ 425.

Example 91

Preparation of Compound 179, (S)-2-amino-1-(2-benzyl-4-(3-(cyclopentyloxy)-4-methoxyphenyl)piperazin-1-yl)ethanone, hydrochloride salt

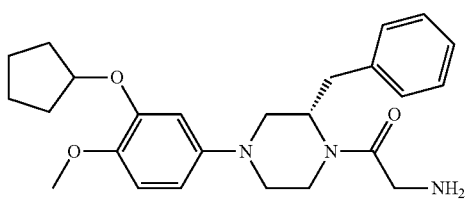 [SMILES: COc1ccc(N2CCN(C(=O)CN)[C@@H](Cc3ccccc3)C2)cc1OC1CCCC1]

A solution of (S)-3-Benzyl-1-(3-cyclopentyloxy-4-methoxy-phenyl)-piperazine (73 mg, 0.2 mmol) and BOC-glycine (35 mg, 0.2 mmol) in DMF (1.0 mL) at room temperature was treated with diisopropylethylamine (35 µL, 0.2 mmol) followed by 2-(7-Aza-1H-benzotriazole-1-yl)-1,1,3,3-tetramethyluronium hexafluorophosphate (HATU) (84 mg, 0.22 mmol). The reaction mixture was stirred for 2 h then partitioned between EtOAc (10 mL) and a saturated aqueous NaHCO$_3$ solution (10 mL). The organic component was isolated and further washed with brine (10 mL) then dried over MgSO$_4$, filtered, and evaporated to an oil which was purified by silica gel flash chromatography with 40% EtOAc/hexane as eluant to afford intermediate {2-[(S)-2-Benzyl-4-(3-cyclopentyloxy-4-methoxy-phenyl)-piperazin-1-yl]-2-oxo-ethyl}-carbamic acid tert-butyl ester as a foam (85 mg, 81%). LC/MS 7.46 min, [M+1]$^+$ 524.

The intermediate {2-[(S)-2-Benzyl-4-(3-cyclopentyloxy-4-methoxy-phenyl)-piperazin-1-yl]-2-oxo-ethyl}-carbamic acid tert-butyl ester was dissolved in a 4 N solution of hydrogen chloride in dioxane and stirred for 2 h then evaporated to a solid which was filtered and washed with diethyl ether to afford the title compound as a colorless solid (42 mg, 49% based on trihydrochloride salt). LC/MS (Method A) 4.66 min, [M+1]$^+$ 424.

Example 92

Preparation of Compound 180, (S)-1-(2-benzyl-4-(3-(cyclopentyloxy)-4-methoxyphenyl)piperazin-1-yl)-2-(methylamino)ethanone, hydrochloride salt

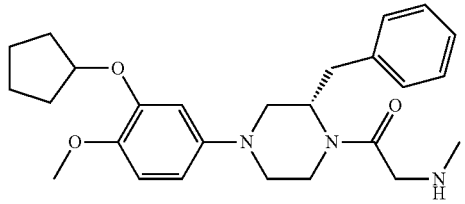 [SMILES: CNCC(=O)N1CCN(c2ccc(OC)c(OC3CCCC3)c2)C[C@@H]1Cc1ccccc1]

The title compound was prepared by the method outlined for Example 91 using BOC-sarcosine as the acid coupling component. The intermediate and title compound were isolated as a foam and solid respectively (74 and 86%, based on trihydrochloride salt). LC/MS (Method A) 7.46 and 4.72 min, [M+1]$^+$ 539 and 438.

Example 93

Preparation of Compound 181, (S)-1-(2-benzyl-4-(7-methoxy-3H-spiro[benzofuran-2,1'-cyclopentane]-4-yl)piperazin-1-yl)-2-hydroxyethanone

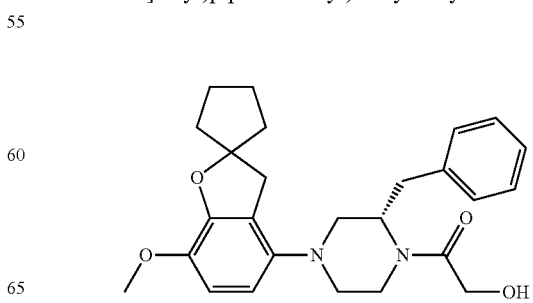

The title compound was prepared by the method outlined for Example 90 using 4-[(S)-3-benzyl-1-piperzinyl]-7-methoxy-spiro[benzofuran-2(3H), 1'-cyclopentane] as the amine component. The intermediate and title compound were isolated as oils (67 and 37%). LC/MS (Method A) 7.60 and 6.68 min, [M+1]$^+$ 527 and 437.

Example 94

Preparation of Compound 182, (S)-1-(2-benzyl-4-(1-cyclopentyl-3-ethyl-1H-indazol-6-yl)piperazin-1-yl)-2-hydroxyethanone

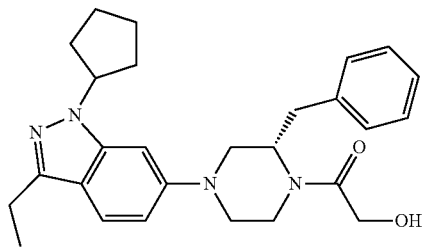 [SMILES: CCc1nn(C2CCCC2)c2cc(N3CCN(C(=O)CO)[C@@H](Cc4ccccc4)C3)ccc12]

The title compound was prepared by the method outlined for Example 90 using 6-((S)-3-Benzyl-piperazin-1-yl)-1-cyclopentyl-3-ethyl-1H-indazole as the amine component. The intermediate and title compound were isolated as oils (73 and 49%). LC/MS (Method A) 8.03 and 7.12 min, [M+1]$^+$ 537 and 447.

Example 95

Preparation of Compound 183, (S)-2-(2-benzyl-4-(3-(cyclopentyloxy)-4-methoxyphenyl)piperazin-1-yl)acetamide

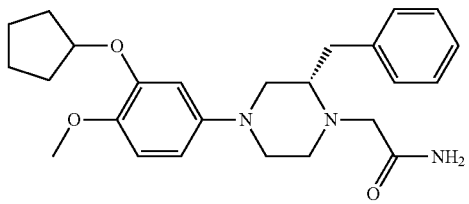 [SMILES: COc1ccc(N2CCN(CC(N)=O)[C@@H](Cc3ccccc3)C2)cc1OC1CCCC1]

A solution of the bishydrochloride salt of (S)-3-Benzyl-1-(3-cyclopentyloxy-4-methoxy-phenyl)-piperazine (110 mg, 0.25 mmol) in THF (2 mL) at room temperature was treated with diisopropylethylamine (165 µL, 1.0 mmol) followed by 2-bromoacetamide (42 mg, 0.3 mmol). The reaction mixture was heated at 50° C. for 8 h and an additional amount of bromide (42 mg, 0.3 mmol) then added. The reaction mixture was then stirred for an additional 16 h at room temperature and evaporated. The crude reaction was then partitioned between EtOAc (3 mL) and a saturated aqueous NaHCO$_3$ solution (3 mL). The organic phase was isolated and further washed with an additional portion of a saturated aqueous NaHCO$_3$ solution (3 mL) and brine (2×3 mL). The organic component was dried over MgSO$_4$, filtered, and evaporated to an oil which was purified by silica gel flash chromatography with 80% EtOAc/hexane then 5% MeOH/EtOAc as eluant to afford the title compound as an oil (23 mg, 22%). LC/MS (Method A) 5.09 min, [M+1]$^+$ 424.

Example 96

Preparation of Compound 184, (S)-methyl 2-(2-benzyl-4-(3-(cyclopentyloxy)-4-methoxyphenyl)piperazin-1-yl)acetate

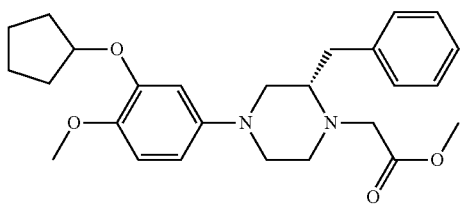 [SMILES: COC(=O)CN1CCN(c2ccc(OC)c(OC3CCCC3)c2)C[C@@H]1Cc1ccccc1]

A solution of the bishydrochloride salt of (S)-3-Benzyl-1-(3-cyclopentyloxy-4-methoxy-phenyl)-piperazine (110 mg, 0.25 mmol) in THF (2 mL) at room temperature was treated with diisopropylethylamine (165 µL, 1.0 mmol) followed by 2-bromo methylacetate (95 µL, 1.0 mmol). The reaction mixture was stirred for 16 h at room temperature and evaporated. The crude reaction was then partitioned between EtOAc (3 mL) and a saturated aqueous NaHCO$_3$ solution (1 mL). The organic phase was isolated and further washed with an additional portion of a saturated aqueous NaHCO$_3$ solution (2×2 mL) and brine (2×2 mL). The organic component was dried over MgSO$_4$, filtered, and evaporated to an oil, which was purified by silica gel flash chromatography with 25% EtOAc/hexane as eluant to afford the title compound as an oil (82 mg, 75%). $^1$H NMR (CDCl$_3$) 7.32-7.18 (m, 5 H), 6.73 (d, J=8.8, 1 H), 6.37 (d, J=2.6, 1H), 6.33 (dd, J=8.6, 2.6, 1 H), 4.62 (m, 1 H), 3.76 (s, 3 H), 3.76 (s, 3 H), 3.58 (s, 2 H), 3.24-3.19 (m, 1 H), 3.14-2.90 (m, 6 H), 2.75-2.66 (m, 2 H), 2.04-1.78 (m, 6 H), 1.58-1.56 (m, 2 H). $^{13}$C NMR 171.2, 148.4, 146.2, 144.6, 139.0, 129.5 (CH), 128.7 (CH), 126.5 (CH) 113.3 (CH), 108.0 (CH), 106.4 (CH), 76.8 (CH), 60.5 (CH), 56.8 (CH$_3$), 55.5 (CH$_2$), 55.0 (CH$_2$), 51.9 (CH$_2$), 51.5 (CH$_3$), 50.2 (CH$_2$), 35.2 (CH$_2$), 33.0 (CH$_2$), 24.2 (CH$_2$). LC/MS (Method A) 5.74 min, [M+1]$^+$ 439.

Example 97

Preparation of Compound 185, (S)-2-(2-benzyl-4-(3-(cyclopentyloxy)-4-methoxyphenyl)piperazin-1-yl)ethanol

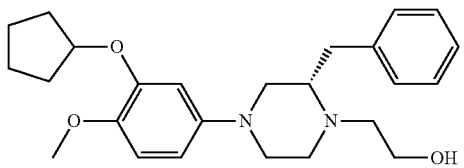 [SMILES: COc1ccc(N2CCN(CCO)[C@@H](Cc3ccccc3)C2)cc1OC1CCCC1]

A solution of [(S)-2-Benzyl-4-(3-cyclopentyloxy-4-methoxy-phenyl)-piperazin-1-yl]-acetic acid methyl ester (110 mg, 0.25 mmol) in THF (2 mL) at room temperature was treated with a 1 N THF solution of lithium aluminum hydride (750 µL, 0.75 mmol) and allowed to stir for 12 h. The reaction mixture was quenched with an aqueous 15% NaOH solution (250 µL) followed by water (250 µL) and THF (2 mL). the reaction mixture was then treated with MgSO$_4$, filtered, and evaporated. The residue was then dissolved in EtOAc (3 mL), retreated with MgSO$_4$, filtered, and evaporated to afford the title compound as an oil (75 mg, 73%). $^1$H NMR (CDCl$_3$) 7.33-7.20 (m, 5 H), 6.75 (d, J=8.6, 1 H), 6.40 (d, J=2.6, 1 H), 6.34 (dd, J=8.6, 2.9, 1 H), 4.67-4.64 (m, 1 H), 3.78 (s, 3 H), 3.76-3.65 (m, 2 H), 3.22-2.74 (m, 12 H), 1.88-1.67 (m, 6 H), 1.62-1.58 (m, 2 H). $^{13}$C NMR 148.5, 146.5, 144.7, 139.6, 129.5 (CH), 128.8 (CH), 126.5 (CH) 113.4 (CH), 108.1 (CH), 106.5 (CH), 80.5 (CH), 61.6 (CH), 58.1 (CH$_2$), 56.9 (CH$_3$), 55.5 (CH$_2$), 53.9 (CH$_2$), 49.7 (CH$_2$), 48.4 (CH$_2$), 33.0 (CH$_2$), 33.0 (CH$_2$), 24.2 (CH$_2$). LC/MS (Method A) 4.81 min, [M+1]$^+$ 411.

Example 98

Preparation of Compound 186, (S)-2-(2-benzyl-4-(3-(cycloperayloxy)-4-methoxyphenyl)piperazin-1-yl)acetic acid

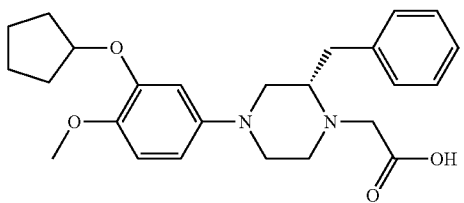 [SMILES: COc1ccc(N2CCN(CC(=O)O)[C@@H](Cc3ccccc3)C2)cc1OC1CCCC1]

A solution of [(S)-2-Benzyl-4-(3-cyclopentyloxy-4-methoxy-phenyl)-piperazin-1-yl]-acetic acid methyl ester (342 mg, 0.78 mmol) in THF (5 mL) at room temperature was treated with an aqueous solution (1 mL) containing lithium hydroxide monohydrate (36 mg, 0.86 mmol). The reaction mixture was allowed to stir for 2 h and then evaporated to a small volume. The reaction mixture was then dissolved in water (5 mL) and the pH adjusted to ~7 with 1 N HCl to precipitate a solid. The precipitate was then triturated with water (2×5 mL) and dried under a stream of nitrogen to afford the title compound as a colorless solid (318 mg, 96%). $^1$H NMR (CDCl$_3$) 7.27-7.18 (m, 5 H), 6.67 (d, J=8.6, 1 H), 6.55 (br s, OH), 6.31-6.24 (m, 2 H), 4.59-4.57 (m, 1 H), 3.89-3.77 (m, 2 H), 3.74 (s, 3 H), 3.51 (br s, 2 H), 3.27 (br s, 3 H), 3.15-3.02 (m, 3 H), 1.79-1.77 (m, 6 H), 1.57-1.43 (m, 2 H). LC/MS (Method A) 5.34 min, [M+1]$^+$ 425.

Example 99

Preparation of Compound 187, (S)-2-(2-benzyl-4-(7-methoxy-3H-spiro[benzofuran-2,1'-cyclopentane]-4-yl)piperazin-1-yl)acetic acid

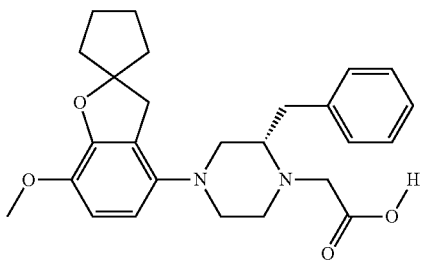 [SMILES: COc1ccc(N2CCN(CC(=O)O)[C@@H](Cc3ccccc3)C2)c2c1OC1(CCCC1)C2]

The title compound was prepared by the methods outlined for Examples 96/98 using 4-[(S)-3-benzyl-1-piperzinyl]-7-methoxy-spiro[benzofuran-2(3H),1'-cyclopentane] as the amine component. The intermediate and title compound were isolated as an oil and tan solid respectively (65 and 98%). LC/MS (Method A) 5.65 and 5.29 min, [M+1]$^+$ 452 and 437.

Example 100

Preparation of Compound 188, (S)-2-(2-benzyl-4-(1-cyclopentyl-3-ethyl-1H-indazol-6-yl)piperazin-1-yl)acetic acid

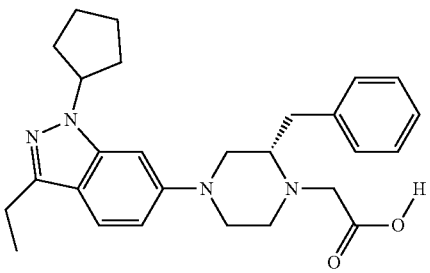 [SMILES: CCc1nn(C2CCCC2)c2cc(N3CCN(CC(=O)O)[C@@H](Cc4ccccc4)C3)ccc12]

The title compound was prepared by the methods outlined for Examples 96/98 using 6-((S)-3-Benzyl-piperazin-1-yl)-1-cyclopentyl-3-ethyl-1H-indazole as the amine component. The intermediate and title compound were isolated as an oil and tan solid respectively (77 and 94%). LC/MS (Method A) 6.37 and 5.65 min, [M+1]$^+$ 462 and 447.

Example 101

Preparation of Compound 189, (S)-2-(2-benzyl-4-(3-(cyclopentyloxy)-4-methoxyphenyl)piperazin-1-yl)-N-methylacetamide

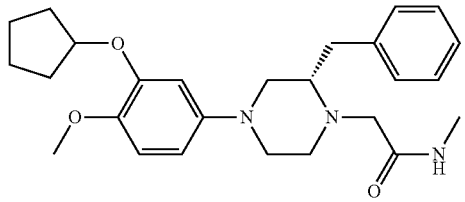 [SMILES: CNC(=O)CN1CCN(c2ccc(OC)c(OC3CCCC3)c2)C[C@@H]1Cc1ccccc1]

A solution of [(S)-2-Benzyl-4-(3-cyclopentyloxy-4-methoxy-phenyl)-piperazin-1-yl]-acetic acid (21.2 mg, 0.05 mmol) in CH$_2$Cl$_2$ (0.5 mL) at 0° C. was treated with catalytic 4-dimethylaminopyridine (DMAP) (~1 mg) and N,N'-dicyclohexylcarbodiimide (DCC) (11.3 mg, 0.055 mmol) followed 5 min later by a 2 M THF solution of methylamine (30 µL, 0.06 mmol). The reaction mixture was stirred for 16 h, evaporated, and purified by silica gel flash chromatography with 50% EtOAc/hexane, then 100% EtOAc, then 5% MeOH/EtOAc as eluant to afford the title compound as an oil (6.4 mg, 29%). LC/MS (Method A) 5.09 min, [M+1]$^+$ 438.

Example 102

Preparation of Compound 190, (S)-2-(2-benzyl-4-(3-(cyclopentyloxy)-4-methoxyphenyl)piperazin-1-yl)acetohydrazide

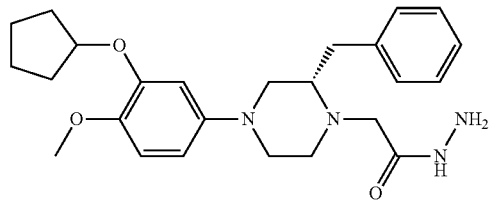 [SMILES: COc1ccc(N2CCN(CC(=O)NN)[C@@H](Cc3ccccc3)C2)cc1OC1CCCC1]

The title compound was prepared by the method outlined for Example 101 using hydrazine hydrate as the amine component. The title compound was isolated as an oil (51%). LC/MS (Method A) 4.84 min, [M+1]$^+$ 439.

Example 103

Preparation of Compound 191, (S)-2-(2-benzyl-4-(3-(cyclopentyloxy)-4-methoxyphenyl)piperazin-1-yl)-N'-methylacetohydrazide

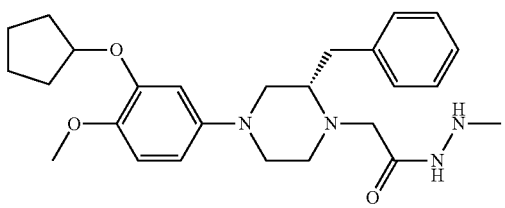 [SMILES: CNNC(=O)CN1CCN(c2ccc(OC)c(OC3CCCC3)c2)C[C@@H]1Cc1ccccc1]

The title compound was prepared by the method outlined for Example 101 using methylhydrazine as the amine component. The title compound was isolated as an oil (73%). LC/MS (Method A) 4.90 min, [M+1]$^+$ 453.

Example 104

Preparation of Compound 192, (S)-2-(2-benzyl-4-(3-(cyclopentyloxy)-4-methoxyphenyl)piperazin-1-yl)-N',N'-dimethylacetohydrazide

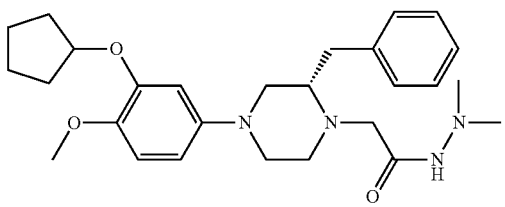 [SMILES: COc1ccc(N2CCN(CC(=O)NN(C)C)[C@@H](Cc3ccccc3)C2)cc1OC1CCCC1]

The title compound was prepared by the method outlined for Example 101 using N,N-dimethylhydrazine as the amine component. The title compound was isolated as an oil (54%). LC/MS (Method A) 5.04 min, [M+1]$^+$ 467.

Example 105

Preparation of Compound 193, (S)-2-(2-benzyl-4-(3-(cyclopentyloxy)-4-methoxyphenyl)piperazin-1-yl)-N-methoxyacetamide

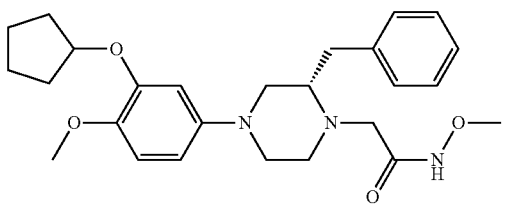

The title compound was prepared by the method outlined for Example 101 using O-methylhydroxylamine hydrochloride (with 1 equivalent of triethylamine to neutralize hydrochloride salt) as the amine component. The title compound was isolated as an oil (57%). LC/MS (Method A) 5.28 min, [M+1]$^+$ 454.

Example 106

Preparation of Compound 194, (S)-2-(2-benzyl-4-(3-(cyclopentyloxy)-4-methoxyphenyl)piperazin-1-yl)-N-ethoxyacetamide

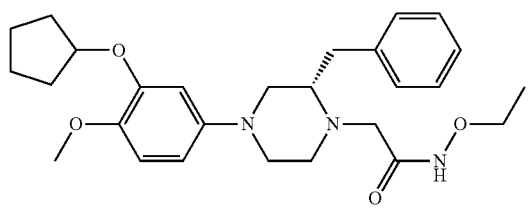 [SMILES: CCONC(=O)CN1CCN(c2ccc(OC)c(OC3CCCC3)c2)C[C@@H]1Cc1ccccc1]

The title compound was prepared by the method outlined for Example 101 using O-ethylhydroxylamine hydrochloride (with 1 equivalent of triethylamine to neutralize hydrochloride salt) as the amine component. The title compound was isolated as an oil (72%). LC/MS (Method A) 5.30 min, [M+1]$^+$ 468.

Example 107

Preparation of Compound 195, (S)-2-(2-benzyl-4-(3-(cyclopentyloxy)-4-methoxyphenyl)piperazin-1-yl)-N-isobutoxyacetamide

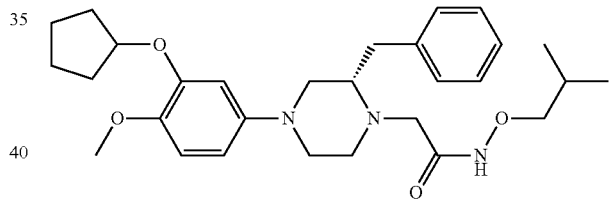

The title compound was prepared by the method outlined for Example 101 using O-isobutylhydroxylamine hydrochloride (with 1 equivalent of triethylamine to neutralize hydrochloride salt) as the amine component. The title compound was isolated as an oil (67%). LC/MS (Method A) 5.78 min, [M+1]$^+$ 496.

Example 108

Preparation of Compound 196, (S)-2-(2-benzyl-4-(3-(cyclopentyloxy)-4-methoxyphenyl)piperazin-1-yl)-N-phenoxyacetamide

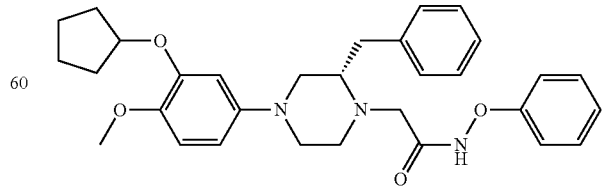

The title compound was prepared by the method outlined for Example 101 using 0-phenylhydroxylamine hydrochloride (with 1 equivalent of triethylamine to neutralize hydrochloride salt) as the amine component. The title compound was isolated as an oil (66%). LC/MS (Method A) 6.13 min, [M+1]+ 516.

Example 109

Preparation of Compound 197, (S)—N-(allyloxy)-2-(2-benzyl-4-(3-(cyclopentyloxy)-4-methoxyphenyl)piperazin-1-yl)acetamide

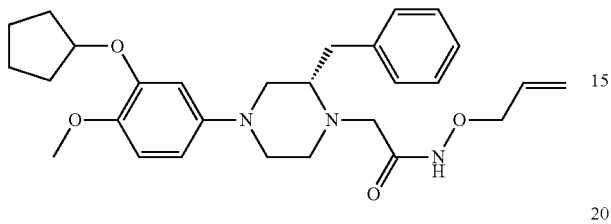

The title compound was prepared by the method outlined for Example 101 using O-allylhydroxylamine hydrochloride (with 1 equivalent of triethylamine to neutralize hydrochloride salt) as the amine component. The title compound was isolated as an oil (71%). LC/MS (Method A) 5.46 min, [M+1]+ 480.

Example 110

Preparation of Compound 198, (S)-2-(2-benzyl-4-(3-(cyclopentyloxy)-4-methoxyphenyl)piperazin-1-yl)-N-(benzyloxy)acetamide

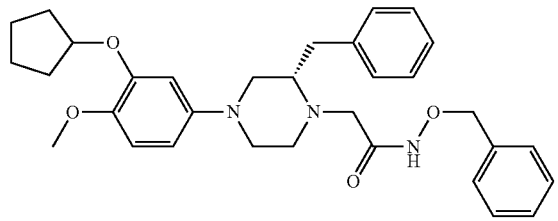 [SMILES: COc1ccc(N2CCN(CC(=O)NOCc3ccccc3)[C@@H](Cc3ccccc3)C2)cc1OC1CCCC1]

The title compound was prepared by the method outlined for Example 101 using O-benzylhydroxylamine hydrochloride (with 1 equivalent of triethylamine to neutralize hydrochloride salt) as the amine component. The title compound was isolated as an oil (72%). LC/MS (Method A) 5.90 min, [M+1]+ 530.

Example 111

Preparation of Compound 199, (S)-2-(2-benzyl-4-(3-(cyclopentyloxy)-4-methoxyphenyl)piperazin-1-yl)-N-hydroxyacetamide

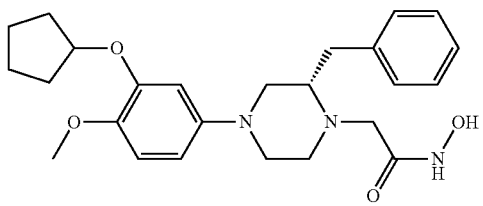 [SMILES: COc1ccc(N2CCN(CC(=O)NO)[C@@H](Cc3ccccc3)C2)cc1OC1CCCC1]

A solution of 2-[(S)-2-Benzyl-4-(3-cyclopentyloxy-4-methoxy-phenyl)-piperazin-1-yl]-N-benzyloxy-acetamide (30 mg, 0.057 mmol) was dissolved in MeOH (10 mL), purged with a stream of nitrogen, treated with 20% Pd/C (100 mg, 50% water content), and hydrogenated under 40 psi pressure of hydrogen for 4 h. The crude reaction mixture was then purged with nitrogen, filtered, and evaporated. The crude product was then dissolved in chloroform (5 mL) and filtered through a nylon syringe filter to remove residual Pd/C. The organic solution was evaporated to afford the title compound as a colorless foam (14 mg, 56%). LC/MS (Method A) 5.03 min, [M+1]+ 440.

Example 112

Preparation of Compound 200, (S)-2-(2-benzyl-4-(8-methoxy-2-(trifluoromethyl)quinolin-5-yl)piperazin-1-yl)acetic acid

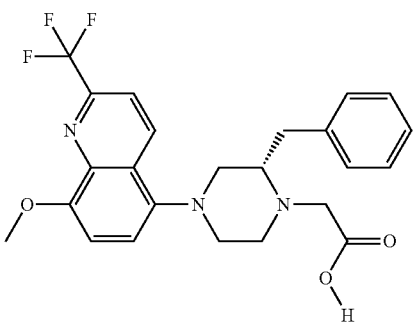 [SMILES: COc1ccc(N2CCN(CC(=O)O)[C@@H](Cc3ccccc3)C2)c2ccc(C(F)(F)F)nc12]

The title compound was prepared by the method outlined for Examples 96/98 using (S)-5-(3-benzylpiperazin-1-yl)-8-methoxy-2-(trifluoromethyl)quinoline as the amine component. The intermediate [(S)-2-Benzyl-4-(8-methoxy-2-trifluoromethyl-quinolin-5-yl)-piperazin-1-yl]-acetic acid ethyl ester and title compound were isolated as yellow solids (88 and 98%). LC/MS (Method A) 5.58 min, [M+1]+ 460.

Example 113

Preparation of Compound 201, (S)-1-(2-benzyl-4-(8-methoxy-2-(trifluoromethyl)quinolin-5-yl)piperazin-1-yl)-2-hydroxyethanone

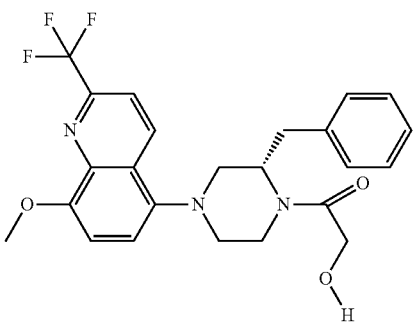 [SMILES: COc1ccc(N2CCN(C(=O)CO)[C@@H](Cc3ccccc3)C2)c2ccc(C(F)(F)F)nc12]

The title compound was prepared by the method outlined for Example 90 using (S)-5-(3-benzylpiperazin-1-yl)-8-methoxy-2-(trifluoromethyl)quinoline as the amine component. The title compound was isolated as a yellow solid (5% for 2 steps). LC/MS (Method A) 6.61 min, [M+1]⁺ 460.

Example 114

Preparation of Compound 202, (S)—N-(allyloxy)-2-(2-benzyl-4-(8-methoxy-2-(trifluoromethyl)quinolin-5-yl)piperazin-1-yl)acetamide

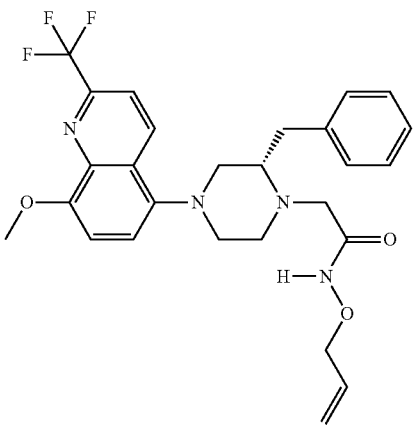 [SMILES: C=CCONC(=O)CN1CCN(c2ccc(OC)c3nc(C(F)(F)F)ccc23)C[C@@H]1Cc1ccccc1]

A solution of (S)-2-(2-benzyl-4-(8-methoxy-2-(trifluoromethyl)quinolin-5-yl)piperazin-1-yl)acetic acid (115 mg, 0.25 mmol) in CH₂Cl₂ (2 mL) at 0-5° C. was treated with O-allylhydroxylamine hydrochloride (31 mg, 0.28 mmol), triethylamine (38 µL, 0.28 mmol), catalytic DMAP, and finally DCC (57 mg, 0.28 mmol). The reaction mixture was stirred for 3 h after which time the mixture was treated with EtOAc (5 mL), filtered and evaporated. The residue was purified by silica gel flash chromatography with 50% EtOAc/hexane, then 100% EtOAc, as eluant to afford the title compound as an oil (88 mg, 68%). LC/MS (Method A) 5.66 min, [M+1]⁺ 515.

Example 115

Preparation of Compound 203, (S)-2-(2-benzyl-4-(8-methoxy-2-(trifluoromethyl)quinolin-5-yl)piperazin-1-yl)-N-hydroxyacetamide

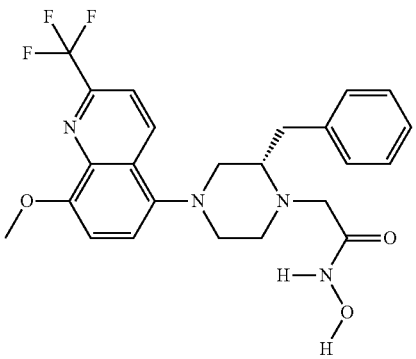 [SMILES: COc1ccc(N2CCN(CC(=O)NO)[C@@H](Cc3ccccc3)C2)c2ccc(C(F)(F)F)nc12]

A solution of (S)-2-(2-benzyl-4-(8-methoxy-2-(trifluoromethyl)quinolin-5-yl)piperazin-1-yl)acetic acid (184 mg, 0.40 mmol) in CH₂Cl₂ (4 mL) at 0-5° C. was treated with O-(tetrahydro-2H-pyran-2-yl)hydroxylamine (49 mg, 0.42 mmol), catalytic DMAP, and finally DCC (87 mg, 0.42 mmol). The reaction mixture was stirred for 3 h after which time the mixture was treated with EtOAc (5 mL), filtered and evaporated. The residue was purified by silica gel flash chromatography with 100% EtOAc, as eluant to afford intermediate 24(S)-2-benzyl-4-(8-methoxy-2-(trifluoromethyl)quinolin-5-yl)piperazin-1-yl)-N-(tetrahydro-2H-pyran-2-yloxy)acetamide as an oil (166 mg, 74%). LC/MS (Method A) 5.76 min, [M+1]⁺ 559.

The intermediate 24(S)-2-benzyl-4-(8-methoxy-2-(trifluoromethyl)quinolin-5-yl)piperazin-1-yl)-N-(tetrahydro-2H-pyran-2-yloxy)acetamide (130 mg, 0.23 mmol) was dissolved in MeOH (5 mL) and water (1 mL) and treated with a 4 N HCl solution in dioxane (250 mL). The resulting mixture was allowed to stir for 16 h after which time the reaction was evaporated to a small volume and partitioned between EtOAc (20 mL) and water (10 mL). The solution was adjusted to pH~7 with a saturated aqueous NaHCO₃ solution and the organic portion further washed with brine (2×5 mL), dried over Na₂SO₄, filtered, and evaporated to afford the title compound as a yellow solid (108 mg, 97%). LC/MS (Method A) 5.16 min, [M+1]⁺ 475.

Example 116

Preparation of Compound 204, (S)-2-(2-benzyl-4-(8-methoxy-2-(trifluoromethyl)quinolin-5-yl)piperazin-1-yl)acetamide

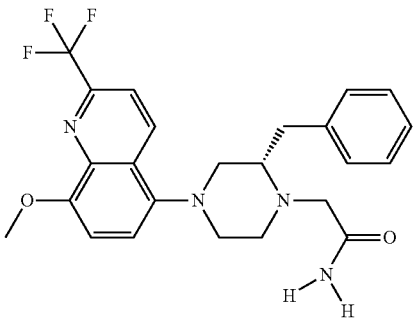 [SMILES: COc1ccc(N2CCN(CC(N)=O)[C@@H](Cc3ccccc3)C2)c2ccc(C(F)(F)F)nc12]

[(S)-2-Benzyl-4-(8-methoxy-2-trifluoromethyl-quinolin-5-yl)-piperazin-1-yl]-acetic acid ethyl ester in a 7 N solution of ammonia in MeOH (10 mL) was treated with catalytic amount of sodium cyanide and allowed to stir for 24 h. The reaction mixture was then evaporated, washed with water and air dried to afford the title compound as a yellow solid (180 mg, 79%). LC/MS (Method B) 2.57 min, [M+1]⁺ 459.

Example 117

Preparation of Compound 205, (S)-2-(2-benzyl-4-(8-methoxy-2-(trifluoromethyl)quinolin-5-yl)piperazin-1-yl)-N-methylacetamide

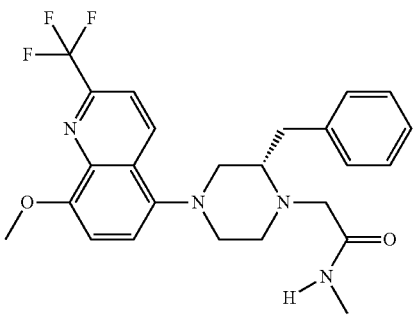 [SMILES: CNC(=O)CN1CCN(c2ccc(OC)c3nc(C(F)(F)F)ccc23)C[C@@H]1Cc1ccccc1]

A solution of [(S)-2-Benzyl-4-(8-methoxy-2-trifluoromethyl-quinolin-5-yl)-piperazin-1-yl]-acetic acid ethyl ester in a 33% methylamine solution in EtOH (5 mL) was treated with catalytic amount of sodium cyanide and allowed to stir for 48 h. The reaction mixture was then evaporated, washed with water and air dried to afford the title compound as a yellow solid (68 mg, 63%). LC/MS (Method B) 2.82 min, [M+1]$^+$ 472.

Example 118

Preparation of Compound 206, (S)-2-(2-benzyl-4-(8-methoxy-2-(trifluoromethyl)quinolin-5-yl)piperazin-1-yl)-N-ethylacetamide

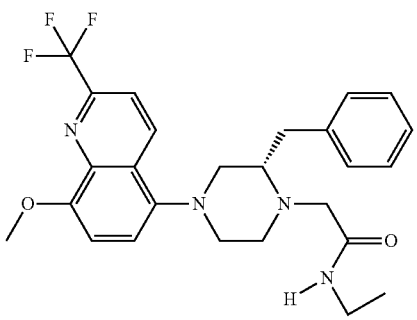 [SMILES: CCNC(=O)CN1CCN(c2ccc(OC)c3nc(C(F)(F)F)ccc23)C[C@@H]1Cc1ccccc1]

The title compound was prepared by the method outlined for Example 117 using [(S)-2-Benzyl-4-(8-methoxy-2-trifluoromethyl-quinolin-5-yl)-piperazin-1-yl]-acetic acid ethyl ester and a 2 M THF solution of ethylamine. The title compound was isolated as a yellow solid (68 mg, 63%). LC/MS (Method B) 2.82 min, [M+1]$^+$ 486.

Example 119

Preparation of Compound 207, (S)-2-(2-(4-fluorobenzyl)-4-(8-methoxy-2-(trifluoromethyl)quinolin-5-yl)piperazin-1-yl)acetic acid

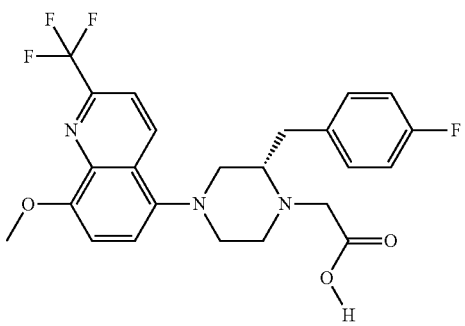 [SMILES: COc1ccc(N2CCN(CC(=O)O)[C@@H](Cc3ccc(F)cc3)C2)c2ccc(C(F)(F)F)nc12]

The title compound was prepared by the method outlined for Example 96/98 using (S)-5-(3-(4-fluorobenzyl)piperazin-1-yl)-8-methoxy-2-(trifluoromethyl)quinoline as the amine component. The title compound was isolated as a yellow solid (74%). LC/MS (Method B) 2.90 min, [M+1]$^+$ 478.

Example 120

Preparation of Compound 208, (S)-2-(2-(4-fluorobenzyl)-4-(8-methoxy-2-(trifluoromethyl)quinolin-5-yl)piperazin-1-yl)acetamide

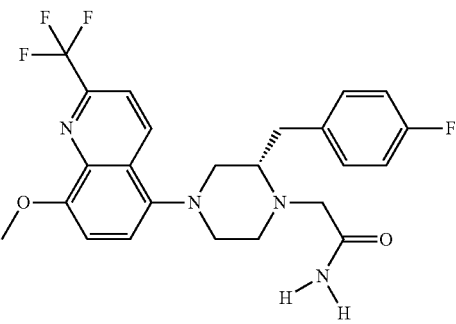 [SMILES: COc1ccc(N2CCN(CC(N)=O)[C@@H](Cc3ccc(F)cc3)C2)c2ccc(C(F)(F)F)nc12]

The title compound was prepared by the method outlined for Example 116 using (S)-2-(2-benzyl-4-(8-methoxy-2-(trifluoromethyl)quinolin-5-yl)piperazin-1-yl)acetic acid. The title compound was isolated as a yellow solid (77%). LC/MS (Method B) 2.67 min, [M+1]$^+$ 477.

Example 121

Preparation of Compound 209, (S)-4-(2-benzyl-4-(3-(cyclopentyloxy)-4-methoxyphenyl)piperazin-1-yl)-4-oxobutanoic acid

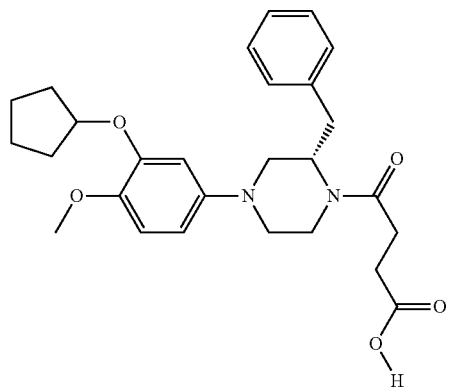 [SMILES: COc1ccc(N2CCN(C(=O)CCC(=O)O)[C@@H](Cc3ccccc3)C2)cc1OC1CCCC1]

A solution of (S)-3-Benzyl-1-(3-cyclopentyloxy-4-methoxy-phenyl)-piperazine (550 mg, 1.5 mmol) in THF (10 mL) was treated with triethylamine (231 μL, 1.65 mmol) followed by ethylsuccinyl chloride (223 μL, 1.58 mmol). The reaction mixture was stirred for 3 h then partitioned between EtOAc (10 mL) and a saturated aqueous solution of NaHCO$_3$ (10 mL). The organic extract was dried over MgSO$_4$, filtered, and evaporated to an oil, which was purified by silica gel flash chromatography with 25%, 30%, then 40% EtOAc/hexanes as eluant to afford intermediate (S)-ethyl 4-(2-benzyl-4-(3-(cyclopentyloxy)-4-methoxyphenyl)piperazin-1-yl)-4-oxobutanoate as a yellow liquid (690 mg, 93%). LC/MS (Method A) 7.49 min, [M+1]$^+$ 495.

The intermediate (S)-ethyl 4-(2-benzyl-4-(3-(cyclopentyloxy)-4-methoxyphenyl)piperazin-1-yl)-4-oxobutanoate (124 mg, 0.25 mmol) was dissolved in THF (4 mL) and treated with LiOH (12 mg, 0.5 mmol) in water (1 mL) and stirred for 24 h. The reaction mixture was evaporated to half-volume, diluted with water (5 mL) and the pH adjusted to pH~7 with a 1 N solution of hydrochloric acid. The resulting precipitate was filtered with the aid of water and air dried to afford the title compound as a solid (82 mg, 70%). LC/MS (Method A) 6.72 min, [M+1]$^+$ 467.

Example 122

Preparation of Compound 210, (S)-3-(2-benzyl-4-(3-(cyclopentyloxy)-4-methoxyphenyl)piperazin-1-yl)propanoic acid

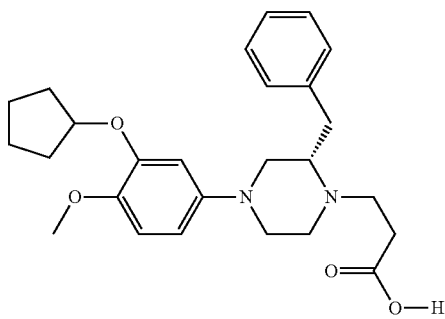 [SMILES: COc1ccc(N2CCN(CCC(=O)O)[C@@H](Cc3ccccc3)C2)cc1OC1CCCC1]

A solution of (S)-3-Benzyl-1-(3-cyclopentyloxy-4-methoxy-phenyl)-piperazine (366 mg, 1.0 mmol) in acetonitrile (6 mL) was treated with triethylamine (699 μL, 5.0 mmol) followed by ethyl bromopropionate (640 μL, 5.0 mmol). The sealed reaction mixture was stirred at 70° C. for 20 h then evaporated and the residue partitioned between EtOAc (10 mL) and a saturated aqueous solution of NaHCO$_3$ (10 mL). The organic extract was dried over MgSO$_4$, filtered, and evaporated to an oil, which was purified by silica gel flash chromatography with 30%, then 50% EtOAc/hexanes as eluant to afford intermediate (S)-ethyl 3-(2-benzyl-4-(3-(cyclopentyloxy)-4-methoxyphenyl)piperazin-1-yl)-3-oxopropanoate as a clear oil (329 mg, 71%). LC/MS (Method A) 5.62 min, [M+1]$^+$ 467.

The intermediate (S)-ethyl 3-(2-benzyl-4-(3-(cyclopentyloxy)-4-methoxyphenyl) piperazin-1-yl)-3-oxopropanoate (117 mg, 0.25 mmol) was dissolved in THF (4 mL) and treated with LiOH (12 mg, 0.5 mmol) in water (1 mL) and stirred for 24 h. The reaction mixture was evaporated to half-volume, diluted with water (5 mL) and the pH adjusted to pH~7 with a 1 N solution of hydrochloric acid. The resulting precipitate was filtered with the aid of water and air dried to afford the title compound as a solid (97 mg, 88%). LC/MS (Method A) 5.31 min, [M+1]$^+$ 439.

Example 123

Preparation of Compound 211, (S)-3-(2-benzyl-4-(3-(cyclopentyloxy)-4-methoxyphenyl)piperazin-1-yl)propan-1-ol

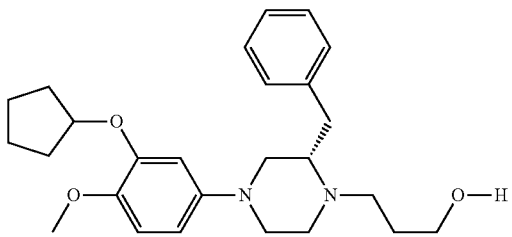 [SMILES: COc1ccc(N2CCN(CCCO)[C@@H](Cc3ccccc3)C2)cc1OC1CCCC1]

A solution of intermediate (S)-ethyl 3-(2-benzyl-4-(3-(cyclopentyloxy)-4-methoxyphenyl) piperazin-1-yl)-3-oxopropanoate (117 mg, 0.25 mmol) in THF (2 mL) was treated with a 1 N THF solution of lithium aluminum hydride (500 μL, 0.5 mmol) and stirred for 1 h. After this time the reaction mixture was quenched with ice water (250 μL) followed by a 5% NaOH solution (500 uL) and solid MgSO$_4$. The material was dissolved in EtOAc, filtered and evaporated to afford the title compound as a burgundy colored oil (103 mg, 97%). LC/MS (Method A) 5.15 min, [M+1]$^+$ 425.

Example 124

Preparation of Compound 212, (S)-4-(2-benzyl-4-(3-(cyclopentyloxy)-4-methoxyphenyl)piperazin-1-yl)butan-1-ol

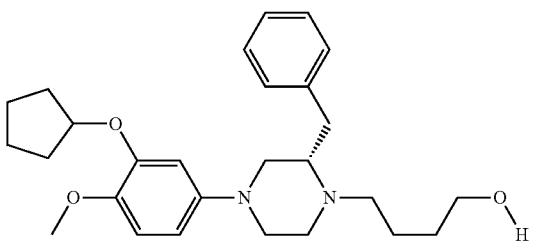 [SMILES: COc1ccc(N2CCN(CCCCO)[C@@H](Cc3ccccc3)C2)cc1OC1CCCC1]

A solution of intermediate (S)-ethyl 4-(2-benzyl-4-(3-(cyclopentyloxy)-4-methoxyphenyl)piperazin-1-yl)-4-oxobutanoate (124 mg, 0.25 mmol) in THF (2 mL) was treated with a 1 N THF solution of lithium aluminum hydride (1.0 mL, 1.0 mmol) and stirred for 1 h. After this time the reaction mixture was quenched with ice water (500 μL) followed by a 5% NaOH solution (500 μL) and solid MgSO$_4$. The material was dissolved in EtOAc, filtered and evaporated to afford the title compound as a burgundy colored oil (77 mg, 70%). LC/MS (Method A) 5.22 min, [M+1]$^+$ 439.

Example 125

Preparation of Compound 213, (S)-1-(2-benzyl-4-(3-(cyclopentyloxy)-4-methoxyphenyl)piperazin-1-yl)-4-hydroxybutan-1-one

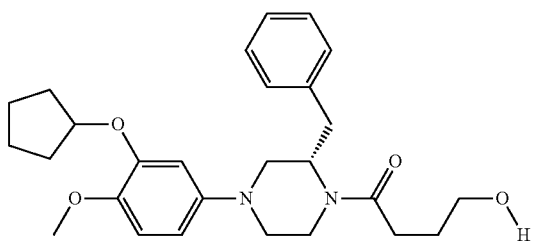 [SMILES: COc1ccc(N2CCN(C(=O)CCCO)[C@@H](Cc3ccccc3)C2)cc1OC1CCCC1]

A solution of ester intermediate (S)-ethyl 4-(2-benzyl-4-(3-(cyclopentyloxy)-4-methoxyphenyl)piperazin-1-yl)-4-oxobutanoate (247 mg, 0.50 mmol) and sodium borohydride (47 mg, 1.3 mmol) in THF (4 mL) was brought to reflux and MeOH (242 µL, 6.0 mmol) added drop-wise over a 1 h period. The reaction mixture was allowed to heat at reflux for a further 16 h and then quenched with a few drops of a 1 N HCl solution. The reaction was partitioned between EtOAc (20 mL) and a saturated aqueous solution of NaHCO$_3$ (10 mL). The organic extract was further washed with brine then dried over MgSO$_4$, filtered, and evaporated to an oil that was purified by silica gel flash chromatography with 30%, then 40% EtOAc/hexanes as eluant to afford the title compound as an oil (67 mg, 30%). LC/MS (Method A) 6.66 min, [M+1]$^+$ 453.

Example 126

Preparation of Compound 214, (S)-4-(2-benzyl-4-(3-(cyclopentyloxy)-4-methoxyphenyl)piperazin-1-yl)butanoic acid

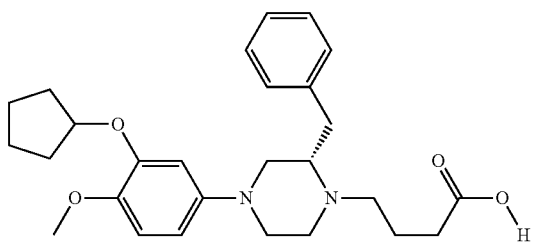 [SMILES: COc1ccc(N2CCN(CCCC(=O)O)[C@@H](Cc3ccccc3)C2)cc1OC1CCCC1]

The title compound was prepared by the method outlined for Example 122 using ethyl bromobutyrate as the alkyl halide. Intermediate (S)-ethyl 4-(2-benzyl-4-(3-(cyclopentyloxy)-4-methoxyphenyl)piperazin-1-yl)butanoate was purified by silica gel flash chromatography with 30%, then 45% EtOAc/hexanes as eluant to afford an oil (47 mg, 39%). LC/MS (Method A) 5.58 min, [M+1]$^+$ 481. The title compound was isolated as a colorless solid (30 mg, 68%). LC/MS (Method A) 5.39 min, [M+1]$^+$ 453.

Example 127

Preparation of Compound 215, (S)-3-(2-benzyl-4-(3-(cyclopentyloxy)-4-methoxyphenyl)piperazin-1-yl)-3-oxopropanoic acid

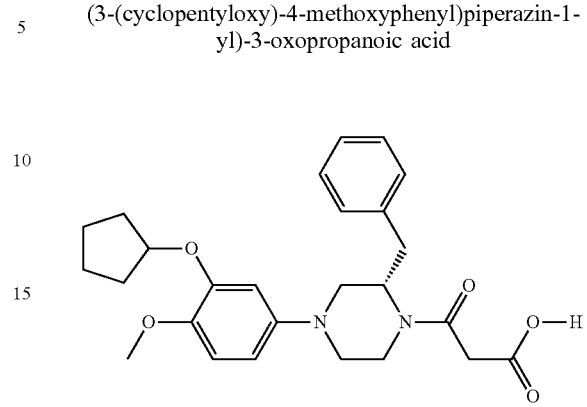

The title compound was prepared by the method outlined for Example 121 using ethyl malonylchloride as the acyl halide. The intermediate (S)-ethyl 3-(2-benzyl-4-(3-(cyclopentyloxy)-4-methoxyphenyl)piperazin-1-yl)-3-oxopropanoate was purified by silica gel flash chromatography with 40%, then 50% EtOAc/hexanes as eluant to afford an oil (210 mg, 88%). LC/MS (Method A) 7.37 min, [M+1]$^+$ 481. (S)-ethyl 3-(2-benzyl-4-(3-(cyclopentyloxy)-4-methoxyphenyl)piperazin-1-yl)-3-oxopropanoate (96 mg, 0.20 mmol) was then hydrolyzed to afford the title compound as a colorless solid (30 mg, 68%). LC/MS (Method A) 5.39 min, [M+1]$^+$ 453.

Example 128

Preparation of Compound 216, (S)-1-(2-benzyl-4-(3-(cyclopentyloxy)-4-methoxyphenyl)piperazin-1-yl)-3-hydroxypropan-1-one

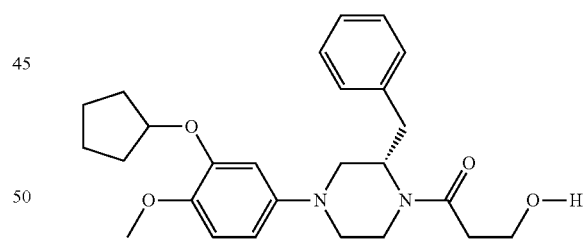

A solution of ((S)-ethyl 3-(2-benzyl-4-(3-(cyclopentyloxy)-4-methoxyphenyl)piperazin-1-yl)-3-oxopropanoate (96 mg, 0.20 mmol) and sodium borohydride (30 mg, 0.80 mmol) in THF (4 mL) was brought to reflux and MeOH (242 µL, 6.0 mmol) added drop-wise over a 1 h period. The reaction mixture was allowed to heat at reflux for an additional 16 h and then quenched with a few drops of a 1 N HCl solution. The reaction was partitioned between EtOAc (10 mL) and a saturated aqueous solution of NaHCO$_3$ (10 mL). The organic extract was further washed with brine then dried over MgSO$_4$, filtered, and evaporated to an oil that was purified by silica gel flash chromatography with EtOAc as eluant to afford the title compound as an oil (51 mg, 58%). LC/MS (Method A) 4.34 min, [M+1]$^+$ 439.

Example 129

Preparation of Compound 217, (S)-3-(2-benzyl-4-(3-(cyclopentyloxy)-4-methoxyphenyl)piperazin-1-yl)-3-oxopropanamide

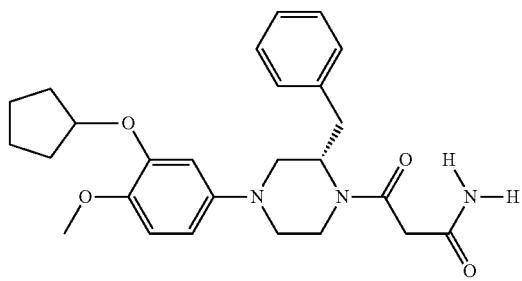

A solution of (S)-ethyl 3-(2-benzyl-4-(3-(cyclopentyloxy)-4-methoxyphenyl)piperazin-1-yl)-3-oxopropanoate (120 mg, 0.25 mmol) in a 7 N solution of ammonia in MeOH (10 mL) was treated with catalytic amount of sodium cyanide and allowed to stir for 24 h. The reaction mixture was then evaporated, washed with water and air dried to afford the title compound as a solid (97 mg, 86%). LC/MS (Method B) 3.12 min, [M+1]$^+$ 452.

Example 130

Preparation of Compound 218, (S)-3-(2-benzyl-4-(3-(cyclopentyloxy)-4-methoxyphenyl)piperazin-1-yl)-N-methyl-3-oxopropanamide

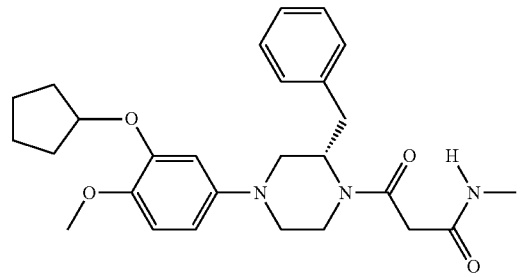

A solution of (S)-ethyl 3-(2-benzyl-4-(3-(cyclopentyloxy)-4-methoxyphenyl)piperazin-1-yl)-3-oxopropanoate (120 mg, 0.25 mmol) in a 33% methylamine solution in EtOH (5 mL) was treated with catalytic amount of sodium cyanide and allowed to stir for 48 h. The reaction mixture was then evaporated, washed with water and air dried to afford the title compound as a pale yellow foam (102 mg, 87%). LC/MS (Method B) 3.34 min, [M+1]$^+$ 366.

Example 131

Preparation of Compound 219, (S)-1-((S)-2-benzyl-4-(3-(cyclopentyloxy)-4-methoxyphenyl)piperazin-1-yl)-3-hydroxybutan-1-one

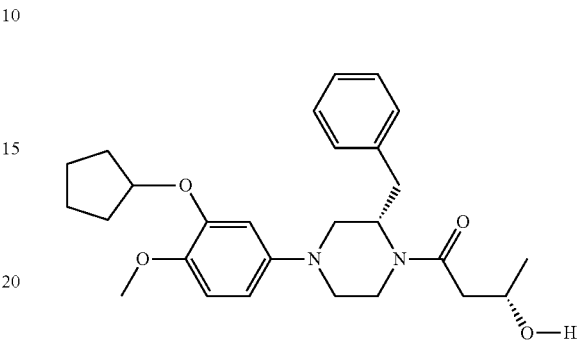

A solution of (S)-3-Benzyl-1-(3-cyclopentyloxy-4-methoxy-phenyl)-piperazine (92 mg, 0.25 mmol) in CH$_2$Cl$_2$ (1 mL) at 0-5° C. was treated with (S)-3-hydroxybutanoic acid (29 mg, 0.28 mmol), a catalytic amount of DMAP, and DCC (57 mg, 0.28 mmol). The reaction mixture was allowed to warm to room temperature and stir 6 h. After this time the reaction mixture was evaporated and the residue purified by silica gel flash chromatography with 50% EtOAc/hexanes as eluant to afford the title compound as an oil (64 mg, 57%). LC/MS (Method B) 3.53 min, [M+1]$^+$ 453.

Example 132

Preparation of Compound 220, (R)-1-((S)-2-benzyl-4-(3-(cyclopentyloxy)-4-methoxyphenyl)piperazin-1-yl)-3-hydroxybutan-1-one

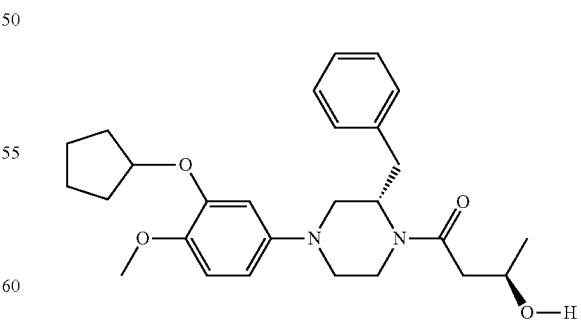

The title compound was prepared by the method outlined for Example 131 using (S)-3-hydroxybutanoic acid and was isolated as an oil (61 mg, 54%). LC/MS (Method B) 3.55 min, [M+1]$^+$ 453.

Example 133

Preparation of Compound 221, (S)-1-(2-benzyl-4-(3-(cyclopentyloxy)-4-methoxyphenyl)piperazin-1-yl)-3-hydroxy-3-methylbutan-1-one

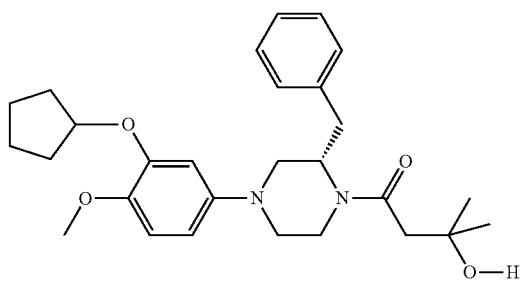

The title compound was prepared by the method outlined for Example 131 using the 3-hydroxy-3-methylbutyric acid and was isolated as an oil (42 mg, 36%). LC/MS (Method B) 3.84 min, [M+1]$^+$ 467.

Example 134

Preparation of Compound 222, (S)-2-(2-benzyl-4-(3-(cyclopentyloxy)-4-methoxyphenyl)piperazin-1-yl)-2-oxoacetic acid

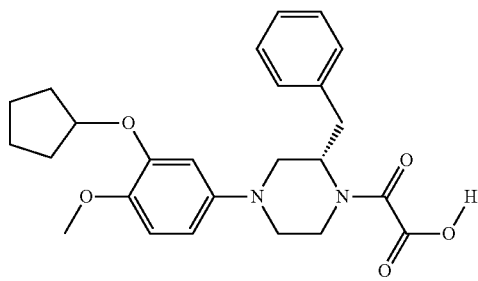

The title compound was prepared by the method outlined for Example 121 using ethyl chlorooxoacetate to afford intermediate (S)-ethyl 2-(2-benzyl-4-(3-(cyclopentyloxy)-4-methoxyphenyl)piperazin-1-yl)-2-oxoacetate (108 mg, 92%). LC/MS (Method B) 4.13 min, [M+1]$^+$ 467. The intermediate was then hydrolyzed with LiOH as described in Example 121 to afford the title compound as a colorless solid (54 mg, 57%). LC/MS (Method B) 3.68 min, [M+1]$^+$ 439.

Example 135

Preparation of Compound 223, (S)-4-(2-benzyl-4-(3-(cyclopentyloxy)-4-methoxyphenyl)piperazin-1-yl)-4-oxobutanamide

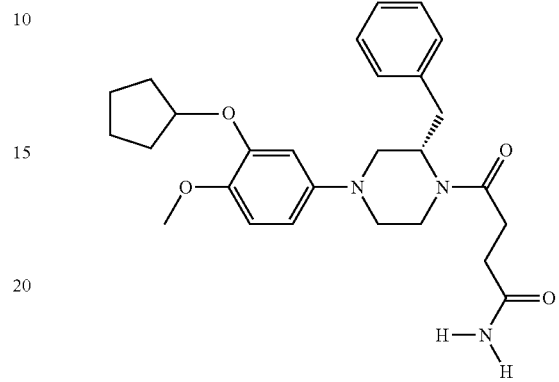

A solution of (S)-ethyl 4-(2-benzyl-4-(3-(cyclopentyloxy)-4-methoxyphenyl)piperazin-1-yl)-4-oxobutanoate (124 mg, 0.25 mmol) in a 7 N ammonia solution in MeOH (5 mL) was treated with catalytic amount of sodium cyanide and allowed to stir for 48 h. The reaction mixture was then evaporated, washed with water and air dried to afford the title compound as a colorless foam (103 mg, 86%). LC/MS (Method B) 3.24 min, [M+1]$^+$ 466.

Example 136

Preparation of Compound 224, (S)-4-(2-benzyl-4-(3-(cyclopentyloxy)-4-methoxyphenyl)piperazin-1-yl)-N-methyl-4-oxobutanamide

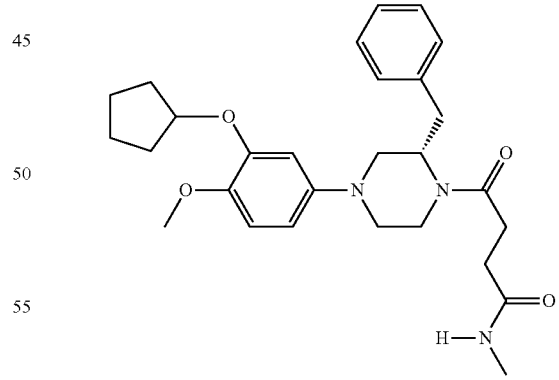

A solution of (S)-ethyl 4-(2-benzyl-4-(3-(cyclopentyloxy)-4-methoxyphenyl)piperazin-1-yl)-4-oxobutanoate (124 mg, 0.25 mmol) in a 33% methylamine solution in EtOH (5 mL) was treated with catalytic amount of sodium cyanide and allowed to heat at 50° C. for 3 days. The reaction mixture was then evaporated, washed with water and air dried to afford the title compound as a colorless foam (100 mg, 83%). LC/MS (Method B) 3.23 min, [M+1]$^+$ 480.

Example 137

Preparation of Compound 225, (S)-2-(2-benzyl-4-(3-(cyclopentyloxy)-4-methoxyphenyl)piperazin-1-yl)-2-oxoacetamide

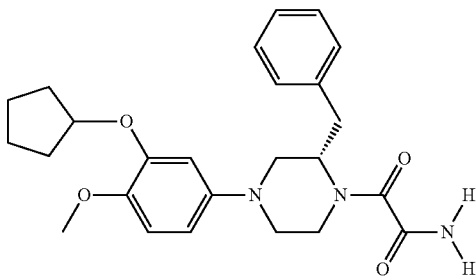

A solution of (S)-ethyl 2-(2-benzyl-4-(3-(cyclopentyloxy)-4-methoxyphenyl)piperazin-1-yl)-2-oxoacetate (245 mg, 0.525 mmol) in a 7 N ammonia solution in MeOH (10 mL) was treated with catalytic amount of sodium cyanide and allowed to stir for 48 h. The reaction mixture was then evaporated, washed with water and air dried to afford a residue then purified by silica gel flash chromatography with 50% then 75% EtOAc/hexanes as eluant to afford the title compound as colorless foam (180 mg, 78%). LC/MS (Method B) 3.31 min, [M+1]$^+$ 438.

Example 138

Preparation of Compound 226, (S)-2-(2-benzyl-4-(3-(cyclopentyloxy)-4-methoxyphenyl)piperazin-1-yl)-N-methyl-2-oxoacetamide

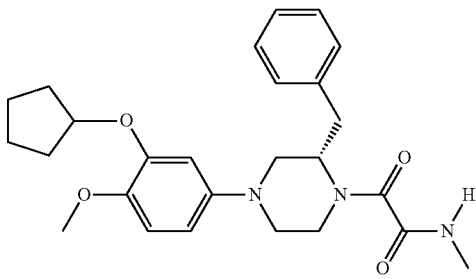

A solution of (S)-ethyl 2-(2-benzyl-4-(3-(cyclopentyloxy)-4-methoxyphenyl)piperazin-1-yl)-2-oxoacetate (117 mg, 0.25 mmol) in 33% methylamine solution in EtOH (5 mL) was treated with catalytic amount of sodium cyanide and allowed to heat in a sealed tube at 80° C. for 24 h. The reaction mixture was then evaporated, washed with water and air dried to afford a residue then purified by silica gel flash chromatography with 50% EtOAc/hexanes as eluant to afford the title compound as colorless foam (90 mg, 80%). LC/MS (Method B) 3.58 min, [M+1]$^+$ 452.

Example 139

Preparation of Compound 227, (1R,3S)-3-((S)-2-benzyl-4-(3-(cyclopentyloxy)-4-methoxyphenyl)piperazine-1-carbonyl)cyclopentanecarboxylic acid

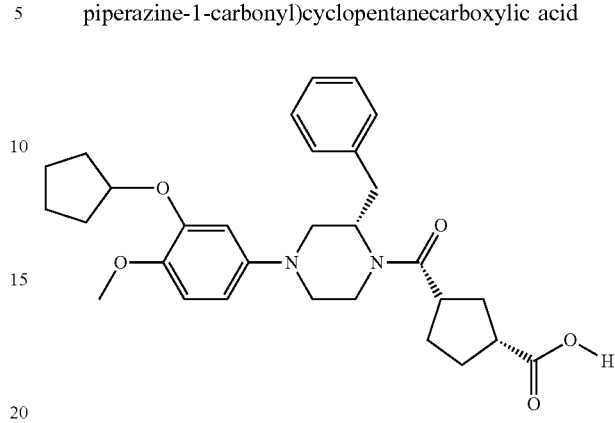

A solution of (S)-3-Benzyl-1-(3-cyclopentyloxy-4-methoxy-phenyl)-piperazine (92 mg, 0.25 mmol) in CH$_2$Cl$_2$ (1 mL) at 0-5° C. was treated with a catalytic amount of DMAP and (1S,3R)-3-(methoxycarbonyl)cyclopentanecarboxylic acid (47 mg, 0.28 mmol) followed by DCC (57 mg, 0.28 mmol). The reaction mixture was allowed to warm to room temperature and stir 1 h. After this time the reaction mixture was evaporated and the residue purified by silica gel flash chromatography with 30% then 50% EtOAc/hexanes as eluant to afford intermediate (1R,3S)-3-[(S)-2-Benzyl-4-(3-cyclopentyloxy-4-methoxy-phenyl)-piperazine-1-carbonyl]-cyclopentanecarboxylic acid methyl ester as an oil (109 mg, 84%). LC/MS (Method B) 4.14 min, [M+1]$^+$ 521. The intermediate (1R,3S)-3-[(S)-2-Benzyl-4-(3-cyclopentyloxy-4-methoxy-phenyl)-piperazine-1-carbonyl]-cyclopentanecarboxylic acid methyl ester was then hydrolyzed with LiOH as described in Example 121, to afford the title compound as a colorless solid (85 mg, 80%) LC/MS (Method B) 3.68 min, [M+1]$^+$ 507.

Example 140

Preparation of Compound 228, (R)-2-amino-1-((S)-2-benzyl-4-(3-(cyclopentyloxy)-4-methoxyphenyl)piperazin-1-yl)-3-hydroxy-3-methylbutan-1-one

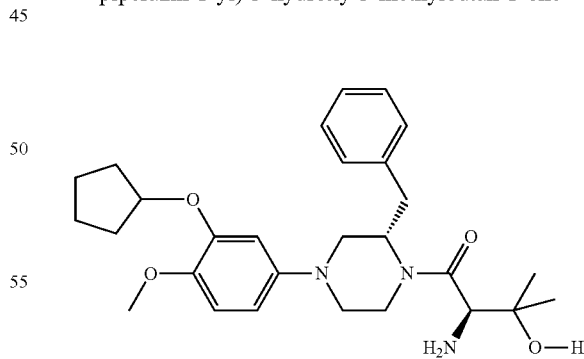

A solution of (S)-3-Benzyl-1-(3-cyclopentyloxy-4-methoxy-phenyl)-piperazine (92 mg, 0.25 mmol) in CH$_2$Cl$_2$ (1 mL) and DMF (500 µL) at 0-5° C. was treated with diisopropylethylamine (87 µL, 0.50 mmol), (R)-2-(tert-butoxycarbonylamino)-3-hydroxy-3-methylbutanoic acid (64 mg, 0.28 mmol), followed by HATU (105 mg, 0.28). The reaction mixture was allowed to warm to room temperature and stir for 3 h. After this time the reaction mixture was evaporated and the residue purified by silica gel flash chromatography with 30% then 40% EtOAc/hexanes as eluant to afford the intermediate {(R)-1-[(S)-2-Benzyl-4-(3-cyclopentyloxy-4-methoxy-phenyl)-piperazine-1-carbonyl]-2-hydroxy-2-methyl-propyl}-carbamic acid tert-butyl ester as an oil (100 mg, 69%). LC/MS (Method B) 4.36 min, [M+1]+ 582.

A solution of {(R)-1-[(S)-2-Benzyl-4-(3-cyclopentyloxy-4-methoxy-phenyl)-piperazine-1-carbonyl]-2-hydroxy-2-methyl-propyl}-carbamic acid tert-butyl ester intermediate in CH$_2$Cl$_2$ (1 mL) at 0-5° C. was treated with trifluoroacetic acid and stirred at room temperature for 8 hr. After this time the reaction mixture was evaporated and the residue partitioned between EtOAc (5 ml) and a saturated aqueous solution of NaHCO$_3$ (5 mL). The organic extract was further washed with brine then dried over MgSO$_4$, filtered, and evaporated to afford the title compound as an oil (69 mg, 83%). LC/MS (Method B) 2.97 min, [M+1]+ 482.

Example 141

Preparation of Compound 229, (S)-2-amino-1-((S)-2-benzyl-4-(3-(cyclopentyloxy)-4-methoxyphenyl)piperazin-1-yl)-3-hydroxy-3-methylbutan-1-one

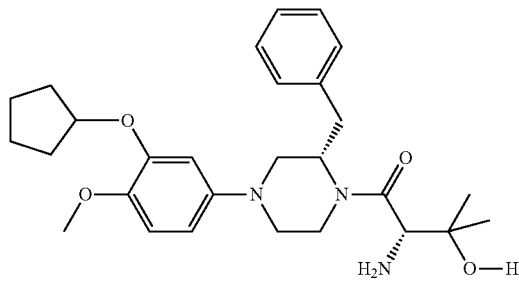

The title compound was prepared by the method outlined for Example 140 using (S)-2-(tert-butoxycarbonylamino)-3-hydroxy-3-methylbutanoic acid. The {(S)-1-[(S)-2-Benzyl-4-(3-cyclopentyloxy-4-methoxy-phenyl)-piperazine-1-carbonyl]-2-hydroxy-2-methyl-propyl}-carbamic acid tert-butyl ester intermediate was isolated as an oil (120 mg, 83%). LC/MS (Method B) 4.33 min, [M+1]+ 582. The title compound was isolated as an oil (76 mg, 76%). LC/MS (Method B) 2.92 min, [M+1]+ 482.

Example 142

Preparation of Compound 230, (S)-3-(2-benzyl-4-(3-(cyclopentyloxy)-4-methoxyphenyl)piperazin-1-yl)-3-oxopropanehydrazide

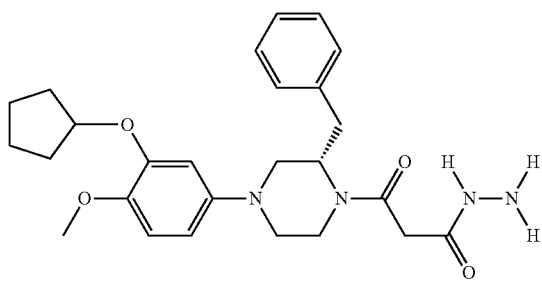

A solution of (S)-Ethyl 3-(2-benzyl-4-(3-(cyclopentyloxy)-4-methoxyphenyl)piperazin-1-yl)-3-oxopropanoate (120 mg, 0.25 mmol) in EtOH (4 mL) was treated with hydrazine hydrate (24 µL 0.50 mmol), a catalytic amount of sodium cyanide, and heated in a sealed tube at 50° C. for 24 hr after which time and additional amount of hydrazine was added (48 µL 1.0 mmol) and the reaction mixture heated at 60° C. for 48 h. After this time the reaction mixture was evaporated, triturated with water and dissolved in EtOAc (2 mL), which was dried over MgSO$_4$, filtered, and evaporated to afford the title compound as a foam (84 mg, 72%). LC/MS (Method B) 3.04 min, [M+1]+ 467.

Example 143

Preparation of Compound 231, (S)-1-(2-benzyl-4-(3-(cyclopentyloxy)-4-methoxyphenyl)piperazine-1-carbonyl)cyclopropanecarboxylic acid

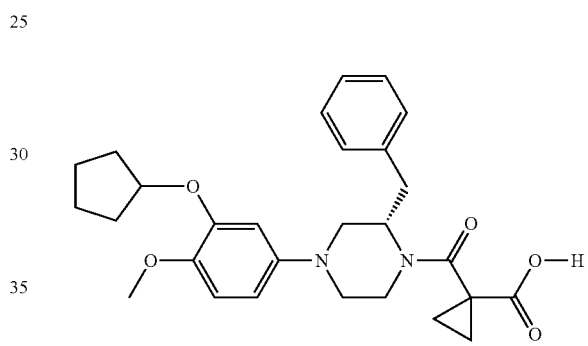

A solution of (S)-3-Benzyl-1-(3-cyclopentyloxy-4-methoxy-phenyl)-piperazine (183 mg, 0.50 mmol) in CH$_2$Cl$_2$ (1 mL) at 0-5° C. was treated with triethylamine (140 µL, 2.0 mmol) followed by a CH$_2$Cl$_2$ solution (2 mL) of methyl 1-(chlorocarbonyl)cyclopropanecarboxylate (90 mg, 0.55 mmol). The reaction mixture was allowed to warm to room temperature and stir for 1 h. After this time the reaction mixture was evaporated and partitioned between EtOAc (3 mL) and a saturated aqueous solution of NaHCO$_3$ (3 mL). The organic extract was further washed with brine then dried over MgSO$_4$, filtered, and evaporated to afford intermediate ester product which was purified by silica gel flash chromatography with 30% then 50% EtOAc/hexanes as eluant to afford intermediate (S)-methyl 1-(2-benzyl-4-(3-(cyclopentyloxy)-4-methoxyphenyl)piperazine-1-carbonyl)cyclopropanecarboxylate ester as an oil (230 mg, 93%). LC/MS (Method B) 4.05 min, [M+1]+ 493. The intermediate (S)-methyl 1-(2-benzyl-4-(3-(cyclopentyloxy)-4-methoxyphenyl)piperazine-1-carbonyl)cyclopropanecarboxylate ester (84 mg, 0.17 mmol) was dissolved in MeOH and treated with an aqueous (1 mL) solution of LiOH (16 mg, 0.68 mmol). The reaction mixture was stirred for 3 days, evaporated, diluted with water and the pH adjusted to pH~6. The water triturated solids were air dried to afford the title compound as a colorless solid (72 mg, 89%). LC/MS (Method B) 3.63 min, [M+1]+ 479.

Example 144

Preparation of Compound 232, (S)-1-(2-benzyl-4-(3-(cyclopentyloxy)-4-methoxyphenyl)piperazine-1-carbonyl)cyclobutanecarboxylic acid

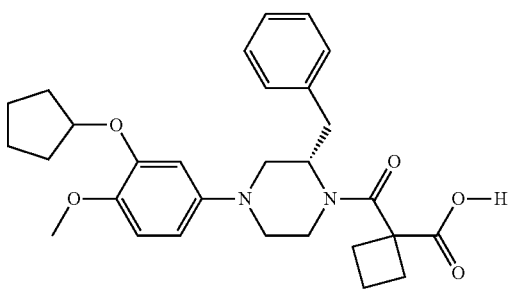 [SMILES: COc1ccc(N2CCN(C(=O)C3(C(=O)O)CCC3)[C@@H](Cc3ccccc3)C2)cc1OC1CCCC1]

The title compound was prepared by the method outlined for Example 143 using methyl 1-(chlorocarbonyl)cyclobutanecarboxylate as acyl halide to afford intermediate (S)-ethyl 1-(2-benzyl-4-(3-(cyclopentyloxy)-4-methoxyphenyl)piperazine-1-carbonyl)cyclobutanecarboxylate (237 mg, 91%). LC/MS (Method B) 4.50 min, [M+1]$^+$ 521. Hydrolysis of (S)-ethyl 1-(2-benzyl-4-(3-(cyclopentyloxy)-4-methoxyphenyl)piperazine-1-carbonyl)cyclobutanecarboxylate at 50° C. for 4 days afforded the title compound as a solid (59 mg, 75%). LC/MS (Method B) 3.88 min, [M+1]$^+$ 493.

Example 145

Preparation of Compound 233, (S)-1-(2-benzyl-4-(3-(cyclopentyloxy)-4-methoxyphenyl)piperazine-1-carbonyl)cyclopropanecarboxamide

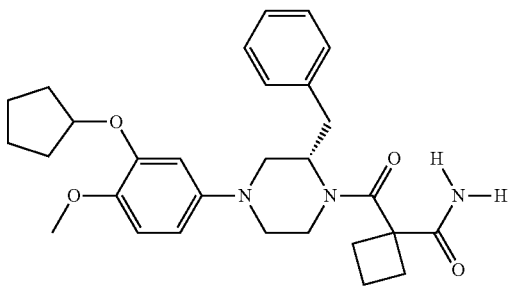 [SMILES: COc1ccc(N2CCN(C(=O)C3(C(N)=O)CCC3)[C@@H](Cc3ccccc3)C2)cc1OC1CCCC1]

A solution of (S)-methyl 1-(2-benzyl-4-(3-(cyclopentyloxy)-4-methoxyphenyl)piperazine-1-carbonyl)cyclopropanecarboxylate (123 mg, 0.25 mmol) was dissolved in a 7 N ammonia solution in MeOH (10 mL), treated with catalytic amount of sodium cyanide, then heated in a sealed tube at 80° C. for 5 days. The reaction mixture was then evaporated, washed with water and air dried to afford a residue then purified by silica gel flash chromatography with 50% then 100% EtOAc/hexanes as eluant to afford the title compound as colorless foam (26 mg, 22%). LC/MS (Method B) 3.49 min, [M+1]$^+$ 478.

Example 146

Preparation of Compound 234, (S)-1-(2-benzyl-4-(3-(cyclopentyloxy)-4-methoxyphenyl)piperazine-1-carbonyl)cyclobutanecarboxamide

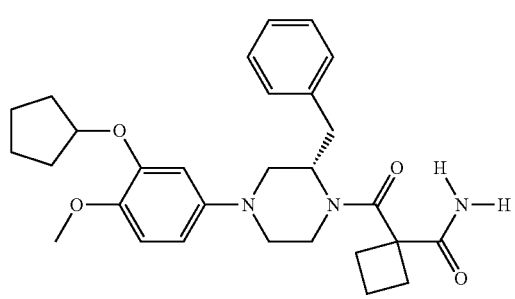 [SMILES: COc1ccc(N2CCN(C(=O)C3(C(N)=O)CCC3)[C@@H](Cc3ccccc3)C2)cc1OC1CCCC1]

The title compound was prepared by the method outlined for Example 145 using (S)-ethyl 1-(2-benzyl-4-(3-(cyclopentyloxy)-4-methoxyphenyl)piperazine-1-carbonyl)cyclobutanecarboxylate and was isolated as colorless foam (4.5 mg, 4%). LC/MS (Method B) 3.75 min, [M+1]$^+$ 492.

Example 147

Preparation of Compound 235, (S)-1-(2-benzyl-4-(3-(cyclopentyloxy)-4-methoxyphenyl)piperazin-1-yl)-2-(thiophen-2-yl)ethane-1,2-dione

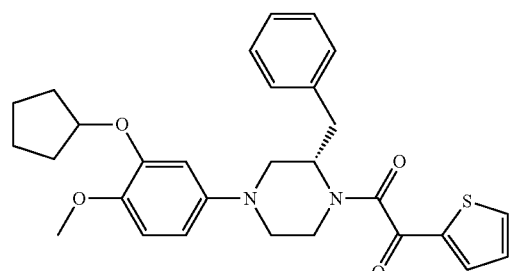

A solution of (S)-3-Benzyl-1-(3-cyclopentyloxy-4-methoxy-phenyl)-piperazine (74 mg, 0.20 mmol) in CH$_2$Cl$_2$ (1 mL) at 0-5° C. was treated with a catalytic amount of 4-dimethylaminopyridine (DMAP) and 2-thiophene glyoxylic acid (37 mg, 0.24 mmol) followed by DCC (50 mg, 0.24 mmol). The reaction mixture was allowed to warm to room temperature and stir for 3 h. After this time the reaction mixture was evaporated and the residue purified by silica gel flash chromatography with 25% then 35% EtOAc/hexanes as eluant to afford the title compound as yellow foam (93 mg, 93%). LC/MS (Method B) 4.27 min, [M+1]$^+$ 505.

Example 148

Preparation of Compound 236, (S)-1-(2-benzyl-4-(3-(cyclopentyloxy)-4-methoxyphenyl)piperazin-1-yl)-2-(thiophen-2-yl)ethanone

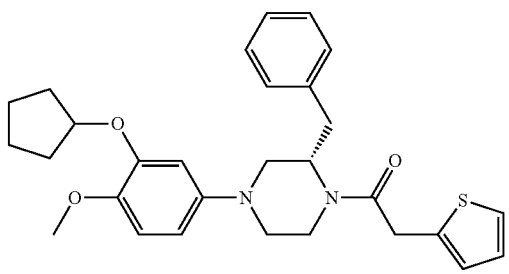 [SMILES: COc1ccc(N2CCN(C(=O)Cc3cccs3)[C@@H](Cc3ccccc3)C2)cc1OC1CCCC1]

The title compound was prepared by the method outlined for Example 147 using 2-(thiophen-2-yl)acetic acid as the acid component and was isolated as an oil (89 mg, 90%). LC/MS (Method B) 4.27 min, [M+1]$^+$ 491.

Example 149

Preparation of Compound 237, (S)-1-(2-benzyl-4-(3-(cyclopentyloxy)-4-methoxyphenyl)piperazin-1-yl)-2-(furan-2-yl)ethanone

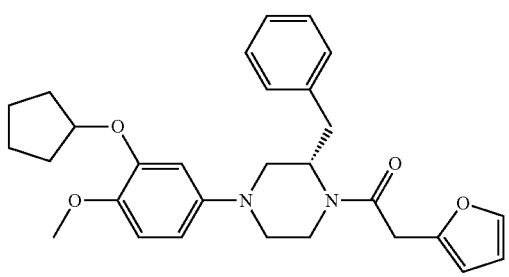 [SMILES: COc1ccc(N2CCN(C(=O)Cc3ccco3)[C@@H](Cc3ccccc3)C2)cc1OC1CCCC1]

The title compound was prepared by the method outlined for Example 147 using 2-(furan-2-yl)acetic acid as the acid component and was isolated as an oil (89 mg, 90%). LC/MS (Method B) 2.75 min, [M+1]$^+$ 475.

Example 150

Preparation of Compound 238, (S)-1-(2-benzyl-4-(3-(cyclopentyloxy)-4-methoxyphenyl)piperazin-1-yl)-2-(thiophen-3-yl)ethanone

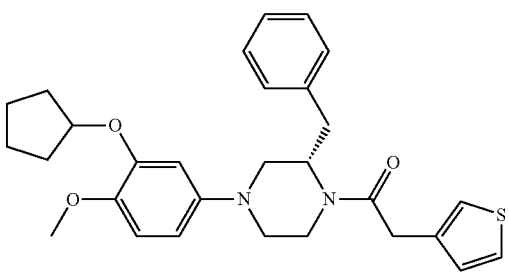 [SMILES: COc1ccc(N2CCN(C(=O)Cc3ccsc3)[C@@H](Cc3ccccc3)C2)cc1OC1CCCC1]

The title compound was prepared by the method outlined for Example 147 using 2-(furan-2-yl)acetic acid as the acid component and was isolated as an oil (114 mg, 93%). LC/MS (Method B) 4.42 min, [M+1]$^+$ 491.

Example 151

Preparation of Compound 239, (S)-1-(2-benzyl-4-(3-(cyclopentyloxy)-4-methoxyphenyl)piperazin-1-yl)-3-(1H-imidazol-5-yl)propan-1-one

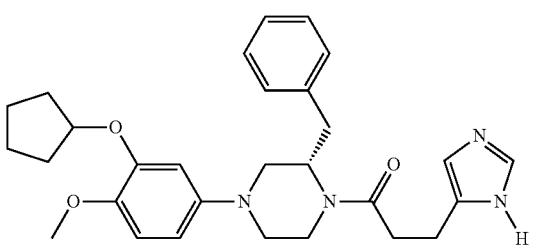 [SMILES: COc1ccc(N2CCN(C(=O)CCc3cnc[nH]3)[C@@H](Cc3ccccc3)C2)cc1OC1CCCC1]

Prepared by the method outlined for Example 147 using 3-(1-trityl-1H-imidazol-4-yl)propanoic acid as the acid component. The residue was purified by silica gel flash chromatography with 25% then 35% EtOAc/hexanes as eluant to afford intermediate trityl-protected product as an oil. The intermediate was then dissolved in $CH_2Cl_2$ (0.5 mL) and treated with triethylsilane (0.5 mL) followed by trifluoroacetic acid (2 mL). The reaction mixture was allowed to stir for 6 h after which time the reaction was evaporated and partitioned between EtOAc (4 mL) and a saturated aqueous solution of $NaHCO_3$ (2 mL). The aqueous extract was further extracted with EtOAc (2×4 mL) then dried over $MgSO_4$, filtered, and evaporated to afford intermediate ester product which was purified by silica gel flash chromatography with 3% then 10% MeOH/$CH_2Cl_2$ as eluant to afford product as an oil (37 mg, 30%). LC/MS (Method B) 2.79 min, [M+1]$^+$ 489. Potency class C.

Example 152

Preparation of Compound 240, (S)-1-(2-benzyl-4-(3-(cyclopentyloxy)-4-methoxyphenyl)piperazin-1-yl)-2-(1H-imidazol-5-yl)ethanone

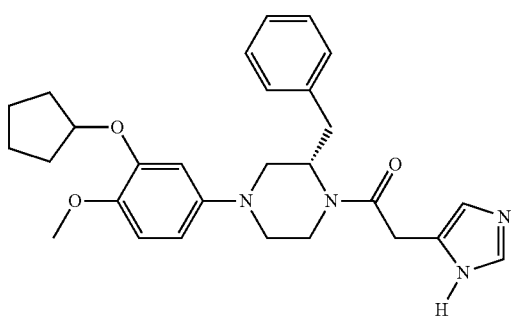 [SMILES: COc1ccc(N2CCN(C(=O)Cc3cnc[nH]3)[C@@H](Cc3ccccc3)C2)cc1OC1CCCC1]

Prepared by the method outlined for Example 151 using 2-(1-trityl-1H-imidazol-4-yl)acetic acid as the acid component. Subsequent deprotection of the trityl-containing intermediate afforded product as a foam (54 mg, 79%). LC/MS (Method B) 0.44 min, [M+1]$^+$475. Potency class A.

Example 153

Preparation of Compound 241, (S)-(2-benzyl-4-(3-(cyclopentyloxy)-4-methoxyphenyl)piperazin-1-yl)(1H-imidazol-4-yl)methanone

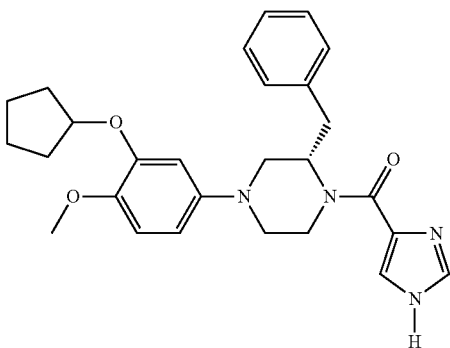 [SMILES: COc1ccc(N2CCN(C(=O)c3c[nH]cn3)[C@@H](Cc3ccccc3)C2)cc1OC1CCCC1]

Prepared by the method outlined for Example 151 using 1-trityl-1H-imidazole-4-carboxylic acid as the acid component. Subsequent deprotection of the trityl-containing intermediate afforded product as a foam (39 mg, 89%). LC/MS (Method B) 0.44 min, [M+1]$^+$461. Potency class B.

Example 154

Preparation of Compound 242, (S)-1-(2-(1H-imidazol-5-yl)ethyl)-2-benzyl-4-(3-(cyclopentyloxy)-4-methoxyphenyl)piperazine

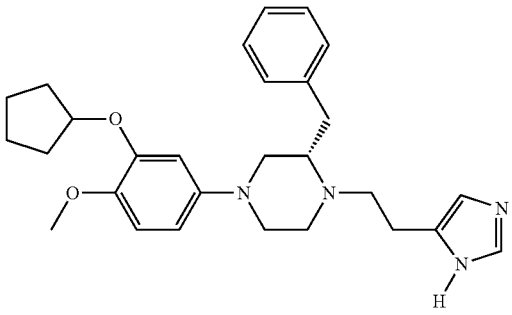 [SMILES: COc1ccc(N2CCN(CCc3cnc[nH]3)[C@@H](Cc3ccccc3)C2)cc1OC1CCCC1]

A solution of trityl protected (S)-1-(2-benzyl-4-(3-(cyclopentyloxy)-4-methoxyphenyl)piperazin-1-yl)-2-(1H-imidazol-5-yl)ethanone intermediate (Intermediate in the Preparation of Compound 240) (243 mg, 0.339 mmol) in THF (5 mL) was treated with a 2M THF solution of borane-dimethylsufide complex (678 uL, 1.36 mmol) and heated at 50 C in a sealed tube for 16 h. The reaction mixture was then cooled and quenched with a 6N HCl solution (500 uL) followed by stirring for 1 h. After this time the reaction mixture was evaporated to a small volume and partitioned between EtOAc (5 mL) and a saturated aqueous solution of NaHCO$_3$ (5 mL). The organic extract was further washed with brine then dried over MgSO$_4$, filtered, and evaporated to afford intermediate trityl-protected product which was purified by silica gel flash chromatography with EtOAc then 10% MeOH/EtOAc as eluant to afford intermediate as a colorless solid (150 mg, 63%). The trityl-protected intermediate was then dissolved in CH$_2$Cl$_2$ (2 mL) and treated with triethylsilane (1 mL) followed by trifluoroacetic acid (2 mL). The reaction mixture was allowed to stir for 16 h after which time the reaction was evaporated and partitioned between EtOAc (4 mL) and a saturated aqueous solution of NaHCO$_3$ (2 mL). The aqueous extract was further extracted with EtOAc (2×4 mL) then dried over MgSO$_4$, filtered, and evaporated to afford intermediate ester product which was purified by silica gel flash chromatography with 3% then 10% MeOH/CH$_2$Cl$_2$ as eluant to afford product as a foam. LC/MS (Method B) 2.30 min, [M+1]$^+$ 461. Potency class C.

Example 155

Preparation of Compound 243, (S)-1-(2-benzyl-4-(3-(cyclopentyloxy)-4-methoxyphenyl)piperazin-1-yl)-2-methylpropan-1-one

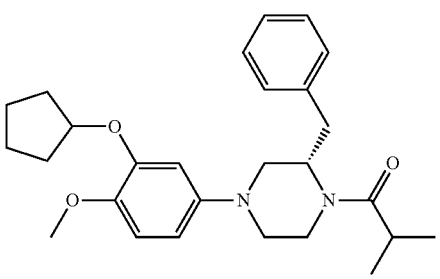 [SMILES: COc1ccc(N2CCN(C(=O)C(C)C)[C@@H](Cc3ccccc3)C2)cc1OC1CCCC1]

A solution of (S)-3-Benzyl-1-(3-cyclopentyloxy-4-methoxy-phenyl)-piperazine (Example 2, Compound 90) (110 mg, 0.25 mmol) in CH$_2$Cl$_2$ (3 mL) at 0-5 C was treated with isobutyl chloride (53 uL, 0.50 mmol). The reaction mixture was allowed to warm to room temperature and stir 3 h. After this time the reaction mixture was treated with a saturated aqueous solution of NaHCO$_3$ (1 mL). The organic portion was then dried over MgSO$_4$, filtered, and evaporated to afford quenched with evaporated and the residue purified by silica gel flash chromatography with 30% then 50% EtOAc/hexanes as eluant to afford product as an oil (100 mg, 83%). LC/MS (Method B) 4.34 min, [M+1]$^+$ 437. Potency class C.

Example 156

Preparation of Compound 244, (S)-1-(2-benzyl-4-(3-(cyclopentyloxy)-4-methoxyphenyl)piperazin-1-yl)propan-1-one

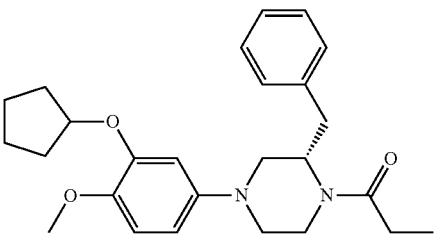 [SMILES: CCC(=O)N1CCN(c2ccc(OC)c(OC3CCCC3)c2)C[C@@H]1Cc1ccccc1]

Prepared by the method outlined for Example 155 using propionyl chloride as the acyl halide. Product as an oil (90 mg, 85%). LC/MS (Method B) 4.10 min, [M+1]$^+$ 423. Potency class B.

Example 157

Preparation of Compound 245, (S)-1-(2-benzyl-4-(3-(cyclopentyloxy)-4-methoxyphenyl)piperazin-1-yl)-2-methoxyethanone

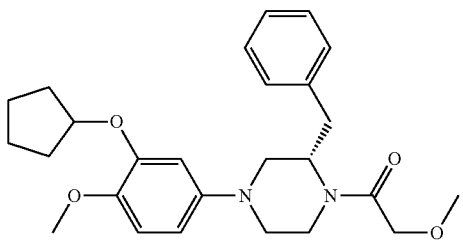 [SMILES: COCC(=O)N1CCN(c2ccc(OC)c(OC3CCCC3)c2)C[C@@H]1Cc1ccccc1]

Prepared by the method outlined for Example 155 using 2-methoxyacetyl chloride as the acyl halide. Product as an oil (100 mg, 91%). LC/MS (Method B) 3.87 min, [M+1]+ 439. Potency class B.

Example 158

Preparation of Compound 246, (S)-(2-benzyl-4-(3-(cyclopentyloxy)-4-methoxyphenyl)piperazin-1-yl)(cyclopropyl)methanone

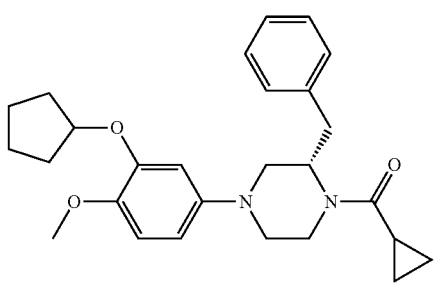 [SMILES: COc1ccc(N2CCN(C(=O)C3CC3)[C@@H](Cc3ccccc3)C2)cc1OC1CCCC1]

Prepared by the method outlined for Example 155 using cyclopropanecarbonyl chloride as the acyl halide. Product as an oil (97 mg, 86%). LC/MS (Method B) 4.24 min, [M+1]+ 435. Potency class ND.

Example 159

Preparation of Compound 247, (S)-1-(2-benzyl-4-(3-(cyclopentyloxy)-4-methoxyphenyl)piperazin-1-yl)-3,3-dimethylbutan-1-one

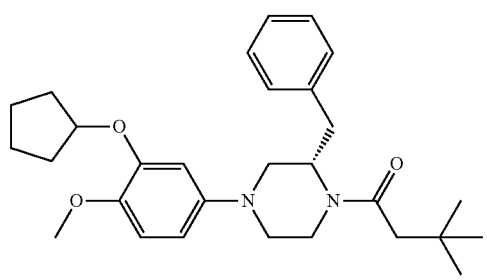 [SMILES: COc1ccc(N2CCN(C(=O)CC(C)(C)C)[C@@H](Cc3ccccc3)C2)cc1OC1CCCC1]

Prepared by the method outlined for Example 155 using 3,3-dimethylbutanoyl chloride as the acyl halide. Product as an oil (79 mg, 70%). LC/MS (Method B) 4.70 min, [M+1]+ 465.

Example 160

Preparation of Compound 248, (S)-1-(4-(3-(cyclopentyloxy)-4-methoxyphenyl)-2-(3-methylbenzyl)piperazin-1-yl)ethanone

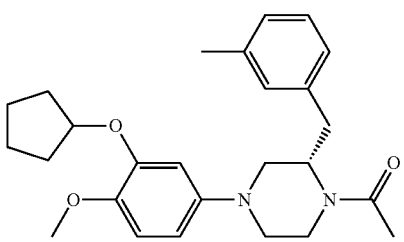 [SMILES: COc1ccc(N2CCN(C(C)=O)[C@@H](Cc3cccc(C)c3)C2)cc1OC1CCCC1]

Prepared by the method outlined for Example 155 using Compound 1, (S)-1-(3-Cyclopentyloxy-4-methoxy-phenyl)-3-(2-methyl-benzyl)-piperazine (Example 1, Compound 89) as the amine component and acetyl chloride as the acyl halide. Product as an oil (25 mg, 60%). LC/MS (Method B) 4.10 min, [M+1]+ 423. Potency class A.

Example 161

Preparation of Compound 249, (S)-1-(4-(3-(cyclopentyloxy)-4-methoxyphenyl)-2-(pyrrolidin-1-ylmethyl)piperazin-1-yl)ethanone

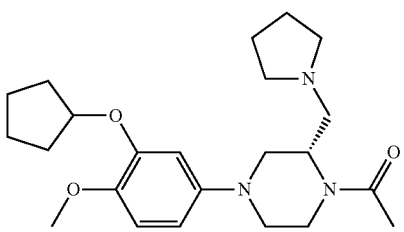 [SMILES: COc1ccc(N2CCN(C(C)=O)[C@@H](CN3CCCC3)C2)cc1OC1CCCC1]

A solution of (S)-1-(3-(cyclopentyloxy)-4-methoxyphenyl)-3-(pyrrolidin-1-ylmethyl)piperazine, dihydrochloride (Example 40, Compound 128) (108 mg, 0.25 mmol) in $CH_2Cl_2$ (5 mL) at 0-5 C was treated with triethylamine (105 uL, 0.75 mmol) followed by acetic anhydride (51 uL, 0.50 mmol). The reaction mixture was allowed to warm to room temperature and stir 16 h. After this time the reaction mixture was treated with a saturated aqueous solution of $NaHCO_3$ (2 mL). The organic portion was then dried over $MgSO_4$, filtered, and evaporated to afford quenched with evaporated and the residue purified by silica gel flash chromatography with 100% EtOAc then 10% MeOH/EtOAc as eluant to afford product as an oil (65 mg, 65%). LC/MS (Method B) 2.22 min, [M+1]+ 402. Potency class C.

Example 162

Preparation of Compound 250, (S)-1-(4-(3-(cyclopentyloxy)-4-methoxyphenyl)-2-(morpholinomethyl)piperazin-1-yl)ethanone

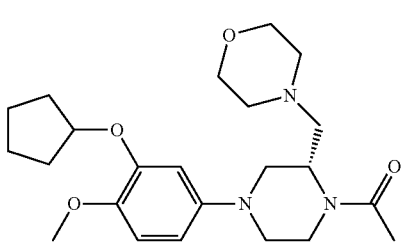 [SMILES: COc1ccc(N2CCN(C(C)=O)[C@@H](CN3CCOCC3)C2)cc1OC1CCCC1]

Prepared by the method outlined for Example 161 using (S)-4-((4-(3-(cyclopentyloxy)-4-methoxyphenyl)piperazin-2-yl)methyl)morpholine dihydrochloride (Example 41, Compound 129), as the amine component Product as an oil (87 mg, 84%). LC/MS (Method B) 2.20 min, [M+1]$^+$ 418. Potency class C.

Example 163

Preparation of Compound 251, (S)-1-(2-((benzyl(methyl)amino)methyl)-4-(3-(cyclopentyloxy)-4-methoxyphenyl)piperazin-1-yl)ethanone

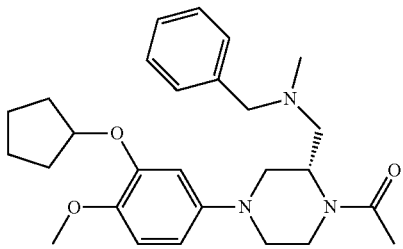 [SMILES: COc1ccc(N2CCN(C(C)=O)[C@@H](CN(C)Cc3ccccc3)C2)cc1OC1CCCC1]

A solution of (S)—N-benzyl-1-(4-(3-(cyclopentyloxy)-4-methoxyphenyl)piperazin-2-yl)-N-methylmethanamine dihydrochloride, (Example 42, Compound 130) (96.5 mg, 0.20 mmol) in CH$_2$Cl$_2$ (2 mL) at 0-5 C was treated with triethylamine (84 ul, 0.60 mmol) followed by acetyl chloride (22 uL, 0.30 mmol). The reaction mixture was allowed to warm to room temperature and stir 1 h. After this time the reaction mixture was treated with a saturated aqueous solution of NaHCO$_3$ (1 mL). The organic portion was then dried over MgSO$_4$, filtered, and evaporated to afford quenched with evaporated and the residue purified by silica gel flash chromatography with 100% EtOAc then 5% MeOH/EtOAc as eluant to afford product as an oil (65 mg, 72%). LC/MS (Method B) 2.57 min, [M+1]$^+$ 452. Potency class ND.

Example 164

Preparation of Compound 252, (S)-1-(4-(3-(cyclopentyloxy)-4-methoxyphenyl)-2-(isoindolin-2-ylmethyl)piperazin-1-yl)ethanone

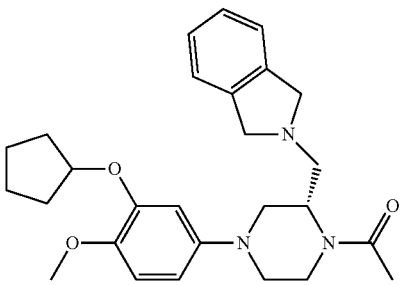 [SMILES: COc1ccc(N2CCN(C(C)=O)[C@@H](CN3Cc4ccccc4C3)C2)cc1OC1CCCC1]

Prepared by the method outlined for Example 163 using (S)-2-((4-(3-(cyclopentyloxy)-4-methoxyphenyl)piperazin-2-yl)methyl)isoindoline dihydrochloride (Example 43, Compound 131). Product as an oil (74 mg, 82%) LC/MS (Method B) 2.54 min, [M+1]$^+$ 450. Potency class B.

Example 165

Preparation of Compound 253, (S)-1-(4-(3-(cyclopentyloxy)-4-methoxyphenyl)-2-((3,4-dihydroisoquinolin-2(1H)-yl)methyl)piperazin-1-yl)ethanone

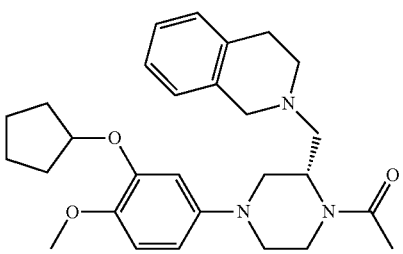 [SMILES: COc1ccc(N2CCN(C(C)=O)[C@@H](CN3CCc4ccccc4C3)C2)cc1OC1CCCC1]

Prepared by the method outlined for Example 163 using (S)-2-((4-(3-(cyclopentyloxy)-4-methoxyphenyl)piperazin-2-yl)methyl)-1,2,3,4-tetrahydroisoquinoline dihydrochloride (Example 44, Compound 132). Product as an oil 75 mg, 81%). LC/MS (Method B) 260 min, [M+1]$^+$ 464. Potency class A.

Example 166

Preparation of Compound 254, (R)-1-(2-(OH-pyrazol-1-yl)methyl)-4-(3-(cyclopentyloxy)-4-ethoxyphenyl)piperazin-1-yl)ethanone

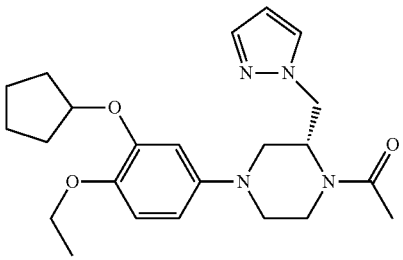 [SMILES: CCOc1ccc(N2CCN(C(C)=O)[C@@H](Cn3cccn3)C2)cc1OC1CCCC1]

The title compound was prepared by the method outlined for Example 163 using (R)-3-((1H-pyrazol-1-yl)methyl)-1-(3-(cyclopentyloxy)-4-ethoxyphenyl)piperazine (Example 45, Compound 133). Product as an oil (31 mg, 94%). LC/MS (Method B) 3.50 min, [M+1]$^+$ 413. Potency class C.

Example 167

Preparation of Compound 255, (S)-1-(4-(3-(cyclopentyloxy)-4-methoxyphenyl)-2-(pyrrolidin-1-ylmethyl)piperazin-1-yl)-2-(5-methyl-1H-1,2,4-triazol-3-yl)ethanone

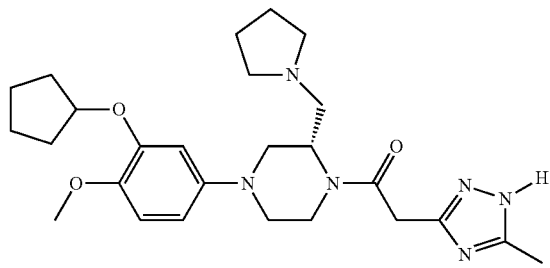 [SMILES: COc1ccc(N2CCN(C(=O)Cc3n[nH]c(C)n3)[C@@H](CN3CCCC3)C2)cc1OC1CCCC1]

A solution of (S)-1-(3-(cyclopentyloxy)-4-methoxyphenyl)-3-(pyrrolidin-1-ylmethyl)piperazine, dihydrochloride (Example 40, Compound 128) (173 mg, 0.40 mmol) in CH$_2$Cl$_2$ (1 mL) and DMF (1 mL) was treated with diisopropylethylamine (348 uL, 2.0 mmol), 2-(5-methyl-1H-1,2,4-triazol-3-yl)acetic acid CAS [720706-28-5] (68 mg, 0.48 mmol) followed by HBTU (162 mg, 0.48 mmol). The reaction mixture was stirred for 16 h after which time the mixture was partitioned between CH$_2$Cl$_2$ (3 mL) and a saturated aqueous solution of NaHCO$_3$ (2 mL). The organic portion was further washed with NaHCO$_3$ (2×3 mL) followed by brine (3 mL). The organic portion was then dried over MgSO$_4$, filtered, and evaporated to afford quenched with evaporated and the residue purified by silica gel flash chromatography with 5% MeOH/EtOAc the 10% MeOH/EtOAc containing 1% NH$_4$OH as eluant to afford product as a foam (123 mg, 64%). LC/MS (Method B) 2.18 min, [M+1]$^+$ 483. Potency class C.

Example 168

Preparation of Compound 256, (S)-1-(4-(3-(cyclopentyloxy)-4-methoxyphenyl)-2-(morpholinomethyl)piperazin-1-yl)-2-(5-methyl-1H-1,2,4-triazol-3-yl)ethanone

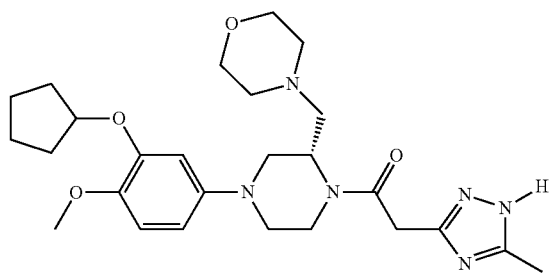 [SMILES: COc1ccc(N2CCN(C(=O)Cc3n[nH]c(C)n3)[C@@H](CN3CCOCC3)C2)cc1OC1CCCC1]

Prepared by the method outlined for Example 167 using (S)-4-((4-(3-(cyclopentyloxy)-4-methoxyphenyl)piperazin-2-yl)methyl)morpholine, dihydrochloride (Example 41, Compound 129). Product as an oil (150 mg, 75%). LC/MS (Method B) 2.15 min, [M+1]$^+$ 499. Potency class A.

Example 169

Preparation of Compound 257, (R)-1-(2-(1H-pyrazol-1-yl)methyl)-4-(3-(cyclopentyloxy)-4-ethoxyphenyl)piperazin-1-yl)-2-(5-methyl-1H-1,2,4-triazol-3-yl)ethanone

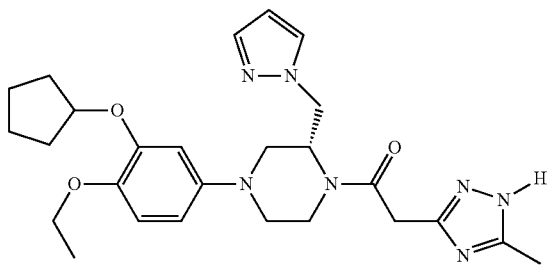 [SMILES: CCOc1ccc(N2CCN(C(=O)Cc3n[nH]c(C)n3)[C@@H](Cn3cccn3)C2)cc1OC1CCCC1]

Prepared by the method outlined for Example 167 using (R)-3-((1H-pyrazol-1-yl)methyl)-1-(3-(cyclopentyloxy)-4-ethoxyphenyl)piperazine (Example 45, Compound 133). Product as an oil (31 mg, 94%). LC/MS (Method B) 3.09 min, [M+1]$^+$ 494. Potency class A.

Example 170

Preparation of Compound 258, (S)-3-(2-benzyl-4-(3-cyclobutoxy-4-methoxyphenyl)piperazin-1-yl)-3-oxopropanoic acid

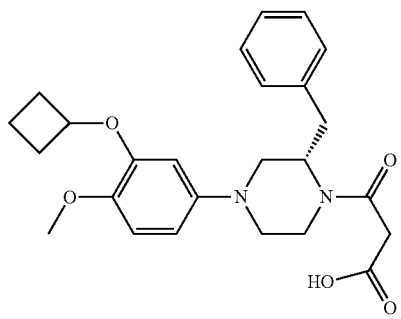 [SMILES: COc1ccc(N2CCN(C(=O)CC(=O)O)[C@@H](Cc3ccccc3)C2)cc1OC1CCC1]

Prepared by the method outlined for Example 127 using chlorocarbonyl-acetic acid ethyl ester and 3(S)-benzyl-1-(3-cyclobutoxy-4-methoxy-phenyl)-piperazine (Example 7, Compound 95) as starting material. Product as an oil (25 mg, 65%). LC/MS (Method B) 2.56 min, [M+1]$^+$ 439. Potency class A.

Example 171

Preparation of Compound 259, (S)-3-(2-benzyl-4-(3-isopropoxy-4-methoxyphenyl)piperazin-1-yl)-3-oxopropanoic acid

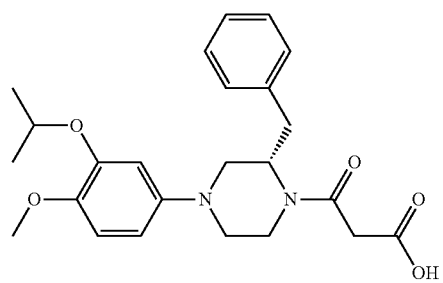 [SMILES: COc1ccc(N2CCN(C(=O)CC(=O)O)[C@@H](Cc3ccccc3)C2)cc1OC(C)C]

Prepared by the method outlined for Example 127 using chlorocarbonyl-acetic acid ethyl ester and 3(S)-benzyl-1-(3-isopropoxy-4-methoxy-phenyl)-piperazine (Example 9, Compound 97) as starting materials. Product as an oil. LC/MS (Method B) 2.36 min, [M+1]$^+$ 439.

Example 172

Preparation of Compound 260, (S)-3-(2-benzyl-4-(3-isopropoxy-4-methoxyphenyl)piperazin-1-yl)-3-oxopropanamide

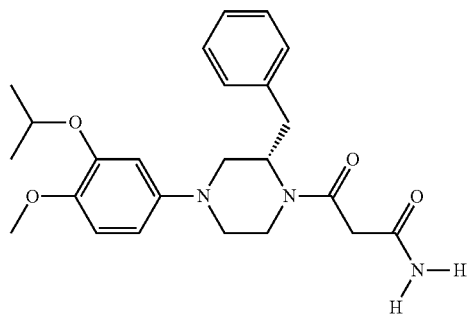 [SMILES: COc1ccc(N2CCN(C(=O)CC(N)=O)[C@@H](Cc3ccccc3)C2)cc1OC(C)C]

Prepared by the method outlined for Example 129 using the intermediate ester in the preparation of 3-[2(S)benzyl-4-(3-isopropoxy-4-methoxy-phenyl)-piperazin-1-yl]-3-oxo-propionic acid (Example 171, Compound 255) as starting materials. Product as an oil. LC/MS (Method B) 2.55 min, [M+1]$^+$ 426. Potency class ND

Example 173

Preparation of Compound 261, (S)-3-(2-benzyl-4-(3-cyclobutoxy-4-methoxyphenyl)piperazin-1-yl)-3-oxopropanamide

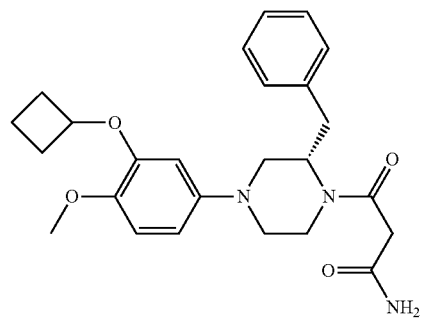 [SMILES: COc1ccc(N2CCN(C(=O)CC(N)=O)[C@@H](Cc3ccccc3)C2)cc1OC1CCC1]

Prepared by the method outlined for Example 129 using the intermediate ester in the preparation of 3-[2(S)benzyl-4-(3-isobutoxy-4-methoxy-phenyl)-piperazin-1-yl]-3-oxo-propionic acid (Example 170, Compound 258) as starting material. Product as an oil. LC/MS (Method B) 3.66 min, [M+1]$^+$ 438. Potency class A.

Example 174

Preparation of Compound 262, (S)-3-(2-benzyl-4-(3-(difluoromethoxy)-4-methoxyphenyl)piperazin-1-yl)-3-oxopropanamide

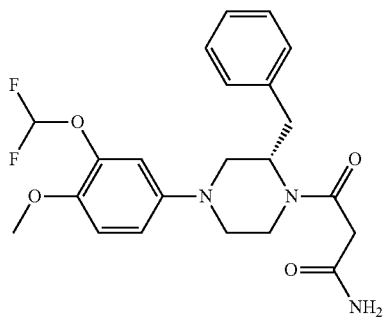 [SMILES: COc1ccc(N2CCN(C(=O)CC(N)=O)[C@@H](Cc3ccccc3)C2)cc1OC(F)F]

Prepared by the method outlined for Example 121 utilizing the intermediate ester from (S)3-benzyl-1-(3-difluoromethoxy-4-methoxy-phenyl)-piperazine (Example 69, Compound 157) followed by the aminolysis transformation outlined in Example 129. Product as an oil. LC/MS (Method B) 2.75 min, [M+1]$^+$ 434.

Example 175

Preparation of Compound 263, (S)-3-(2-benzyl-4-(3-cyclobutoxy-4-(difluoromethoxy)phenyl)piperazin-1-yl)-3-oxopropanamide

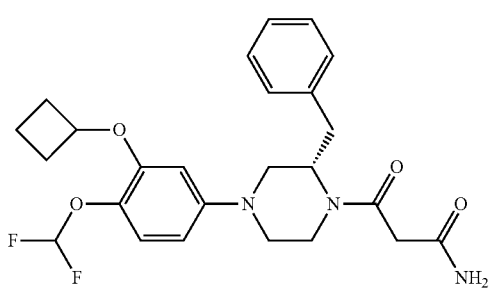 [SMILES: NC(=O)CC(=O)N1CCN(c2ccc(OC(F)F)c(OC3CCC3)c2)C[C@@H]1Cc1ccccc1]

Prepared by the method outlined for Example 121 utilizing the intermediate ester from (S)3-benzyl-1-(3-cyclobutoxy-4-difluoromethoxy-phenyl)-piperazine (Example 4, Compound 92) followed by the aminolysis transformation outlined in Example 129. Product as an oil. LC/MS (Method B) 3.00 min, [M+1]$^+$ 474. Potency class A.

Example 176

Preparation of Compound 264, (S)-3-(2-benzyl-4-(1-cyclobutyl-3-ethyl-1H-indazol-6-yl)piperazin-1-yl)-3-oxopropanamide

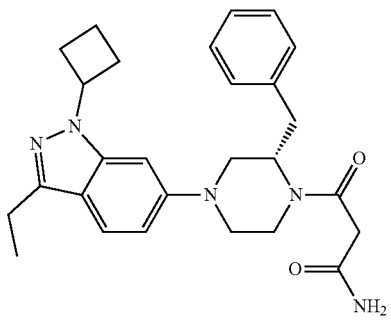 [SMILES: CCc1nn(C2CCC2)c2cc(N3CCN(C(=O)CC(N)=O)[C@@H](Cc4ccccc4)C3)ccc12]

Prepared by the method outlined for Example 121 utilizing the intermediate ester from 6-(S)3-benzyl-piperazin-1-yl)-1-cyclopentyl-3-ethyl-1H-indazole (Example 56, Compound 144) followed by the aminolysis transformation outlined in Example 129. Product as an oil. LC/MS (Method B) 2.88 min, [M+1]$^+$ 460. Potency class A.

Example 177

Preparation of Compound 265, (S)-2-(2-benzyl-4-(3-cyclobutoxy-4-methoxyphenyl)piperazin-1-yl) acetic acid

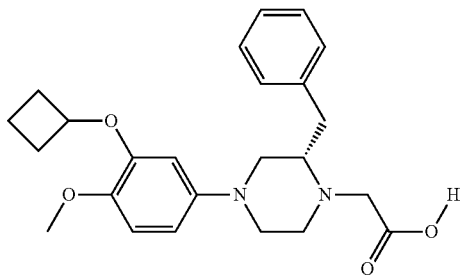 [SMILES: COc1ccc(N2CCN(CC(=O)O)[C@@H](Cc3ccccc3)C2)cc1OC1CCC1]

Prepared by the method outlined for Example 96/98 utilizing 3(S)-benzyl-1-(3-cyclobutoxy-4-methoxy-phenyl)-piperazine (Example 7, Compound 95), Compound 95) as starting materials. Product as an oil (50 mg, 70%). LC/MS (Method B) 3.25 min, [M+1]$^+$ 411.

Example 178

Preparation of Compound 266, (S)-2-(2-benzyl-4-(3-isopropoxy-4-methoxyphenyl)piperazin-1-yl) acetic acid)

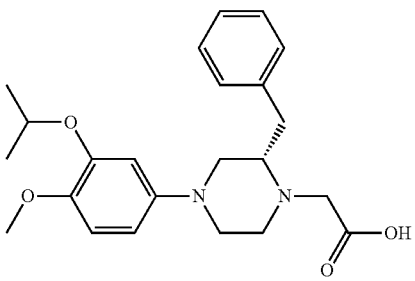 [SMILES: COc1ccc(N2CCN(CC(=O)O)[C@@H](Cc3ccccc3)C2)cc1OC(C)C]

Prepared by the method outlined for Example 96/98 utilizing 3(S)-benzyl-1-(3-isopropoxy-4-methoxy-phenyl)-piperazine (Example 9, Compound 97) as starting materials. Product as an oil. LC/MS (Method B) 3.10 min, [M+1]$^+$ 399. Potency class B.

Example 179

Preparation of Compound 267, (S)-2-(2-benzyl-4-(3-isopropoxy-4-methoxyphenyl)piperazin-1-yl) acetamide

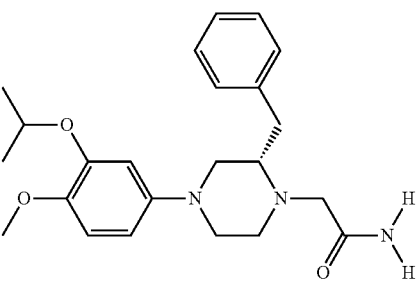 [SMILES: COc1ccc(N2CCN(CC(N)=O)[C@@H](Cc3ccccc3)C2)cc1OC(C)C]

Prepared by the method outlined for Example 95 utilizing the ester intermediate in the synthesis of [2(S)benzyl-4-(3-cyclopentyloxy-4-methoxy-phenyl)-piperazin-1-yl]-acetic acid (Example 178, Compound 266) as starting material. Product as an oil. LC/MS (Method B) 2.66 min, [M+1]$^+$ 398. Potency class ND.

Example 180

Preparation of Compound 268, (S)-2-(2-benzyl-4-(3-cyclobutoxy-4-methoxyphenyl)piperazin-1-yl)acetamide

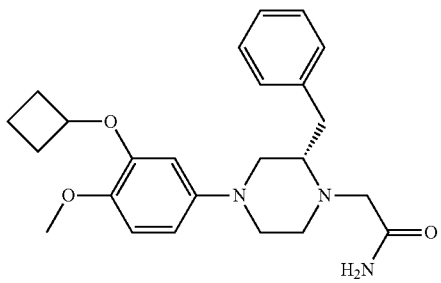 [SMILES: COc1ccc(N2CCN(CC(N)=O)[C@@H](Cc3ccccc3)C2)cc1OC1CCC1]

Prepared by the method outlined for Example 95 utilizing the ester intermediate in the synthesis of [2(S)benzyl-4-(3-cyclopentyloxy-4-methoxy-phenyl)-piperazin-1-yl]-acetic acid (Example 177, Compound 265) as starting material. Product as an oil. LC/MS (Method B) 3.25 min, [M+1]$^+$ 410. Potency class A.

Example 181

Preparation of Compound 269, (S)-3-(2-benzyl-4-(3-(cyclopentyloxy)-4-methoxyphenyl)piperazin-1-yl)propanamide

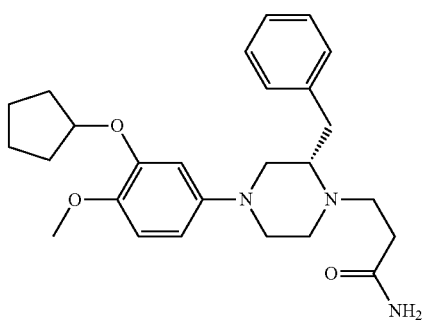 [SMILES: COc1ccc(N2CCN(CCC(N)=O)[C@@H](Cc3ccccc3)C2)cc1OC1CCCC1]

Prepared by the method outlined for Example 129 using the ester intermediate in the synthesis of (S)-3-(2-benzyl-4-(3-(cyclopentyloxy)-4-methoxyphenyl)piperazin-1-yl)propanoic acid (Example 122, Compound 210). Product as an oil. LC/MS (Method B) 2.86 min, [M+1]$^+$ 438. Potency class A.

Example 182

Preparation of Compound 270, (S)-3-(2-benzyl-4-(3-cyclobutoxy-4-methoxyphenyl)piperazin-1-yl)propanamide

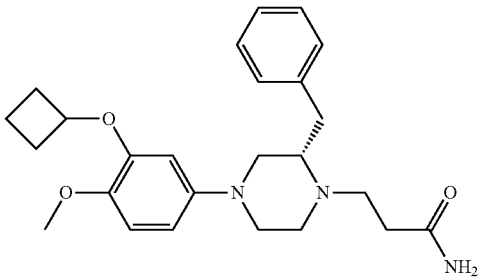 [SMILES: COc1ccc(N2CCN(CCC(N)=O)[C@@H](Cc3ccccc3)C2)cc1OC1CCC1]

Prepared by the method outlined for Example 181 using (S)3-benzyl-1-(3-cyclobutoxy-4-methoxy-phenyl)-piperazine (Example 7, Compound 95) as starting material. Product as an oil (30 mg, 68%). LC/MS (Method B) 3.15 min, [M+1]$^+$ 472. Potency class A.

Example 183

Preparation of Compound 271, (S)-2-(2-benzyl-4-(3-(difluoromethoxy)-4-methoxyphenyl)piperazin-1-yl)acetamide

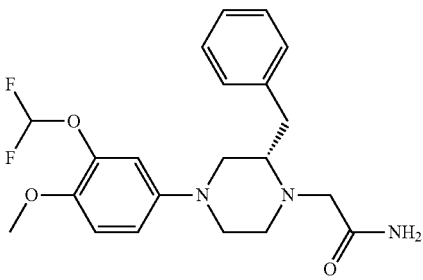 [SMILES: COc1ccc(N2CCN(CC(N)=O)[C@@H](Cc3ccccc3)C2)cc1OC(F)F]

Prepared by the method outlined for Example 95 utilizing (S)3-benzyl-1-(3-difluoromethoxy-4-methoxy-phenyl)-piperazine (Example 69, Compound 157) as starting material. Product as an oil. LC/MS (Method B) 3.65 min, [M+1]$^+$ 406. Potency class B.

Example 184

Preparation of Compound 272, (S)-3-(2-benzyl-4-(3-isopropoxy-4-methoxyphenyl)piperazin-1-yl)propanamide

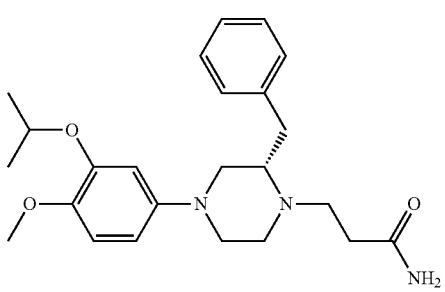 [SMILES: COc1ccc(N2CCN(CCC(N)=O)[C@@H](Cc3ccccc3)C2)cc1OC(C)C]

Prepared by the method outlined for Example 181 using (S) 3-benzyl-1-(3-(1-methylethoxy)-4-methoxy-phenyl)-piperazine (Example 9, Compound 97) as starting material. Product as an oil. LC/MS (Method B) 3.20 min, [M+1]$^+$ 412. Potency class B.

Example 185

Preparation of Compound 273, (S)-2-(2-benzyl-4-(3-cyclobutoxy-4-(difluoromethoxy)phenyl)piperazin-1-yl)acetamide

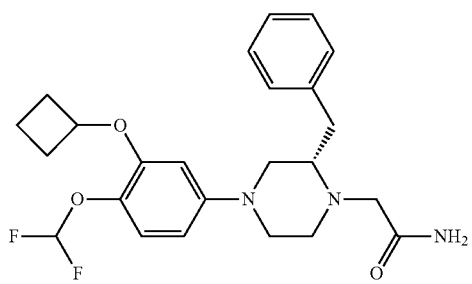 [SMILES: NC(=O)CN1CCN(c2ccc(OC(F)F)c(OC3CCC3)c2)C[C@@H]1Cc1ccccc1]

Prepared by the method outlined in Example 95 using (S)3-benzyl-1-(3-cyclobutoxy-4-difluoromethoxy-phenyl)-piperazine (Example 4, Compound 92) as starting material. Product as an oil. LC/MS (Method B) 3.20 min, [M+1]$^+$ 446. Potency class A.

Example 186

Preparation of Compound 274, (S)-3-amino-1-(2-benzyl-4-(3-cyclobutoxy-4-methoxyphenyl)piperazin-1-yl)propan-1-one

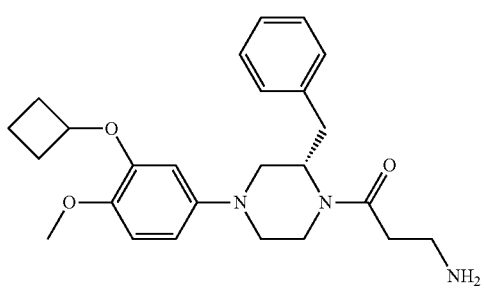 [SMILES: COc1ccc(N2CCN(C(=O)CCN)[C@@H](Cc3ccccc3)C2)cc1OC1CCC1]

Prepared by the method outlined for Example 131 using 3-tert-butoxycarbonylamino-propionic acid and (S)3-benzyl-1-(3-cyclobutoxy-4-methoxy-phenyl)-piperazine (Example 7, Compound 95) as starting materials to afford the BOC-protected intermediate. Removal of the BOC-protecting group was achieved using the method outlined in Example 1. Product as an oil (25 mg, 55%). LC/MS (Method B) 3.75 min, [M+1]$^+$ 424. Potency class C.

Example 187

Preparation of Compound 275, (S)-2-(2-benzyl-4-(1-cyclobutyl-3-ethyl-1H-indazol-6-yl)piperazin-1-yl)acetamide

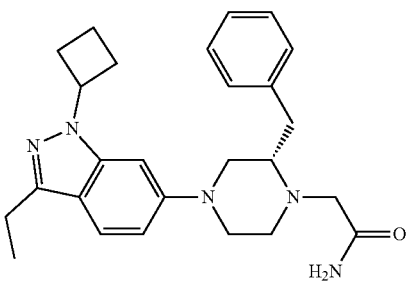 [SMILES: CCc1nn(C2CCC2)c2cc(N3CCN(CC(N)=O)[C@@H](Cc4ccccc4)C3)ccc12]

Prepared by the method outlined for Example 95 using 6-(S)3-benzyl-piperazin-1-yl)-1-cyclobutyl-3-ethyl-1H-indazole (Example 57, Compound 145) as starting material. Product as an oil. LC/MS (Method B) 3.75 min, [M+1]$^+$ 432. Potency class C.

Example 188

Preparation of Compound 276, (S)-3-(2-benzyl-4-(1-cyclobutyl-3-ethyl-1H-indazol-6-yl)piperazin-1-yl)propanamide

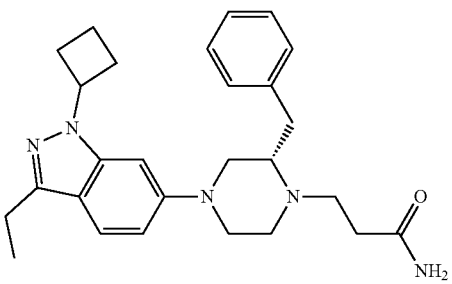 [SMILES: CCc1nn(C2CCC2)c2cc(N3CCN(CCC(N)=O)[C@@H](Cc4ccccc4)C3)ccc12]

Prepared by the method outlined for Example 181 using 6-(S)3-benzyl-piperazin-1-yl)-1-cyclobutyl-3-ethyl-1H-indazole (Example 57, Compound 145) as starting material. Product as an oil. LC/MS (Method B) 3.66 min, [M+1]$^+$ 446. Potency class C.

Example 189

Preparation of Compound 277, (S)-1-(2-benzyl-4-(3-(cyclopentyloxy)-4-methoxyphenyl)piperazin-1-yl)-2-(5-methyl-1H-1,2,4-triazol-3-yl)ethanone

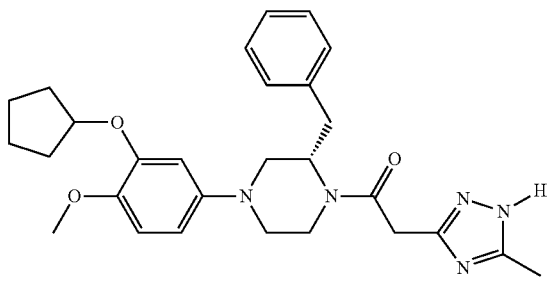 [SMILES: COc1ccc(N2CCN(C(=O)Cc3n[nH]c(C)n3)[C@@H](Cc3ccccc3)C2)cc1OC1CCCC1]

A solution of 3-benzyl-1-(3-cyclopentyloxy-4-methoxy-phenyl)-piperazine (Example 2, Compound 90) (100 mg, 0.273 mmol), in CH$_2$Cl$_2$: DMF (1:1, 3 mL), then treated with (5-methyl-1H[1,2,4]triazol-3-yl)-acetic acid (50.0 mg, 0.355 mmol), followed by the addition of diisopropylethylamine μL, 0.819 mmmol) and HATU (135 mg, 0.355 mmol). (00 The reaction stirred at room temperature for 8 h. The solution was washed with a saturated aqueous solution of NaHCO$_3$ (10 mL) followed by brine (10 mL). The organic portion was dried over MgSO$_4$, filtered and evaporated to an oil which was purified by silica gel flash chromatography with 5% then 10% MeOH/EtOAc as eluant to afford product as a colorless solid (86 mg, 65%). $^1$H NMR (CDCl$_3$) 1.50-1.65 (m, 4 H), 1.70-2.00 (m, 6 H), 2.42 (s, 3 H), 2.46 (s, 2 H), 2.61-2.99 (m, 2 H), 3.21-3.51 (m, 3 H), 3.72-3.99 (m, 4 H), 4.62-4.79 (m, 1 H), 6.38-6.60 (m, 2 H), 6.70-6.82 (m, 1 H), 7.20-7.39 (m, 5 H). $^{13}$C NMR 44.8 (CH$_2$), 53.5 (CH$_2$), 54.8 (CH), 55.3 (CH$_2$), 56.6 (CH$_2$), 63.2 (CH$_2$), 105.4 (CH), 127.1 (CH), 128.2 (CH), 129.0 (CH), 130.0 (CH), 138.0, 139.8 (CH). LC/MS (Method B) 3.32 min, [M+1]$^+$ 490.2.

Example 190

Preparation of Compound 278, ((S)-2-benzyl-4-(3-(cyclopentyloxy)-4-methoxyphenyl)piperazin-1-yl)((2R,4S)-4-hydroxypyrrolidin-2-yl)methanone

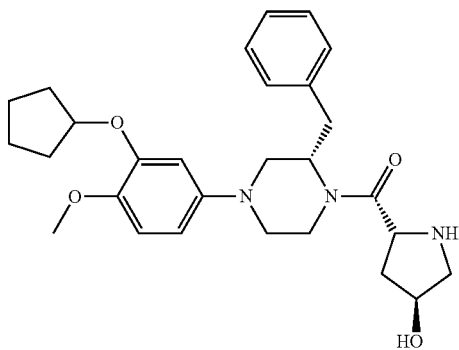

Prepared by the method outlined for Example 131 using (2R,4S)-1-(tert-butoxycarbonyl)-4-hydroxypyrrolidine-2-carboxylic acid as the acid component to afford the BOC-protected intermediate. Removal of the BOC-protecting group was achieved using the method outlined in Example 1. Product as an oil (25 mg, 55%). LC/MS (Method B) 3.25 min, [M+1]$^+$ 480. Potency class C.

Example 191

Preparation of Compound 279, ((S)-2-benzyl-4-(3-(cyclopentyloxy)-4-methoxyphenyl)piperazin-1-yl)((2R,4R)-4-hydroxypyrrolidin-2-yl)methanone

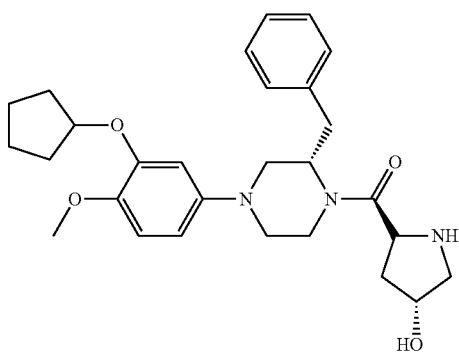

Prepared by the method outlined for Example 131 using (2S,4R)-1-(tert-butoxycarbonyl)-4-hydroxypyrrolidine-2-carboxylic acid as the acid component to afford the BOC-protected intermediate. Removal of the BOC-protecting group was achieved using the method outlined in Example 1. Product as an oil. LC/MS (Method B) 3.80 min, [M+1]$^+$ 480. Potency class C.

Example 192

Preparation of Compound 280, (S)-(2-benzyl-4-(3-(cyclopentyloxy)-4-methoxyphenyl)piperazin-1-yl)(2,4-dimethylthiazol-5-yl)methanone

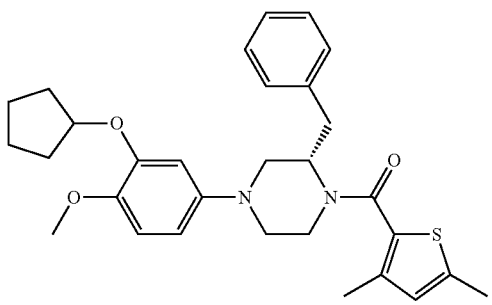 [SMILES: COc1ccc(N2CCN(C(=O)c3sc(C)cc3C)[C@@H](Cc3ccccc3)C2)cc1OC1CCCC1]

Prepared by the method outlined for Example 75 using 2,4-dimethyl-thiazole-5-carboxaldehyde as starting material. Product as an (30 mg, 60%). LC/MS (Method B) 3.70 min, [M+1]$^+$ 506. Potency class C.

Example 193

Preparation of Compound 281, 4-((S)-2-benzyl-4-(3-(cyclopentyloxy)-4-methoxyphenyl)piperazine-1-carbonyl)imidazolidin-2-one

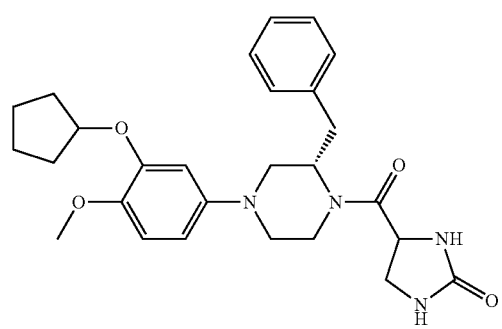 [SMILES: COc1ccc(N2CCN(C(=O)C3CNC(=O)N3)[C@@H](Cc3ccccc3)C2)cc1OC1CCCC1]

A solution of 3-benzyl-1-(3-cyclopentyloxy-4-methoxy-phenyl)-piperazine (Example 2, Compound 90) (100 mg, 0.273 mmol), in CH$_2$Cl$_2$: DMF (1:1, 3 mL), then treated with 2-oxoimidazolidine-4-carboxylic acid (50 mg, 0.321 mmol), followed by the addition of diisopropylethylamine (100 μL, 0.819 mmmol) and PyBOP (198 mg, 0.383 mmol). The reaction stirred at room temperature for 8 h. The solution was washed with a saturated aqueous solution of NaHCO$_3$ (10 mL) followed by brine (10 mL). The organic portion was dried over MgSO$_4$, filtered and evaporated to an oil which was purified by reversed phase HPLC to afford product as a colorless solid (39 mg, 30%). LC/MS (Method B) 3.60 min, [M+1]$^+$ 479. Potency class A.

Example 194

Preparation of Compound 282, (S)-1-(2-benzyl-4-(3-(cyclopentyloxy)-4-methoxyphenyl)piperazin-1-yl)-2-hydroxy-2-methylpropan-1-one

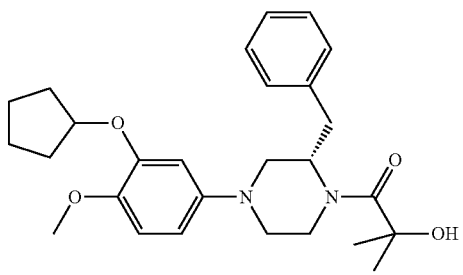 [SMILES: COc1ccc(N2CCN(C(=O)C(C)(C)O)[C@@H](Cc3ccccc3)C2)cc1OC1CCCC1]

Prepared by the method outlined for Example 193 using 2-hydroxy-2-methyl-propionic acid as starting material. Product as an oil (40 mg, 65%). LC/MS (Method B) 3.59 min, [M+1]$^+$ 453. Potency class B.

Example 195

Preparation of Compound 283, (S)-(2-benzyl-4-(3-(cyclopentyloxy)-4-methoxyphenyl)piperazin-1-yl)(1-hydroxycyclopropyl)methanone

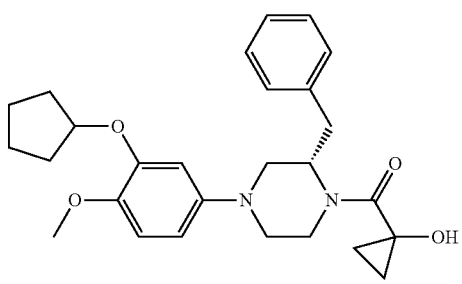 [SMILES: COc1ccc(N2CCN(C(=O)C3(O)CC3)[C@@H](Cc3ccccc3)C2)cc1OC1CCCC1]

Prepared by the method outlined for Example 193 using 1-hydroxy-cyclopropanecarboxylic acid as starting material. Product as an oil (45 mg, 68%). LC/MS (Method B) 3.65 min, [M+1]$^+$ 451. Potency class B.

Example 196

Preparation of Compound 284, (S)-2-(2-benzyl-4-(3-(cyclopentyloxy)-4-methoxyphenyl)piperazin-1-yl)-2-oxoethyl acetate

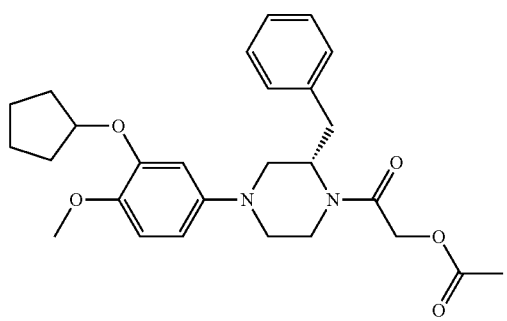 [SMILES: COc1ccc(N2CCN(C(=O)COC(C)=O)[C@@H](Cc3ccccc3)C2)cc1OC1CCCC1]

Prepared by the method outlined for Example 155 using 2-chloro-2-oxoethyl acetate as starting material. Product as an oil (60 mg, 68%). LC/MS (Method B) 3.55 min, [M+1]$^+$ 467. Potency class C.

Example 197

Preparation of Compound 285, (S)-5-(2-benzyl-4-(3-(cyclopentyloxy)-4-methoxyphenyl)piperazine-1-carbonyl)pyrrolidin-2-one

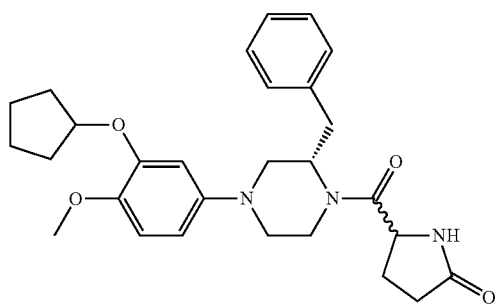 [SMILES: COc1ccc(N2CCN(C(=O)C3CCC(=O)N3)[C@@H](Cc3ccccc3)C2)cc1OC1CCCC1]

Prepared by the method outlined for Example 193 using 5-oxo-pyrrolidine-2-carboxylic acid as starting material. Product as an oil (65 mg, 58%). LC/MS (Method B) 3.15 min, [M+1]$^+$ 478. Potency class B.

Example 198

Preparation of Compound 286, (S)-(2-benzyl-4-(3-(cyclopentyloxy)-4-methoxyphenyl)piperazin-1-yl)(3,4-dihydroxyphenyl)methanone

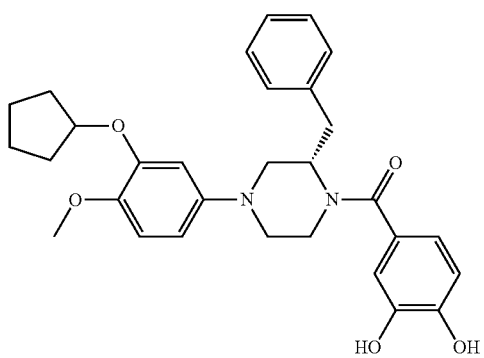 [SMILES: COc1ccc(N2CCN(C(=O)c3ccc(O)c(O)c3)[C@@H](Cc3ccccc3)C2)cc1OC1CCCC1]

Prepared by the method outlined for Example 193 using 3,4-dihydroxy-benzoic acid as starting material. Product as an oil (35 mg, 38%). LC/MS (Method B) 2.75 min, [M+1]$^+$ 503. Potency class C.

Example 199

Preparation of Compound 287, (S)-(2-benzyl-4-(3-(cyclopentyloxy)-4-methoxyphenyl)piperazin-1-yl)(3-hydroxyphenyl)methanone

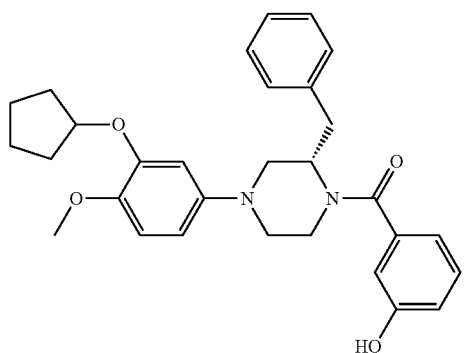 [SMILES: COc1ccc(N2CCN(C(=O)c3cccc(O)c3)[C@@H](Cc3ccccc3)C2)cc1OC1CCCC1]

Prepared by the method outlined for Example 193 using 3-hydroxy-benzoic acid as starting material. Product as an oil (29 mg, 30%). LC/MS (Method B) 2.57 min, [M+1]$^+$ 487. Potency class ND.

Example 200

Preparation of Compound 288, (S)-4-(2-benzyl-4-(3-(cyclopentyloxy)-4-methoxyphenyl)piperazine-1-carbonyl)-1H-imidazol-2(3H)-one

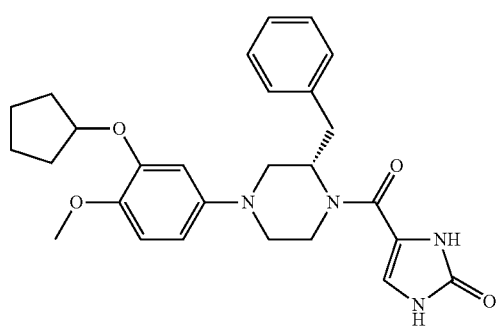 [SMILES: COc1ccc(N2CCN(C(=O)c3c[nH]c(=O)[nH]3)[C@@H](Cc3ccccc3)C2)cc1OC1CCCC1]

Prepared by the method outlined for Example 193 using 2-oxo-2,3-dihydro-1H-imidazole-4-carboxylic acid as starting material. Product as an oil (15 mg, 35%). LC/MS (Method B) 2.89 min, [M+1]$^+$ 477. Potency class B.

Example 201

Preparation of Compound 289, (S)-1-(2-benzyl-4-(3-(cyclopentyloxy)-4-methoxyphenyl)piperazin-1-yl)-2-(2-methyl-1H-imidazol-1-yl)ethanone

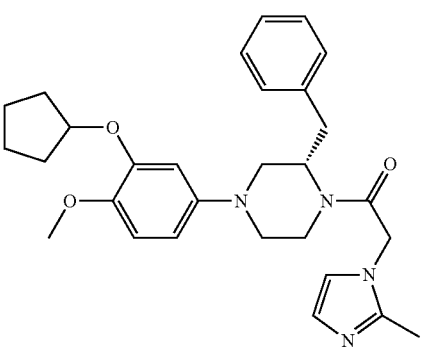 [SMILES: COc1ccc(N2CCN(C(=O)Cn3ccnc3C)[C@@H](Cc3ccccc3)C2)cc1OC1CCCC1]

Prepared by the method outlined for Example 193 using (2-methyl-imidazol-1-yl)-acetic acid as starting material. Product as an oil (20 mg, 50%). LC/MS (Method B) 2.45 min, [M+1]$^+$ 489. Potency class C.

Example 202

Preparation of Compound 290, (S)-1-(2-benzyl-4-(3-(cyclopentyloxy)-4-methoxyphenyl)piperazin-1-yl)-2-(1H-imidazol-1-yl)ethanone

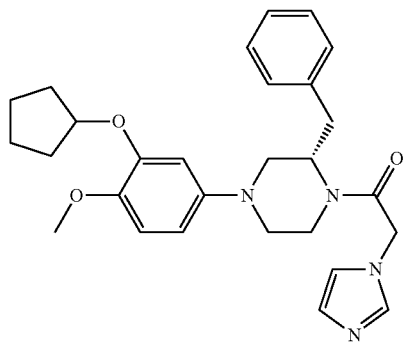 [SMILES: COc1ccc(N2CCN(C(=O)Cn3ccnc3)[C@@H](Cc3ccccc3)C2)cc1OC1CCCC1]

Prepared by the method outlined for Example 193 using imidazol-1-yl-acetic acid as starting material. Product as an oil (20 mg, 50%). LC/MS (Method B) 2.65 min, [M+1]$^+$ 475. Potency class C.

Example 203

Preparation of Compound 291, (S)-1-(2-benzyl-4-(3-(cyclopentyloxy)-4-methoxyphenyl)piperazin-1-yl)-2-(thiazol-5-yl)ethanone

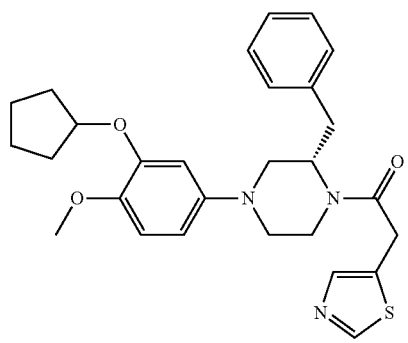 [SMILES: COc1ccc(N2CCN(C(=O)Cc3cncs3)[C@@H](Cc3ccccc3)C2)cc1OC1CCCC1]

Prepared by the method outlined for Example 193 using thiazol-5-yl-acetic acid starting material. Product as an oil (20 mg, 45%). LC/MS (Method B) 3.16 min, [M+1]$^+$ 492. Potency class B.

Example 204

Preparation of Compound 292, (S)-4-((S)-2-benzyl-4-(3-(cyclopentyloxy)-4-methoxyphenyl)piperazine-1-carbonyl)imidazolidin-2-one

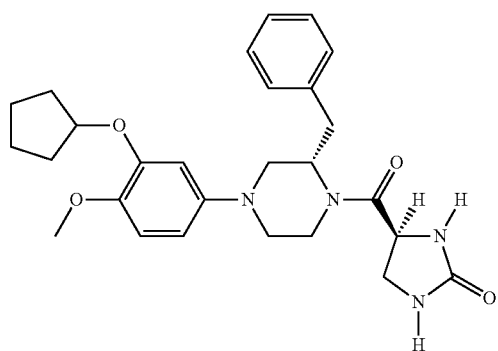 [SMILES: COc1ccc(N2CCN(C(=O)[C@@H]3CNC(=O)N3)[C@@H](Cc3ccccc3)C2)cc1OC1CCCC1]

Prepared by the method outlined for Example 193 using (S)-3-(benzyloxycarbonyl)-2-oxoimidazolidine-4-carboxylic acid CAS [59760-01-9] starting material to afford a Cbz-protected intermediate. The HPLC chromatographed intermediate was dissolved in MeOH and treated to with 10% palladium on carbon. The flask was subjected to hydrogen balloon and stirred vigorously for 2 h. The reaction mixture was then filtered and evaporated to afford clean product as an oil (28% for 2 steps). LC/MS (Method B) 2.89 min, [M+1]$^+$ 479. Potency class A.

Example 205

Preparation of Compound 293, (S)-3-(2-(2-benzyl-4-(3-(cyclopentyloxy)-4-methoxyphenyl)piperazin-1-yl)-2-oxoethyl)-1H-1,2,4-triazol-5(4H)-one

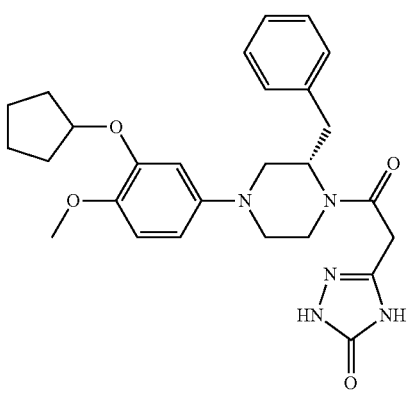 [SMILES: COc1ccc(N2CCN(C(=O)Cc3n[nH]c(=O)[nH]3)[C@@H](Cc3ccccc3)C2)cc1OC1CCCC1]

Prepared by the method outlined for Example 193 using 2-(5-oxo-4,5-dihydro-1H-[1,2,4]triazol-3-yl)-acetamide as starting material. Product as an oil. LC/MS (Method B) 2.78 min, [M+1]$^+$ 492. Potency class B.

Example 206

Preparation of Compound 294, (S)-1-(2-benzyl-4-(3-(cyclopentyloxy)-4-methoxyphenyl)piperazin-1-yl)-2-(2H-tetrazol-5-yl)ethanone

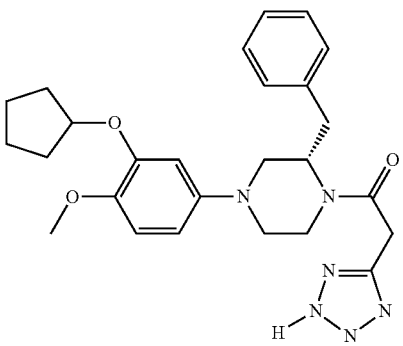 [SMILES: COc1ccc(N2CCN(C(=O)CC3=NNNN3)[C@@H](Cc3ccccc3)C2)cc1OC1CCCC1]

Prepared by the method outlined for Example 193 using (2H-tetrazol-5yl)-acetic acid as starting material. Product as an oil. LC/MS (Method B) 2.56 min, [M+1]$^+$ 477. Potency class A.

Example 207

Preparation of Compound 295, (S)-5-((S)-2-benzyl-4-(3-(cyclopentyloxy)-4-methoxyphenyl)piperazine-1-carbonyl)dihydrofuran-2 (3H)-one

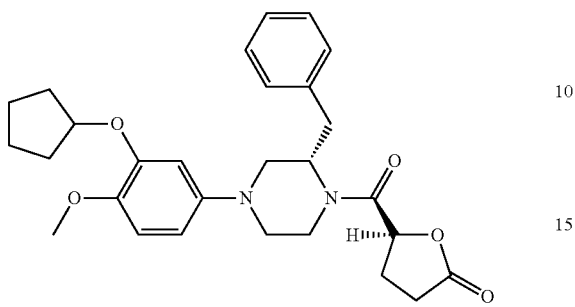

Prepared by the method outlined for Example 193 using (S)-5-oxotetrahydrofuran-2-carboxylic acid as starting material. Product as an oil. LC/MS (Method B) 3.15 min, [M+1]+ 479. Potency class C.

Example 208

Preparation of Compound 296, (R)-5-((S)-2-benzyl-4-(3-(cyclopentyloxy)-4-methoxyphenyl)piperazine-1-carbonyl)dihydrofuran-2(3H)-one

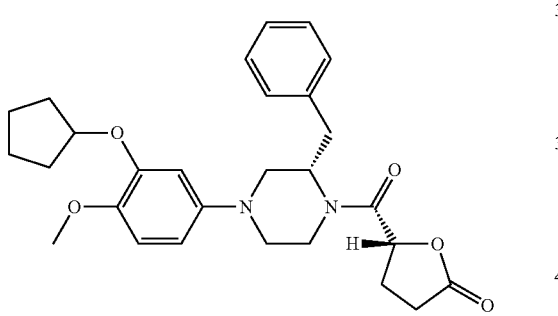

Prepared by the method outlined for Example 193 using (R)-5-oxotetrahydrofuran-2-carboxylic acid as starting material. Product as an oil. LC/MS (Method B) 2.76 min, [M+1]+ 479. Potency class C.

Example 209

Preparation of Compound 297, (S)-(2-benzyl-4-(3-(cyclopentyloxy)-4-methoxyphenyl)piperazin-1-yl)(1-hydroxycyclobutyl)methanone

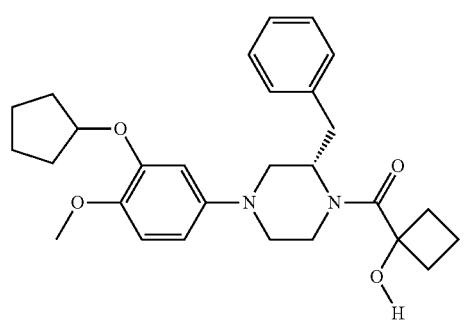 [SMILES: COc1ccc(N2CCN(C(=O)C3(O)CCC3)[C@@H](Cc3ccccc3)C2)cc1OC1CCCC1]

Prepared by the method outlined for Example 193 using 1-hydroxy-cyclobutanecarboxylic acid as starting material. Product as an oil (25 mg, 65%). LC/MS (Method B) 3.56 min, [M+1]+ 465. Potency class B.

Example 210

Preparation of Compound 298, (S)-1-(2-benzyl-4-(3-(cyclopentyloxy)-4-methoxyphenyl)piperazin-1-yl)-2-(2,4-dimethylthiazol-5-yl)ethanone

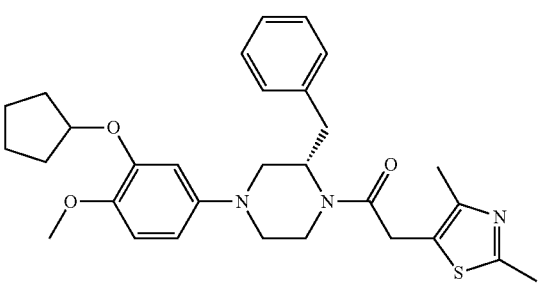 [SMILES: COc1ccc(N2CCN(C(=O)Cc3sc(C)nc3C)[C@@H](Cc3ccccc3)C2)cc1OC1CCCC1]

Prepared by the method outlined for Example 193 using (2,4-dimethyl-thiazol-5-yl)-acetic acid as starting material. Product as an oil. LC/MS (Method B) 2.75 min, [M+1]+ 520. Potency class C.

Example 211

Preparation of Compound 299, 4-((S)-2-benzyl-4-(3-(cyclopentyloxy)-4-methoxyphenyl)piperazine-1-carbonyl)pyrrolidin-2-one

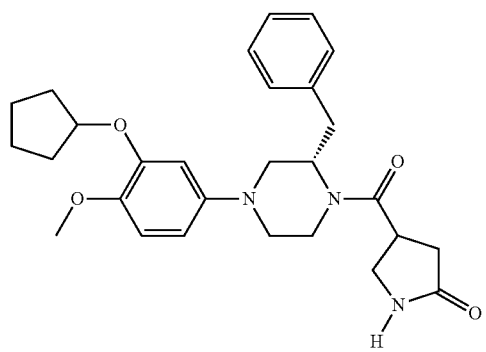 [SMILES: COc1ccc(N2CCN(C(=O)C3CNC(=O)C3)[C@@H](Cc3ccccc3)C2)cc1OC1CCCC1]

Prepared by the method outlined for Example 193 using 5-oxo-pyrrolidine-3-carboxylic acid as starting material. Product as an oil. LC/MS (Method B) 2.50 min, [M+1]+ 478. Potency class B.

Example 212

Preparation of Compound 300, (S)-1-(2-benzyl-4-(3-(cyclopentyloxy)-4-methoxyphenyl)piperazin-1-yl)-2-(furan-2-yl)ethanone

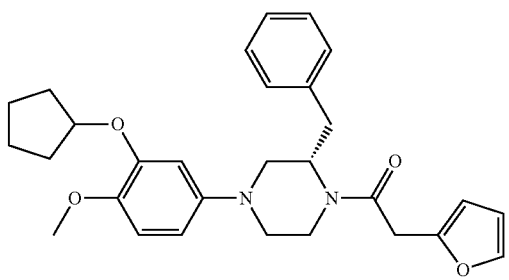 [SMILES: COc1ccc(N2CCN(C(=O)Cc3ccco3)[C@@H](Cc3ccccc3)C2)cc1OC1CCCC1]

Prepared by the method outlined for Example 193 using furan-2-yl-acetic acid as starting material. Product as an oil. LC/MS (Method B) 2.80 min, [M+1]+ 475.

Example 213

Preparation of Compound 301, (S)-1-(2-benzyl-4-(3-(cyclopentyloxy)-4-methoxyphenyl)piperazin-1-yl)-2-(1H-imidazol-2-yl)ethanone

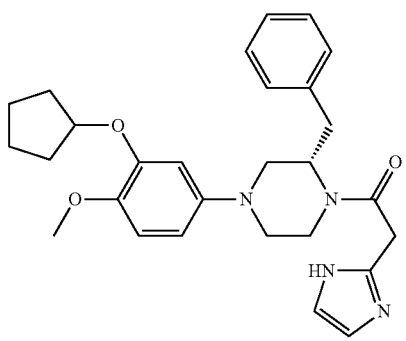 [SMILES: COc1ccc(N2CCN(C(=O)Cc3ncc[nH]3)[C@@H](Cc3ccccc3)C2)cc1OC1CCCC1]

Prepared by the method outlined for Example 189 using 2-(1H-imidazol-2-yl)acetic acid as starting material. Product as an oil (29 mg, 69%). LC/MS (Method B) 2.89 min, [M+1]+ 475. Potency class A.

Example 214

Preparation of Compound 302, (S)-1-(2-benzyl-4-(3-(cyclopentyloxy)-4-methoxyphenyl)piperazin-1-yl)-2-(furan-2-yl)ethane-1,2-dione

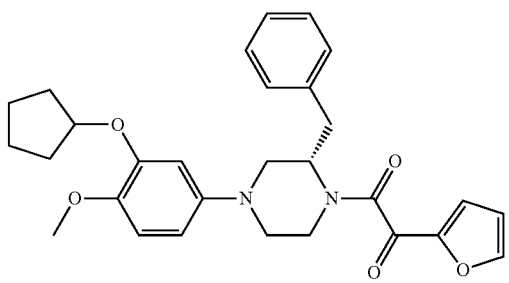 [SMILES: COc1ccc(N2CCN(C(=O)C(=O)c3ccco3)[C@@H](Cc3ccccc3)C2)cc1OC1CCCC1]

Prepared by the method outlined for Example 189 using furan-2-yl-oxo-acetic acid as starting material. Product as an oil (23 mg, 61%). LC/MS (Method B) 2.78 min, [M+1]+ 489. Potency class B.

Example 215

Preparation of Compound 303, (S)-1-(2-benzyl-4-(3-cyclobutoxy-4-methoxyphenyl)piperazin-1-yl)-2-(1H-imidazol-4-yl)ethanone

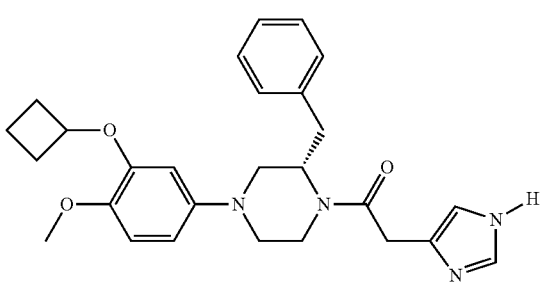 [SMILES: COc1ccc(N2CCN(C(=O)Cc3c[nH]cn3)[C@@H](Cc3ccccc3)C2)cc1OC1CCC1]

Prepared by the method outlined for Example 189 using (1H-imidazol-4-yl)-acetic acid and 3(S)-benzyl-1-(3-cyclobutoxy-4-methoxy-phenyl)-piperazine as starting material. Product as an oil (20 mg, 62%). LC/MS (Method B) 2.89 min, [M+1]+ 461. Potency class A.

Example 216

Preparation of Compound 304, (S)-(2-benzyl-4-(3-(cyclopentyloxy)-4-methoxyphenyl)piperazin-1-yl)(1H-pyrazol-3-yl)methanone

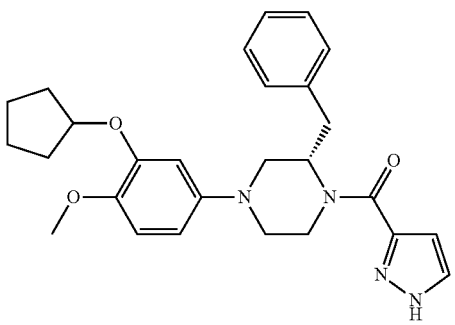 [SMILES: COc1ccc(N2CCN(C(=O)c3cc[nH]n3)[C@@H](Cc3ccccc3)C2)cc1OC1CCCC1]

Prepared by the method outlined for Example 189 using 1H-pyrazole-3-carboxylic acid as starting materials. Product as an oil (30 mg, 60%). LC/MS (Method B) 2.75 min, [M+1]+ 461. Potency class C.

Example 217

Preparation of Compound 305, (S)-1-(2-benzyl-4-(3-(cyclopentyloxy)-4-methoxyphenyl)piperazin-1-yl)-2-(5-methyl-1H-pyrazol-3-yl)ethanone

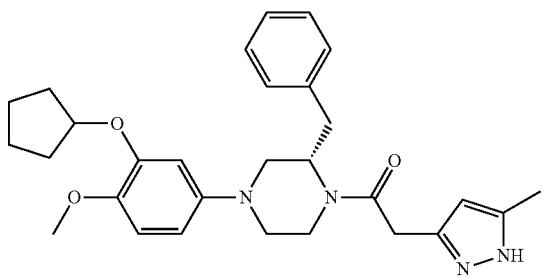 [SMILES: COc1ccc(N2CCN(C(=O)Cc3cc(C)[nH]n3)[C@@H](Cc3ccccc3)C2)cc1OC1CCCC1]

Prepared by the method outlined for Example 189 using (5-methyl-1H-pyrazol-3-yl)-acetic acid as starting material. Product as an oil (25 mg, 65%). LC/MS (Method B) 2.66 min, [M+1]$^+$ 489. Potency class A.

Example 218

Preparation of Compound 306, (S)-1-(2-benzyl-4-(3-(cyclopentyloxy)-4-methoxyphenyl)piperazin-1-yl)-2-(1H-pyrrol-2-yl)ethanone

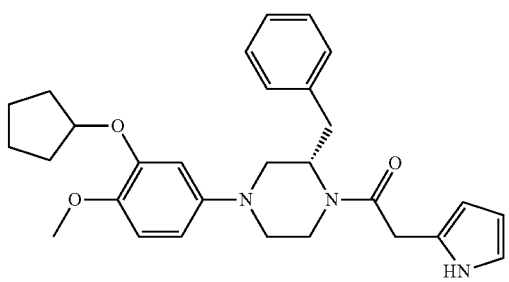 [SMILES: COc1ccc(N2CCN(C(=O)Cc3ccc[nH]3)[C@@H](Cc3ccccc3)C2)cc1OC1CCCC1]

Prepared by the method outlined for Example 189 using (1H-pyrrol-2-yl)-acetic acid as starting material. Product as an oil. LC/MS (Method B) 2.52 min, [M+1]$^+$ 474. Potency class B.

Example 219

Preparation of Compound 307, (S)-1-(2-benzyl-4-(3-(cyclopentyloxy)-4-methoxyphenyl)piperazin-1-yl)-2-(1H-pyrrol-3-yl)ethanone

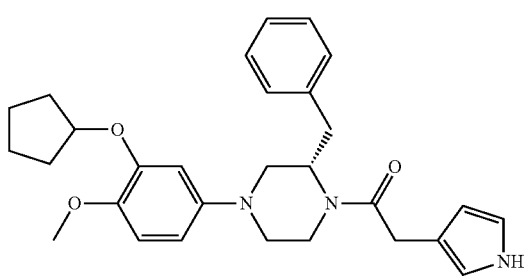 [SMILES: COc1ccc(N2CCN(C(=O)Cc3cc[nH]c3)[C@@H](Cc3ccccc3)C2)cc1OC1CCCC1]

Prepared by the method outlined for Example 189 using (1H-pyrrol-3-yl)-acetic acid as starting material. Product as an oil. LC/MS (Method B) 2.82 min, [M+1]$^+$ 474. Potency class A.

Example 220

Preparation of Compound 308, (S)-1-(2-benzyl-4-(3-(cyclopentyloxy)-4-methoxyphenyl)piperazin-1-yl)-2-(4-methylthiazol-2-yl)ethanone

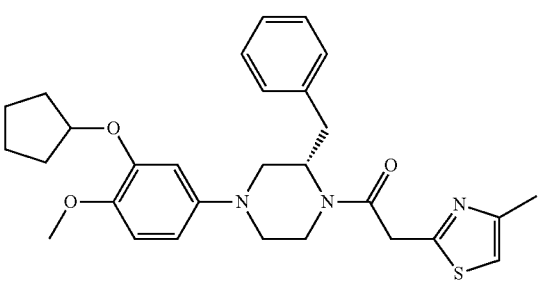 [SMILES: COc1ccc(N2CCN(C(=O)Cc3nc(C)cs3)[C@@H](Cc3ccccc3)C2)cc1OC1CCCC1]

Prepared by the method outlined for Example 189 using (4-methyl-thiazol-2-yl)-acetic acid as starting material. Product as an oil. LC/MS (Method B) 2.84 min, [M+1]$^+$ 506. Potency class A.

Example 221

Preparation of Compound 309, 1-((S)-2-benzyl-4-(3-(cyclopentyloxy)-4-methoxyphenyl)piperazin-1-yl)-2-((S)-pyrrolidin-3-yl)ethanone

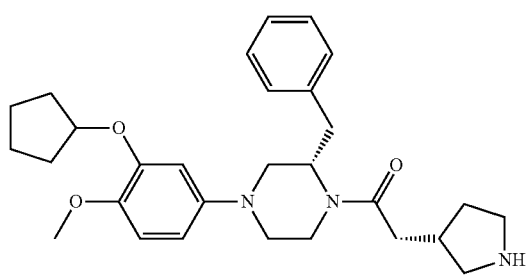

Prepared by the method outlined for Example 189 using (S)-2-(1-(tert-butoxycarbonyl)pyrrolidin-3-yl)acetic acid as starting material to afford the BOC-protected intermediate. Removal of the BOC-protecting group was achieved using the method outlined in Example 1. Product as an oil. LC/MS (Method B) 2.49 min, [M+1]$^+$ 478. Potency class ND.

Example 222

Preparation of Compound 310, 1-((S)-2-benzyl-4-(3-(cyclopentyloxy)-4-methoxyphenyl)piperazin-1-yl)-2-((S)-pyrrolidin-2-yl)ethanone

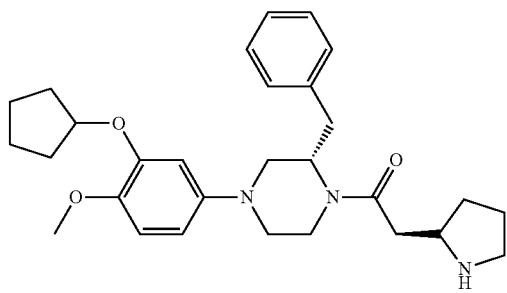

Prepared by the method outlined for Example 189 using (R)-2-(1-(tert-butoxycarbonyl)pyrrolidin-3-yl)acetic acid as starting material to afford the BOC-protected intermediate. Removal of the BOC-protecting group was achieved using the method outlined in Example 1. Product as an oil. LC/MS (Method B) 2.51 min, [M+1]$^+$ 478.

Example 223

Preparation of Compound 311, (S)-ethyl 1-(2-benzyl-4-(3-(cyclopentyloxy)-4-methoxyphenyl)piperazine-1-carbonyl)cyclobutanecarboxylate

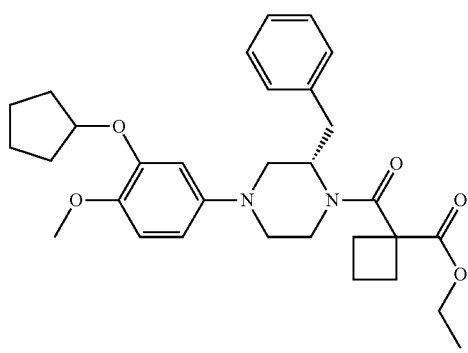 [SMILES: CCOC(=O)C1(C(=O)N2CCN(c3ccc(OC)c(OC4CCCC4)c3)C[C@@H]2Cc2ccccc2)CCC1]

Prepared by the method outlined for Example 131 using cyclobutane-1,1-dicarboxylic acid mono ethyl ester as starting material. Product as an oil. LC/MS (Method B) 3.25 min, [M+1]$^+$ 521.

Example 224

Preparation of Compound 312, (S)-(2-benzyl-4-(3-(cyclopentyloxy)-4-methoxyphenyl)piperazin-1-yl)(1-(hydroxymethyl)cyclobutyl)methanone

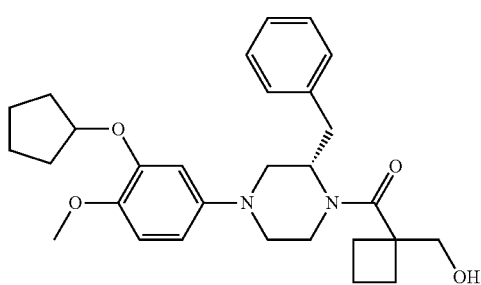 [SMILES: COc1ccc(N2CCN(C(=O)C3(CO)CCC3)[C@@H](Cc3ccccc3)C2)cc1OC1CCCC1]

Prepared by the method outlined for Example 125 using 1-[2(S)benzyl-4-(3-cyclopentyloxy-4-methoxy-phenyl)-piperazine-1-carbonyl]-cyclobutanecarboxylic acid ethyl ester (Example 223, Compound 311) as starting material. Product as an oil. LC/MS (Method B) 2.75 min, [M+1]$^+$ 478. Potency class C.

Example 225

Preparation of Compound 313, 1-((S)-2-benzyl-4-(3-(cyclopentyloxy)-4-methoxyphenyl)piperazin-1-yl)-2-((R)-3-(hydroxymethyl)pyrrolidin-1-yl)ethanone

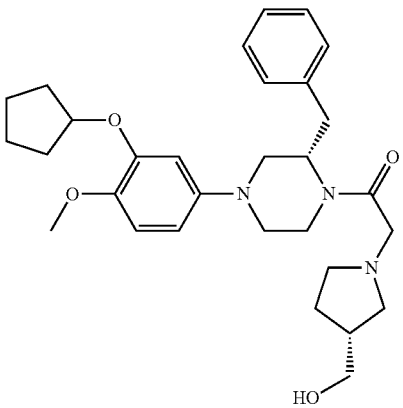 [SMILES: COc1ccc(N2CCN(C(=O)CN3CC[C@@H](CO)C3)[C@@H](Cc3ccccc3)C2)cc1OC1CCCC1]

Prepared by the method outlined for Example 189 using (R)-2-(3-(hydroxymethyl)pyrrolidin-1-yl)acetic acid as starting material. Product as an oil. LC/MS (Method B) 2.56 min, [M+1]$^+$ 508. Potency class ND.

Example 226

Preparation of Compound 314, (S)-1-(2-benzyl-4-(3-cyclobutoxy-4-methoxyphenyl)piperazin-1-yl)-2-(furan-2-yl)ethanone

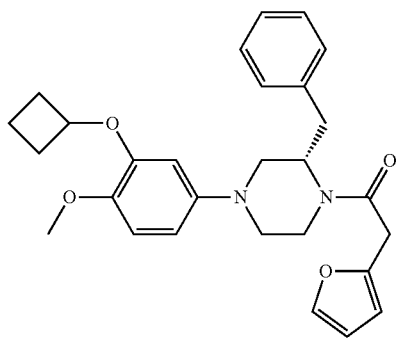 [SMILES: COc1ccc(N2CCN(C(=O)Cc3ccco3)[C@@H](Cc3ccccc3)C2)cc1OC1CCC1]

Prepared by the method outlined for Example 189 using furan-2-yl-acetic acid and 3(S)-benzyl-1-(3-cyclobutoxy-4-methoxy-phenyl)-piperazine (Example 7, Compound 95) as starting materials. Product as an oil. LC/MS (Method B) 2.77 min, [M+1]$^+$ 461. Potency class B.

Example 227

Preparation of Compound 315, (S)-1-(2-benzyl-4-(3-cyclobutoxy-4-methoxyphenyl)piperazine-1-carbonyl)cyclobutanecarboxylic acid

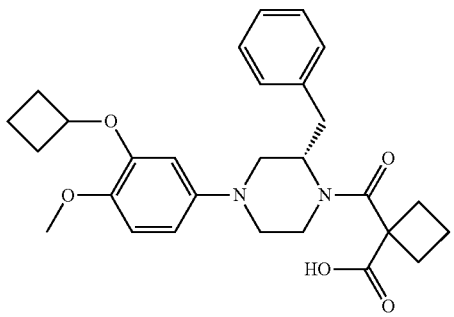 [SMILES: COc1ccc(N2CCN(C(=O)C3(C(=O)O)CCC3)[C@@H](Cc3ccccc3)C2)cc1OC1CCC1]

Prepared by the method outlined for Example 189 using cyclobutanol-,1-dicarboxylic acid mono ethyl ester and 3(S)-benzyl-1-(3-cyclobutoxy-4-methoxy-phenyl)-piperazine (Example 7, Compound 95) to afford intermediate ester which was hydrolyzed as described in Example 98 to afford product as an oil. LC/MS (Method B) 2.82 min, [M+1]$^+$ 479. Potency class A.

Example 228

Preparation of Compound 316, (S)-1-(2-benzyl-4-(3-cyclobutoxy-4-methoxyphenyl)piperazin-1-yl)-2-(2,4-dimethylthiazol-5-yl)ethanone

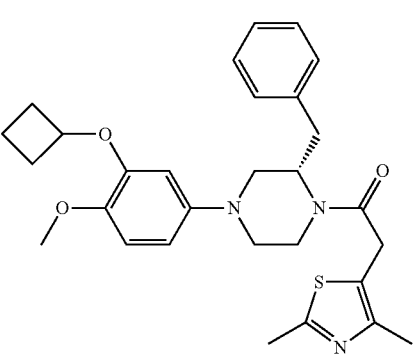 [SMILES: COc1ccc(N2CCN(C(=O)Cc3sc(C)nc3C)[C@@H](Cc3ccccc3)C2)cc1OC1CCC1]

Prepared by the method outlined for Example 189 using (2,4-dimethyl-thiazol-5-yl)-acetic acid and 3(S)-benzyl-1-(3-cyclobutoxy-4-methoxy-phenyl)-piperazine (Example 7, Compound 95) as starting materials to afford product as an oil. LC/MS (Method B) 2.46 min, [M+1]$^+$ 505. Potency class B.

Example 229

Preparation of Compound 317, (S)-1-(2-benzyl-4-(3-(cyclopentyloxy)-4-methoxyphenyl)piperazin-1-yl)-2-(1-methyl-1H-imidazol-4-yl)ethanone

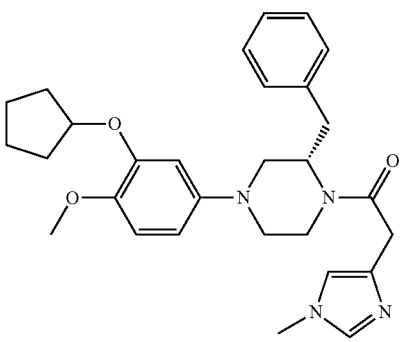 [SMILES: COc1ccc(N2CCN(C(=O)Cc3cn(C)cn3)[C@@H](Cc3ccccc3)C2)cc1OC1CCCC1]

Prepared by the method outlined for Example 189 using (1-methyl-1H-imidazol-4-yl)-acetic acid as starting material. Product as an oil. LC/MS (Method B) 2.76 min, [M+1]$^+$ 489. Potency class A.

Example 230

Preparation of Compound 318, (S)-1-(2-benzyl-4-(3-(cyclopentyloxy)-4-methoxyphenyl)piperazin-1-yl)-2-(1-methyl-1H-imidazol-5-yl)ethanone

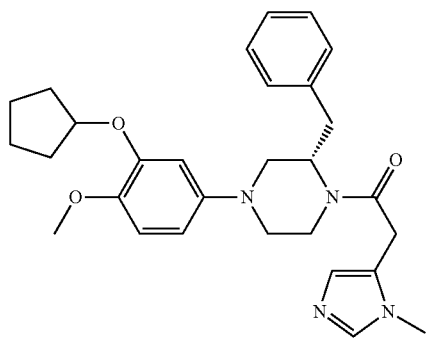 [SMILES: COc1ccc(N2CCN(C(=O)Cc3cncn3C)[C@@H](Cc3ccccc3)C2)cc1OC1CCCC1]

Prepared by the method outlined for Example 189 using (3-methyl-3H-imidazol-4-yl)acetic acid as starting material. Product as an oil. LC/MS (Method B) 2.47 min, [M+1]$^+$ 489. Potency class B.

Example 231

Preparation of Compound 319, 1-((S)-2-benzyl-4-(3-(cyclopentyloxy)-4-methoxyphenyl)piperazin-1-yl)-2-((S)-3-hydroxypyrrolidin-1-yl)ethanone

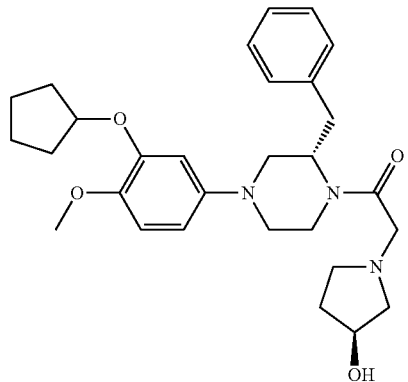 [SMILES: COc1ccc(N2CCN(C(=O)CN3CC[C@H](O)C3)[C@@H](Cc3ccccc3)C2)cc1OC1CCCC1]

Prepared by the method outlined for Example 189 using (3(S)-hydroxy-pyrrolidin-1-yl)-acetic acid as starting material. Product as an oil. LC/MS (Method B) 2.63 min, [M+1]$^+$ 494. Potency class B.

Example 232

Preparation of Compound 320, 1-((S)-2-benzyl-4-(3-(cyclopentyloxy)-4-methoxyphenyl)piperazin-1-yl)-2-((R)-3-hydroxypyrrolidin-1-yl)ethanone

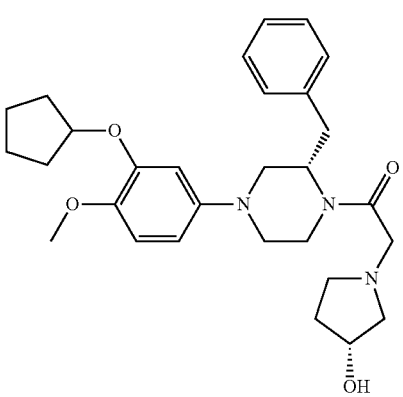 [SMILES: COc1ccc(N2CCN(C(=O)CN3CC[C@@H](O)C3)[C@@H](Cc3ccccc3)C2)cc1OC1CCCC1]

Prepared by the method outlined for Example 189 using (3(R)-hydroxy-pyrrolidin-1-yl)-acetic acid as starting material. Product as an oil. LC/MS (Method B) 2.85 min, [M+1]$^+$ 494. Potency class C.

Example 233

Preparation of Compound 321, 1-((S)-2-benzyl-4-(3-(cyclopentyloxy)-4-methoxyphenyl)piperazin-1-yl)-2-((S)-pyrrolidin-3-yl)ethanone

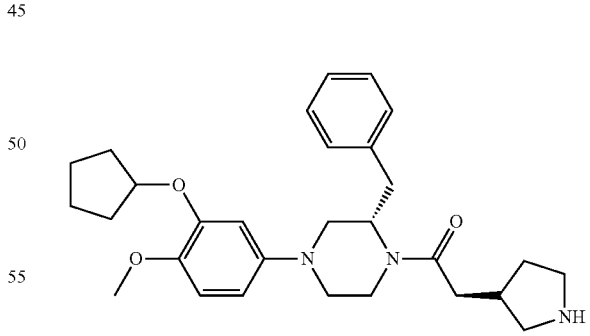

Prepared by the method outlined for Example 189 using 3(S)-carboxymethyl-pyrrolidine-1-carboxylic acid tert-butyl ester as starting material to afford the BOC-protected intermediate. Removal of the BOC-protecting group was achieved using the method outlined in Example 1. Product as an oil. LC/MS (Method B) 2.56 min, [M+1]$^+$ 478. Potency class ND.

Example 234

Preparation of Compound 322, 1-((S)-2-benzyl-4-(3-(cyclopentyloxy)-4-methoxyphenyl)piperazin-1-yl)-2-((S)-3-(hydroxymethyl)pyrrolidin-1-yl)ethanone

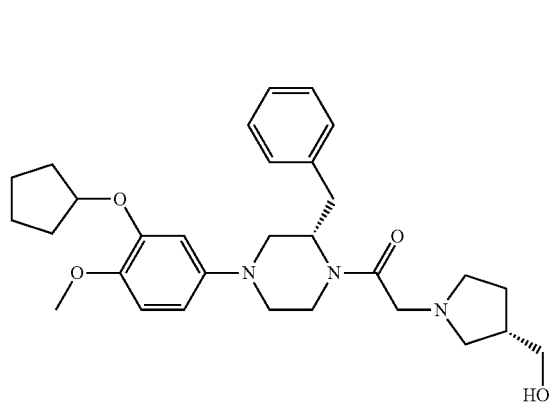 [SMILES: COc1ccc(N2CCN(C(=O)CN3CC[C@H](CO)C3)[C@@H](Cc3ccccc3)C2)cc1OC1CCCC1]

Prepared by the method outlined for Example 189 using (3(S)-hydroxymethyl-pyrrolidin-1-yl)-acetic acid as starting material. Product as an oil. LC/MS (Method B) 2.52 min, [M+1]+ 508. Potency class ND.

Example 235

Preparation of Compound 323, (S)-1-(2-benzyl-4-(3-(cyclopentyloxy)-4-methoxyphenyl)piperazin-1-yl)-2-(1-methyl-1H-imidazol-2-yl)ethanone

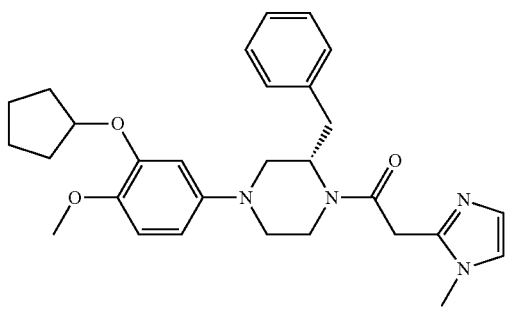 [SMILES: COc1ccc(N2CCN(C(=O)Cc3nccn3C)[C@@H](Cc3ccccc3)C2)cc1OC1CCCC1]

Prepared by the method outlined for Example 189 using (1-methyl-1H-imidazol-2-yl)acetic acid as starting material. Product as an oil. LC/MS (Method B) 2.36 min, [M+1]+ 489. Potency class ND.

Example 236

Preparation of Compound 324, (S)-1-(2-benzyl-4-(3-isopropoxy-4-methoxyphenyl)piperazine-1-carbonyl)cyclobutanecarboxylic acid

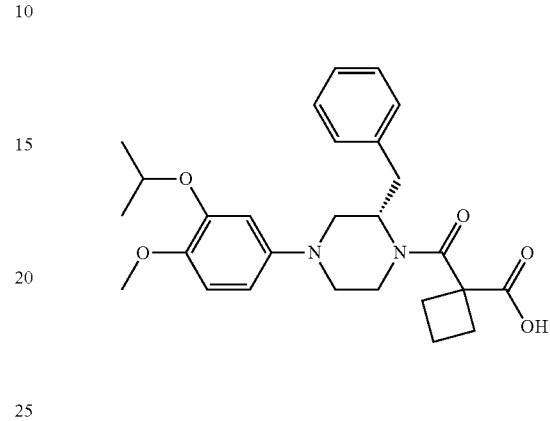

Prepared by the method outlined for Example 189 using cyclobutane 1-,1-dicarboxylic acid mono ethyl ester and 3(S)-benzyl-1-(3-(1-methylethoxy)-4-methoxy-phenyl)-piperazine (Example 9, Compound 97) as starting materials to afford an intermediate ester which was hydrolyzed as described in Example 98 to afford product as an oil. LC/MS (Method B) 2.82 min, [M+1]+ 467. Potency class ND.

Example 237

Preparation of Compound 325, (S)-1-(2-benzyl-4-(3-(cyclopentyloxy)-4-methoxyphenyl)piperazin-1-yl)-2-(5-nitro-1H-1,2,4-triazol-3-yl)ethanone

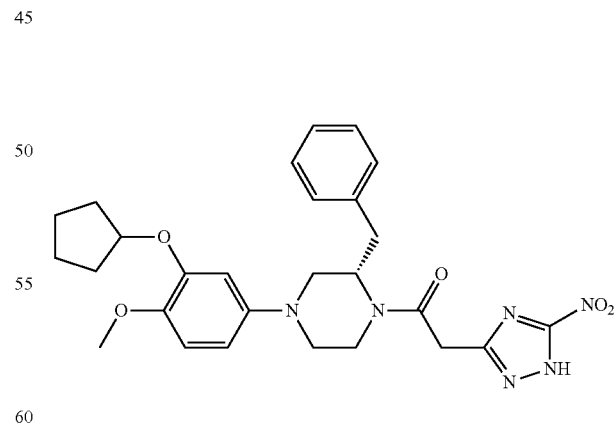

Prepared by the method outlined for Example 189 using (5-Nitro-1H-[1,2,4]triazol-3-yl)-acetic acid as starting material. Product as an oil. LC/MS (Method B) 3.66 min, [M+1]+ 521. Potency class A.

Example 238

Preparation of Compound 326, (S)-1-(2-benzyl-4-(3-cyclobutoxy-4-methoxyphenyl)piperazin-1-yl)-2-(1H-pyrrol-3-yl)ethanone

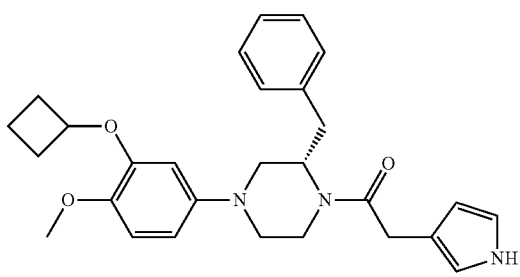 [SMILES: COc1ccc(N2CCN(C(=O)Cc3cc[nH]c3)[C@@H](Cc3ccccc3)C2)cc1OC1CCC1]

Prepared by the method outlined for Example 189 using (1H-pyrrol-3-yl)-acetic acid and 3(S)-benzyl-1-(3-cyclobutoxy-4-methoxy-phenyl)-piperazine (Example 7, Compound 95) as starting materials. Product as an oil. LC/MS (Method B) 2.66 min, [M+1]$^+$ 460. Potency class ND.

Example 239

Preparation of Compound 327, (S)-1-(2-benzyl-4-(3-isopropoxy-4-methoxyphenyl)piperazin-1-yl)-2-(1H-imidazol-5-yl)ethanone

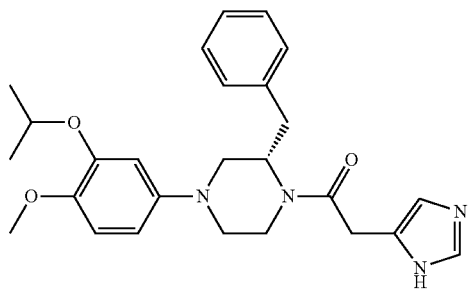 [SMILES: COc1ccc(N2CCN(C(=O)Cc3cnc[nH]3)[C@@H](Cc3ccccc3)C2)cc1OC(C)C]

Prepared by the method outlined for Example 189 using (3H-imidazol-4-yl)-acetic acid and 3(S)-benzyl-1-(3-(1-methylethoxy)-4-methoxy-phenyl)-piperazine (Example 9, Compound 97) as starting materials. Product as an oil. LC/MS (Method B) 2.52 min, [M+1]$^+$ 449. Potency class A.

Example 240

Preparation of Compound 328, (S)-1-(2-benzyl-4-(3-isopropoxy-4-methoxyphenyl)piperazin-1-yl)-2-(1H-pyrrol-3-yl)ethanone

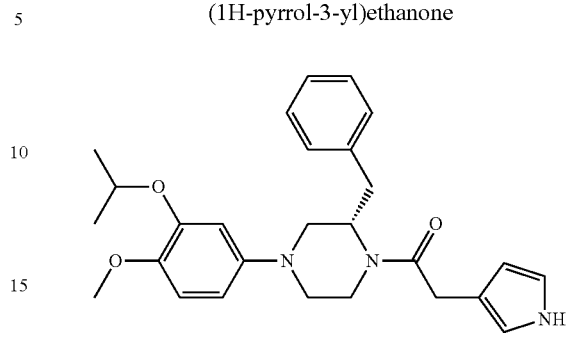

Prepared by the method outlined for Example 189 using (1H-pyrrol-3-yl)-acetic acid and 3(S)-benzyl-1-(3-(1-methylethoxy)-4-methoxy-phenyl)-piperazine (Example 9, Compound 97) as starting materials. Product as an oil. LC/MS (Method B) 2.75 min, [M+1]$^+$ 448. Potency class A.

Example 241

Preparation of Compound 329, (S)-1-(2-benzyl-4-(3-(cyclopentyloxy)-4-methoxyphenyl)piperazin-1-yl)-2-(5-methyl-1H-1,2,4-triazol-3-yl)ethanone

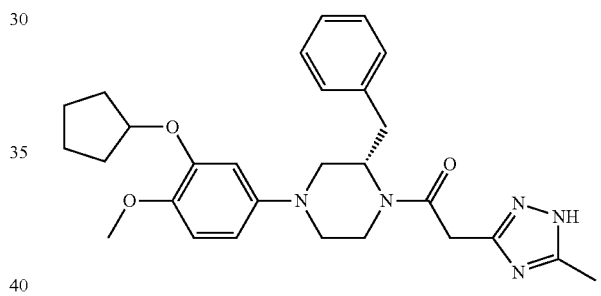

Prepared by the method outlined for Example 189 using (5-methyl-1H-[1,2,4]triazol-3-yl)-acetic acid as starting material. Product as an oil. LC/MS (Method B) 2.35 min, [M+1]$^+$ 490.

Example 242

Preparation of Compound 330, (S)-1-(2-benzyl-4-(3-isopropoxy-4-methoxyphenyl)piperazin-1-yl)-2-(3-methyl-1H-1,2,4-triazol-5-yl)ethanone

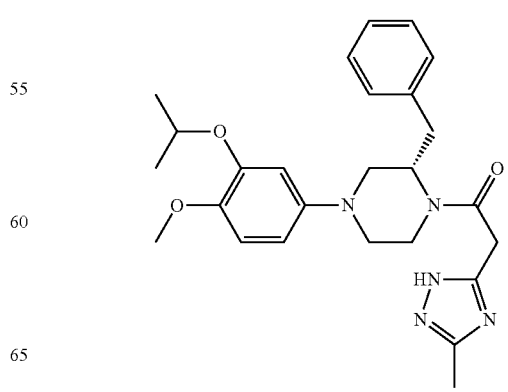

Prepared by the method outlined for Example 189 using 3(S)-benzyl-1-(3-(1-methylethoxy)-4-methoxy-phenyl)-piperazine (Example 9, Compound 97) as starting material. Product as an oil. LC/MS (Method B) 2.54 min, [M+1]+ 464. Potency class A.

Example 243

Preparation of Compound 331, (S)-1-(2-benzyl-4-(3-cyclobutoxy-4-methoxyphenyl)piperazin-1-yl)-2-(3-methyl-1H-1,2,4-triazol-5-yl)ethanone

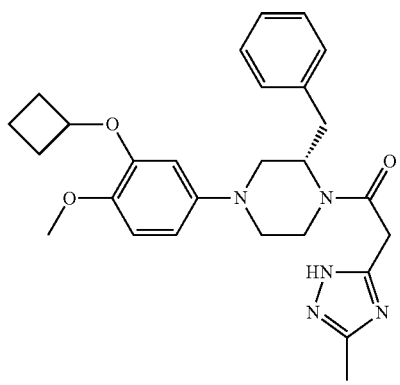 [SMILES: COc1ccc(N2CCN(C(=O)Cc3nc(C)n[nH]3)[C@@H](Cc3ccccc3)C2)cc1OC1CCC1]

Prepared by the method outlined for Example 189 using 3(S)-benzyl-1-(3-cyclobutoxy-4-methoxy-phenyl)-piperazine as starting material. Product as an oil. LC/MS (Method B) 2.46 min, [M+1]+ 475. Potency class A.

Example 244

Preparation of Compound 332, (S)-1-(2-benzyl-4-(3,4-bis(difluoromethoxy)phenyl)piperazin-1-yl)-2-(3-methyl-1H-1,2,4-triazol-5-yl)ethanone

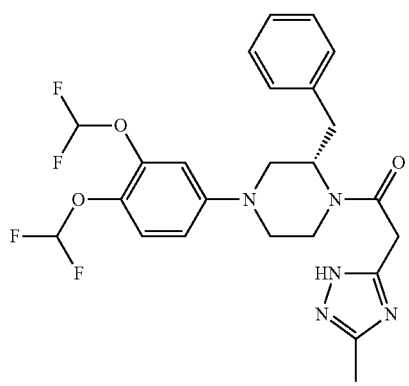 [SMILES: Cc1n[nH]c(CC(=O)N2CCN(c3ccc(OC(F)F)c(OC(F)F)c3)C[C@@H]2Cc2ccccc2)n1]

Prepared by the method outlined for Example 189 using and 3(S)-benzyl-1-(3,4-bis-difluoromethoxy-phenyl)-piperazine as starting material. Product as an oil (30 mg, 68%). LC/MS (Method B) 2.57 min, [M+1]+ 508. Potency class A.

Example 245

Preparation of Compound 333, (S)-1-(2-benzyl-4-(3-isopropoxy-4-methoxyphenyl)piperazin-1-yl)-2-(2H-tetrazol-5-yl)ethanone

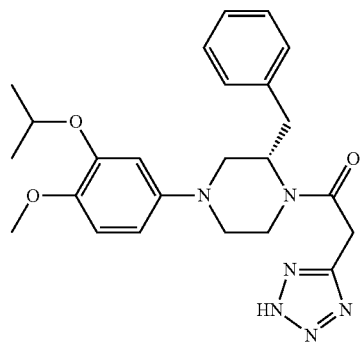 [SMILES: COc1ccc(N2CCN(C(=O)Cc3nn[nH]n3)[C@@H](Cc3ccccc3)C2)cc1OC(C)C]

Prepared by the method outlined for Example 189 using (2H-tetrazol-5-yl)-acetic acid and 3(S)-benzyl-1-(3-(1-methylethoxy)-4-methoxy-phenyl)-piperazine (Example 9, Compound 97) as starting materials. Product as an oil. LC/MS (Method B) 2.50 min, [M+1]+ 450. Potency class B.

Example 246

Preparation of Compound 334, (S)-1-(2-benzyl-4-(3-(cyclopentyloxy)-4-methoxyphenyl)piperazin-1-yl)-2-(1H-1,2,3-triazol-1-yl)ethanone

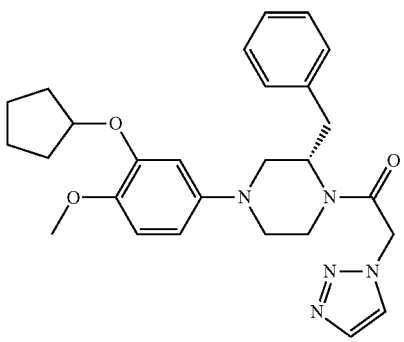 [SMILES: COc1ccc(N2CCN(C(=O)Cn3ccnn3)[C@@H](Cc3ccccc3)C2)cc1OC1CCCC1]

Prepared by the method outlined for Example 189 using [1,2,3]triazol-1-yl-acetic acid as starting material. Product as an oil. LC/MS (Method B) 2.66 min, [M+1]+ 476. Potency class C.

Example 247

Preparation of Compound 335, (S)-1-(2-benzyl-4-(3-cyclobutoxy-4-methoxyphenyl)piperazin-1-yl)-2-(2H-tetrazol-5-yl)ethanone

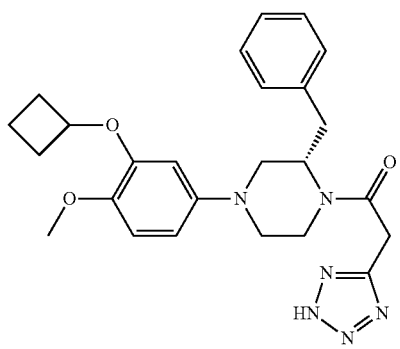 [SMILES: COc1ccc(N2CCN(C(=O)Cc3nn[nH]n3)[C@@H](Cc3ccccc3)C2)cc1OC1CCC1]

Prepared by the method outlined for Example 189 using (2H-tetrazol-5-yl)-acetic acid and 3(S)-benzyl-1-(3-cyclobutoxy-4-methoxy-phenyl)-piperazine (Example 7, Compound 95) as starting materials. Product as an oil (30 mg, 68%). LC/MS (Method B) 2.57 min, [M+1]$^+$ 463. Potency class A.

Example 248

Preparation of Compound 336, (S)-1-(2-benzyl-4-(3-isopropoxy-4-methoxyphenyl)piperazin-1-yl)-2-(5-nitro-1H-1,2,4-triazol-3-yl)ethanone

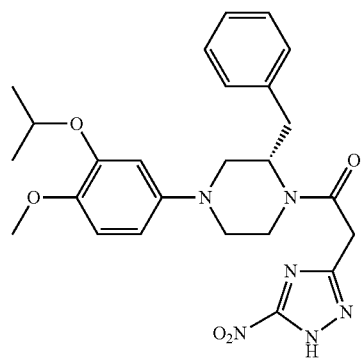 [SMILES: COc1ccc(N2CCN(C(=O)Cc3n[nH]c([N+](=O)[O-])n3)[C@@H](Cc3ccccc3)C2)cc1OC(C)C]

Prepared by the method outlined for Example 189 using (5-Nitro-1H-[1,2,4]triazol-3-yl)-acetic acid and 3(S)-benzyl-1-(3-(1-methylethoxy)-4-methoxy-phenyl)-piperazine (Example 9, Compound 97) as starting materials. Product as an oil. LC/MS (Method B) 3.10 min, [M+1]$^+$ 495. Potency class C.

Example 249

Preparation of Compound 337, (S)-2-(3-amino-1H-1,2,4-triazol-5-yl)-1-(2-benzyl-4-(3-isopropoxy-4-methoxyphenyl)piperazin-1-yl)ethanone

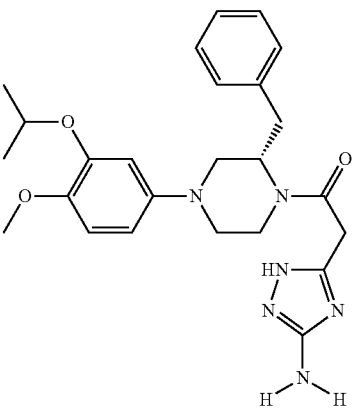 [SMILES: COc1ccc(N2CCN(C(=O)Cc3nc(N)n[nH]3)[C@@H](Cc3ccccc3)C2)cc1OC(C)C]

A solution of 1-[2(S)benzyl-4-(3-isopropoxy-4-methoxy-phenyl)-piperazin-1-yl]-2-(5-nitro-1H-[1,2,4]triazol-3-yl)-ethanone (Example 248, Compound 336) in MeOH (10 mL) was treated with 10% Palladium on Carbon (200 mg, 0.66 mmol) and ammonium formate (50 mg, 1.66 mmol). The reaction mixture was heated at 65 C for 1 h after which time the reaction was cooled and filtered with the aid of MeOH (20 mL) and EtOAc (20 mL). The organic portion was dried over MgSO$_4$, filtered, and evaporated to an oil which was purified by silica gel flash chromatography with 5% then 10% MeOH/EtOAc as eluant to afford product as an oil. $^1$H NMR (CDCl$_3$) 12.00-11.90 (br, 1 H), 7.39-7.25 (m, 2 H), 7.24-7.20 (m, 3 H), 6.79 (d, J=8, 1 H), 6.50-6.43 (m, 1 H), 6.37-6.34 (m, 1 H), 6.00-5.90 (br, 2 H), 4.50-433 (m, 2 H), 3.64 (s, 3 H), 3.54-3.33 (m, 4 H). 3.22-3.09 (m, 3 H), 3.00-2.92 (m, 1 H), 2.74-2.60 (m, 1 H), 2.55-2.37 (m, 3 H), 1.19 (d, J=6.4, 6 H). LC/MS (Method B) 3.66 min, [M+1]$^+$ 465. Potency class A.

Example 250

Preparation of Compound 338, (S)-1-(2-benzyl-4-(3-cyclobutoxy-4-methoxyphenyl)piperazin-1-yl)-2-(5-nitro-1H-1,2,4-triazol-3-yl)ethanone

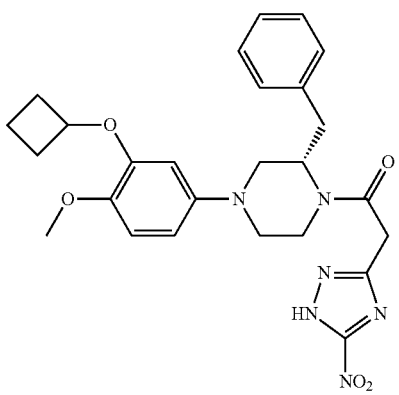 [SMILES: COc1ccc(N2CCN(C(=O)Cc3n[nH]c([N+](=O)[O-])n3)[C@@H](Cc3ccccc3)C2)cc1OC1CCC1]

Prepared by the method outlined for Example 189 using (5-Nitro-1H-[1,2,4]triazol-3-yl)-acetic acid and 3(S)-benzyl-1-(3-cyclobutoxy-4-methoxy-phenyl)-piperazine (Example 7, Compound 95) as starting materials to afford product as an oil. LC/MS (Method B) 3.18 min, [M+1]+ 507. Potency class B.

Example 251

Preparation of Compound 339, (S)-2-(5-amino-1H-1,2,4-triazol-3-yl)-1-(2-benzyl-4-(3-cyclobutoxy-4-methoxyphenyl)piperazin-1-yl)ethanone

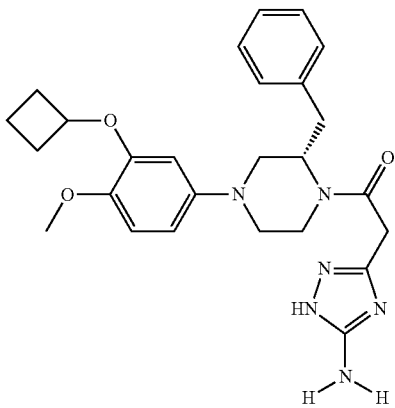 [SMILES: COc1ccc(N2CCN(C(=O)Cc3n[nH]c(N)n3)[C@@H](Cc3ccccc3)C2)cc1OC1CCC1]

Prepared by the method outlined for Example 249 using 1-[2(S)benzyl-4-(3-cyclobutoxy-4-methoxy-phenyl)-piperazin-1-yl]-2-(5-nitro-1H-[1,2,4]triazol-3-yl)-ethanone (Example 250, Compound 338) as starting materials to afford product as an oil. LC/MS (Method B) 3.25 min, [M+1]+ 477. Potency class A.

Example 252

Preparation of Compound 340, (S)-1-(2-benzyl-4-(3-cyclobutoxy-4-methoxyphenyl)piperazin-1-yl)-2-(pyrimidin-2-yl)ethanone

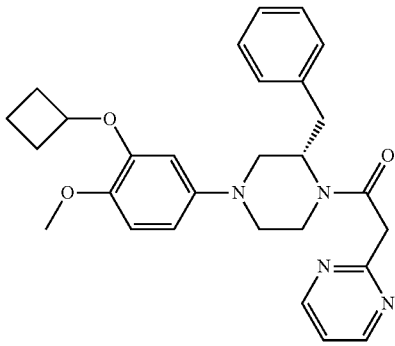 [SMILES: COc1ccc(N2CCN(C(=O)Cc3ncccn3)[C@@H](Cc3ccccc3)C2)cc1OC1CCC1]

Prepared by the method outlined for Example 189 using pyrimidin-2-yl-acetic acid and and 3(S)-benzyl-1-(3-cy clobutoxy-4-methoxy-phenyl)-piperazine (Example 7, Compound 95) as starting materials. Product as an oil. LC/MS (Method B) 2.51 min, [M+1]+ 473. Potency class A.

Example 253

Preparation of Compound 341, (S)-1-(2-benzyl-4-(3-isopropoxy-4-methoxyphenyl)piperazin-1-yl)-2-(pyridin-2-yl)ethanone

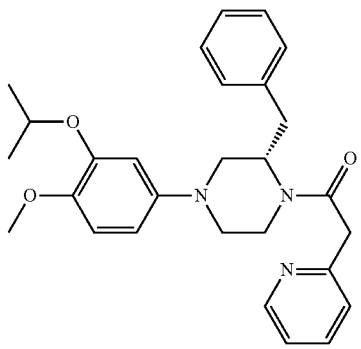

Prepared by the method outlined for Example 189 using pyridine-2-yl-acetic acid and 3(S)-benzyl-1-(3-(1-methylethoxy)-4-methoxy-phenyl)-piperazine (Example 9, Compound 97) as starting materials. Product as an oil (30 mg, 68%). LC/MS (Method B) 2.45 min, [M+1]+ 460. Potency class B.

Example 254

Preparation of Compound 342, (S)-1-(2-benzyl-4-(3-cyclobutoxy-4-methoxyphenyl)piperazin-1-yl)-2-(pyridin-2-yl)ethanone

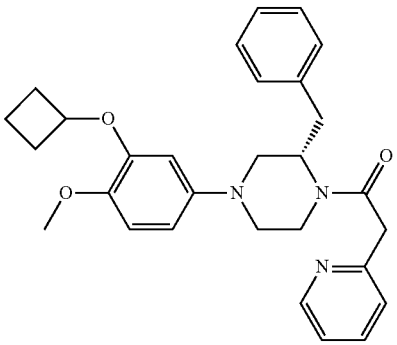 [SMILES: COc1ccc(N2CCN(C(=O)Cc3ccccn3)[C@@H](Cc3ccccc3)C2)cc1OC1CCC1]

Prepared by the method outlined for Example 189 using pyridine-2-yl-acetic acid and (S)3-benzyl-1-(3-cyclobutoxy-4-methoxy-phenyl)-piperazine (Example 7, Compound 95) as starting materials. Product as an oil. LC/MS (Method B) 2.57 min, [M+1]+ 472. Potency class A.

Example 255

Preparation of Compound 343, (S)-1-(2-benzyl-4-(3-isopropoxy-4-methoxyphenyl)piperazin-1-yl)-2-(pyrimidin-2-yl)ethanone

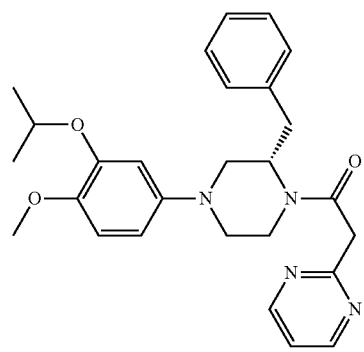 [SMILES: COc1ccc(N2CCN(C(=O)Cc3ncccn3)[C@@H](Cc3ccccc3)C2)cc1OC(C)C]

Prepared by the method outlined for Example 189 using pyrimidin-2-yl-acetic acid and 3(S)-benzyl-1-(3-(1-methylethoxy)-4-methoxy-phenyl)-piperazine (Example 9, Compound 97) as starting materials. Product as an oil. LC/MS (Method B) 2.67 min, [M+1]+ 461. Potency class B.

Example 256

Preparation of Compound 344, (S)-1-(2-benzyl-4-(3-cyclobutoxy-4-(difluoromethoxy)phenyl)piperazin-1-yl)-2-(1H-imidazol-4-yl)ethanone

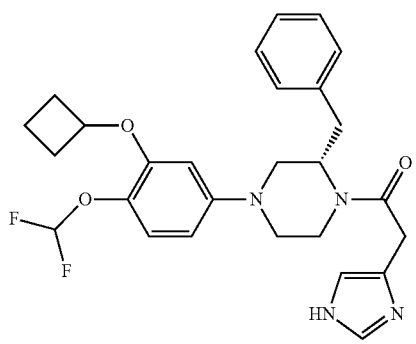 [SMILES: O=C(Cc1c[nH]cn1)N1CCN(c2ccc(OC(F)F)c(OC3CCC3)c2)C[C@@H]1Cc1ccccc1]

Prepared by the method outlined for Example 189 using (1H-imidazol-4-yl)-acetic acid and (S)3-benzyl-1-(3-cyclobutoxy-4-difluoromethoxy-phenyl)-piperazine (Example 4, Compound 92) as starting materials. Product as an oil. LC/MS (Method B) 2.54 min, [M+1]+ 497. Potency class A.

Example 257

Preparation of Compound 345, (S)-1-(2-benzyl-4-(3-cyclobutoxy-4-(difluoromethoxy)phenyl)piperazin-1-yl)-2-(5-methyl-1H-1,2,4-triazol-3-yl)ethanone

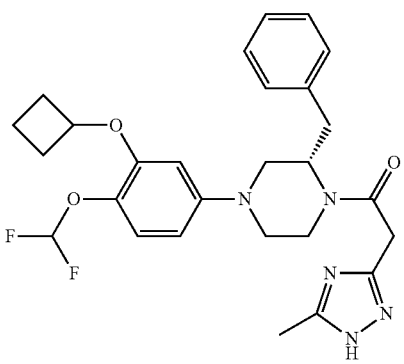 [SMILES: Cc1nc(CC(=O)N2CCN(c3ccc(OC(F)F)c(OC4CCC4)c3)C[C@@H]2Cc2ccccc2)n[nH]1]

Prepared by the method outlined for Example 189 using (5-methyl-1H-[1,2,4]triazol-3-yl)-acetic acid and (S)3-benzyl-1-(3-cyclobutoxy-4-difluoromethoxy-phenyl)-piperazine (Example 4, Compound 92) as starting materials. Product as an oil. LC/MS (Method B) 2.66 min, [M+1]+ 512. Potency class A.

Example 258

Preparation of Compound 346, (S)-1-(2-benzyl-4-(3-(difluoromethoxy)-4-methoxyphenyl)piperazin-1-yl)-2-(5-methyl-1H-1,2,4-triazol-3-yl)ethanone

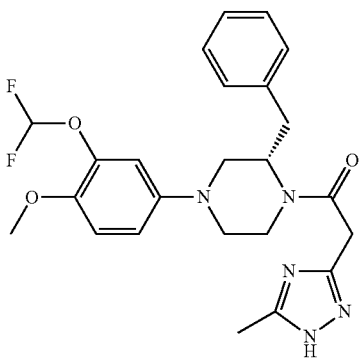 [SMILES: COc1ccc(N2CCN(C(=O)Cc3n[nH]c(C)n3)[C@@H](Cc3ccccc3)C2)cc1OC(F)F]

Prepared by the method outlined for Example 189 using (5-methyl-1H-[1,2,4]triazol-3-yl)-acetic acid and (S)3-benzyl-1-(3-difluoromethoxy-4-methoxy-phenyl)-piperazine (Example 69, Compound 157) as starting materials. Product as an oil. LC/MS (Method B) 2.57 min, [M+1]+ 472. Potency class A.

Example 259

Preparation of Compound 347, (S)-1-(2-benzyl-4-(3-(difluoromethoxy)-4-methoxyphenyl)piperazin-1-yl)-2-(1H-imidazol-4-yl)ethanone

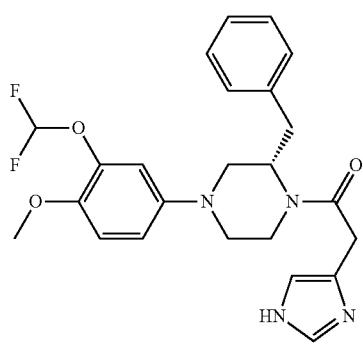 [SMILES: COc1ccc(N2CCN(C(=O)Cc3c[nH]cn3)[C@@H](Cc3ccccc3)C2)cc1OC(F)F]

Prepared by the method outlined for Example 189 using (1H-imidazol-4-yl)-acetic acid and (S)3-benzyl-1-(3-difluoromethoxy-4-methoxy-phenyl)-piperazine (Example 69, Compound 157) as starting materials. Product as an oil. LC/MS (Method B) 3.14 min, [M+1]$^+$ 457. Potency class C.

Example 260

Preparation of Compound 348, (S)-1-(2-benzyl-4-(3-cyclobutoxy-4-methoxyphenyl)piperazin-1-yl)-3-(methylamino)propan-1-one

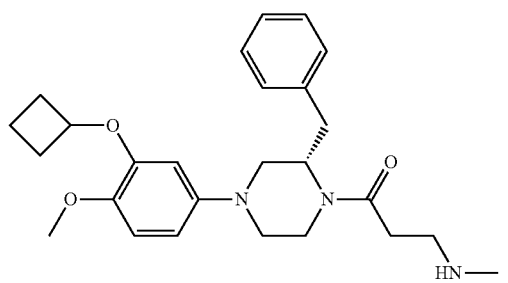 [SMILES: CNCCC(=O)N1CCN(c2ccc(OC)c(OC3CCC3)c2)C[C@@H]1Cc1ccccc1]

Prepared by the method outlined for Example 189 using 3-(tert-butoxycarbonyl-methyl-amino)-propionic acid and (S)3-benzyl-1-(3-cyclobutoxy-4-methoxy-phenyl)-piperazine (Example 7, Compound 95) as starting materials to afford the BOC-protected intermediate. Removal of the BOC-protecting group was achieved using the method outlined in Example 1. Product as an oil (25 mg, 55%). LC/MS (Method B) 3.75 min, [M+1]$^+$ 438. Potency class C.

Example 261

Preparation of Compound 349, (S)-2-amino-1-(2-benzyl-4-(3-cyclobutoxy-4-methoxyphenyl)piperazin-1-yl)ethanone

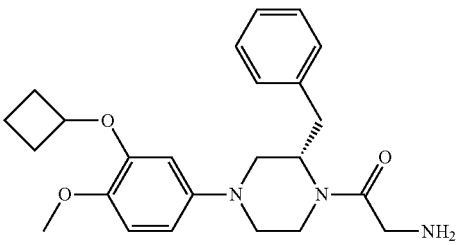 [SMILES: COc1ccc(N2CCN(C(=O)CN)[C@@H](Cc3ccccc3)C2)cc1OC1CCC1]

Prepared by the method outlined for Example 91 using tert-butoxycarbonylamino acetic acid and (S)3-benzyl-1-(3-cyclobutoxy-4-methoxy-phenyl)-piperazine (Example 7, Compound 95) as staring materials to afford product as an oil. LC/MS (Method B) 3.55 min, [M+1]$^+$ 410. Potency class C.

Example 262

Preparation of Compound 350, (S)-1-(2-benzyl-4-(3-cyclobutoxy-4-methoxyphenyl)piperazin-1-yl)-2-(methylamino)ethanone

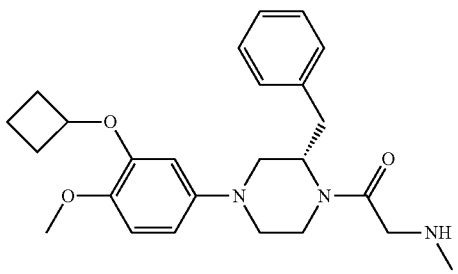 [SMILES: CNCC(=O)N1CCN(c2ccc(OC)c(OC3CCC3)c2)C[C@@H]1Cc1ccccc1]

Prepared by the method outlined for Example 92 using (S)3-benzyl-1-(3-cyclobutoxy-4-methoxy-phenyl)-piperazine (Example 7, Compound 95) as starting material to afford product as an oil. LC/MS (Method B) 3.65 min, [M+1]$^+$ 424. Potency class C.

Example 263

Preparation of Compound 351, (S)-2-amino-1-(2-benzyl-4-(1-cyclobutyl-3-ethyl-1H-indazol-6-yl)piperazin-1-yl)ethanone

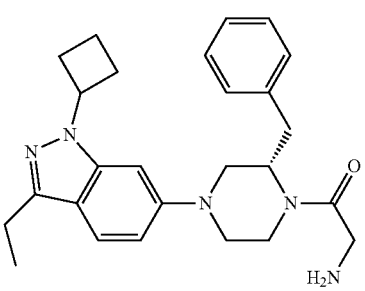 [SMILES: CCc1nn(C2CCC2)c2cc(N3CCN(C(=O)CN)[C@@H](Cc4ccccc4)C3)ccc12]

Prepared by the method outlined for Example 91 using 64(S)3-benzyl-piperazin-1-yl)-1-cyclobutyl-3-ethyl-1H-indazole (Example 56, Compound 144) as starting material to afford product as an oil. LC/MS (Method B) 3.35 min, [M+1]+ 432. Potency class C.

Example 264

Preparation of Compound 352, (S)-1-(2-benzyl-4-(1-cyclobutyl-3-ethyl-1H-indazol-6-yl)piperazin-1-yl)-2-(pyridin-2-yl)ethanone

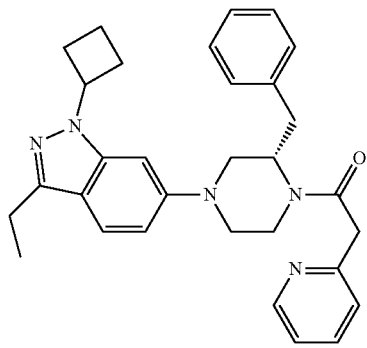 [SMILES: CCc1nn(C2CCC2)c2cc(N3CCN(C(=O)Cc4ncccn4)[C@@H](Cc4ccccc4)C3)ccc12]

Prepared by the method outlined for Example 189 using pyridine-2-yl-acetic acid and 6-((S)3-benzyl-piperazin-1-yl)-1-cyclobutyl-3-ethyl-1H-indazole (Example 56, Compound 144) as starting materials. Product as an oil (30 mg, 68%). LC/MS (Method B) 2.76 min, [M+1]+ 494. Potency class C.

Example 265

Preparation of Compound 353, (S)-1-(2-benzyl-4-(1-cyclobutyl-3-ethyl-1H-indazol-6-yl)piperazin-1-yl)-2-(pyrimidin-2-yl)ethanone

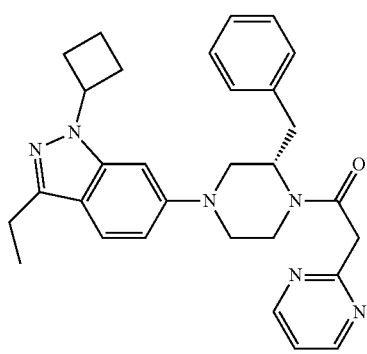

Prepared by the method outlined for Example 189 using pyrimidin-2-yl-acetic acid and 6-((S)3-benzyl-piperazin-1-yl)-1-cyclobutyl-3-ethyl-1H-indazole (Example 56, Compound 144) as starting materials. Product as an oil. LC/MS (Method B) 2.46 min, [M+1]+ 495. Potency class C.

Example 266

Preparation of Compound 354, (S)-1-(2-benzyl-4-(1-cyclobutyl-3-ethyl-1H-indazol-6-yl)piperazin-1-yl)-2-(5-nitro-1H-1,2,4-triazol-3-yl)ethanone

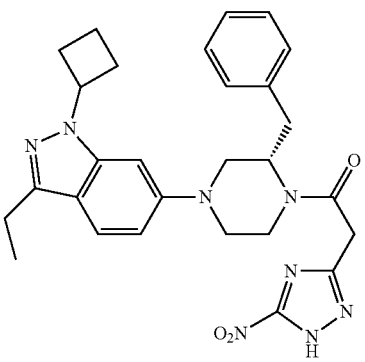 [SMILES: CCc1nn(C2CCC2)c2cc(N3CCN(C(=O)Cc4n[nH]c([N+](=O)[O-])n4)[C@@H](Cc4ccccc4)C3)ccc12]

Prepared by the method outlined for Example 189 using (5-Nitro-1H-[1,2,4]triazol-3-yl)-acetic acid and ester 6-(S) 3-benzyl-piperazin-1-yl)-1-cyclobutyl-3-ethyl-1H-indazole (Example 56, Compound 144) as starting materials. Product as an oil. LC/MS (Method B) 2.56 min, [M+1]+ 529. Potency class ND.

Example 267

Preparation of Compound 355, (S)-2-(5-amino-1H-1,2,4-triazol-3-yl)-1-(2-benzyl-4-(1-cyclobutyl-3-ethyl-1H-indazol-6-yl)piperazin-1-yl)ethanone

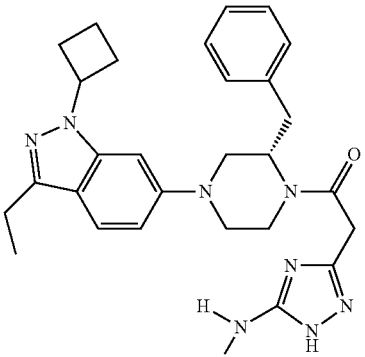

Prepared by the method outlined for Example 249 using 1-[(S)2-benzyl-4-(cyclobutyl-3-ethyl-1Hindazol-6yl)-piperazin-1-yl]-2-(5-nitro-1H-[1,2,4]triazol-3-yl)-ethanone (Example 266, Compound 354) as starting material. Product as an oil. LC/MS (Method B) 2.76 min, [M+1]+ 499. Potency class A.

Example 268

Preparation of Compound 356, (S)-1-(2-benzyl-4-(3-cyclobutoxy-4-(difluoromethoxy)phenyl)piperazin-1-yl)-2-(pyrimidin-2-yl)ethanone

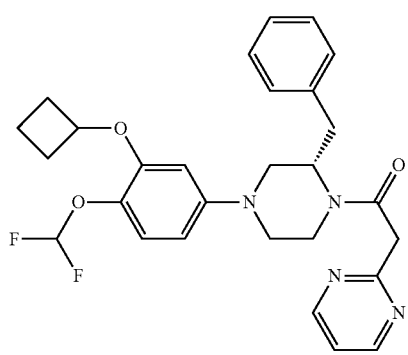 [SMILES: O=C(Cc1ncccn1)N1CCN(c2ccc(OC(F)F)c(OC3CCC3)c2)C[C@@H]1Cc1ccccc1]

Prepared by the method outlined for Example 189 using pyrimidin-2-yl-acetic acid and (S)3-benzyl-1-(3-cyclobutoxy-4-difluoromethoxy-phenyl)-piperazine (Example 4, Compound 92) as starting materials. Product as an oil. LC/MS (Method B) 2.86 min, [M+1]+ 509. Potency class B.

Example 269

Preparation of Compound 357, (S)-1-(2-benzyl-4-(3-(difluoromethoxy)-4-methoxyphenyl)piperazin-1-yl)-2-(pyrimidin-2-yl)ethanone

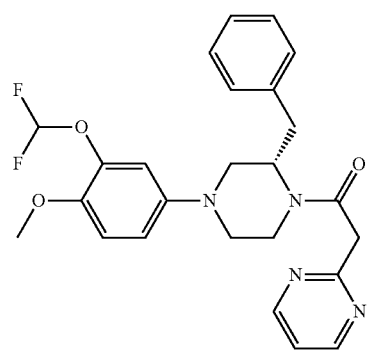 [SMILES: COc1ccc(N2CCN(C(=O)Cc3ncccn3)[C@@H](Cc3ccccc3)C2)cc1OC(F)F]

Prepared by the method outlined for Example 189 using pyrimidin-2-yl-acetic acid and (S)3-benzyl-1-(3-difluoromethoxy-4-methoxy-phenyl)-piperazine (Example 69, Compound 157) as starting materials. Product as an oil. LC/MS (Method B) 2.46 min, [M+1]+ 468. Potency class ND.

Example 270

Preparation of Compound 358, (S)-1-(2-benzyl-4-(3-(difluoromethoxy)-4-methoxyphenyl)piperazin-1-yl)-2-(pyridin-2-yl)ethanone

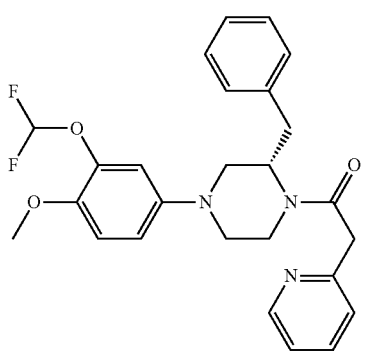 [SMILES: COc1ccc(N2CCN(C(=O)Cc3ccccn3)[C@@H](Cc3ccccc3)C2)cc1OC(F)F]

Prepared by the method outlined for Example 189 using pyridin-2-yl-acetic acid and (S)3-benzyl-1-(3-difluoromethoxy-4-methoxy-phenyl)-piperazine (Example 69, Compound 157) as starting materials. Product as an oil. LC/MS (Method B) 2.56 min, [M+1]+ 468. Potency class ND.

Example 271

Preparation of Compound 359, (S)-5-((2-benzyl-4-(3-(cyclopentyloxy)-4-methoxyphenyl)piperazin-1-yl)methyl)-2,4-dimethylthiazole

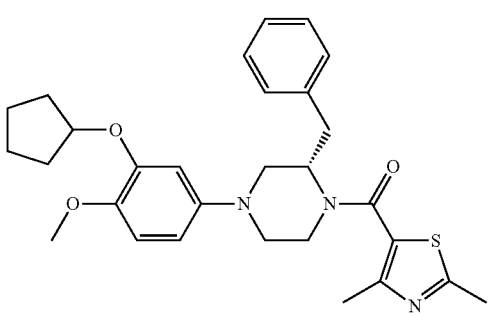 [SMILES: COc1ccc(N2CCN(C(=O)c3sc(C)nc3C)[C@@H](Cc3ccccc3)C2)cc1OC1CCCC1]

Prepared by the method outlined for Example 75 using 2,4-dimethyl-thiazole-5-carbaldehyde as starting material. Product as an oil (30 mg, 60%). LC/MS (Method B) 3.55 min, [M+1]+ 492. Potency class C.

Example 272

Preparation of Compound 360, (S)-(2-benzyl-4-(3-(cyclopentyloxy)-4-methoxyphenyl)piperazin-1-yl)(4-(hydroxymethyl)phenyl)methanone

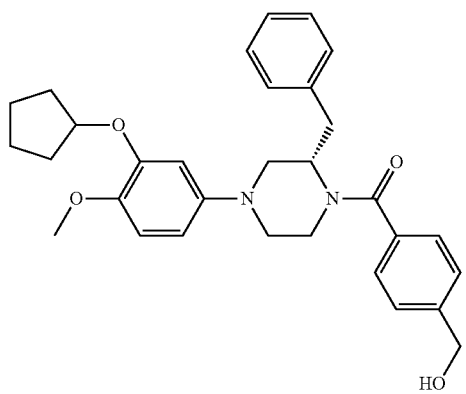 [SMILES: COc1ccc(N2CCN(C(=O)c3ccc(CO)cc3)[C@@H](Cc3ccccc3)C2)cc1OC1CCCC1]

Prepared by the method outlined for Example 189 using 4-hydroxymethyl-benzoic acid as starting material. Product as an oil (30 mg, 39%). LC/MS (Method B) 2.57 min, [M+1]$^+$ 501. Potency class C.

Example 273

Preparation of Compound 361, (S)-34(2-benzyl-4-(3-(cyclopentyloxy)-4-methoxyphenyl)piperazin-1-yl)methyl)phenol

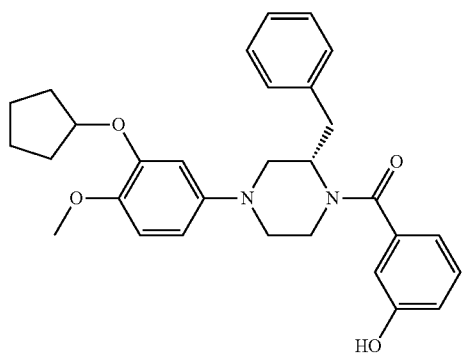 [SMILES: COc1ccc(N2CCN(C(=O)c3cccc(O)c3)[C@@H](Cc3ccccc3)C2)cc1OC1CCCC1]

Prepared by the method outlined for Example 75 using 3-hydroxy-benzaldehyde as starting material. Product as an oil. LC/MS (Method B) 2.67 min, [M+1]$^+$ 473. Potency class C.

Example 274

Preparation of Compound 362, (S)-4-((2-benzyl-4-(3-(cyclopentyloxy)-4-methoxyphenyl)piperazin-1-yl)methyl)phenol

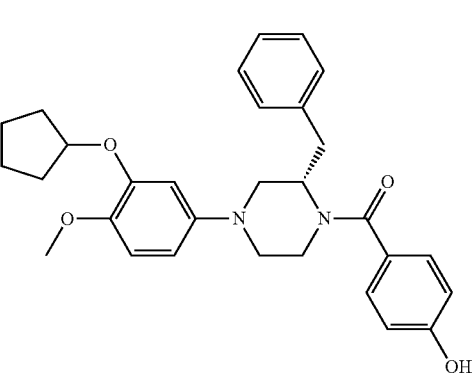 [SMILES: COc1ccc(N2CCN(C(=O)c3ccc(O)cc3)[C@@H](Cc3ccccc3)C2)cc1OC1CCCC1]

Prepared by the method outlined for Example 75 using 4-hydroxy-benzaldehyde as starting material. Product as an oil. LC/MS (Method B) 2.67 min, [M+1]$^+$ 473. Potency class C.

Example 275

Preparation of Compound 363, (S)-1-(2-benzyl-4-(8-methoxy-2-(trifluoromethyl)quinolin-5-yl)piperazin-1-yl)-2-(1H-1,2,4-triazol-5-yl)ethanone

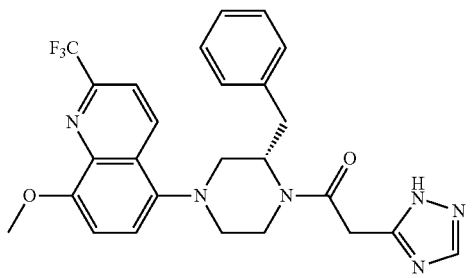 [SMILES: COc1ccc(N2CCN(C(=O)Cc3ncn[nH]3)[C@@H](Cc3ccccc3)C2)c2ccc(C(F)(F)F)nc12]

A solution of (S)-5-(3-benzylpiperazin-1-yl)-8-methoxy-2-(trifluoromethyl)quinoline (Example 65, Compound 153) (100.0 mg, 0.25 mmol), (4H-[1,2,4]triazol-3-yl)-acetic acid ethyl ester (83 mg, 0.50 mmol), sodium cyanide (24 mg, 0.50 mmol), and DMSO (2 mL). The reaction mixture was heated in a heat block at 100 C for 24 h then cooled to room temperature, diluted with EtOAc, and washed with water followed by brine. The organic portion was dried over MgSO$_4$, filtered, evaporated and purified by silica gel flash chromatography to afford product as a colorless solid (0.9 mg, 0.7%). LC/MS (Method B) 3.32 min, [m/z=510.9].

Example 276

Preparation of Compound 364, (S)-1-(4-(3-(cyclopentyloxy)-4-methoxyphenyl)-2-isobutylpiperazin-1-yl)-2-(1H-imidazol-4-yl)ethanone

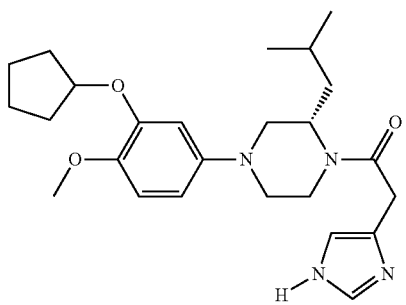 [SMILES: COc1ccc(N2CCN(C(=O)Cc3c[nH]cn3)[C@@H](CC(C)C)C2)cc1OC1CCCC1]

Prepared by the method outlined for Example 189 using 2-(1H-imidazol-4-yl)acetic acid and (S)-1-(3-cyclopentyloxy-4-methoxy-phenyl)-3-isobutyl-piperazine (Example 33, Compound 121) as starting materials. Product as a light brown solid (11%). LC/MS (Method B) 2.69 min, [M+1]$^+$ 441.1. Potency class A.

Example 277

Preparation of Compound 365, (S)-1-(4-(3-(cyclopropylmethoxy)-4-(difluoromethoxy)phenyl)-2-isobutylpiperazin-1-yl)-2-(1H-imidazol-4-yl)ethanone

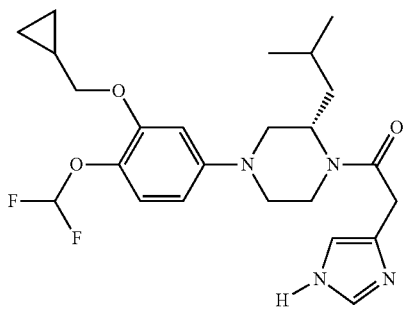 [SMILES: CC(C)C[C@H]1CN(c2ccc(OC(F)F)c(OCC3CC3)c2)CCN1C(=O)Cc1c[nH]cn1]

Prepared by the method outlined for Example 189 using 2-(1H-imidazol-4-yl)acetic acid and (S)-1-(3-cyclopropylmethoxy-4-difluoromethoxy-phenyl)-3-isobutyl-piperazine (Example 37, Compound 125) as starting materials. Product as an off-white solid (14%). LC/MS (Method B) 2.94 min, [M+1]$^+$ 463.0. Potency class B.

Example 278

Preparation of Compound 366, (S)-1-(4-(3-(cyclopentyloxy)-4-(difluoromethoxy)phenyl)-2-isobutylpiperazin-1-yl)-2-(1H-imidazol-4-yl)ethanone

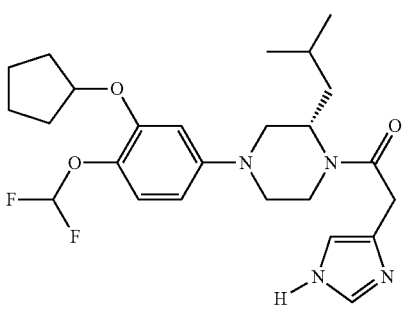 [SMILES: CC(C)C[C@H]1CN(c2ccc(OC(F)F)c(OC3CCCC3)c2)CCN1C(=O)Cc1c[nH]cn1]

Prepared by the method outlined for Example 189 using 2-(1H-imidazol-4-yl)acetic acid and (S)-1-(3-cyclopentyloxy-4-difluoromethoxy-phenyl)-3-isobutyl-piperazine (Example 36, Compound 124) as starting materials. Product as an off-white solid (20%). LC/MS (Method B) 3.04 min, [M+1]$^+$ 477.1. Potency class B.

Example 279

Preparation of Compound 367, (S)-1-(4-(3-cyclobutoxy-4-methoxyphenyl)-2-isobutylpiperazin-1-yl)-2-(1H-imidazol-4-yl)ethanone

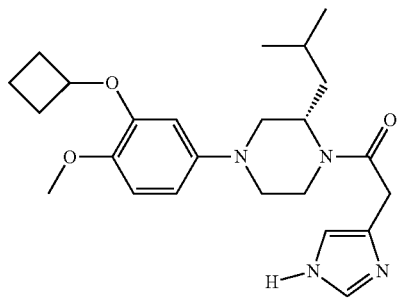 [SMILES: COc1ccc(N2CCN(C(=O)Cc3c[nH]cn3)[C@@H](CC(C)C)C2)cc1OC1CCC1]

Prepared by the method outlined for Example 189 using 2-(1H-imidazol-4-yl)acetic acid and (S)-1-(3-cyclobutyloxy-4-methoxy-phenyl)-3-isobutyl-piperazine (Example 34, Compound 122) as starting materials. Product as a light brown solid (17%). LC/MS (Method B) 2.57 min, [M+1]$^+$ 427.0. Potency class A.

Example 280

Preparation of Compound 368, (S)-ethyl 3-(4-(3-(cyclopentyloxy)-4-methoxyphenyl)-2-isobutylpiperazin-1-yl)-3-oxopropanoate

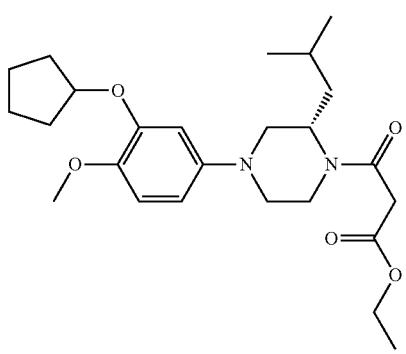 [SMILES: CCOC(=O)CC(=O)N1CCN(c2ccc(OC)c(OC3CCCC3)c2)C[C@@H]1CC(C)C]

Prepared by the method outlined for Example 127 ester intermediate using (S)-1-(3-cyclopentyloxy-4-methoxyphenyl)-3-isobutyl-piperazine (Example 33, Compound 121) as starting material. Product as an oil (17%). LC/MS (Method B) 4.12 min, [M+1]⁺ 447.1. Potency class C.

Example 281

Preparation of Compound 369, (S)-1-(4-(3-cyclobutoxy-4-methoxyphenyl)-2-isobutylpiperazin-1-yl)-2-(1-methyl-1H-imidazol-4-yl)ethanone

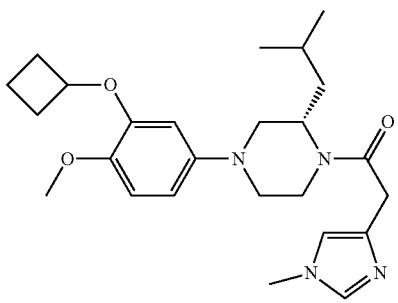 [SMILES: COc1ccc(N2CCN(C(=O)Cc3cn(C)cn3)[C@@H](CC(C)C)C2)cc1OC1CCC1]

Prepared by the method outlined for Example 189 using 2-(1-methyl-1H-imidazol-4-yl)acetic acid and (S)-1-(3-cyclobutlyoxy-4-methoxy-phenyl)-3-isobutyl-piperazine (Example 34, Compound 122) as starting materials. Product as an oil (13.5%). LC/MS (Method B) 2.6 min, [M+1]⁺ 441.1. Potency class B.

Example 282

Preparation of Compound 370, (S)-3-(4-(3-(cyclopentyloxy)-4-methoxyphenyl)-2-isobutylpiperazin-1-yl)-3-oxopropanamide

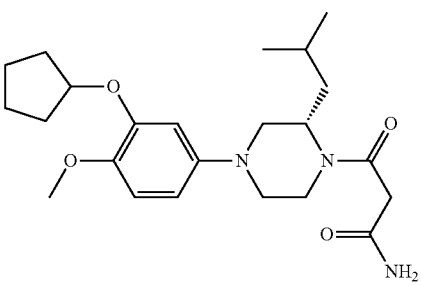 [SMILES: COc1ccc(N2CCN(C(=O)CC(N)=O)[C@@H](CC(C)C)C2)cc1OC1CCCC1]

Prepared by the method outlined for Example 129 using 3-[4-(3-cyclopentyloxy-4-methoxy-phenyl)-2-isobutyl-piperazin-1-yl]-3-oxo-propionic acid ethyl ester (Example 280, Compound 368) as starting material to afford product as a colorless solid (40.9%). LC/MS (Method B) 3.35 min, [M+1]⁺ 418.1. Potency class ND.

Example 283

Preparation of Compound 371, (S)-ethyl 3-(4-(3-(cyclopropylmethoxy)-4-(difluoromethoxy)phenyl)-2-isobutylpiperazin-1-yl)-3-oxopropanoate

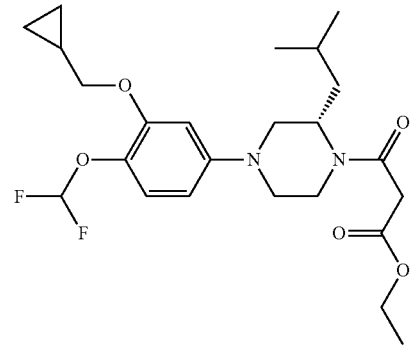 [SMILES: CCOC(=O)CC(=O)N1CCN(c2ccc(OC(F)F)c(OCC3CC3)c2)C[C@@H]1CC(C)C]

Prepared by the method outlined for Example 127 ester intermediate using (S)-1-(3-cyclopropylmethoxy-4-difluoromethoxy-phenyl)-3-isobutyl-piperazine (Example 37, Compound 125) as starting material. Product as an oil (78%). LC/MS (Method B) 4.27 min, [M+1]⁺ 469.1. Potency class ND.

Example 284

Preparation of Compound 372, (S)-ethyl 3-(4-(3-(cyclopentyloxy)-4-(difluoromethoxy)phenyl)-2-isobutylpiperazin-1-yl)-3-oxopropanoate

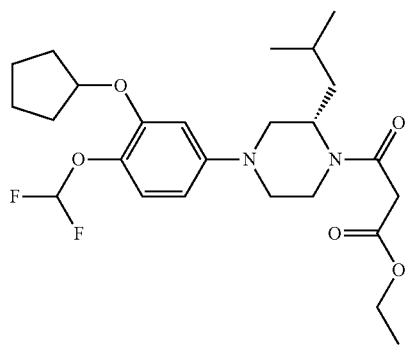 [SMILES: CCOC(=O)CC(=O)N1CCN(c2ccc(OC(F)F)c(OC3CCCC3)c2)C[C@@H]1CC(C)C]

Prepared by the method outlined for Example 127 ester intermediate using (S)-1-(3-cyclopentyloxy-4-difluoromethoxy-phenyl)-3-isobutyl-piperazine (Example 36, Compound 124) as starting material. Product as an oil (79%). LC/MS (Method B) 4.5 min, [M+1]$^+$ 483.1. Potency class ND.

Example 285

Preparation of Compound 373, (S)-1-(4-(3-(cyclopropylmethoxy)-4-(difluoromethoxy)phenyl)-2-isobutylpiperazin-1-yl)-2-(5-methyl-1-H-1,2,4-triazol-3-yl)ethanone

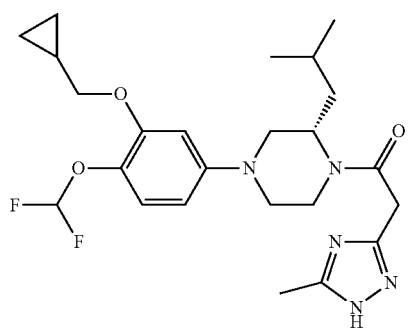 [SMILES: Cc1nc(CC(=O)N2CCN(c3ccc(OC(F)F)c(OCC4CC4)c3)C[C@@H]2CC(C)C)n[nH]1]

Prepared by the method outlined for Example 189 using (S)-1-(3-cyclopropylmethoxy-4-difluoromethoxy-phenyl)-3-isobutyl-piperazine (Example 37, Compound 125) as starting material. Product as a colorless solid (35.5%). LC/MS (Method B) 3.5 min, [M+1]$^+$ 478.1. Potency class A.

Example 286

Preparation of Compound 374, (S)-1-(4-(3-(cyclopentyloxy)-4-(difluoromethoxy)phenyl)-2-isobutylpiperazin-1-yl)-2-(5-methyl-1H-1,2,4-triazol-3-yl)ethanone

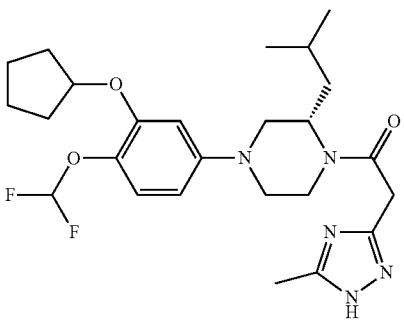 [SMILES: Cc1nc(CC(=O)N2CCN(c3ccc(OC(F)F)c(OC4CCCC4)c3)C[C@@H]2CC(C)C)n[nH]1]

Prepared by the method outlined for Example 189 using (S)-1-(3-Cyclopentyloxy-4-difluoromethoxy-phenyl)-3-isobutyl-piperazine (Example 36, Compound 124) as starting material. Product as a colorless solid (37.5%). LC/MS (Method B) 3.72 min, [M+1]$^+$ 492.1. Potency class A.

Example 287

Preparation of Compound 375, (S)-3-(4-(3-(cyclopropylmethoxy)-4-(difluoromethoxy)phenyl)-2-isobutylpiperazin-1-yl)-3-oxopropanamide

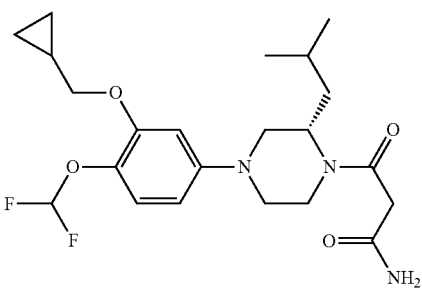 [SMILES: CC(C)C[C@H]1CN(c2ccc(OC(F)F)c(OCC3CC3)c2)CCN1C(=O)CC(N)=O]

Prepared by the method outlined for Example 129 using (S)-1-(3-cyclopropylmethoxy-4-difluoromethoxy-phenyl)-3-isobutyl-piperazine (Example 37, Compound 125) as starting material. Product as a colorless solid (63%). LC/MS (Method B) 3.62 min, [M+1]$^+$ 440.1. Potency class ND.

Example 288

Preparation of Compound 376, (S)-3-(4-(3-(cyclopentyloxy)-4-(difluoromethoxy)phenyl)-2-isobutylpiperazin-1-yl)-3-oxopropanamide

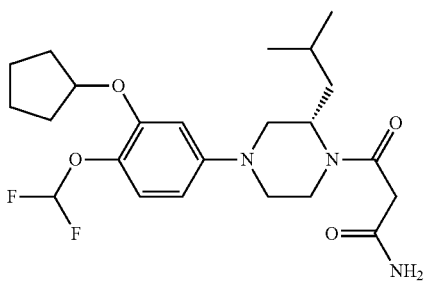 [SMILES: CC(C)C[C@H]1CN(c2ccc(OC(F)F)c(OC3CCCC3)c2)CCN1C(=O)CC(N)=O]

Prepared by the method outlined for Example 129 using (S)-1-(3-cyclopentyloxy-4-difluoromethoxy-phenyl)-3-isobutyl-piperazine (Example 36, Compound 124) as starting material. Product as an oil (65%). LC/MS (Method B) 3.82 min, [M+1]$^+$ 454.1. Potency class ND.

Example 289

Preparation of Compound 377, (S)-1-(2-isobutyl-4-(3-isopropoxy-4-methoxyphenyl)piperazin-1-yl)-2-(5-methyl-1H-1,2,4-triazol-3-yl)ethanone

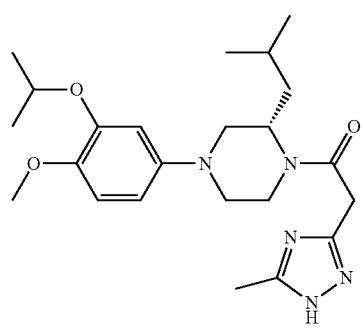 [SMILES: COc1ccc(N2CCN(C(=O)Cc3n[nH]c(C)n3)[C@@H](CC(C)C)C2)cc1OC(C)C]

Prepared by the method outlined for Example 189 using (S)-1-(3-isopropoxy-4-methoxy-phenyl)-3-isobutyl-piperazine (Example 35, Compound 123) as starting material. Product as an off-white solid (49%). LC/MS (Method B) 2.97 min, [M+1]$^+$ 430.0. Potency class B.

Example 290

Preparation of Compound 378, (S)-2-(1H-imidazol-4-yl)-1-(2-isobutyl-4-(3-isopropoxy-4-methoxyphenyl)piperazin-1-yl)ethanone

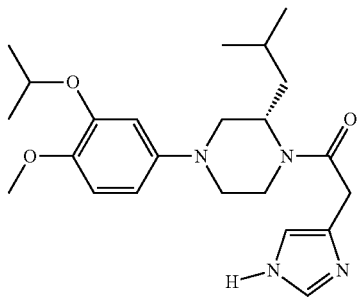 [SMILES: COc1ccc(N2CCN(C(=O)Cc3c[nH]cn3)[C@@H](CC(C)C)C2)cc1OC(C)C]

Prepared by the method outlined for Example 189 using 2-(1H-imidazol-4-yl)acetic acid and (S)-1-(3-isopropoxy-4-methoxy-phenyl)-3-isobutyl-piperazine (Example 35, Compound 123) as starting materials. Product as an off-white solid (32%). LC/MS (Method B) 2.52 min, [M+1]$^+$ 415.1. Potency class B.

Example 291

Preparation of Compound 379, (S)-1-(2-benzyl-4-(3-ethyl-1-isopropyl-1H-indazol-6-yl)piperazin-1-yl)ethanone

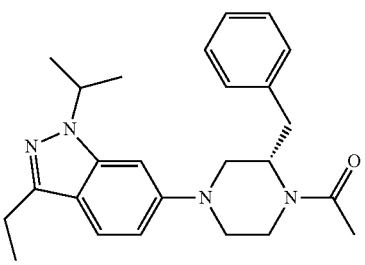 [SMILES: CCc1nn(C(C)C)c2cc(N3CCN(C(C)=O)[C@@H](Cc4ccccc4)C3)ccc12]

Prepared by the method outlined for Example 87 using 64(S)-3-Benzyl-piperazin-1-yl)-1-isopropyl-3-ethyl-1H-indazole (Example 59, Compound 147) as starting material. Product as a light brown solid (61%). LC/MS (Method B) 3.82 min, [M+1]$^+$ 405.6. Potency class C.

Example 292

Preparation of Compound 380, (S)-1-(2-benzyl-4-(1-cyclopentyl-3-ethyl-1H-indazol-6-yl)piperazin-1-yl)-2-(3-methyl-1H-1,2,4-triazol-5-yl)ethanone

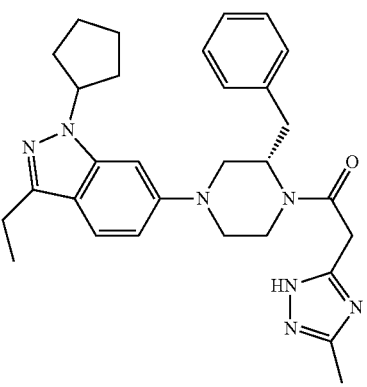 [SMILES: CCc1nn(C2CCCC2)c2cc(N3CCN(C(=O)Cc4nc(C)n[nH]4)[C@@H](Cc4ccccc4)C3)ccc12]

Prepared by the method outlined for Example 189 using 64(S)-3-Benzyl-piperazin-1-yl)-1-cyclopentyl-3-ethyl-1H-indazole (Example 56, Compound 144) as starting material. Product as a colorless solid (48.2%). LC/MS (Method B) 3.62 min, [M+1]+ 512.1. Potency class A.

Example 293

Preparation of Compound 381, (S)-1-(2-benzyl-4-(3-ethyl-1-isopropyl-1H-indazol-6-yl)piperazin-1-yl)-2-(3-methyl-1H-1,2,4-triazol-5-yl)ethanone

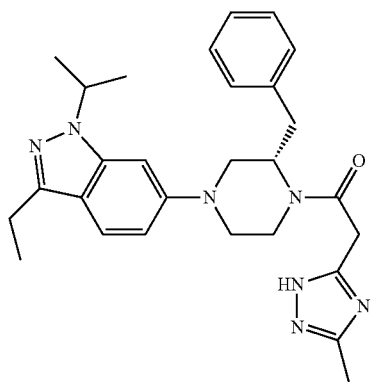 [SMILES: CCc1nn(C(C)C)c2cc(N3CCN(C(=O)Cc4nc(C)n[nH]4)[C@@H](Cc4ccccc4)C3)ccc12]

Prepared by the method outlined for Example 189 using 64(S)-3-Benzyl-piperazin-1-yl)-1-isopropyl-3-ethyl-1H-indazole (Example 59, Compound 147) as starting material. Product as a colorless solid (61%). LC/MS (Method B) 3.25 min, [M+1]+ 486.1. Potency class A.

Example 294

Preparation of Compound 382, (S)-3-(2-benzyl-4-(3-ethyl-1-isopropyl-1H-indazol-6-yl)piperazin-1-yl)-3-oxopropanamide

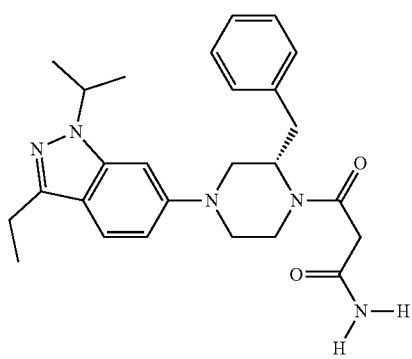 [SMILES: CCc1nn(C(C)C)c2cc(N3CCN(C(=O)CC(N)=O)[C@@H](Cc4ccccc4)C3)ccc12]

Prepared by the method outlined for Example 129 using 64(S)-3-Benzyl-piperazin-1-yl)-1-isopropyl-3-ethyl-1H-indazole (Example 59, Compound 147) as starting material. Product as a colorless solid (79%). LC/MS (Method B) 3.42 min, [M+1]+ 448.1. Potency class C.

Example 295

Preparation of Compound 383, (S)-2-(2-benzyl-4-(3-ethyl-1-isopropyl-1H-indazol-6-yl)piperazin-1-yl)acetamide

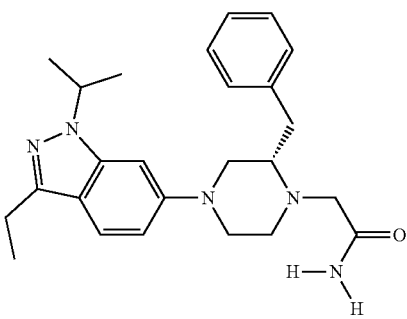 [SMILES: CCc1nn(C(C)C)c2cc(N3CCN(CC(N)=O)[C@@H](Cc4ccccc4)C3)ccc12]

Prepared by the method outlined for Example 95 using 64(S)-3-Benzyl-piperazin-1-yl)-1-isopropyl-3-ethyl-1H-indazole (Example 59, Compound 147) as starting material. Product as a colorless solid (78%). LC/MS (Method B) 3.35 min, [M+1]+ 420.1. Potency class C.

Example 296

Preparation of Compound 384, (S)-1-(2-benzyl-4-(3-(cyclopentyloxy)-4-methoxyphenyl)piperazin-1-yl)-2-(pyridin-2-yl)ethanone

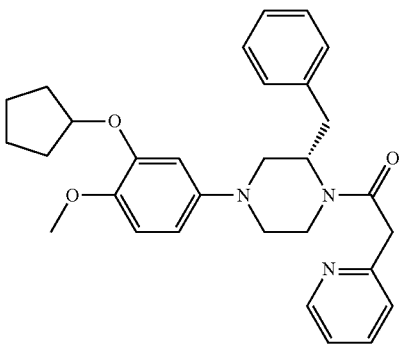

Prepared by the method outlined for Example 189 using 2-(pyridin-2-yl)acetic acid as starting material. Product as a light yellow solid (2.6%). LC/MS (Method B) 3.25 min, [M+1]+ 486.0. Potency class A.

Example 297

Preparation of Compound 385, (S)-1-(2-benzyl-4-(3-(cyclopentyloxy)-4-methoxyphenyl)piperazin-1-yl)-2-(pyridin-3-yl)ethanone

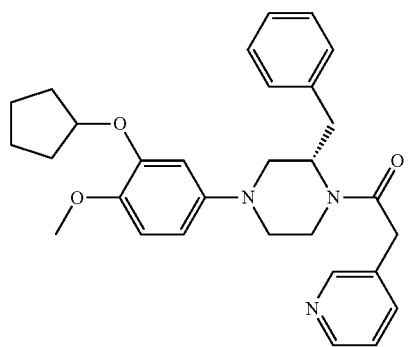

Prepared by the method outlined for Example 189 using 2-(pyridin-3-yl)acetic acid as starting material. Product as an oil (38.7%). LC/MS (Method B) 2.99 min, [M+1]+ 486.1. Potency class A.

Example 298

Preparation of Compound 386, (S)-1-(2-benzyl-4-(3-(cyclopentyloxy)-4-methoxyphenyl)piperazin-1-yl)-2-(pyridin-4-yl)ethanone

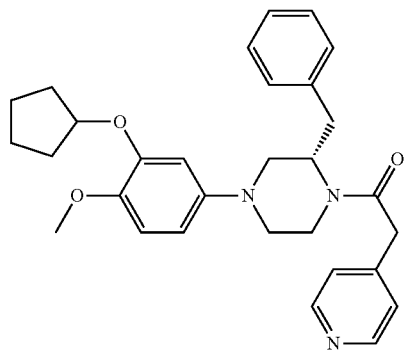 [SMILES: COc1ccc(N2CCN(C(=O)Cc3ccncc3)[C@@H](Cc3ccccc3)C2)cc1OC1CCCC1]

Prepared by the method outlined for Example 189 using 2-(pyridin-4-yl)acetic acid as starting material. Product as an off-white solid (30.4%). LC/MS (Method B) 2.88 min, [M+1]+ 486.1. Potency class C.

Example 299

Preparation of Compound 387, (S)-1-(2-benzyl-4-(3-(cyclopentyloxy)-4-methoxyphenyl)piperazin-1-yl)-2-(pyrazin-2-yl)ethanone

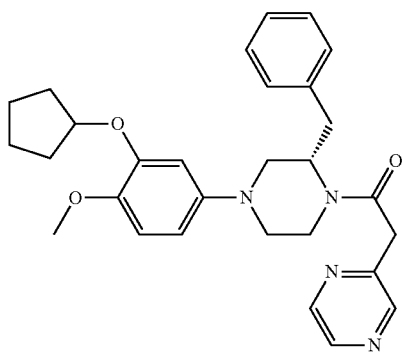 [SMILES: COc1ccc(N2CCN(C(=O)Cc3cnccn3)[C@@H](Cc3ccccc3)C2)cc1OC1CCCC1]

Prepared by the method outlined for Example 189 using 2-(pyrazin-2-yl)acetic acid as starting material. Product as an off-white solid (30.6%). LC/MS (Method B) 3.77 min, [M+1]+ 487.0. Potency class B.

Example 300

Preparation of Compound 388, (S)-1-(2-benzyl-4-(3-(cyclopentyloxy)-4-methoxyphenyl)piperazin-1-yl)-2-(pyrimidin-2-yl)ethanone

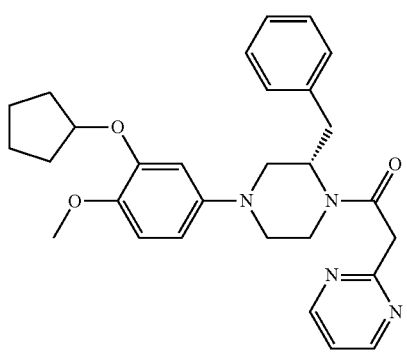 [SMILES: COc1ccc(N2CCN(C(=O)Cc3ncccn3)[C@@H](Cc3ccccc3)C2)cc1OC1CCCC1]

Prepared by the method outlined for Example 189 using 2-(pyrimidin-2-yl)acetic acid as starting material. Product as a colorless solid (29%). LC/MS (Method B) 3.7 min, [M+1]+ 487.0. Potency class A.

Example 301

Preparation of Compound 389, (S)-1-(4-(3-(cyclopentyloxy)-4-methoxyphenyl)-2-isobutylpiperazin-1-yl)-2-(5-methyl-1H-1,2,4-triazol-3-yl)ethanone

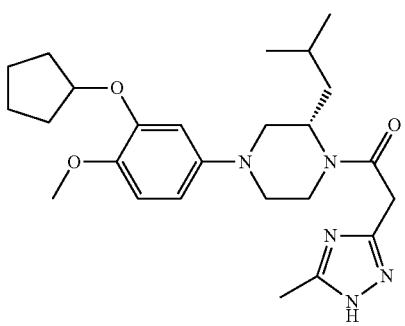 [SMILES: COc1ccc(N2CCN(C(=O)Cc3n[nH]c(C)n3)[C@@H](CC(C)C)C2)cc1OC1CCCC1]

Prepared by the method outlined for Example 189 using (S)-1-(3-cyclopentyloxy-4-methoxy-phenyl)-3-isobutyl-piperazine as starting material. Product was obtained as an off-white solid (3%). LC/MS (Method B) 3.24 min, [M+1]$^+$ 456.

Example 302

Preparation of Compound 390, (S)-1-(2-benzyl-4-(3-(cyclopentyloxy)-4-methoxyphenyl)piperazin-1-yl)-2-(pyrimidin-4-yl)ethanone

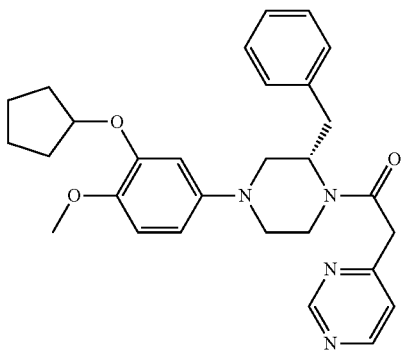 [SMILES: COc1ccc(N2CCN(C(=O)Cc3ccncn3)[C@@H](Cc3ccccc3)C2)cc1OC1CCCC1]

Prepared by the method outlined for Example 189 using 2-(pyrimidin-4-yl)acetic acid as starting material. Product was obtained as an off-white solid (14%). LC/MS (Method B) 3.7 min, [M+1]$^+$ 487.

Example 303

Preparation of Compound 391, (S)-2-benzyl-4-(1-cyclopentyl-3-methyl-1H-indazol-6-yl)piperazine-1-carboxamide

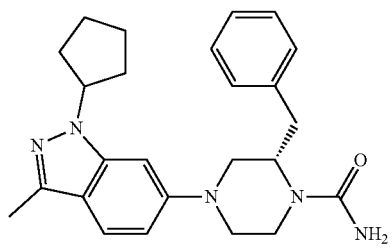 [SMILES: Cc1nn(C2CCCC2)c2cc(N3CCN(C(N)=O)[C@@H](Cc4ccccc4)C3)ccc12]

A solution of 6-((S)-3-benzyl-piperazin-1-yl)-1-cyclopentyl-3-methyl-1H-indazole (44 mg, 0.12 mmol) in CH$_2$Cl$_2$ (1 mL) was treated with diisopropylethylamine (21 µL, 0.12 mmol) followed by trimethylsilyl isocyanate (31 µL, 0.24 mmol). The reaction mixture was stirred for 16 h after which time an additional equivalent of TMS-isocyanate was added and the reaction mixture was stirred an additional 16 h. The reaction mixture was evaporated and purified by reverse phase HPLC. Product was obtained as a colorless solid (18 mg, 36%). LC/MS (Method B) 3.64 min, [M+1]$^+$ 418.

Example 304

Preparation of Compound 392, (S)-4-(3-cyclobutoxy-4-methoxyphenyl)-2-isobutylpiperazine-1-carboxamide

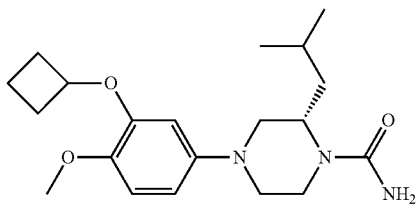 [SMILES: COc1ccc(N2CCN(C(N)=O)[C@@H](CC(C)C)C2)cc1OC1CCC1]

Prepared by the method outlined for Example 303 using (S)-1-(3-cyclobutlyoxy-4-methoxy-phenyl)-3-isobutyl-piperazine as starting material. Product was obtained as an oil (12%). LC/MS (Method B) 3.27 min, [M+1]$^+$ 362.

Example 305

Preparation of Compound 393, (S)-2-isobutyl-4-(3-isopropoxy-4-methoxyphenyl)piperazine-1-carboxamide

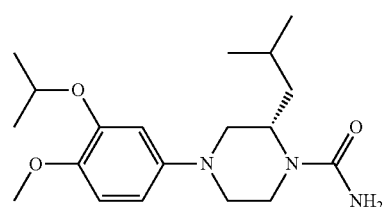

Prepared by the method outlined for Example 303 using (S)-1-(3-isopropoxy-4-methoxy-phenyl)-3-isobutyl-piperazine as starting material. Product was obtained as an oil (47%). LC/MS (Method B) 3.12 min, [M+1]⁺ 350.

Example 306

Preparation of Compound 394, (S)-2-benzyl-4-(1-cyclobutyl-3-ethyl-1H-indazol-6-yl)piperazine-1-carboxamide

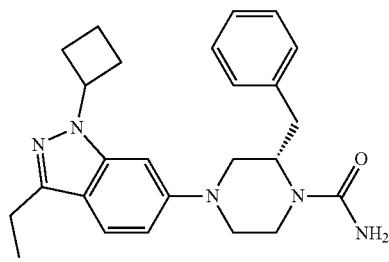 [SMILES: CCc1nn(C2CCC2)c2cc(N3CCN(C(N)=O)[C@@H](Cc4ccccc4)C3)ccc12]

Prepared by the method outlined for Example 303 using 64(S)-3-benzyl-piperazin-1-yl)-1-cyclobutyl-3-ethyl-1H-indazole as starting material. Product was obtained as a colorless solid (66%). LC/MS (Method B) 3.70 min, [M+1]⁺ 418.

Example 307

Preparation of Compound 395, (S)-4-(1-cyclobutyl-3-ethyl-1H-indazol-6-yl)-2-isobutylpiperazine-1-carboxamide

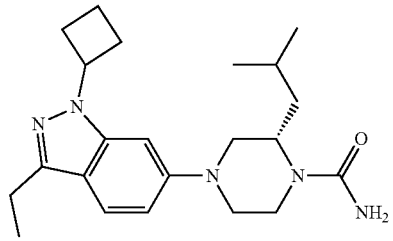 [SMILES: CCc1nn(C2CCC2)c2cc(N3CCN(C(N)=O)[C@@H](CC(C)C)C3)ccc12]

Prepared by the method outlined for Example 303 using (S)-1-cyclobutyl-3-ethyl-6-(3-isobutylpiperazin-1-yl)-1H-indazole as staring material. Product was obtained as a colorless solid (60%). LC/MS (Method B) 3.67 min, [M+1]⁺ 384.

Example 308

Preparation of Compound 396, (S)-2-benzyl-4-(1,3-diethyl-1H-indazol-6-yl)piperazine-1-carboxamide

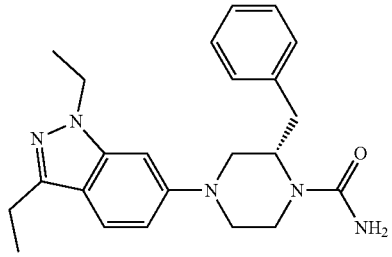 [SMILES: CCc1nn(CC)c2cc(N3CCN(C(N)=O)[C@@H](Cc4ccccc4)C3)ccc12]

Prepared by the method outlined for Example 303 using 64(S)-3-Benzyl-piperazin-1-yl)-1-ethyl-3-ethyl-1H-indazole as starting material. Product was obtained as a colorless solid (54%). LC/MS (Method B) 3.30 min, [M+1]⁺ 392.

Example 309

Preparation of Compound 397, (S)-4-(3-(cyclopentyloxy)-4-methoxyphenyl)-2-(isoindolin-2-ylmethyl)piperazine-1-carboxamide

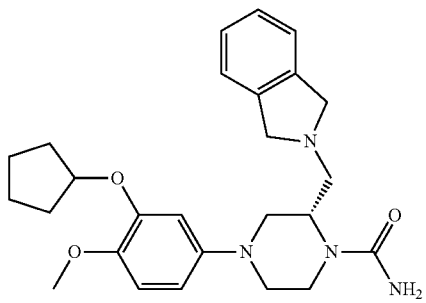 [SMILES: COc1ccc(N2CCN(C(N)=O)[C@@H](CN3Cc4ccccc4C3)C2)cc1OC1CCCC1]

Prepared by the method outlined for Example 303 using 2-[4-(S)-3-cyclopentyloxy-4-methoxy-phenyl)-piperazin-2-ylmethyl]2,3-dihydro-1H-isoindole as starting material. Product was obtained as an oil (10 mg, 75%). LC/MS (Method B) 2.76 min, [M+1]⁺ 451.

Example 310

Preparation of Compound 398, (S)-4-(3-(cyclopentyloxy)-4-methoxyphenyl)-2-((3,4-dihydroisoquinolin-2(1H)-yl)methyl)piperazine-1-carboxamide

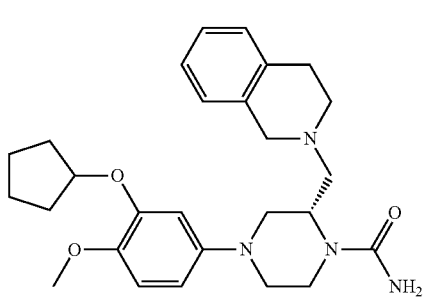 [SMILES: COc1ccc(N2CCN(C(N)=O)[C@@H](CN3CCc4ccccc4C3)C2)cc1OC1CCCC1]

Prepared by the method outlined for Example 303 using 2-[4-(3-cyclopentyloxy-4-methoxy-phenyl)-piperazin-2-yl-methyl]1,2,3,4-tetrahydro-isoquinoline as starting material. Product was obtained as an oil (10 mg, 73%). LC/MS (Method B) 2.66 min, [M+1]+ 465.

Example 311

Preparation of Compound 399, (S)-1-(2-benzyl-4-(3-(cyclopentyloxy)-4-methoxyphenyl)piperazin-1-yl)-2-(2-fluorophenyl)ethanone

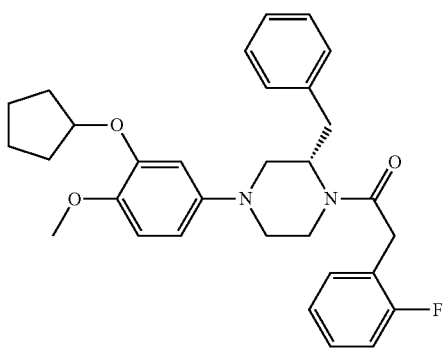 [SMILES: COc1ccc(N2CCN(C(=O)Cc3ccccc3F)[C@@H](Cc3ccccc3)C2)cc1OC1CCCC1]

Prepared by the method outlined for Example 189 using 2-(2-fluorophenyl)acetic acid and (S)-3-benzyl-1-(3-cyclopentyloxy-4-methoxy-phenyl)-piperazine as starting materials. Product was obtained as an off-white solid (50%). LC/MS (Method B) 4.53 min, [M+1]+ 503.

Example 312

Preparation of Compound 400, (S)-1-(2-benzyl-4-(3-(cyclopentyloxy)-4-methoxyphenyl)piperazin-1-yl)-2-(2,6-difluorophenyl)ethanone

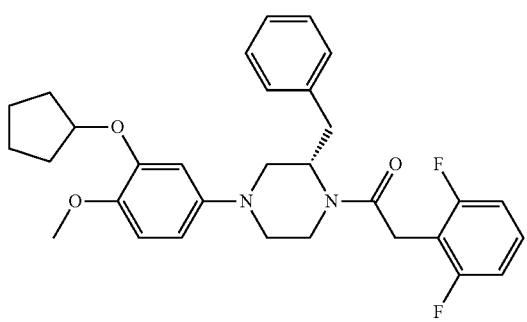 [SMILES: COc1ccc(N2CCN(C(=O)Cc3c(F)cccc3F)[C@@H](Cc3ccccc3)C2)cc1OC1CCCC1]

Prepared by the method outlined for Example 189 using 2-(2,6-difluorophenyl)acetic acid and (S)-3-benzyl-1-(3-cyclopentyloxy-4-methoxy-phenyl)-piperazine as starting materials. Product was obtained as an off-white solid (33%). LC/MS (Method B) 4.6 min, [M+1]+ 521.

Example 313

Preparation of Compound 401, (S)-1-(2-benzyl-4-(3-ethyl-1-isopropyl-1H-indazol-6-yl)piperazin-1-yl)-2-(3-methyl-1,2,4-oxadiazol-5-yl)ethanone

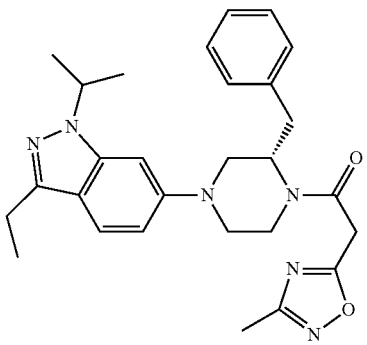 [SMILES: CCc1nn(C(C)C)c2cc(N3CCN(C(=O)Cc4nc(C)no4)[C@@H](Cc4ccccc4)C3)ccc12]

Prepared by the method outlined for Example 275 using 6-((S)-3-benzyl-piperazin-1-yl)-1-isopropyl-3-ethyl-1H-indazole and methyl (3-methyl-1,2,4-oxadiazol-5-yl)acetate as starting materials. Product was obtained as a colorless solid (64%). LC/MS (Method B) 3.95 min, [M+1]+ 487.

Example 314

Preparation of Compound 402, (S)-1-(2-benzyl-4-(3-ethyl-1-isopropyl-1H-indazol-6-yl)piperazin-1-yl)-2-(oxazol-5-yl)ethanone

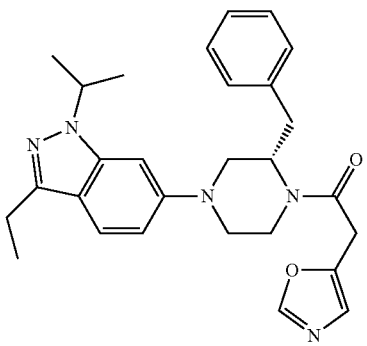 [SMILES: CCc1nn(C(C)C)c2cc(N3CCN(C(=O)Cc4cnco4)[C@@H](Cc4ccccc4)C3)ccc12]

Prepared by the method outlined for Example 189 using 2-(oxazol-5-yl)acetic acid and 6-((S)-3-benzyl-piperazin-1-yl)-1-isopropyl-3-ethyl-1H-indazole as starting materials. Product was obtained as a light brown solid (34%). LC/MS (Method B) 3.77 min, [M+1]+ 472.

Example 315

Preparation of Compound 403, (S)-1-(2-benzyl-4-(3-ethyl-1-isopropyl-1H-indazol-6-yl)piperazin-1-yl)-2-(4H-1,2,4-triazol-3-yl)ethanone

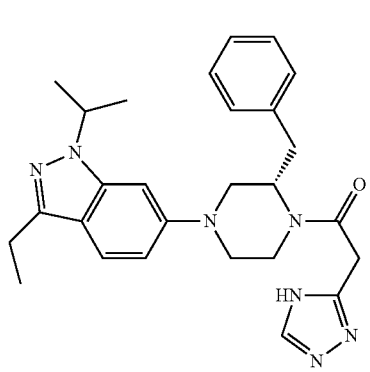 [SMILES: CCc1nn(C(C)C)c2cc(N3CCN(C(=O)Cc4nnc[nH]4)[C@@H](Cc4ccccc4)C3)ccc12]

Prepared by the method outlined for Example 275 using ethyl 2-(4H-1,2,4-triazol-3-yl)acetate and 6-((S)-3-benzyl-piperazin-1-yl)-1-isopropyl-3-ethyl-1H-indazole as starting materials. Product was obtained as an off-white solid (39%). LC/MS (Method B) 3.34 min, [M+1]$^+$ 472.

Example 316

Preparation of Compound 404, (S)-1-(2-benzyl-4-(3-ethyl-1-isopropyl-1H-indazol-6-yl)piperazin-1-yl)-2-(pyrimidin-2-yl)ethanone

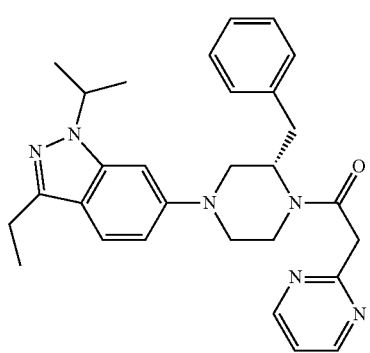 [SMILES: CCc1nn(C(C)C)c2cc(N3CCN(C(=O)Cc4ncccn4)[C@@H](Cc4ccccc4)C3)ccc12]

Prepared by the method outlined for Example 189 using 2-(pyrimidin-2-yl)acetic acid and 6-((S)-3-benzyl-piperazin-1-yl)-1-isopropyl-3-ethyl-1H-indazole as starting materials. Product was obtained as a colorless solid (64%). LC/MS (Method B) 3.7 min, [M+1]$^+$ 483.

Example 317

Preparation of Compound 405, (S)-1-(2-benzyl-4-(3-ethyl-1-isopropyl-1H-indazol-6-yl)piperazin-1-yl)-2-hydroxyethanone

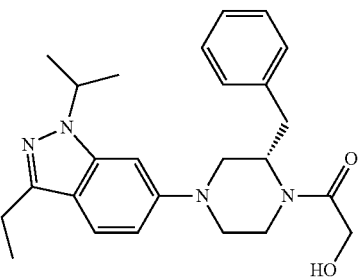 [SMILES: CCc1nn(C(C)C)c2cc(N3CCN(C(=O)CO)[C@@H](Cc4ccccc4)C3)ccc12]

Prepared by the method outlined for Example 90 using and 64(S)-3-benzyl-piperazin-1-yl)-1-isopropyl-3-ethyl-1H-indazole as starting material. Product was obtained as a colorless solid (76%). LC/MS (Method B) 3.69 min, [M+1]$^+$ 421.

Example 318

Preparation of Compound 406, (S)-1-(2-benzyl-4-(1-cyclobutyl-3-ethyl-1H-indazol-6-yl)piperazin-1-yl)-2-(5-methyl-4H-1,2,4-triazol-3-yl)ethanone

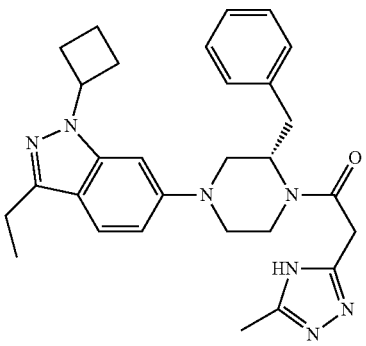 [SMILES: CCc1nn(C2CCC2)c2cc(N3CCN(C(=O)Cc4nnc(C)[nH]4)[C@@H](Cc4ccccc4)C3)ccc12]

Prepared by the method outlined for Example 189 using 6-((S)-3-benzyl-piperazin-1-yl)-1-cyclobutyl-3-ethyl-1H-indazole as starting material. Product was obtained as an off-white solid (73%). LC/MS (Method B) 3.44 min, [M+1]$^+$ 498.

Example 319

Preparation of Compound 407, (S)-2-amino-1-(2-benzyl-4-(3-ethyl-1-isopropyl-1H-indazol-6-yl)piperazin-1-yl)ethanone

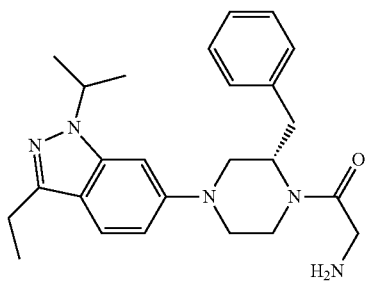 [SMILES: CCc1nn(C(C)C)c2cc(N3CCN(C(=O)CN)[C@@H](Cc4ccccc4)C3)ccc12]

Prepared by the method outlined for Example 91 using 64(S)-3-benzyl-piperazin-1-yl)-1-isopropyl-3-ethyl-1H-indazole. Product was obtained as a pale yellow solid (82%). LC/MS (Method B) 2.54 min, [M+1]$^+$ 420.

Example 320

Preparation of Compound 408, (S)-2-benzyl-4-(3-ethyl-1-isopropyl-1H-indazol-6-yl)piperazine-1-carboxamide

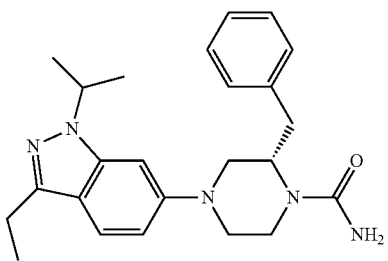 [SMILES: CCc1nn(C(C)C)c2cc(N3CCN(C(N)=O)[C@@H](Cc4ccccc4)C3)ccc12]

Prepared by the method outlined for Example 303 using 6-((S)-3-benzyl-piperazin-1-yl)-1-isopropyl-3-ethyl-1H-indazole as starting material. Product was obtained as an off-white solid (35%). LC/MS (Method B) 3.55 min, [M+1]$^+$ 406.

Example 321

Preparation of Compound 409, (S)-1-(4-(3-cyclobutoxy-4-methoxyphenyl)-2-isobutylpiperazin-1-yl)-2-(oxazol-5-yl)ethanone

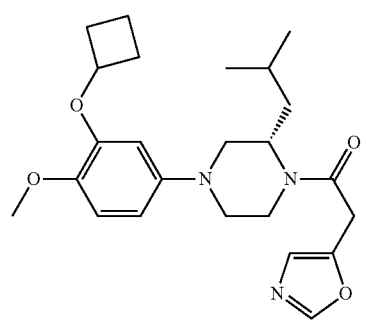 [SMILES: COc1ccc(N2CCN(C(=O)Cc3cnco3)[C@@H](CC(C)C)C2)cc1OC1CCC1]

Prepared by the method outlined for Example 189 using 2-(oxazol-5-yl)acetic acid and (S)-1-(3-cyclobutlyoxy-4-methoxy-phenyl)-3-isobutyl-piperazine as starting material. Product was obtained as an oil (4%). LC/MS (Method B) 3.62 min, [M+1]$^+$ 428.

Example 322

Preparation of Compound 410, (S)-1-(4-(3-cyclobutoxy-4-methoxyphenyl)-2-isobutylpiperazin-1-yl)-2-(3-methyl-1,2,4-oxadiazol-5-yl)ethanone

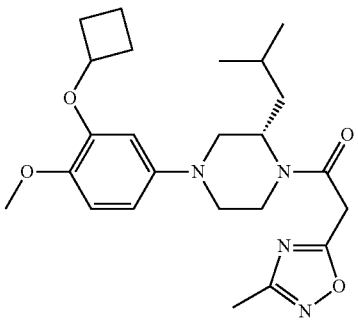 [SMILES: COc1ccc(N2CCN(C(=O)Cc3nc(C)no3)[C@@H](CC(C)C)C2)cc1OC1CCC1]

Prepared by the method outlined for Example 275 using methyl-(3-methyl-1,2,4-oxadiazol-5-yl)acetic acid and (S)-1-(3-cyclobutlyoxy-4-methoxy-phenyl)-3-isobutyl-piperazine as starting materials. Product was obtained as an off-white solid (4%). LC/MS (Method B) 3.8 min, [M+1]$^+$ 443.

Example 323

Preparation of Compound 411, (S)-1-(2-benzyl-4-(1-cyclobutyl-3-ethyl-1H-indazol-6-yl)piperazin-1-yl)-2-(5-ethyl-4H-1,2,4-triazol-3-yl)ethanone

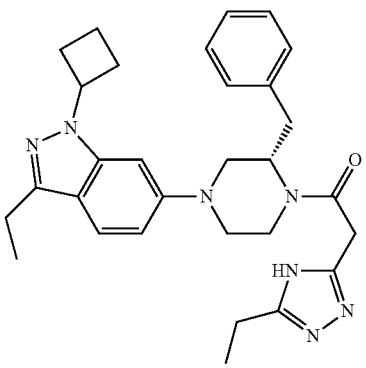 [SMILES: CCc1nnc(CC(=O)N2CCN(c3ccc4c(CC)nn(C5CCC5)c4c3)C[C@@H]2Cc2ccccc2)[nH]1]

Prepared by the method outlined for Example 275 using methyl (5-ethyl-1H-1,2,4-triazol-3-yl)acetate and 6-((S)-3-benzyl-piperazin-1-yl)-1-cyclobutyl-3-ethyl-1H-indazole as starting materials. Product was obtained as a light yellow solid (16%). LC/MS (Method B) 3.56 min, [M+1]$^+$ 512.

Example 324

Preparation of Compound 412, (S)-1-(2-benzyl-4-(1-cyclobutyl-3-ethyl-1H-indazol-6-yl)piperazin-1-yl)-2-(5-(trifluoromethyl)-4H-1,2,4-triazol-3-yl)ethanone

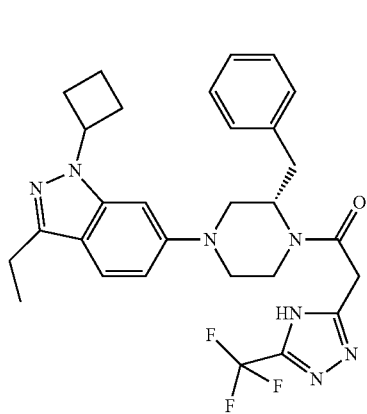 [SMILES: CCc1nn(C2CCC2)c2cc(N3CCN(C(=O)Cc4nnc(C(F)(F)F)[nH]4)[C@@H](Cc4ccccc4)C3)ccc12]

Prepared by the method outlined for Example 275 using methyl [5-(trifluoromethyl)-1H-1,2,4-triazol-3-yl]acetate and 6-((S)-3-benzyl-piperazin-1-yl)-1-cyclobutyl-3-ethyl-1H-indazole as starting materials. Product was obtained as an off-white solid (11%). LC/MS (Method B) 4.25 min, [M+1]$^+$ 552.

Example 325

Preparation of Compound 413, (S)-1-(2-benzyl-4-(1-cyclobutyl-3-ethyl-1H-indazol-6-yl)piperazin-1-yl)-2-(5-isopropyl-4H-1,2,4-triazol-3-yl)ethanone

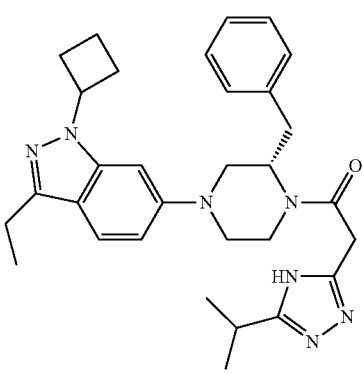 [SMILES: CCc1nn(C2CCC2)c2cc(N3CCN(C(=O)Cc4nnc(C(C)C)[nH]4)[C@@H](Cc4ccccc4)C3)ccc12]

Prepared by the method outlined for Example 275 using methyl (5-isopropyl-1H-1,2,4-triazol-3-yl)acetate and 6-((S)-3-benzyl-piperazin-1-yl)-1-cyclobutyl-3-ethyl-1H-indazole as starting materials. Product as a light brown solid (35%). LC/MS (Method B) 3.72 min, [M+1]$^+$ 526.

Example 326

Preparation of Compound 414, (S)-1-(4-(3-cyclobutoxy-4-methoxyphenyl)-2-(4-fluorobenzyl)piperazin-1-yl)-2-(1H-pyrazol-4-yl)ethanone

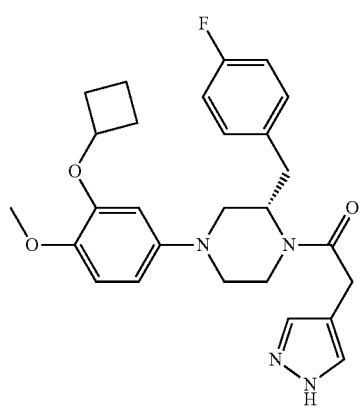 [SMILES: COc1ccc(N2CCN(C(=O)Cc3cn[nH]c3)[C@@H](Cc3ccc(F)cc3)C2)cc1OC1CCC1]

Prepared by the method outlined for Example 275 using methyl 1H-pyrazol-4-ylacetate and (S)-1-(3-cyclobutoxy-4-methoxyphenyl)-3-(4-fluorobenzyl)piperazine as starting materials. Product was obtained as a colorless solid (58%). LC/MS 3.44 min, [M+1]$^+$ 479.

Example 327

Preparation of Compound 415, (S)-1-(4-(3-cyclobutoxy-4-methoxyphenyl)-2-(4-fluorobenzyl)piperazin-1-yl)-2-(5-methyl-1H-1,2,4-triazol-3-yl)ethanone

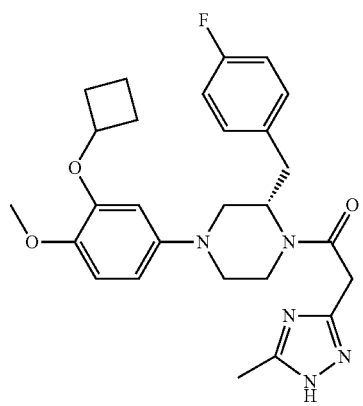 [SMILES: COc1ccc(N2CCN(C(=O)Cc3n[nH]c(C)n3)[C@@H](Cc3ccc(F)cc3)C2)cc1OC1CCC1]

Prepared by the method outlined for Example 189 using (S)-1-(3-cyclobutoxy-4-methoxyphenyl)-3-(4-fluorobenzyl)piperazine as starting material. Product was obtained as a colorless solid (79%). LC/MS 3.16 min, [M+1]$^+$ 494.

Example 328

Preparation of Compound 416, (S)-1-(4-(3-cyclobutoxy-4-methoxyphenyl)-2-(4-fluorobenzyl)piperazin-1-yl)-2-(pyrimidin-2-yl)ethanone

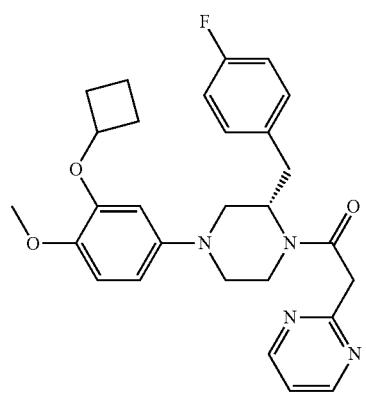 [SMILES: COc1ccc(N2CCN(C(=O)Cc3ncccn3)[C@@H](Cc3ccc(F)cc3)C2)cc1OC1CCC1]

Prepared by the method outlined for Example 189 using (S)-1-(3-cyclobutoxy-4-methoxyphenyl)-3-(4-fluorobenzyl)piperazine and 2-(pyrimidin-2-yl)acetic acid as starting materials. Product was obtained as a colorless solid (81%). LC/MS 3.59 min, [M+1]$^+$ 491.

Example 329

Preparation of Compound 417, 1-((S)-4-(1-cyclobutyl-3-ethyl-1H-indazol-6-yl)-2-(4-fluorobenzyl)piperazin-1-yl)-2-(5-methyl-3H-1,2,4-triazol-3-yl)ethanone

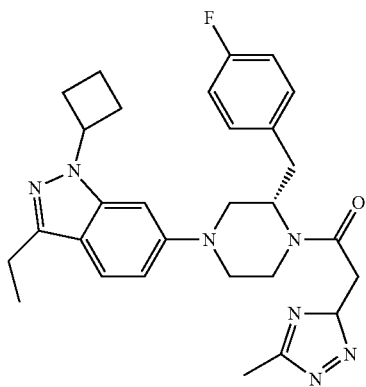 [SMILES: CCc1nn(C2CCC2)c2cc(N3CCN(C(=O)CC4N=NC(C)=N4)[C@@H](Cc4ccc(F)cc4)C3)ccc12]

Prepared by the method outlined for Example 189 using (S)-1-cyclobutyl-3-ethyl-6-(3-(4-fluorobenzyl)piperazin-1-yl)-1H-indazole as starting material. Product was obtained as a colorless solid (71%). LC/MS 3.47 min, [M+1]$^+$ 516.

Example 330

Preparation of Compound 418, (S)-4-(3-cyclobutoxy-4-methoxyphenyl)-2-(4-fluorobenzyl)piperazine-1-carboxamide

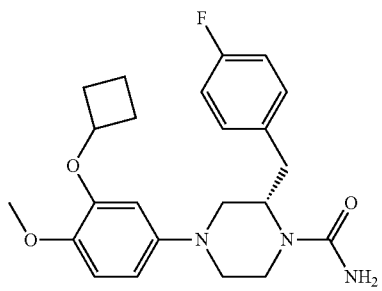 [SMILES: COc1ccc(N2CCN(C(N)=O)[C@@H](Cc3ccc(F)cc3)C2)cc1OC1CCC1]

Prepared by the method outlined for Example 303 using (S)-1-(3-cyclobutoxy-4-methoxyphenyl)-3-(4-fluorobenzyl)piperazine. Product was obtained as a colorless solid (82%). LC/MS 3.39 min, [M+1]$^+$ 414.

Example 331

Preparation of Compound 419, (S)-2-(2-benzyl-4-(2-chloro-8-methoxyquinolin-5-yl)piperazin-1-yl)acetamide

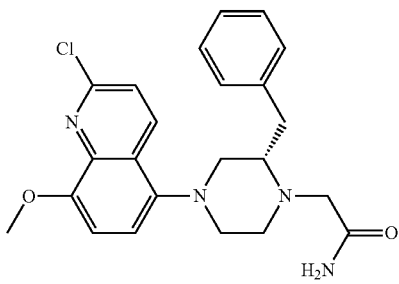 [SMILES: COc1ccc(N2CCN(CC(N)=O)[C@@H](Cc3ccccc3)C2)c2ccc(Cl)nc12]

Prepared by the method outlined for Example 95 using (S)-5-(3-benzylpiperazin-1-yl)-2-chloro-8-methoxyquinoline as starting material. Product was obtained as a yellow solid (34%). LC/MS 2.38 min, [M+1]$^+$ 425.

Example 332

Preparation of Compound 420, (S)-2-(2-(4-fluorobenzyl)-4-(8-methoxy-2-(trifluoromethyl)quinolin-5-yl)piperazin-1-yl)acetamide

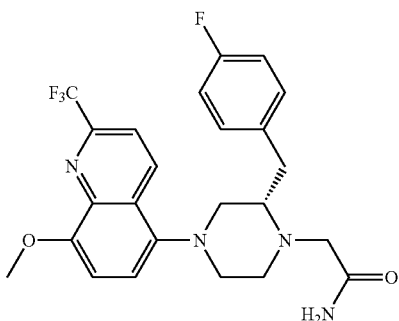

Prepared by the method outlined for Example 95 using (S)-5-(3-(4-fluorobenzyl)piperazin-1-yl)-2-chloro-8-methoxyquinoline as starting material. Product was obtained as a yellow solid (77%). LC/MS 2.67 min, [M+1]+ 477.

Example 333

Preparation of Compound 421, (S)-2-(2-(4-fluorobenzyl)-4-(8-methoxy-2-(trifluoromethyl)quinolin-5-yl)piperazin-1-yl)acetic acid

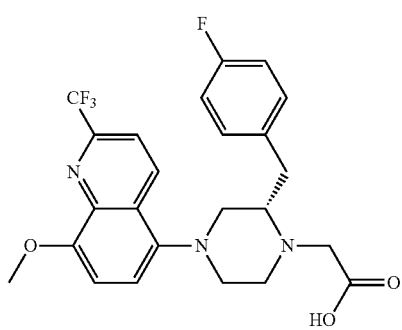 [SMILES: COc1ccc(N2CCN(CC(=O)O)[C@@H](Cc3ccc(F)cc3)C2)c2ccc(C(F)(F)F)nc12]

Prepared by the method outlined for Examples 96/98 using (S)-5-(3-(4-fluorobenzyl)piperazin-1-yl)-2-chloro-8-methoxyquinoline as starting material. Product was obtained as a yellow solid (74%). LC/MS (Method B) 2.90 min, [M+1]+ 478.

Example 334

Preparation of Compound 422, (S)-2-(2-benzyl-4-(2,8-dimethoxyquinolin-5-yl)piperazin-1-yl)acetamide

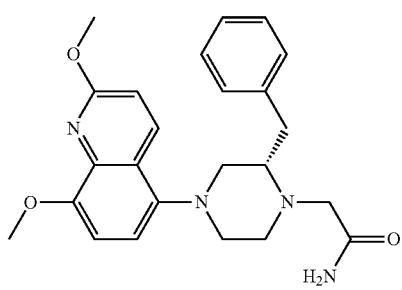 [SMILES: COc1ccc2c(N3CCN(CC(N)=O)[C@@H](Cc4ccccc4)C3)ccc(OC)c2n1]

A stirred solution of (S)-2-(2-benzyl-4-(2-chloro-8-methoxyquinolin-5-yl)piperazin-1-yl)acetamide (40 mg, 0.1 mmol) in MeOH (1.2 mL) was treated with sodium methoxide (1.0 mL, 4.4 mmol) as a 25% solution in MeOH. The reaction mixture was allowed to stir for 18 h, then evaporated and purified by silica gel chromatography eluting with EtOAc to afford product as a yellow solid (23 mg, 55%). $^1$H NMR (MeOH-d$_4$) 8.24-8.40 (br s, 1 H), 7.10-7.24 (m, 5 H), 7.03 (d, J=8.2, 1 H), 6.94 (d, J=8.4, 1 H), 6.82-6.88 (m, 1 H), 4.03 (s, 3 H), 3.97 (s, 3 H), 3.42-3.56 (m, 1 H), 2.94-3.27 (m, 8 H), 2.64-2.85 (m, 2 H). LC/MS 2.34 min, [M+1]+ 421.

Example 335

Preparation of Compound 423, (S)-1-(2-benzyl-4-(1-cyclobutyl-3-ethyl-1H-indazol-6-yl)piperazin-1-yl)-2-(1H-pyrazol-4-yl)ethanone

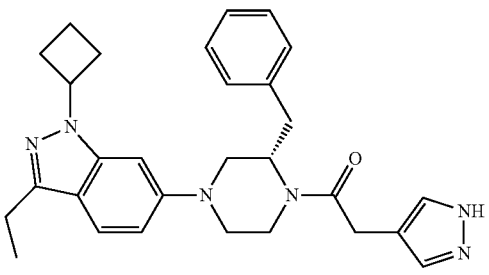 [SMILES: CCc1nn(C2CCC2)c2cc(N3CCN(C(=O)Cc4cn[nH]c4)[C@@H](Cc4ccccc4)C3)ccc12]

Prepared by the method outlined for Example 275 using 6-(3-benzyl-piperazin-1-yl)-1-cyclobutyl-3-ethyl-1H-indazole (185 mg, 0.494 mmol) and (1H-pyrazol-4-yl)-acetic acid methyl ester (148 mg, 1.06 mmol) with heating for 5 days to afford product as a colorless solid (31 mg, 13%). LC/MS (Method B) 3.70 min, [M+1]+ 483.

Example 336

Preparation of Compound 424, (S)-1-(2-benzyl-4-(1-cyclobutyl-3-ethyl-1H-indazol-6-yl)piperazin-1-yl)-2-(1-ethyl-1H-pyrazol-4-yl)ethanone

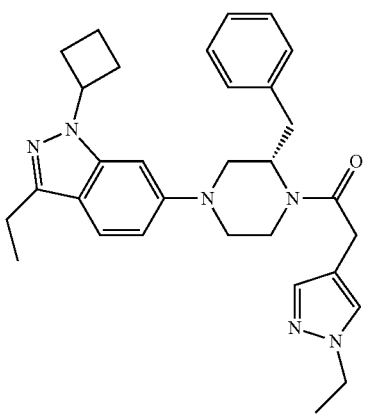 [SMILES: CCc1nn(C2CCC2)c2cc(N3CCN(C(=O)Cc4cnn(CC)c4)[C@@H](Cc4ccccc4)C3)ccc12]

A solution of (S)-1-(2-benzyl-4-(1-cyclobutyl-3-ethyl-1H-indazol-6-yl)piperazin-1-yl)-2-(1H-pyrazol-4-yl)ethanone (101 mg, 0.21 mmol) in DMF (1 mL) was treated with sodium hydride (10 mg, 0.25 mmol) as a 60% dispersion in mineral oil. Once bubbling subsided, ethyl iodide (18 µL, 0.23 mmol) was added and the mixture was heated to 60° C. for 24 h. The reaction mixture was diluted with EtOAc (30 mL) and washed with water (5 mL) followed by brine (5 mL). The organic layer was dried over Na$_2$SO$_4$, filtered, and evaporated. The crude residue was purified by silica gel chromatography eluting with a 0-10% MeOH in CH$_2$Cl$_2$ gradient to afford product as a colorless solid (48 mg, 44%). LC/MS 4.03 min, [M+1]+ 511.

Example 337

Preparation of Compound 425, (S)-1-(2-benzyl-4-(1-cyclobutyl-3-ethyl-1H-indazol-6-yl)piperazin-1-yl)-2-(1-isopropyl-1H-pyrazol-4-yl)ethanone

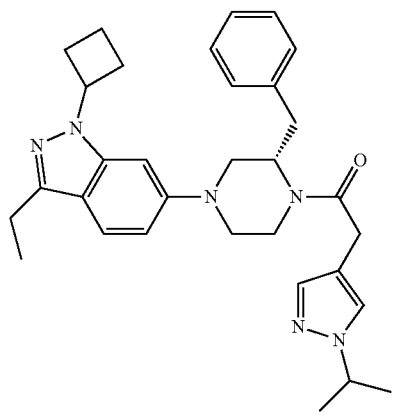 [SMILES: CCc1nn(C2CCC2)c2cc(N3CCN(C(=O)Cc4cnn(C(C)C)c4)[C@@H](Cc4ccccc4)C3)ccc12]

Prepared by the method outlined for Examples 336 using 2-bromopropane. Product was obtained as a colorless solid (35%). LC/MS 4.18 min, [M+1]$^+$ 525.

Example 338

Preparation of Compound 426, 1-((S)-2-benzyl-4-(4-methoxy-3-((S)-1-methylpyrrolidin-3-yloxy)phenyl)piperazin-1-yl)ethanone

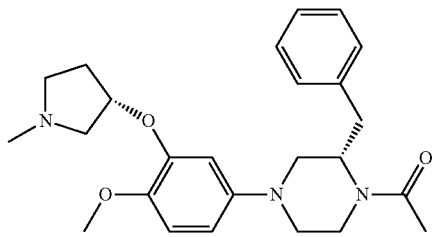 [SMILES: COc1ccc(N2CCN(C(C)=O)[C@@H](Cc3ccccc3)C2)cc1O[C@H]1CCN(C)C1]

Into a 25 mL screw-cap vial were added (S)-3-benzyl-1-[4-methoxy-3-(1-methyl-pyrrolidin-(S)-3-yloxy)-phenyl]-piperazine dihydrochloride (88 mg, 0.19 mmol), acetic andydride (62 µL, 0.65 mmol), and pyridine (2 mL). The reaction mixture was stirred at room temperature for 4 h, then concentrated. Purification by silica gel flash chromatography with a 0-20% MeOH/CH$_2$Cl$_2$ gradient afforded the title compound as a tan solid (63 mg, 77%). LC/MS (Method B) 0.91 min, [M+1]$^+$ 424.

Example 339

Preparation of Compound 427, (S)-1-(2-benzyl-4-(4-methoxy-3-(1-methylpiperidin-4-yloxy)phenyl)piperazin-1-yl)ethanone

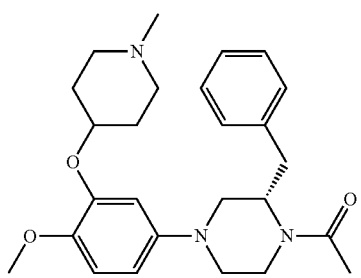 [SMILES: COc1ccc(N2CCN(C(C)=O)[C@@H](Cc3ccccc3)C2)cc1OC1CCN(C)CC1]

Prepared using the same procedure described in Example 338 from (S)-3-benzyl-1-[4-methoxy-3-(1-methyl-piperidin-4-yloxy)-phenyl]-piperazine dihydrochloride (103 mg, 0.22 mmol) and acetic anhydride (200 µL, 2.11 mmol), and pyridine (2 mL) to afford the title compound as brown waxy solid (47 mg, 49%). LC/MS (Method B) 2.32 min, [M+1]$^+$ 338.

Example 340

Preparation of Compound 428, (S)-methyl 2-benzyl-4-(3-cyclobutoxy-4-methoxyphenyl)piperazine-1-carboxylate

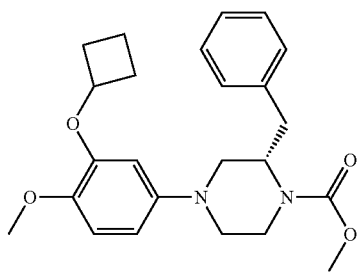 [SMILES: COC(=O)N1CCN(c2ccc(OC)c(OC3CCC3)c2)C[C@@H]1Cc1ccccc1]

Prepared using the same procedure described in Example 89 from (S)-3-benzyl-1-(3-cyclobutoxy-4-methoxy-phenyl)-piperazine (188 mg, 0.535 mmol), diisopropylethylamine (200 µL, 1.15 mmol), and methyl chloroformate (62 µL, 0.81 mmol) to afford the title compound as a yellow solid (107 mg, 49%). LC/MS (Method B) 4.17 min, [M+1]$^+$ 411.

Example 341

Preparation of Compound 429, (S)-3-(2-benzyl-4-(3-cyclopropoxy-4-methoxyphenyl)piperazin-1-yl)-3-oxopropanamide

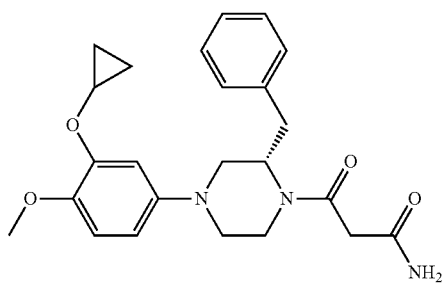 [SMILES: COc1ccc(N2CCN(C(=O)CC(N)=O)[C@@H](Cc3ccccc3)C2)cc1OC1CC1]

Prepared using the same procedure described in Examples 121/129 from (S)-3-benzyl-1-(3-cyclopropoxy-4-methoxyphenyl)-piperazine (111 mg, 0.328 mmol) and ethylmalonyl chloride (107 mg, 0.71 mmol) to obtain the intermediate ester, which was treated with methanolic ammonia and catalytic NaCN to afford the title compound as a white solid (37 mg, 27% overall). LC/MS (Method B) 3.14 min, [M+1]$^+$ 424.

Example 342

Preparation of Compound 430, (S)-3-(2-benzyl-4-(3-(cyclopentyloxy)-4-(difluoromethoxy)phenyl)piperazin-1-yl)-3-oxopropanamide

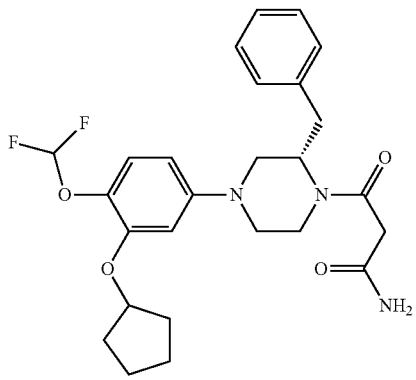 [SMILES: NC(=O)CC(=O)N1CCN(c2ccc(OC(F)F)c(OC3CCCC3)c2)C[C@@H]1Cc1ccccc1]

Prepared using the same procedure described in Examples 121/129 from (S)-3-benzyl-1-(3-cyclopentyloxy-4-difluoromethoxy-phenyl)-piperazine (152 mg, 0.345 mmol) and ethylmalonyl chloride (66 µL, 0.51 mmol) to obtain the intermediate ester, which was treated with methanolic ammonia and catalytic NaCN to afford the title compound as a white solid (101 mg, 60% overall). LC/MS (Method B) 3.67 min, [M+1]$^+$ 488.

Example 343

Preparation of Compound 431, (S)-3-(2-benzyl-4-(3-(cyclopropylmethoxy)-4-(difluoromethoxy)phenyl)piperazin-1-yl)-3-oxopropanamide

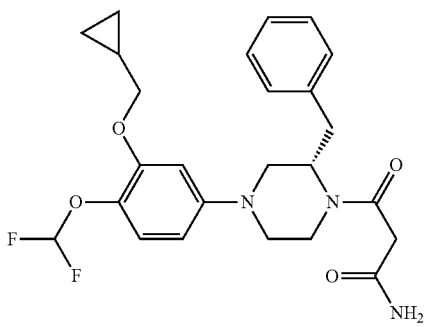 [SMILES: NC(=O)CC(=O)N1CCN(c2ccc(OC(F)F)c(OCC3CC3)c2)C[C@@H]1Cc1ccccc1]

Prepared using the same procedure described in Examples 121/129 from (S)-3-benzyl-1-(3-cyclopropylmethoxy-4-difluoromethoxy-phenyl)-piperazine (156 mg, 0.367 mmol) and ethylmalonyl chloride (68 µL, 0.52 mmol) to obtain the intermediate ester, which was treated with methanolic ammonia and catalytic NaCN to afford the title compound as a white solid (65 mg, 37% overall). LC/MS (Method B) 3.69 min, [M+1]$^+$ 474.

Example 344

Preparation of Compound 432, (S)-3-(2-benzyl-4-(3,4-bis(difluoromethoxy)phenyl)piperazin-1-yl)-3-oxopropanamide

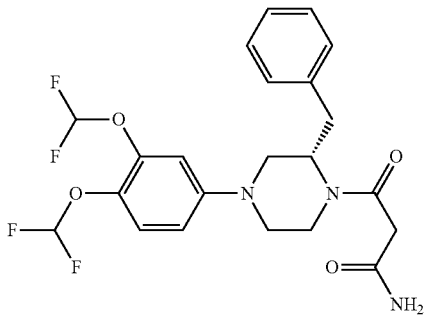 [SMILES: NC(=O)CC(=O)N1CCN(c2ccc(OC(F)F)c(OC(F)F)c2)C[C@@H]1Cc1ccccc1]

Prepared using the same procedure described in Examples 121/129 from (S)-3-benzyl-1-(3,4-bis-difluoromethoxy-phenyl)-piperazine hydrochloride (90 mg, 0.21 mmol) and ethylmalonyl chloride (50 µL, 0.39 mmol) to obtain the intermediate ester, which was treated with methanolic ammonia and catalytic NaCN to afford the title compound as a white solid (59 mg, 58% overall). LC/MS (Method B) 3.47 min, [M+1]$^+$ 470.

Example 345

Preparation of Compound 433, (S)-3-(2-benzyl-4-(1-cyclopentyl-3-ethyl-1H-indazol-6-yl)piperazin-1-yl)-3-oxopropanamide

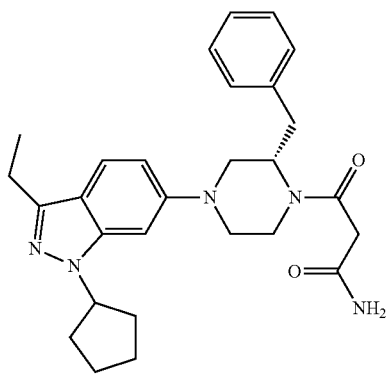 [SMILES: CCc1nn(C2CCCC2)c2cc(N3CCN(C(=O)CC(N)=O)[C@@H](Cc4ccccc4)C3)ccc12]

Prepared using the same procedure described in Examples 121/129 from 6-((S)-3-benzyl-piperazin-1-yl)-1-cyclopentyl-3-ethyl-1H-indazole (85 mg, 0.22 mmol) and ethylmalonyl chloride (45 µL, 0.35 mmol) to obtain the intermediate ester, which was treated with methanolic ammonia and catalytic NaCN to afford the title compound as a tan solid (44 mg, 42% overall). LC/MS (Method B) 3.54 min, [M+1]$^+$ 474.

Example 346

Preparation of Compound 434, (S)-3-(2-benzyl-4-(8-methoxy-2-(trifluoromethyl)quinolin-5-yl)piperazin-1-yl)-3-oxopropanamide

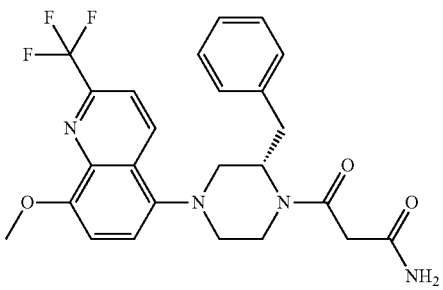 [SMILES: COc1ccc(N2CCN(C(=O)CC(N)=O)[C@@H](Cc3ccccc3)C2)c2ccc(C(F)(F)F)nc12]

Prepared using the same procedure described in Example 121/129 from 5-((S)-3-benzyl-piperazin-1-yl)-8-methoxy-2-trifluoromethyl-quinoline (200 mg, 0.498 mmol) and ethylmalonyl chloride (93 mg, 0.62 mmol) to obtain the intermediate ester, which was treated with methanolic ammonia and catalytic NaCN to afford the title compound as a yellow solid (155 mg, 65% overall). LC/MS (Method B) 3.35 min, [M+1]$^+$ 487.

Example 347

Preparation of Compound 435, (S)-1-(2-benzyl-4-(3-cyclobutyl-1-ethyl-1H-indazol-5-yl)piperazin-1-yl)-2-hydroxyethanone

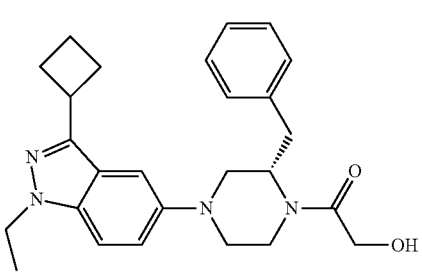 [SMILES: CCn1nc(C2CCC2)c2cc(N3CCN(C(=O)CO)[C@@H](Cc4ccccc4)C3)ccc21]

Prepared using the same procedure described in Example 90 from 5-(3-benzyl-piperazin-1-yl)-3-cyclobutyl-1-ethyl-1H-indazole (161 mg, 0.430 mmol) and acetoxyacetyl chloride (70 µL, 0.65 mmol) to obtain the intermediate acetyl ester (LC/MS (Method B) 3.95 min, [M+1]$^+$ 475.0), which was treated with 1 M KOH in MeOH to afford the title compound as a yellow solid (105 mg, 56% overall). LC/MS (Method B) 3.75 min, [M+1]$^+$ 433.

Example 348

Preparation of Compound 436, (S)-1-(2-benzyl-4-(3-(cyclopentyloxy)-4-methoxyphenyl)piperazin-1-yl)-2-(4H-1,2,4-triazol-3-yl)ethanone

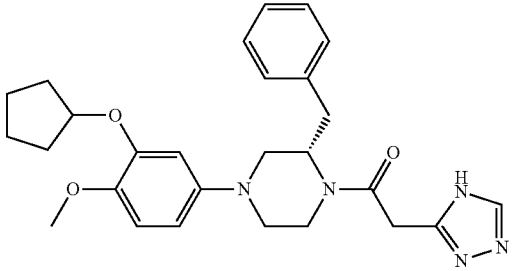 [SMILES: COc1ccc(N2CCN(C(=O)Cc3nnc[nH]3)[C@@H](Cc3ccccc3)C2)cc1OC1CCCC1]

Prepared using the same procedure described in Example 275 with (S)-3-benzyl-1-(3-cyclopentyloxy-4-methoxy-phenyl)-piperazine and (4H-[1,2,4]triazol-3-yl)-acetic acid ethyl ester as starting material. The product was obtained as an off-white solid (105 mg, 20%). LC/MS (Method B) 3.39 min, [M+1]$^+$ 476.

Example 349

Preparation of Compound 437, (S)-1-(2-benzyl-4-(3-(cyclopentyloxy)-4-methoxyphenyl)piperazin-1-yl)-2-(1H-pyrazol-4-yl)ethanone

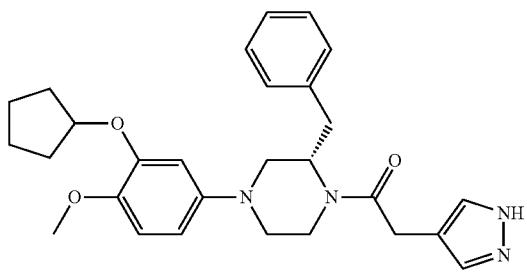 [SMILES: COc1ccc(N2CCN(C(=O)Cc3cn[nH]c3)[C@@H](Cc3ccccc3)C2)cc1OC1CCCC1]

Prepared using the same procedure described in Example 275 from (S)-3-benzyl-1-(3-cyclopentyloxy-4-methoxyphenyl)-piperazine and (1H-pyrazol-4-yl)-acetic acid methyl ester with heating for 15 days to afford the title compound as an off-white solid (12 mg, 7%). LC/MS (Method B) 3.60 min, [M+1]$^+$ 475.

Example 350

Preparation of Compound 438, (S)-1-(2-benzyl-4-(3-(cyclopentyloxy)-4-methoxyphenyl)piperazin-1-yl)-2-(oxazol-5-yl)ethanone

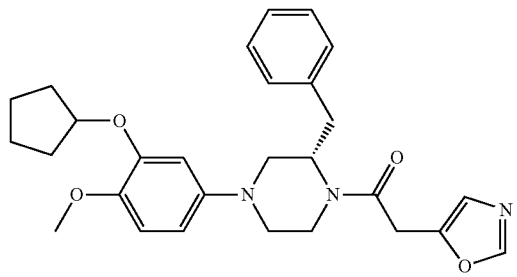 [SMILES: COc1ccc(N2CCN(C(=O)Cc3cnco3)[C@@H](Cc3ccccc3)C2)cc1OC1CCCC1]

Prepared using the same procedure described in Example 275 from (S)-3-benzyl-1-(3-cyclopentyloxy-4-methoxyphenyl)-piperazine and oxazol-5-yl-acetic acid methyl ester with heating for 5 days to afford the title compound as tan solid (13 mg, 10%). LC/MS (Method B) 3.84 min, [M+1]$^+$ 476.

Example 351

Preparation of Compound 439, (S)-1-(2-benzyl-4-(3-(cyclopentyloxy)-4-methoxyphenyl)piperazin-1-yl)-2-(3-methyl-1,2,4-oxadiazol-5-yl)ethanone

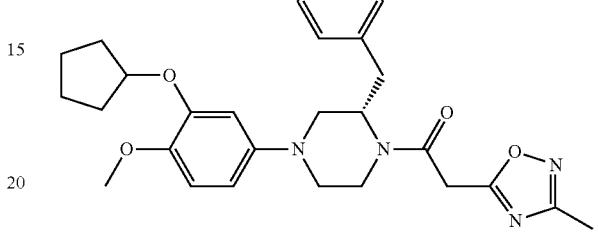

Prepared using the same procedure described in Example 275 from (S)-3-benzyl-1-(3-cyclopentyloxy-4-methoxyphenyl)-piperazine and (3-methyl-[1,2,4]oxadiazol-5-yl)-acetic acid methyl ester with heating for 2 days to afford the title compound as tan solid (65 mg, 34%). LC/MS (Method B) 4.05 min, [M+1]$^+$ 491.

Example 352

Preparation of Compound 440, (S)-1-(2-benzyl-4-(3-cyclopropoxy-4-methoxyphenyl)piperazin-1-yl)-2-(4H-1,2,4-triazol-3-yl)ethanone

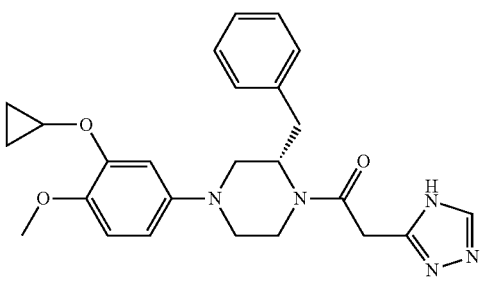 [SMILES: COc1ccc(N2CCN(C(=O)Cc3nnc[nH]3)[C@@H](Cc3ccccc3)C2)cc1OC1CC1]

Prepared using the same procedure described in Example 275 from (S)-3-benzyl-1-(3-cyclopropyloxy-4-methoxyphenyl)-piperazine and (4H-[1,2,4]triazol-3-yl)-acetic acid ethyl ester with heating for 7 days to afford the title compound as a yellow solid (20 mg, 15%). LC/MS (Method B) 3.12 min, [M+1]$^+$ 448.

Example 353

Preparation of Compound 441, (S)-1-(2-benzyl-4-(3-cyclobutoxy-4-methoxyphenyl)piperazin-1-yl)-2-(oxazol-5-yl)ethanone

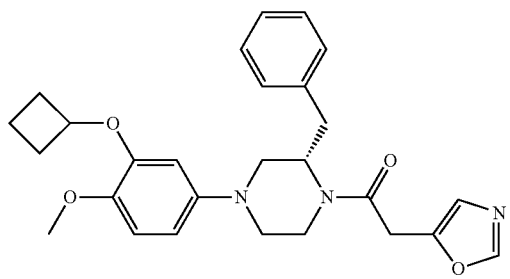 [SMILES: COc1ccc(N2CCN(C(=O)Cc3cnco3)[C@@H](Cc3ccccc3)C2)cc1OC1CCC1]

Prepared using the same procedure described in Example 275 from (S)-3-benzyl-1-(3-cyclobutyloxy-4-methoxy-phenyl)-piperazine and oxazol-5-yl-acetic acid methyl ester with heating for 5 days to afford the title compound as tan solid (22 mg, 17%). LC/MS (Method B) 3.59 min, $[M+1]^+$ 462.

Example 354

Preparation of Compound 442, (S)-1-(2-benzyl-4-(3-cyclobutoxy-4-methoxyphenyl)piperazin-1-yl)-2-(3-methyl-1,2,4-oxadiazol-5-yl)ethanone

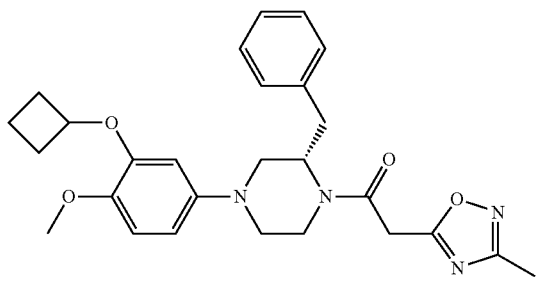 [SMILES: COc1ccc(N2CCN(C(=O)Cc3nc(C)no3)[C@@H](Cc3ccccc3)C2)cc1OC1CCC1]

Prepared using the same procedure described in Example 275 from (S)-3-benzyl-1-(3-cyclobutyloxy-4-methoxy-phenyl)-piperazine and (3-methyl-[1,2,4]oxadiazol-5-yl)-acetic acid methyl ester with heating for 5 days to afford the title compound as an off-white solid (49 mg, 35%). LC/MS (Method B) 3.80 min, $[M+1]^+$ 477.

Example 355

Preparation of Compound 443, (S)-1-(2-benzyl-4-(3-cyclobutoxy-4-methoxyphenyl)piperazin-1-yl)-2-(3-(trifluoromethyl)-1H-1,2,4-triazol-5-yl)ethanone

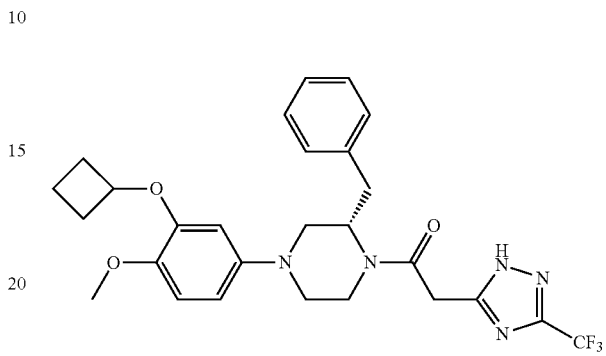

Prepared using the same procedure described in Example 275 from (S)-3-benzyl-1-(3-cyclobutyloxy-4-methoxy-phenyl)-piperazine and (5-trifluoromethyl-2H-[1,2,4]triazol-3-yl)-acetic acid methyl ester with heating for 5 days to afford the title compound as tan solid (24 mg, 15%). LC/MS (Method B) 3.94 min, $[M+1]^+$ 530.

Example 356

Preparation of Compound 444, (S)-1-(2-benzyl-4-(3-cyclobutoxy-4-methoxyphenyl)piperazin-1-yl)-2-(1H-pyrazol-4-yl)ethanone

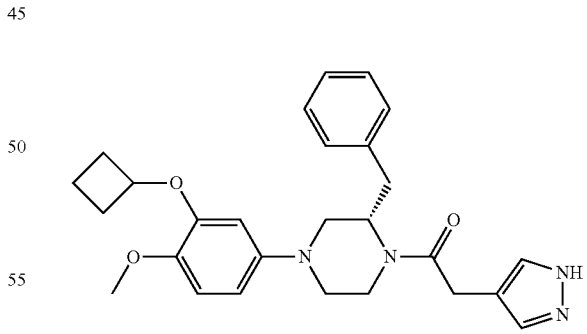

Prepared using the same procedure described in Example 275 from (S)-3-benzyl-1-(3-cyclobutyloxy-4-methoxy-phenyl)-piperazine and (1H-pyrazol-4-yl)-acetic acid methyl ester with heating for 17 days to afford the title compound as an off-white solid (20 mg, 14%). LC/MS (Method B) 3.42 min, $[M+1]^+$ 461.

Example 357

Preparation of Compound 445, (S)-1-(2-benzyl-4-(3-cyclobutoxy-4-methoxyphenyl)piperazin-1-yl)-2-(2-methyloxazol-5-yl)ethanone

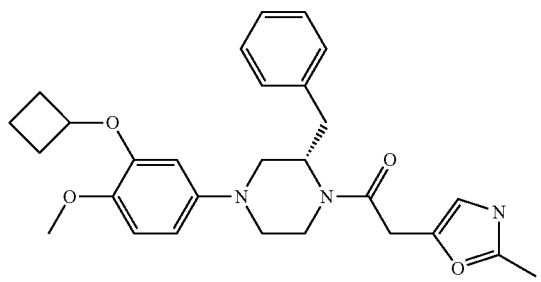

Prepared using the same procedure described in Example 275 from (S)-3-benzyl-1-(3-cyclobutyloxy-4-methoxy-phenyl)-piperazine and (2-methyl-oxazol-5-yl)-acetic acid methyl ester with heating for 12 h to afford the title compound as tan solid (110 mg, 54%). LC/MS (Method B) 3.62 min, [M+1]$^+$ 476.

Example 358

Preparation of Compound 446, (S)-1-(2-benzyl-4-(3-cyclobutoxy-4-methoxyphenyl)piperazin-1-yl)-2-(3-isopropyl-1H-1,2,4-triazol-5-yl)ethanone

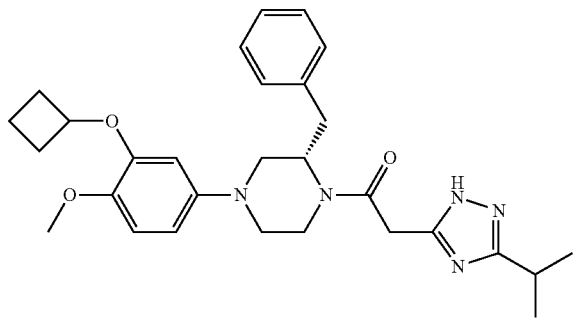 [SMILES: COc1ccc(N2CCN(C(=O)Cc3nc(C(C)C)n[nH]3)[C@@H](Cc3ccccc3)C2)cc1OC1CCC1]

Prepared using the same procedure described in Example 275 from (S)-3-benzyl-1-(3-cyclobutyloxy-4-methoxy-phenyl)-piperazine and (5-isopropyl-2H-[1,2,4]triazol-3-yl)-acetic acid ethyl ester with heating for 10 h to afford the title compound as tan solid (96 mg, 25%). LC/MS (Method B) 3.39 min, [M+1]$^+$ 504.

Example 359

Preparation of Compound 447, (S)-1-(2-benzyl-4-(3-cyclobutoxy-4-methoxyphenyl)piperazin-1-yl)-2-(3-ethyl-1H-1,2,4-triazol-5-yl)ethanone

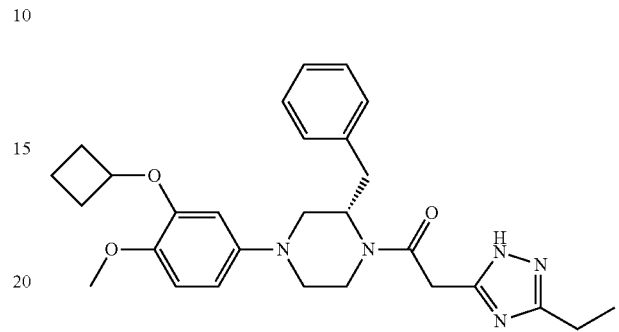

Prepared using the same procedure described in Example 275 from (S)-3-benzyl-1-(3-cyclobutyloxy-4-methoxy-phenyl)-piperazine and (5-ethyl-2H-[1,2,4]triazol-3-yl)-acetic acid ethyl ester with heating for 15 days to afford the title compound as tan solid (60 mg, 19%). LC/MS (Method B) 3.22 min, [M+1]$^+$ 490.

Example 360

Preparation of Compound 448, (S)-1-(2-benzyl-4-(3-cyclobutoxy-4-methoxyphenyl)piperazin-1-yl)-2-(1-methyl-1H-pyrazol-4-yl)ethanone

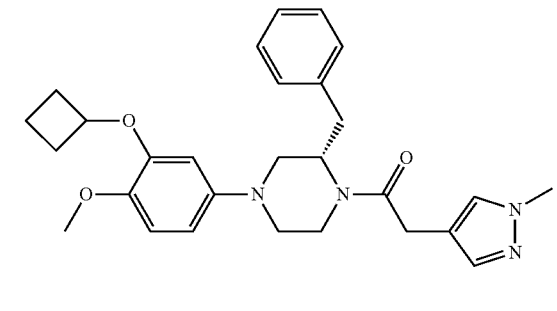 [SMILES: COc1ccc(N2CCN(C(=O)Cc3cnn(C)c3)[C@@H](Cc3ccccc3)C2)cc1OC1CCC1]

Prepared using the same procedure described in Example 275 from (S)-3-benzyl-1-(3-cyclobutyloxy-4-methoxy-phenyl)-piperazine and (1-methyl-1H-pyrazol-4-yl)-acetic acid methyl ester [prepared by treatment of (1H-pyrazol-4-yl)-acetic acid methyl ester with NaH followed by MeI; used as obtained after aqueous workup] with heating for 15 days to afford the title compound as a tan solid (12 mg, 4%). LC/MS (Method B) 3.55 min, [M+1]$^+$ 475.

Example 361

Preparation of Compound 449, (S)-1-(2-benzyl-4-(1-cyclobutyl-3-ethyl-1H-indazol-6-yl)piperazin-1-yl)-2-(4H-1,2,4-triazol-3-yl)ethanone

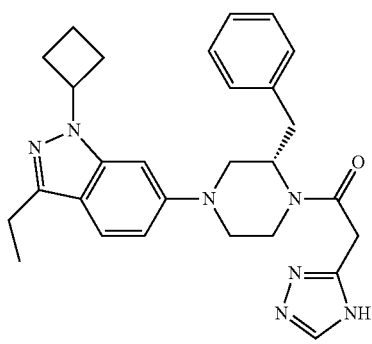 [SMILES: CCc1nn(C2CCC2)c2cc(N3CCN(C(=O)Cc4nnc[nH]4)[C@@H](Cc4ccccc4)C3)ccc12]

Prepared using the same procedure described in Example 275 from 6-(3-benzyl-piperazin-1-yl)-1-cyclobutyl-3-ethyl-1H-indazole and (4H-[1,2,4]triazol-3-yl)-acetic acid ethyl ester with heating for 5 days to afford the title compound as a colorless solid (72 mg, 27%). LC/MS (Method B) 3.52 min, [M+1]$^+$ 484.

Example 362

Preparation of Compound 450, (S)-1-(2-benzyl-4-(3-cyclobutyl-1-ethyl-1H-indazol-5-yl)piperazin-1-yl)-2-(4H-1,2,4-triazol-3-yl)ethanone

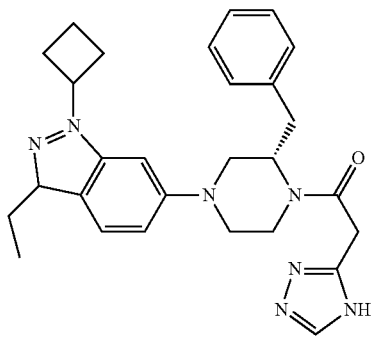

Prepared using the same procedure described in Example 275 from 5-((S)-3-benzyl-piperazin-1-yl)-3-cyclobutyl-1-ethyl-1H-indazole and (4H-[1,2,4]triazol-3-yl)-acetic acid ethyl ester with heating for 7 days to afford the title compound as a colorless solid (19 mg, 10%). LC/MS (Method B) 3.39 min, [M+1]$^+$ 484.

Example 363

Preparation of Compound 451, (S)-1-(2-benzyl-4-(8-methoxy-2-(trifluoromethyl)quinolin-5-yl)piperazin-1-yl)-2-(1H-1,2,4-triazol-5-yl)ethanone

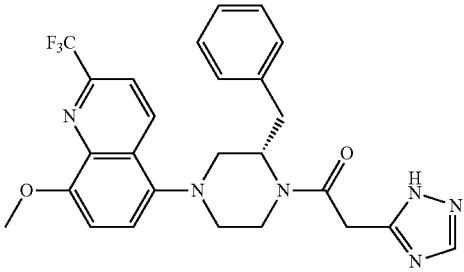 [SMILES: COc1ccc(N2CCN(C(=O)Cc3ncn[nH]3)[C@@H](Cc3ccccc3)C2)c2ccc(C(F)(F)F)nc12]

Prepared using the same procedure described in Example 275 from 5-((S)-3-benzyl-piperazin-1-yl)-8-methoxy-2-trifluoromethyl-quinoline and (4H-[1,2,4]triazol-3-yl)-acetic acid ethyl ester with heating for 7 days to afford the title compound as a colorless solid (0.9 mg, 0.7%). LC/MS (Method B) 3.32 min, [M+1]$^+$ 511.

Example 364

Preparation of Compound 452, (S)-1-(2-benzyl-4-(3-cyclobutoxy-4-methoxyphenyl)piperazin-1-yl)-2-(4H-1,2,4-triazol-3-yl)ethanone

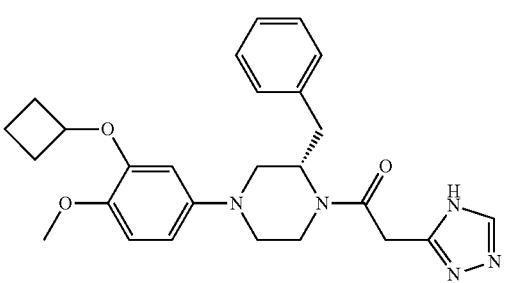 [SMILES: COc1ccc(N2CCN(C(=O)Cc3nnc[nH]3)[C@@H](Cc3ccccc3)C2)cc1OC1CCC1]

Prepared using the same procedure described in Example 275 from (S)-3-benzyl-1-(3-cyclobutyloxy-4-methoxy-phenyl)-piperazine and (4H-[1,2,4]triazol-3-yl)-acetic acid ethyl ester with heating for 15 days to afford the title compound as a yellow solid (75 mg, 19%). LC/MS (Method B) 3.17 min, [M+1]$^+$ 462.

Example 365

Preparation of Compound 453, (S)-1-(2-benzyl-4-(3-isopropoxy-4-methoxyphenyl)piperazin-1-yl)-2-(4H-1,2,4-triazol-3-yl)ethanone

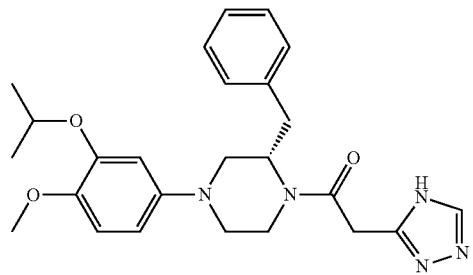 [SMILES: COc1ccc(N2CCN(C(=O)Cc3nnc[nH]3)[C@@H](Cc3ccccc3)C2)cc1OC(C)C]

Prepared using the same procedure described in Example 275 from (S)-3-benzyl-1-(3-isopropoxy-4-methoxy-phenyl)-piperazine and (4H-[1,2,4]triazol-3-yl)-acetic acid ethyl ester with heating for 5 days to afford the title compound as a yellow solid (94 mg, 25%). LC/MS (Method B) 3.12 min, [M+1]$^+$ 450.

Example 366

Preparation of Compound 454, (S)-1-(2-benzyl-4-(3-cyclobutoxy-4-(difluoromethoxy)phenyl)piperazin-1-yl)-2-(4H-1,2,4-triazol-3-yl)ethanone

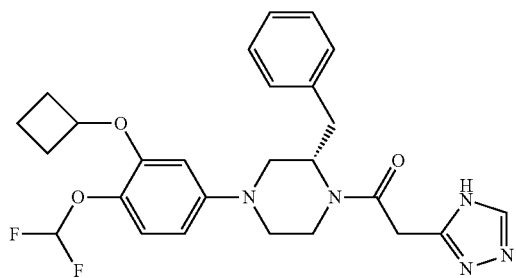 [SMILES: O=C(Cc1nnc[nH]1)N1CCN(c2ccc(OC(F)F)c(OC3CCC3)c2)C[C@@H]1Cc1ccccc1]

Prepared using the same procedure described in Example 275 from (S)-3-benzyl-1-(3-cyclobutoxy-4-difluoromethoxy-phenyl)-piperazine and (4H-[1,2,4]triazol-3-yl)-acetic acid ethyl ester with heating for 15 days to afford the title compound as a yellow solid (87 mg, 32%). LC/MS (Method B) 3.64 min, [M+1]$^+$ 498.

Example 367

Preparation of Compound 455, (S)-1-(2-benzyl-4-(3-(cyclopentyloxy)-4-(difluoromethoxy)phenyl)piperazin-1-yl)-2-(1H-imidazol-4-yl)ethanone

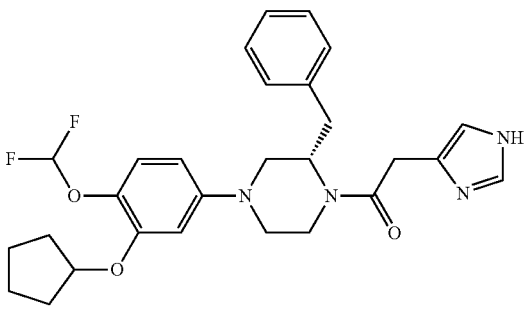 [SMILES: O=C(Cc1c[nH]cn1)N1CCN(c2ccc(OC(F)F)c(OC3CCCC3)c2)C[C@@H]1Cc1ccccc1]

Prepared using the same procedure described in Example 189 from (S)-3-benzyl-1-(3-cyclopentyloxy-4-difluoromethoxy-phenyl)-piperazine and (1H-imidazol-4-yl)-acetic acid to afford the title compound as colorless solid (46 mg, 26%). LC/MS (Method B) 2.77 min, [M+1]$^+$ 511.

Example 368

Preparation of Compound 456, (S)-1-(2-benzyl-4-(1-cyclopentyl-3-ethyl-1H-indazol-6-yl)piperazin-1-yl)-2-(1H-imidazol-4-yl)ethanone

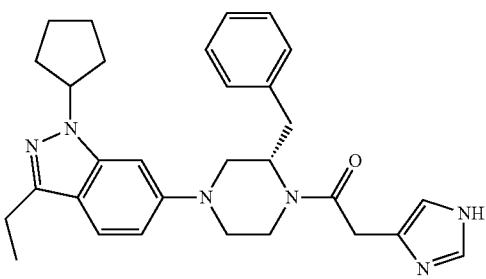 [SMILES: CCc1nn(C2CCCC2)c2cc(N3CCN(C(=O)Cc4c[nH]cn4)[C@@H](Cc4ccccc4)C3)ccc12]

Prepared using the same procedure described in Example 189 from (S)-6-(3-Benzyl-piperazin-1-yl)-1-cyclopentyl-3-ethyl-1H-indazole and (1H-imidazol-4-yl)-acetic acid to afford the title compound as colorless solid (66 mg, 50%). LC/MS (Method B) 2.68 min, [M+1]$^+$ 497.

Example 369

Preparation of Compound 457, (S)-1-(2-benzyl-4-(3-(cyclopropylmethoxy)-4-(difluoromethoxy)phenyl)piperazin-1-yl)-2-(1H-imidazol-5-yl)ethanone

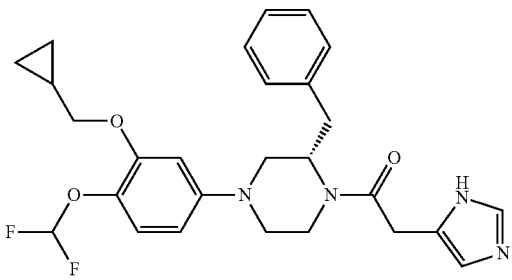 [SMILES: O=C(Cc1cnc[nH]1)N1CCN(c2ccc(OC(F)F)c(OCC3CC3)c2)C[C@@H]1Cc1ccccc1]

Prepared using the same procedure described in Example 189 from (S)-3-benzyl-1-(3-cyclopropylmethoxy-4-difluoromethoxy-phenyl)-piperazine and (1H-imidazol-4-yl)-acetic acid to afford the title compound as colorless solid (62 mg, 35%). LC/MS (Method B) 2.80 min, [M+1]+ 497.

Example 370

Preparation of Compound 458, (S)-1-(2-benzyl-4-(3,4-bis(difluoromethoxy)phenyl)piperazin-1-yl)-2-(1H-imidazol-5-yl)ethanone

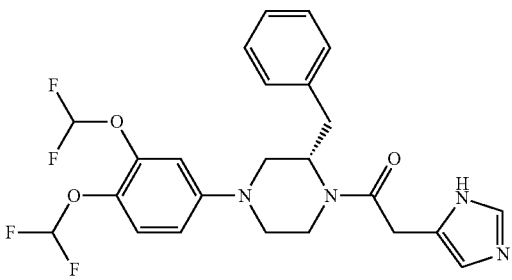 [SMILES: O=C(Cc1cnc[nH]1)N1CCN(c2ccc(OC(F)F)c(OC(F)F)c2)C[C@@H]1Cc1ccccc1]

Prepared using the same procedure described in Example 189 from (S)-3-benzyl-1-(3,4-bis-difluoromethoxy-phenyl)-piperazine and (1H-imidazol-4-yl)-acetic acid to afford the title compound as colorless solid (55 mg, 45%). LC/MS (Method B) 2.72 min, [M+1]+ 493.

Example 371

Preparation of Compound 459, 1-((S)-2-benzyl-4-(4-methoxy-3-((S)-1-methylpyrrolidin-3-yloxy)phenyl)piperazin-1-yl)-2-(5-methyl-1H-1,2,4-triazol-3-yl)ethanone

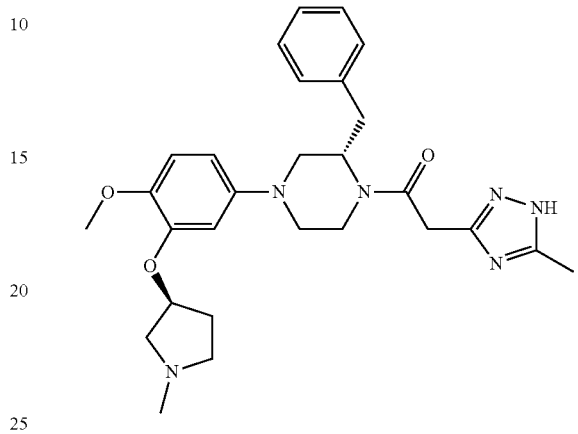

Prepared using the same procedure described in Example 189 from (S)-3-benzyl-1-[4-methoxy-3-(1-methyl-pyrrolidin-(S)-3-yloxy)-phenyl]-piperazine and (5-methyl-1H-[1,2,4]triazol-3-yl)-acetic acid to afford the title compound as white solid (58 mg, 51%). LC/MS (Method B) 2.04 min, [M+1]+ 505.

Example 372

Preparation of Compound 460, (S)-2-(5-amino-M-1,2,4-triazol-3-yl)-1-(2-benzyl-4-(3-(cyclopentyloxy)-4-methoxyphenyl)piperazin-1-yl)ethanone

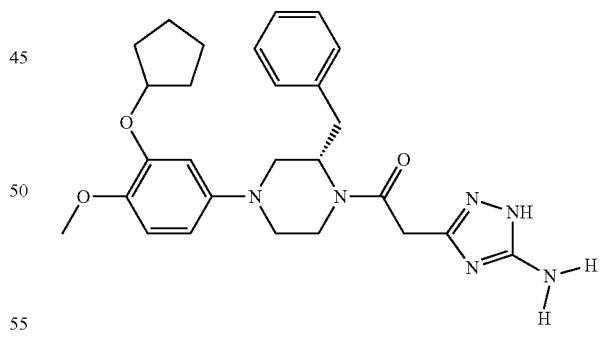

Prepared using the same procedure described in Example 189 from (S)-3-benzyl-1-(3-cyclopentyloxy-4-methoxyphenyl)-piperazine and (5-nitro-1H-[1,2,4]triazol-3-yl)-acetic acid to afford (S)-1-[2-Benzyl-4-(3-cyclopentyloxy-4-methoxy-phenyl)-piperazin-1-yl]-2-(5-nitro-1H-[1,2,4]triazol-3-yl)-ethanone as white solid (58 mg). The resulting nitrotriazole was reduced with 10% Pd/C under 1 atm of hydrogen in MeOH to afford the title compound as an off-white solid (15 mg, 39% overall). LC/MS (Method B) 2.20 min, [M+1]+ 491.

Example 373

Preparation of Compound 461, (S)-1-(2-benzyl-4-(4-methoxy-3-(1-methylpiperidin-4-yloxy)phenyl)piperazin-1-yl)-2-(5-methyl-4H-1,2,4-triazol-3-yl)ethanone

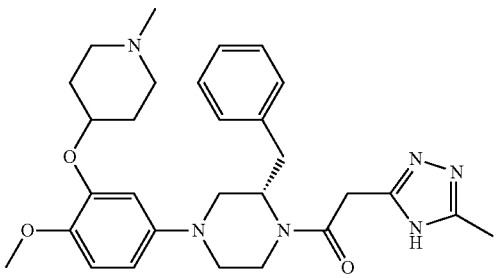

Prepared using the same procedure described in Example 189 from (S)-3-benzyl-1-[4-methoxy-3-(1-methyl-piperidin-4-yloxy)-phenyl]-piperazine dihydrochloride and (5-methyl-1H-[1,2,4]triazol-3-yl)-acetic acid to afford the title compound as colorless solid (20 mg, 17%). LC/MS (Method B) 2.10 min, [M+1]$^+$ 519.

Example 374

Preparation of Compound 462, (S)-1-(2-benzyl-4-(3-cyclopropoxy-4-methoxyphenyl)piperazin-1-yl)-2-(3-methyl-1H-1,2,4-triazol-5-yl)ethanone

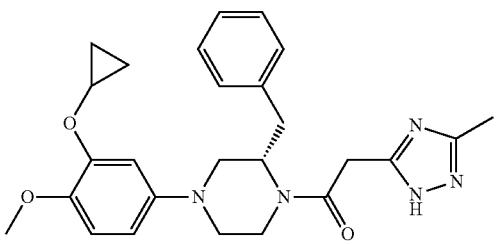

Prepared using the same procedure described in Example 189 from (S)-3-benzyl-1-(3-cyclopropoxy-4-methoxy-phenyl)-piperazine and (5-methyl-1H-[1,2,4]triazol-3-yl)-acetic acid to afford the title compound as colorless solid (53 mg, 40%). LC/MS (Method B) 3.02 min, [M+1]$^+$ 462.

Example 375

Preparation of Compound 463, (S)-1-(2-benzyl-4-(1-cyclobutyl-3-isopropyl-1H-indazol-6-yl)piperazin-1-yl)-2-(5-methyl-4H-1,2,4-triazol-3-yl)ethanone

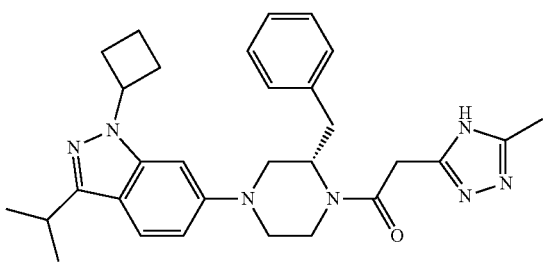 [SMILES: Cc1nnc(CC(=O)N2CCN(c3ccc4c(C(C)C)nn(C5CCC5)c4c3)C[C@@H]2Cc2ccccc2)[nH]1]

Prepared using the same procedure described in Example 189 from 6-((S)-3-benzyl-piperazin-1-yl)-1-cyclobutyl-3-isopropyl-1H-indazole and (5-methyl-1H-[1,2,4]triazol-3-yl)-acetic acid to afford the title compound as colorless solid (35 mg, 25%). LC/MS (Method B) 3.62 min, [M+1]$^+$ 512.

Example 376

Preparation of Compound 464, (S)-1-(2-benzyl-4-(3-cyclobutyl-1-ethyl-1H-indazol-5-yl)piperazin-1-yl)-2-(3-methyl-1H-1,2,4-triazol-5-yl)ethanone

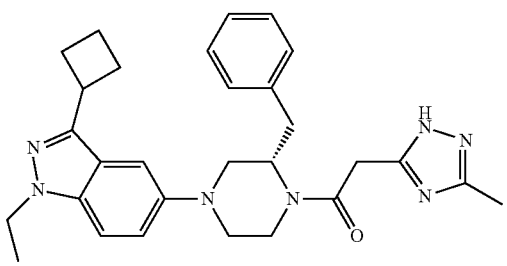 [SMILES: CCn1nc(C2CCC2)c2cc(N3CCN(C(=O)Cc4nc(C)n[nH]4)[C@@H](Cc4ccccc4)C3)ccc21]

Prepared using the same procedure described in Example 189 from 5-((S)-3-benzyl-piperazin-1-yl)-3-cyclobutyl-1-ethyl-1H-indazole and (5-methyl-1H-[1,2,4]triazol-3-yl)-acetic acid to afford the title compound as colorless solid (61 mg, 37%). LC/MS (Method B) 3.32 min, [M+1]$^+$ 498.

Example 377

Preparation of Compound 465, (S)-1-(2-benzyl-4-(8-methoxy-2-(trifluoromethyl)quinolin-5-yl)piperazin-1-yl)-2-(3-methyl-1H-1,2,4-triazol-5-yl)ethanone

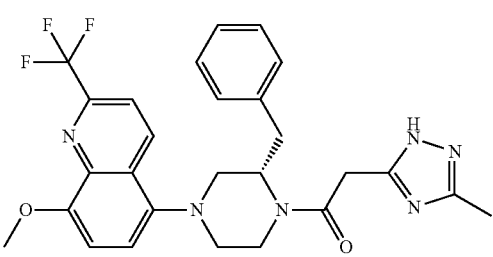

Prepared using the same procedure described in Example 189 from 5-((S)-3-benzyl-piperazin-1-yl)-8-methoxy-2-trifluoromethyl-quinoline and (5-methyl-1H-[1,2,4]triazol-3-yl)-acetic acid to afford the title compound as colorless solid (17 mg, 12%). LC/MS (Method B) 3.22 min, [M+1]$^+$ 525.

Example 378

Preparation of Compound 466, (S)-1-(2-benzyl-4-(3-cyclobutoxy-4-methoxyphenyl)piperazin-1-yl)-2-(2-methyl-1H-imidazol-5-yl)ethanone

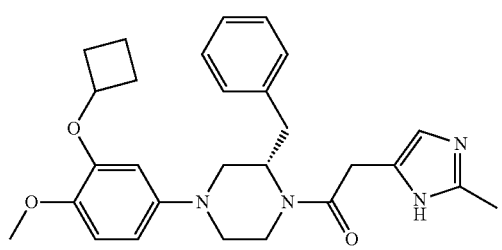

Prepared using the same procedure described in Example 189 from (S)-3-benzyl-1-(3-cyclobutoxy-4-methoxy-phenyl)-piperazine and (2-methyl-1-trityl-1H-imidazol-4-yl)-acetic acid [CAS 168632-03-9] to afford the N-trityl-protected intermediate, which was treated as described in Example 151 with TFA in the presence of triethylsilane to afford the title compound as colorless solid (146 mg, 49% overall). LC/MS (Method B) 2.79 min, [M+1]$^+$ 475.

Example 379

Preparation of Compound 467, (S)-2-benzyl-4-(3-(cyclopentyloxy)-4-methoxyphenyl)piperazine-1-sulfonamide

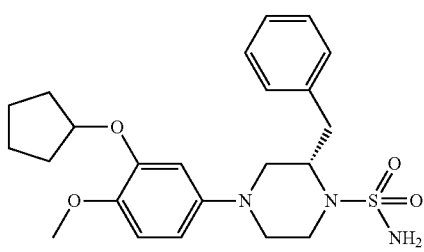 [SMILES: COc1ccc(N2CCN(S(N)(=O)=O)[C@@H](Cc3ccccc3)C2)cc1OC1CCCC1]

Into a 25 mL round bottomed flask were added (S)-3-benzyl-1-(3-cyclopentyloxy-4-methoxy-phenyl)-piperazine (188 mg, 0.513 mmol), sulfamide (103 mg, 1.07 mmol) and 1,4-dioxane (3 mL). The reaction mixture was refluxed under nitrogen for 3.5 h then cooled to room temperature and adsorbed onto silica gel. Purification by silica gel flash chromatography with a 0-100% EtOAc/Hexanes gradient to afford product as tan solid (165 mg, 72%). LC/MS (Method B) 3.90 min, [M+1]$^+$ 446.

Example 380

Preparation of Compound 468, (S)-2-benzyl-4-(3-cyclobutoxy-4-methoxyphenyl)piperazine-1-sulfonamide

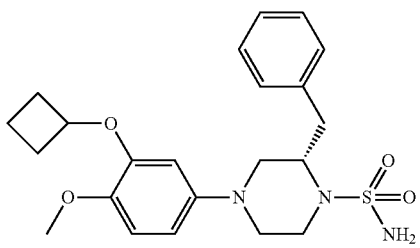 [SMILES: COc1ccc(N2CCN(S(N)(=O)=O)[C@@H](Cc3ccccc3)C2)cc1OC1CCC1]

Prepared using the same procedure described in Example 379 from (S)-3-benzyl-1-(3-cyclobutyloxy-4-methoxy-phenyl)-piperazine to afford the title compound as an off-white solid (201 mg, 72%). LC/MS (Method B) 3.67 min, [M+1]$^+$ 432.

Example 381

Preparation of Compound 469, (S)-2-benzyl-4-(8-methoxy-2-(trifluoromethyl)quinolin-5-yl)piperazine-1-sulfonamide

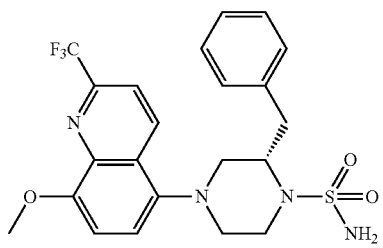 [SMILES: COc1ccc(N2CCN(S(N)(=O)=O)[C@@H](Cc3ccccc3)C2)c2ccc(C(F)(F)F)nc12]

Prepared using the same procedure described in Example 379 from (S)-5-(3-benzyl-piperazin-1-yl)-8-methoxy-2-trifluoromethyl-quinoline to afford the title compound as yellow solid (180 mg, 75%). LC/MS (Method B) 3.77 min, [M+1]$^+$ 481.

Example 382

Preparation of Compound 470, (S)-2-benzyl-4-(3-(cyclopentyloxy)-4-methoxyphenyl)piperazine-1-carboxamide

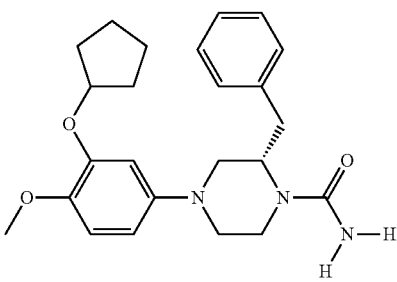 [SMILES: COc1ccc(N2CCN(C(N)=O)[C@@H](Cc3ccccc3)C2)cc1OC1CCCC1]

Prepared using the same procedure described in Example 303 from (S)-3-benzyl-1-(3-cyclopentyloxy-4-methoxyphenyl)-piperazine afford product as a colorless solid (125 mg, 68%). LC/MS (Method B) 3.54 min, [M+1]⁺ 410.

Example 383

Preparation of Compound 471, (S)-2-benzyl-4-(3-cyclobutoxy-4-methoxyphenyl)piperazine-1-carboxamide

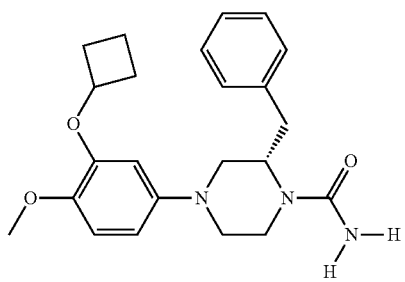 [SMILES: COc1ccc(N2CCN(C(N)=O)[C@@H](Cc3ccccc3)C2)cc1OC1CCC1]

Prepared using the same procedure described in Example 303 from (S)-3-benzyl-1-(3-cyclobutoxy-4-methoxy-phenyl)-piperazine to afford the title compound as an off-white solid (168 mg, 75%). LC/MS (Method B) 3.37 min, [M+1]⁺ 396.

Example 384

Preparation of Compound 472, (S)-2-benzyl-4-(3-cyclopropoxy-4-methoxyphenyl)piperazine-1-carboxamide

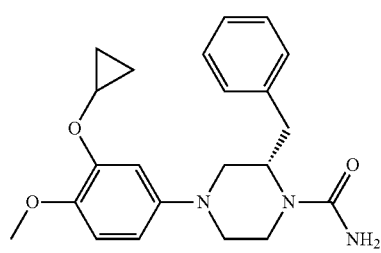 [SMILES: COc1ccc(N2CCN(C(N)=O)[C@@H](Cc3ccccc3)C2)cc1OC1CC1]

Prepared using the same procedure described in Example 303 from (S)-3-benzyl-1-(3-cycloproplyloxy-4-methoxyphenyl)-piperazine to afford the title compound as an off-white solid (63 mg, 47%). LC/MS (Method B) 3.29 min, [M+1]⁺ 382.

Example 385

Preparation of Compound 473, (S)-2-benzyl-4-(3-(1,3-difluoropropan-2-yloxy)-4-methoxyphenyl) piperazine-1-carboxamide

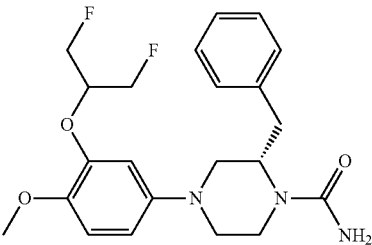 [SMILES: COc1ccc(N2CCN(C(N)=O)[C@@H](Cc3ccccc3)C2)cc1OC(CF)CF]

Prepared using the same procedure described in Example 303 from (S)-3-benzyl-1-[3-(2-fluoro-1-fluoromethyl-ethoxy)-4-methoxy-phenyl]-piperazine to afford the title compound as tan solid (69 mg, 29%). LC/MS (Method B) 3.22 min, [M+1]⁺ 420.

Example 386

Preparation of Compound 474, (S)-2-benzyl-4-(3-cyclobutoxy-4-(difluoromethoxy)phenyl)piperazine-1-carboxamide

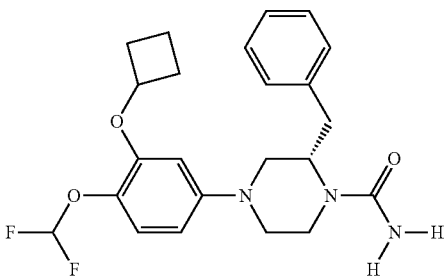 [SMILES: NC(=O)N1CCN(c2ccc(OC(F)F)c(OC3CCC3)c2)C[C@@H]1Cc1ccccc1]

Prepared using the same procedure described in Example 303 from (S)-3-benzyl-1-(3-cyclobutoxy-4-difluoromethoxy-phenyl)-piperazine to afford the title compound as an off-white solid (130 mg, 64%). LC/MS (Method B) 3.85 min, [M+1]⁺ 432.

Example 387

Preparation of Compound 475, (S)-2-benzyl-4-(3-isopropoxy-4-methoxyphenyl)piperazine-1-carboxamide

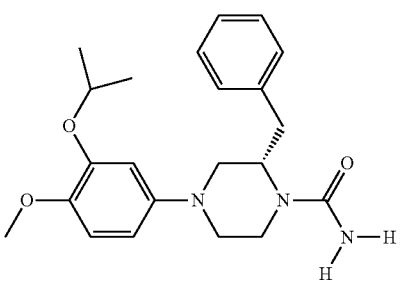 [SMILES: COc1ccc(N2CCN(C(N)=O)[C@@H](Cc3ccccc3)C2)cc1OC(C)C]

Prepared using the same procedure described in Example 303 from (S)-3-benzyl-1-(3-isopropoxy-4-methoxy-phenyl)-piperazine to afford the title compound as an off-white solid (135 mg, 57%). LC/MS (Method B) 3.24 min, [M+1]+ 384.

Example 388

Preparation of Compound 476, (S)-2-benzyl-4-(8-methoxy-2-(trifluoromethyl)quinolin-5-yl)piperazine-1-carboxamide

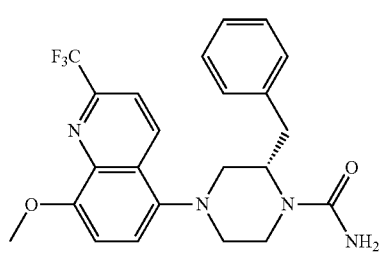 [SMILES: COc1ccc(N2CCN(C(N)=O)[C@@H](Cc3ccccc3)C2)c2ccc(C(F)(F)F)nc12]

Prepared using the same procedure described in Example 303 from (S)-5-(3-benzyl-piperazin-1-yl)-8-methoxy-2-trifluoromethyl-quinoline to afford the title compound as a yellow solid (33 mg, 20%). LC/MS (Method B) 3.45 min, [M+1]+ 445.

Example 389

Preparation of Compound 477, (S)-2-benzyl-4-(3-cyclobutoxy-4-methoxyphenyl)-N-methylpiperazine-1-carboxamide

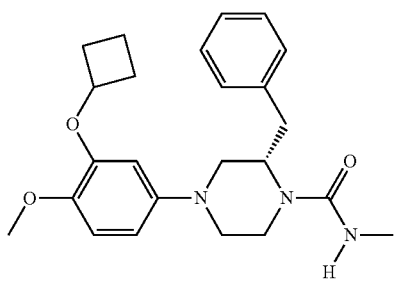

Prepared using the same procedure described in Example 88 from (S)-3-benzyl-1-(3-cyclobutoxy-4-methoxy-phenyl)-piperazine to afford the title compound as a yellow solid (72 mg, 43%). LC/MS (Method B) 3.50 min, [M+1]+ 410.

Example 390

Preparation of Compound 478, (S)-2-(2-benzyl-4-(3-(cyclopentyloxy)-4-(difluoromethoxy)phenyl)piperazin-1-yl)acetic acid

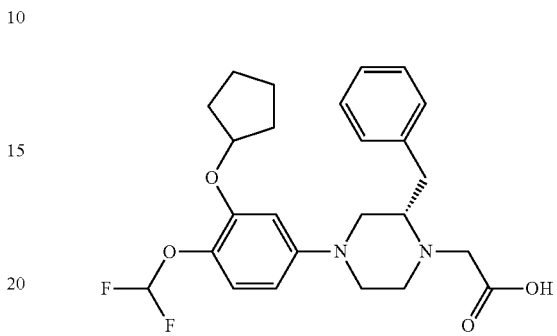

Prepared using the same procedure described in Examples 96/98 from (S)-3-benzyl-1-(3-cyclopentyloxy-4-difluoromethoxy-phenyl)-piperazine and methyl bromoacetate to afford the intermediate methyl ester [LC/MS (Method B) 3.62 min, [M+1]+ 475.1]. Hydrolysis with a 1M KOH in MeOH afforded the title compound as a tan powder (115 mg, 73% overall). LC/MS (Method B) 3.13 min, [M+1]+ 461.

Example 391

Preparation of Compound 479, (S)-2-(2-benzyl-4-(3,4-bis(difluoromethoxy)phenyl)piperazin-1-yl)acetic acid

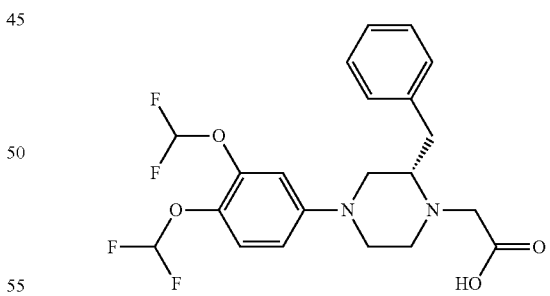

Prepared using the same procedure described in Example 96/98 from (S)-3-benzyl-1-(3,4-bis-difluoromethoxy-phenyl)-piperazine hydrochloride and methyl bromoacetate to afford the intermediate methyl ester [LC/MS (Method B) 3.40 min, [m/z=457]]. Hydrolysis with 1M KOH in MeOH afforded the title compound as a tan powder (121 mg, 75% overall). LC/MS (Method B) 2.95 min, [M+1]+ 443.

Example 392

Preparation of Compound 480, (S)-2-(2-benzyl-4-(3-(cyclopropylmethoxy)-4-(difluoromethoxy)phenyl)piperazin-1-yl)acetic acid

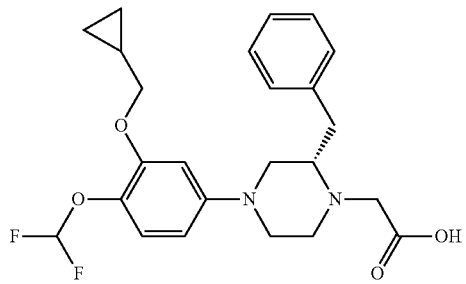 [SMILES: O=C(O)CN1CCN(c2ccc(OC(F)F)c(OCC3CC3)c2)C[C@@H]1Cc1ccccc1]

Prepared using the same procedure described in Example 96/98 from (S)-3-Benzyl-1-(3-cyclopropylmethoxy-4-difluoromethoxy-phenyl)-piperazine hydrochloride (and methyl bromoacetate to afford the intermediate methyl ester [LC/MS (Method B) 3.49 min, [M+1]$^+$461]]. Hydrolysis with 1M KOH in MeOH afforded the title compound as a tan powder (98 mg, 62% overall). LC/MS (Method B) 3.20 min, [M+1]$^+$ 447.

Example 393

Preparation of Compound 481, (S)-2-(2-benzyl-4-(8-methoxy-2-methylquinolin-5-yl)piperazin-1-yl)acetic acid

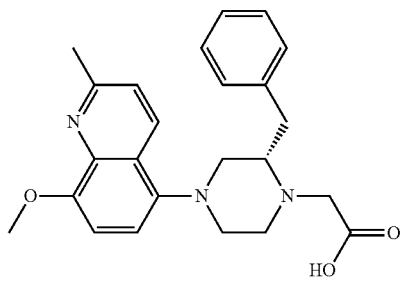 [SMILES: COc1ccc(N2CCN(CC(=O)O)[C@@H](Cc3ccccc3)C2)c2ccc(C)nc12]

Prepared using the same procedure described in Example 96/98 from 5-((S)-3-benzyl-piperazin-1-yl)-8-methoxy-2-methyl-quinoline and methyl bromoacetate to afford the intermediate methyl ester [LC/MS (Method B) 1.84 min, [m/z=420.0]]. Hydrolysis of the intermediate ester (118 mg, 0.28 mmol) with 1M KOH in MeOH afforded the title compound as a yellow powder (82 mg, 72% overall). LC/MS (Method B) 1.68 min, [M+1]$^+$ 406.

Example 394

Preparation of Compound 482, (S)-2-(2-benzyl-4-(8-methoxy-2-(trifluoromethyl)quinolin-5-yl)piperazin-1-yl)acetic acid

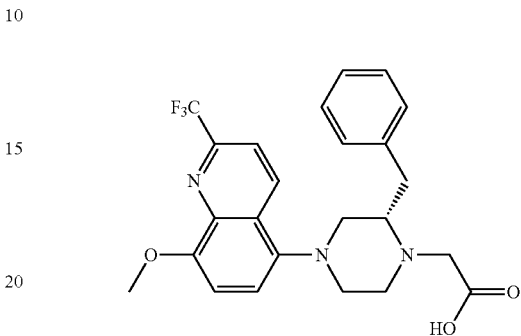

Prepared using the same procedure described in Example 96/98 from 5-((S)-3-benzyl-piperazin-1-yl)-8-methoxy-2-trifluoromethyl-quinoline and methyl bromoacetate to afford the intermediate methyl ester [LC/MS (Method B) 3.05 min, [M+1]$^+$ 474]]. Hydrolysis of the intermediate ester (1.29 g, 2.72 mmol) with 1M KOH in MeOH afforded the title compound as a yellow powder (1.20 g, 96%). LC/MS (Method B) 1.68 min, [M+1]$^+$ 474.

Example 395

Preparation of Compound 483, (S)-2-(2-benzyl-4-(8-methoxy-2-methylquinolin-5-yl)piperazin-1-yl) acetic acid

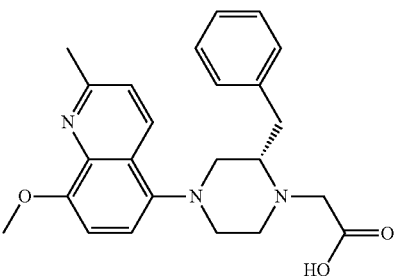 [SMILES: COc1ccc(N2CCN(CC(=O)O)[C@@H](Cc3ccccc3)C2)c2ccc(C)nc12]

Prepared using the same procedure described in Example 96/98 from 5-((S)-3-benzyl-piperazin-1-yl)-8-methoxy-2-methyl-quinoline and methyl bromoacetate to afford the intermediate methyl ester {LC/MS (Method B) 1.84 min, [M+1]$^+$ 420.0]} (235 mg, 94%). Treatment of the intermediate ester (118 mg, 0.28 mmol) with 1N KOH in MeOH afforded the title compound as an off-white solid (82 mg, 72%). LC/MS (Method B) 1.68 min, [M+1]$^+$ 406.

Example 396

Preparation of Compound 484, (S)-2-(2-benzyl-4-(8-methoxy-2-methylquinolin-5-yl)piperazin-1-yl)acetamide

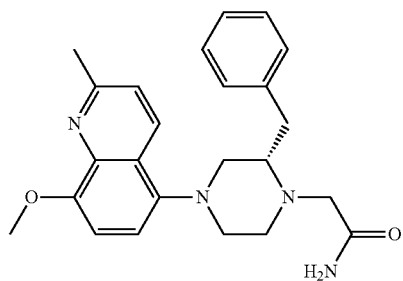 [SMILES: COc1ccc(N2CCN(CC(N)=O)[C@@H](Cc3ccccc3)C2)c2ccc(C)nc12]

Prepared using the same procedure described in Example 96/129 from 5-((S)-3-benzyl-piperazin-1-yl)-8-methoxy-2-methyl-quinoline and methyl bromoacetate to afford the intermediate methyl ester {LC/MS (Method B) 1.84 min, [M+1]$^+$ 420.0]} (235 mg, 94%). Treatment of the intermediate ester (118 mg, 0.28 mmol) with 7N methanolic ammonia (8 mL) with catalytic NaCN afforded the title compound as a yellow solid (74 mg, 65%). LC/MS (Method B) 1.67 min, [M+1]$^+$ 405.

Example 397

Preparation of Compound 485, (S)-2-(2-benzyl-4-(3-cyclopropoxy-4-methoxyphenyl)piperazin-1-yl)acetamide

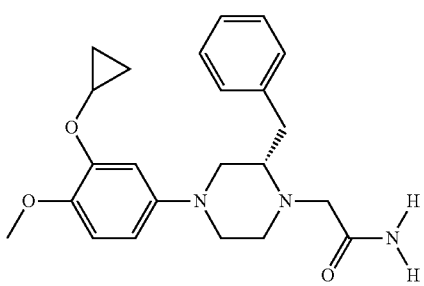 [SMILES: COc1ccc(N2CCN(CC(N)=O)[C@@H](Cc3ccccc3)C2)cc1OC1CC1]

Prepared using the same procedure described in Example 96/129 from (S)-3-benzyl-1-(3-cyclopropoxy-4-methoxyphenyl)-piperazine and methyl bromoacetate to afford the intermediate methyl ester, which was treated with 7N methanolic ammonia (3 mL) with catalytic NaCN afforded the title compound as a pink solid (19 mg, 16% overall). LC/MS (Method B) 2.40 min, [M+1]$^+$ 396.

Example 398

Preparation of Compound 486, (S)-2-(2-benzyl-4-(3-(cyclopentyloxy)-4-(difluoromethoxy)phenyl)piperazin-1-yl)acetamide

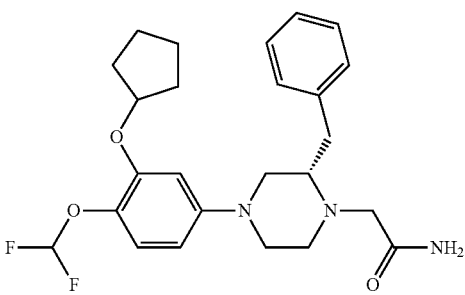 [SMILES: NC(=O)CN1CCN(c2ccc(OC(F)F)c(OC3CCCC3)c2)C[C@@H]1Cc1ccccc1]

Prepared using the same procedure described in Example 96/129 from (S)-3-benzyl-1-(3-cyclopentyloxy-4-difluoromethoxy-phenyl)-piperazine hydrochloride and methyl bromoacetate to afford the intermediate methyl ester, which was treated with 7N methanolic ammonia (3 mL) with catalytic NaCN afforded the title compound as a yellow solid (40 mg, 48% overall). LC/MS (Method B) 3.32 min, [M+1]$^+$ 460.

Example 399

Preparation of Compound 487, (S)-2-(2-benzyl-4-(3,4-bis(difluoromethoxy)phenyl)piperazin-1-yl)acetamide

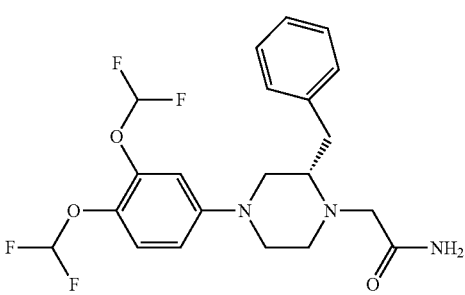 [SMILES: NC(=O)CN1CCN(c2ccc(OC(F)F)c(OC(F)F)c2)C[C@@H]1Cc1ccccc1]

Prepared using the same procedure described in Example 96/129 from (S)-3-benzyl-1-(3,4-bis-difluoromethoxy-phenyl)-piperazine hydrochloride and methyl bromoacetate to afford the intermediate methyl ester, which was treated with 7N methanolic ammonia (3 mL) with catalytic NaCN afforded the title compound as a yellow viscous oil (54 mg, 44% overall). LC/MS (Method B) 2.85 min, [M+1]$^+$ 442.

Example 400

Preparation of Compound 488, (S)-2-(2-benzyl-4-(3-(cyclopropylmethoxy)-4-(difluoromethoxy)phenyl)piperazin-1-yl)acetamide

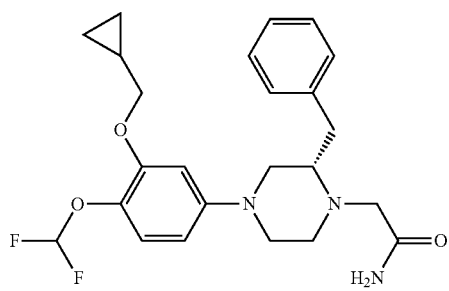 [SMILES: NC(=O)CN1CCN(c2ccc(OC(F)F)c(OCC3CC3)c2)C[C@@H]1Cc1ccccc1]

Prepared using the same procedure described in Example 96/129 from (S)-3-benzyl-1-(3-cyclopropylmethoxy-4-difluoromethoxy-phenyl)-piperazine hydrochloride and methyl bromoacetate to afford the intermediate methyl ester, which was treated with 7N methanolic ammonia (3 mL) with catalytic NaCN afforded the title compound as a yellow viscous oil (44 mg, 23% overall). LC/MS (Method B) 2.90 min, [M+1]$^+$ 446.

Example 401

Preparation of Compound 489, (S)-2-(2-benzyl-4-(8-methoxy-2-(trifluoromethyl)quinolin-5-yl)piperazin-1-yl)acetamide

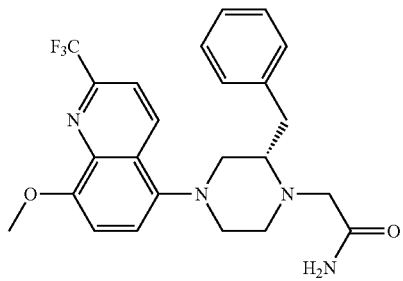

Prepared using the same procedure described in Example 96/129 from 5-((S)-3-benzyl-piperazin-1-yl)-8-methoxy-2-trifluoromethyl-quinoline and methyl bromoacetate to afford the intermediate methyl ester in quantitative yield {LC/MS (Method B) 3.04 min, [M+1]$^+$ 473.9]}. Treatment of the intermediate ester (235 mg, 0.49 mmol) with methanolic ammonia (3 mL, 7N) and catalytic NaCN afforded the title compound as a yellow solid (180 mg, 79%). LC/MS (Method B) 2.57 min, [M+1]$^+$ 459.

Example 402

Preparation of Compound 490, (S)-2-(2-benzyl-4-(8-methoxy-2-(trifluoromethyl)quinolin-5-yl)piperazin-1-yl)-N-methylacetamide

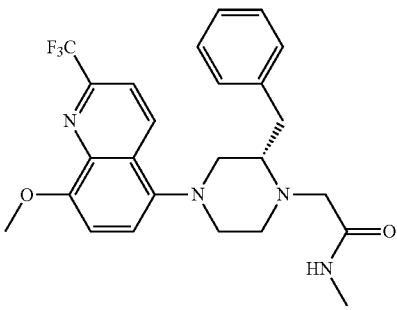 [SMILES: CNC(=O)CN1CCN(c2ccc(OC)c3nc(C(F)(F)F)ccc23)C[C@@H]1Cc1ccccc1]

Prepared using the same procedure described in Example 96/130 from 5-((S)-3-benzyl-piperazin-1-yl)-8-methoxy-2-trifluoromethyl-quinoline and methyl bromoacetate to afford the intermediate methyl ester in quantitative yield {LC/MS (Method B) 3.04 min, [M+1]$^+$ 473.9]}. Treatment of the intermediate ester (108 mg, 0.23 mmol) with ethanolic methylamine (3 mL, 33% w/w solution) with catalytic NaCN afforded the title compound as a yellow solid (68 mg, 63%). LC/MS (Method B) 2.82 min, [M+1]$^+$ 473.

Example 403

Preparation of Compound 491, (S)-2-(2-benzyl-4-(8-methoxy-2-(trifluoromethyl)quinolin-5-yl)piperazin-1-yl)-1-morpholinoethanone

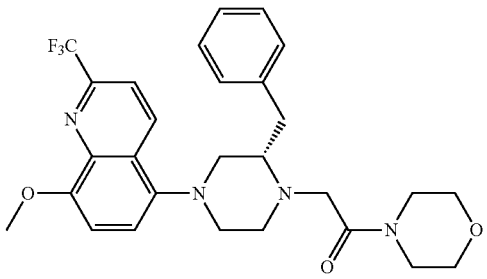 [SMILES: COc1ccc(N2CCN(CC(=O)N3CCOCC3)[C@@H](Cc3ccccc3)C2)c2ccc(C(F)(F)F)nc12]

Prepared using the same procedure described in Example 96/130 from 5-((S)-3-benzyl-piperazin-1-yl)-8-methoxy-2-trifluoromethyl-quinoline and methyl bromoacetate to afford the intermediate methyl ester in quantitative yield {LC/MS (Method B) 3.04 min, [M+1]$^+$ 473.9]}. Treatment of the intermediate ester (110 mg, 0.23 mmol) with morpholine (54 mg, 62 mmol) with catalytic NaCN in DMSO at 100 C afforded the title compound as a yellow solid (26 mg, 21%). LC/MS (Method B) 2.67 min, [M+1]$^+$ 529.

Example 404

Preparation of Compound 492, (S)-2-(2-benzyl-4-(8-methoxy-2-(trifluoromethyl)quinolin-5-yl)piperazin-1-yl)-N-ethylacetamide

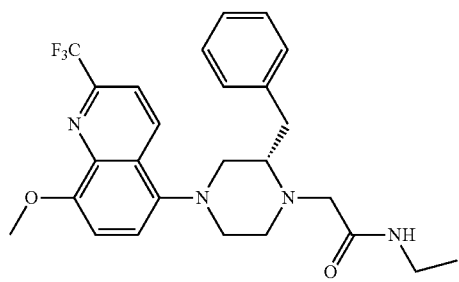 [SMILES: CCNC(=O)CN1CCN(c2ccc(OC)c3nc(C(F)(F)F)ccc23)C[C@@H]1Cc1ccccc1]

Prepared using the same procedure described in Example 96/130 from 5-((S)-3-benzyl-piperazin-1-yl)-8-methoxy-2-trifluoromethyl-quinoline and methyl bromoacetate (to afford the intermediate methyl ester in quantitative yield {LC/MS (Method B) 3.04 min, [M+1]$^+$ 473.9]}. Treatment of the intermediate ester (133 mg, 0.28 mmol) with ethylamine (2 mL, 2 M in THF) and catalytic NaCN in DMSO at 60 C afforded the title compound as a yellow waxy solid (1.6 mg, 0.5%). LC/MS (Method B) 2.82 min, [M+1]$^+$ 487.

Example 405

Preparation of Compound 493, (S)-2-(2-benzyl-4-(3-(cyclopentyloxy)-4-methoxyphenyl)piperazin-1-yl)acetonitrile

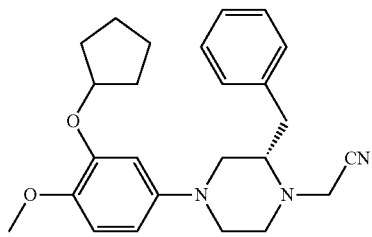 [SMILES: COc1ccc(N2CCN(CC#N)[C@@H](Cc3ccccc3)C2)cc1OC1CCCC1]

Into a 25 mL screw-cap vial were added 3-benzyl-1-(3-cyclopentyloxy-4-methoxy-phenyl)-piperazine (104 mg, 0.28 mmol), chloroacetonitrile (25 µL, 0.39 mmol), K$_2$CO$_3$ (88 mg, 0.64 mmol), and DMF (2 mL). The reaction mixture was heated at 60° C. for 8 h then cooled to room temperature. The reaction mixture was concentrated and adsorbed onto silica gel then purified by silica gel flash chromatography with a 0-10% MeOH/CH2Cl2 gradient to afford product as a light green solid (65 mg, 57%). LC/MS (Method B) 3.84 min, [M+1]$^+$ 406.

Example 406

Preparation of Compound 494, (S)-2-(2-benzyl-4-(8-methoxy-2-(trifluoromethyl)quinolin-5-yl)piperazin-1-yl)acetonitrile

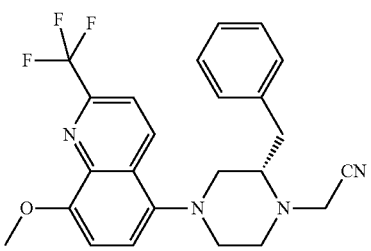 [SMILES: COc1ccc(N2CCN(CC#N)[C@@H](Cc3ccccc3)C2)c2ccc(C(F)(F)F)nc12]

Prepared using the same procedure described in Example 405 from 5-((S)-3-benzyl-piperazin-1-yl)-8-methoxy-2-trifluoromethyl-quinoline and chloroacetonitrile to afford the title compound as a yellow solid (26 mg, 21%). LC/MS (Method B) 4.10 min, [M+1]$^+$ 441.

Example 407

Preparation of Compound 495, (S)-3-(2-benzyl-4-(3-(cyclopentyloxy)-4-methoxyphenyl)piperazin-1-yl)propanenitrile

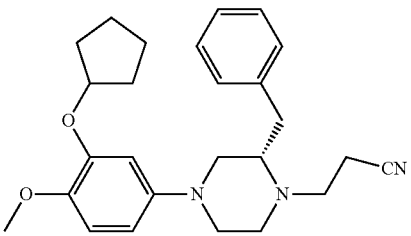 [SMILES: COc1ccc(N2CCN(CCC#N)[C@@H](Cc3ccccc3)C2)cc1OC1CCCC1]

Into a 25 mL screw-cap vial were added 3-benzyl-1-(3-cyclopentyloxy-4-methoxy-phenyl)-piperazine (206 mg, 0.562 mmol), acrylonitrile (55 µL, 0.83 mmol), triethylamine (500 µL), and MeOH (5 mL). The reaction mixture was heated at 60° C. for 4 h then cooled to room temperature. The reaction mixture was concentrated and adsorbed onto silica gel then purified by silica gel flash chromatography with a 0-10% MeOH/CH2Cl2 gradient to afford the title compound as a yellow waxy solid (181 mg, 77%). LC/MS (Method B) 2.77 min, [M+1]$^+$ 420.

Example 408

Preparation of Compound 496, (S)-3-(2-benzyl-4-(8-methoxy-2-(trifluoromethyl)quinolin-5-yl)piperazin-1-yl)propanamide

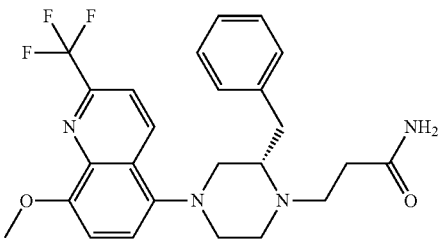 [SMILES: COc1ccc(N2CCN(CCC(N)=O)[C@@H](Cc3ccccc3)C2)c2ccc(C(F)(F)F)nc12]

Into a 5 mL microwave vial were added 5(S)-3-benzyl-piperazin-1-yl)-8-methoxy-2-trifluoromethyl-quinoline (210 mg, 0.524 mmol), ethyl acrylate (300 µL, 2.76 mmol), and toluene (3 mL). The reaction mixture was heated in a microwave with stirring at 200° C. for 2 h. The reaction mixture was concentrated and adsorbed onto silica gel then purified by silica gel flash chromatography with a 0-100% EtOAc/hexanes gradient to afford the intermediate ethyl ester as a brown oil {(192 mg, 73%). LC/MS (Method B) 2.95 min, [M+1]$^+$ 501.9]}. Treatment of the intermediate ester (107 mg, 0.21 mmol) with methanolic ammonia (3 mL, 7N) and catalytic NaCN afforded the title compound as a yellow solid (25 mg, 25%). LC/MS (Method B) 2.57 min, [M+1]$^+$ 459.

Example 409

Preparation of Compound 497, (S)-1-(2-benzyl-4-(8-methoxy-2-(trifluoromethyl)quinolin-5-yl)piperazin-1-yl)propan-2-one

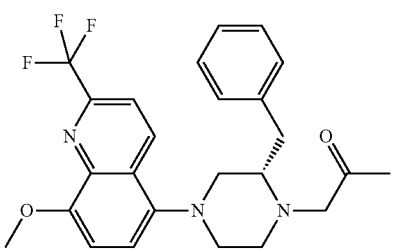 [SMILES: COc1ccc(N2CCN(CC(C)=O)[C@@H](Cc3ccccc3)C2)c2ccc(C(F)(F)F)nc12]

Prepared using the same procedure described in Example 405 from 5-((S)-3-benzyl-piperazin-1-yl)-8-methoxy-2-trifluoromethyl-quinoline (254 mg, 0.63 mmol) and chloroacetone (60 µL), to afford the title compound as yellow solid (288 mg, 98%). LC/MS (Method B) 2.67 min, [M+1]$^+$ 458.

Example 410

Preparation of Compound 498, (S)-2-(2-benzyl-4-(3-cyclobutoxy-4-methoxyphenyl)piperazin-1-yl)pyrimidine

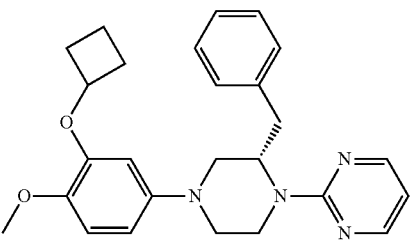 [SMILES: COc1ccc(N2CCN(c3ncccn3)[C@@H](Cc3ccccc3)C2)cc1OC1CCC1]

Into a 25 mL screw-cap vial were added 3-benzyl-1-(3-cyclobutyloxy-4-methoxy-phenyl)-piperazine (149 mg, 0.42 mmol), 2-chloropyrimidine (60 mg, 0.53 mmol), diisopropylethylamine (150 µL, 0.86 mmol), and DMSO (2 mL). The reaction mixture was heated at 100° C. for 12 h then cooled to room temperature. The reaction mixture was diluted with EtOAc and washed 3× with water followed by brine, concentrated, and adsorbed onto silica gel and purified by silica gel flash chromatography with a 0-50% EtOAc/Hexanes gradient to afford the title compound as a an off-white solid (43 mg, 23%). LC/MS (Method B) 4.62 min, [[M+1]$^+$ 431

Example 411

Preparation of Compound 499, (S)-6-(3-benzyl-4-(pyrazin-2-yl)piperazin-1-yl)-3-ethyl-1-isopropyl-1H-indazole

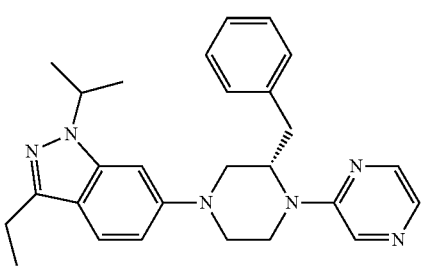 [SMILES: CCc1nn(C(C)C)c2cc(N3CCN(c4cnccn4)[C@@H](Cc4ccccc4)C3)ccc12]

Prepared using the same procedure described in Example 410 from 6-(3-benzyl-piperazin-1-yl)-3-ethyl-1-isopropyl-1H-indazole and chloropyrazine to afford the title compound as a yellow solid (7 mg, 12%). LC/MS (Method B) 4.47 min, [M+1]$^+$ 441.

Example 412

Preparation of Compound 500, (S)-6-(2-benzyl-4-(1-cyclobutyl-3-ethyl-1H-indazol-6-yl)piperazin-1-yl)pyridin-2-amine

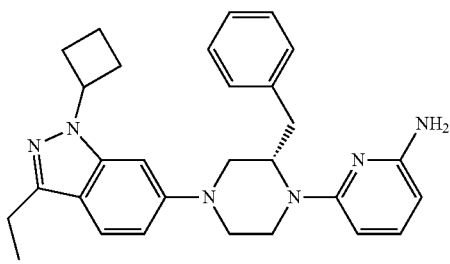 [SMILES: CCc1nn(C2CCC2)c2cc(N3CCN(c4cccc(N)n4)[C@@H](Cc4ccccc4)C3)ccc12]

Prepared using the same procedure described in Example 410 from 6-(3-benzyl-piperazin-1-yl)-1-cyclobutyl-3-ethyl-1H-indazole and 2-chloro-6-nitro-pyridine to afford the intermediate 6-[3-benzyl-4-(6-nitro-pyridin-2-yl)-piperazin-1-yl]-1-cyclobutyl-3-ethyl-1H-indazole {20.5 mg; LC/MS (Method B) 5.09 min, [M+1]$^+$ 497]}. The nitro-intermediate was reduced with sodium hydrosulfite (48 mg, 0.28 mmol) in 50:50 THF/water at room temperature to obtain the title compound as a tan solid (6 mg, 2% overall). LC/MS (Method B) 4.02 min, [M+1]$^+$ 467.

Example 413

Preparation of Compound 501, (S)-6-(3-benzyl-4-(pyridin-3-yl)piperazin-1-yl)-1-cyclobutyl-3-ethyl-1H-indazole

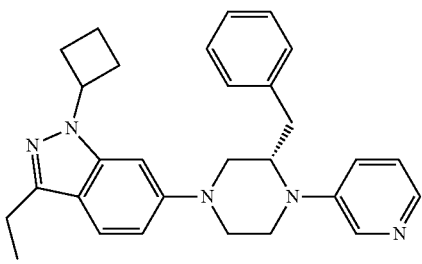 [SMILES: CCc1nn(C2CCC2)c2cc(N3CCN(c4cccnc4)[C@@H](Cc4ccccc4)C3)ccc12]

Into a 40 mL septum-cap vial were added sodium tert-butoxide (68 mg, 0.71 mmol), 2-dicyclohexylphosphino-N'—(N,N-dimethylamino)biphenyl (28 mg, 0.07 mmol), and Pd$_2$(dba)$_3$ (0.03 mmol). The vial was sealed and evacuated/purged 5× with nitrogen. A solution of 6-((S)-3-benzyl-piperazin-1-yl)-1-cyclobutyl-3-ethyl-1H-indazole (185 mg, 0.49 mmol) and 3-bromopyridine (158 mg, 1.02 mmol) in 3 mL of toluene was added, and the reaction mixture was heated at 100° C. for 15 h. The reaction mixture was cooled, filtered, concentrated, and purified by silica gel flash chromatography with a 0-100% EtOAc/Hexanes gradient to afford the title compound as a tan solid (30 mg, 13%). LC/MS (Method B) 3.10 min, [M+1]$^+$ 452.

Example 414

Preparation of Compound 502, (S)-2-(2-benzyl-4-(1-cyclobutyl-3-ethyl-1H-indazol-6-yl)piperazin-1-yl)thiazole

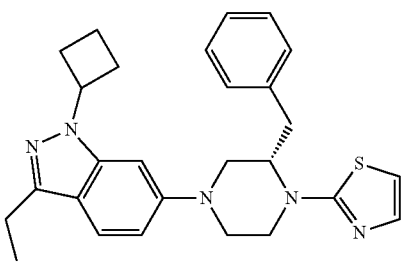 [SMILES: CCc1nn(C2CCC2)c2cc(N3CCN(c4nccs4)[C@@H](Cc4ccccc4)C3)ccc12]

Prepared using the same procedure described in Example 413 from 6-((S)-3-benzyl-piperazin-1-yl)-1-cyclobutyl-3-ethyl-1H-indazole and 2-chlorothiazole to afford the title compound as a colorless solid (152 mg, 64%). LC/MS (Method B) 4.60 min, [M+1]$^+$ 458.

Example 415

Preparation of Compound 503, (S)-5-(4((1H-imidazol-2-yl)methyl)-3-benzylpiperazin-1-yl)-8-methoxy-2-(trifluoromethyl)quinoline

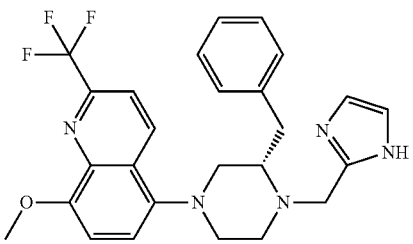 [SMILES: COc1ccc(N2CCN(Cc3ncc[nH]3)[C@@H](Cc3ccccc3)C2)c2ccc(C(F)(F)F)nc12]

Prepared using the same procedure described in Example 75 from 5-((S)-3-benzyl-piperazin-1-yl)-8-methoxy-2-trifluoromethyl-quinoline and 1H-imidazole-2-carbaldehyde to afford the title compound as a yellow solid (39 mg, 27%). LC/MS (Method B) 2.85 min, [M+1]$^+$ 482.

Example 416

Preparation of Compound 504, (S)-1-(2-benzyl-4-(3-(cyclopentyloxy)-4-methoxyphenyl)piperazin-1-yl)-2-(1-isopropyl-1H-imidazol-4-yl)ethanone

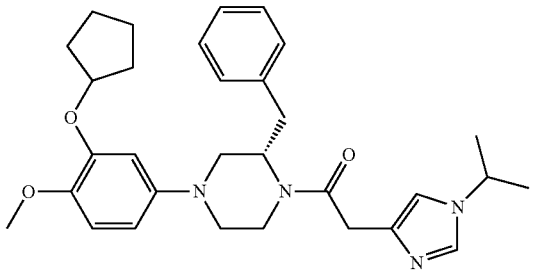 [SMILES: COc1ccc(N2CCN(C(=O)Cc3cn(C(C)C)cn3)[C@@H](Cc3ccccc3)C2)cc1OC1CCCC1]

Prepared using the same procedure described in Example 336 using 1-[(S)-2-benzyl-4-(3-cyclopentyloxy-4-methoxy-phenyl)-piperazin-1-yl]-2-(1H-imidazol-4-yl)-ethanone and 2-bromopropane to afford the title compound as an orange solid (67 mg, 20% overall). LC/MS (Method B) 2.88 min, [M+1]+ 517.

Example 417

Preparation of Compound 505, ((S)-2-benzyl-4-(3-(cyclopentyloxy)-4-methoxyphenyl)piperazin-1-yl)((S)-3-hydroxypyrrolidin-1-yl)methanone

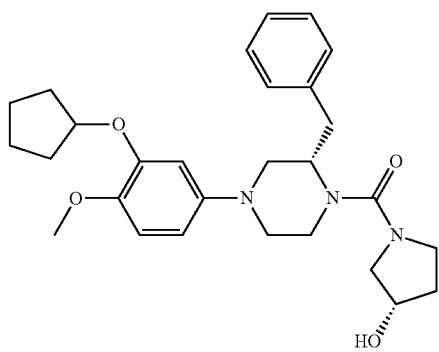 [SMILES: COc1ccc(N2CCN(C(=O)N3CC[C@H](O)C3)[C@@H](Cc3ccccc3)C2)cc1OC1CCCC1]

A solution of (S)-3-benzyl-1-(3-cyclopentyloxy-4-methoxy-phenyl)-piperazine (50 mg, 0.137 mmol) in CH₂Cl₂ (1 mL) at 0° C. was treated with triphosgene (25 mg, 0.084 mmol) followed by diisopropylethylamine (30 μL, 0.182 mmol). The reaction was allowed to warm to room temperature and stirred for 20 min then cooled to 0° C. and treated with an additional portion of diisopropylethylamine followed by pyrrolidin-3(S)-ol (30 μL, 0.37 mmol). The reaction mixture was allowed to warm to room temperature and stirred 16 h then quenched with MeOH, evaporated and purified by chromatography on silica gel using 5% MeOH/CH₂Cl₂ as eluant to afford the title compound as an oil (26 mg, 55%). LC/MS (Method B) 3.75 min, [M+1]+ 480.

Example 418

Preparation of Compound 506, ((S)-2-benzyl-4-(3-(cyclopentyloxy)-4-methoxyphenyl)piperazin-1-yl)((R)-3-hydroxypyrrolidin-1-yl)methanone

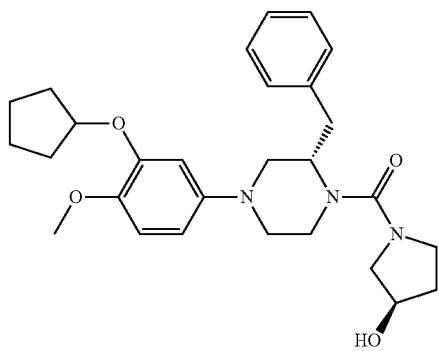 [SMILES: COc1ccc(N2CCN(C(=O)N3CC[C@@H](O)C3)[C@@H](Cc3ccccc3)C2)cc1OC1CCCC1]

Prepared by the method outlined for Example 417 utilizing pyrrolidin-3(R)-ol to afford the title compound as an oil (25 mg, 55%). LC/MS (Method B) 3.75 min, [M+1]+ 480.

Example 419

Preparation of Compound 507, (S)-2-benzyl-4-(3-(cyclopentyloxy)-4-methoxyphenyl)-N-(3-hydroxyphenyl)piperazine-1-carboxamide

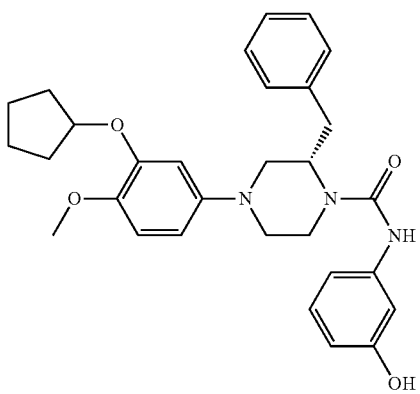 [SMILES: COc1ccc(N2CCN(C(=O)Nc3cccc(O)c3)[C@@H](Cc3ccccc3)C2)cc1OC1CCCC1]

Prepared by the method outlined for Example 417 with 3-amino-phenol to afford the title compound as an oil (55 mg, 55%). LC/MS (Method B) 2.67 min, [M+1]+ 502.

Example 420

Preparation of Compound 508, (S)-2-benzyl-4-(3-(cyclopentyloxy)-4-methoxyphenyl)-N-(3-(hydroxymethyl)phenyl)piperazine-1-carboxamide

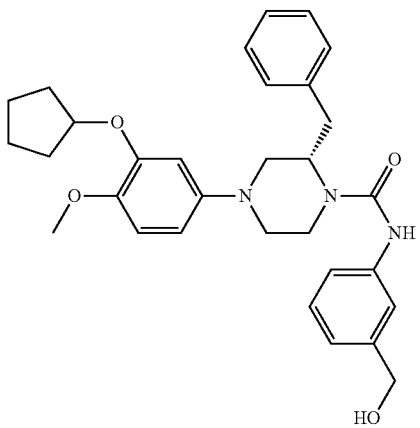 [SMILES: COc1ccc(N2CCN(C(=O)Nc3cccc(CO)c3)[C@@H](Cc3ccccc3)C2)cc1OC1CCCC1]

Prepared by the method outlined for Example 417 with (3-amino-phenyl)-methanol to afford the title compound as an oil (55 mg, 58%). LC/MS (Method B) 2.77 min, [M+1]+ 516.

Example 421

Preparation of Compound 509, methyl 1-((S)-2-benzyl-4-(3-(cyclopentyloxy)-4-methoxyphenyl)piperazine-1-carbonyl)pyrrolidine-3-carboxylate

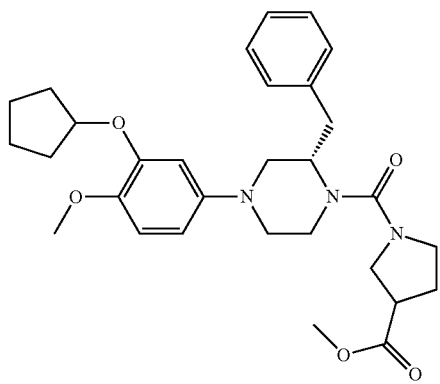 [SMILES: COC(=O)C1CCN(C(=O)N2CCN(c3ccc(OC)c(OC4CCCC4)c3)C[C@@H]2Cc2ccccc2)C1]

Prepared by the method outlined for Example 417 with pyrrolidine-3-carboxylic acid methyl ester to afford the title compound as an oil (32 mg, 40%). LC/MS (Method B) 2.47 min, [M+1]⁺ 522.

Example 422

Preparation of Compound 510, 14(S)-2-benzyl-4-(3-(cyclopentyloxy)-4-methoxyphenyl)piperazine-1-carbonyl)pyrrolidine-3-carboxylic acid

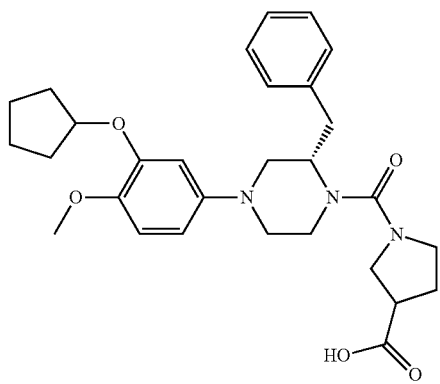 [SMILES: COc1ccc(N2CCN(C(=O)N3CCC(C(=O)O)C3)[C@@H](Cc3ccccc3)C2)cc1OC1CCCC1]

Prepared by the method outlined for Example 98 for hydrolysis of 142(S)-benzyl-4-(3-cyclopentyloxy-4-methoxy-phenyl)-piperazine-1-carbonyl]-pyrrolidine-3-carboxylic acid methyl ester (Example 421, Compound 509) to afford the title compound as an oil. LC/MS (Method B) 2.57 min, [M+1]⁺ 508.

Example 423

Preparation of Compound 511, ((S)-2-benzyl-4-(3-(cyclopentyloxy)-4-methoxyphenyl)piperazin-1-yl)(3-(hydroxymethyl)pyrrolidin-1-yl)methanone

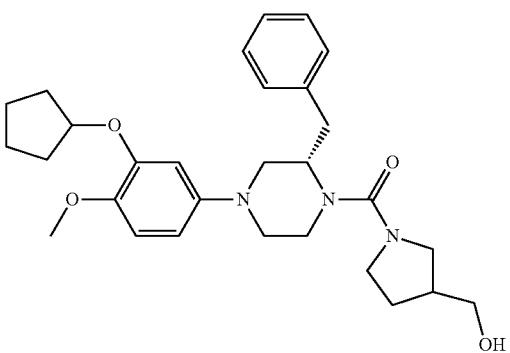 [SMILES: COc1ccc(N2CCN(C(=O)N3CCC(CO)C3)[C@@H](Cc3ccccc3)C2)cc1OC1CCCC1]

Prepared by the method outlined for Example 417 with pyrrolidin-3-yl-methanol to afford the title compound as an oil (20 mg, 45%). LC/MS (Method B) 2.55 min, [M+1]⁺ 494.

Example 424

Preparation of Compound 512, ((S)-2-benzyl-4-(3-(cyclopentyloxy)-4-methoxyphenyl)piperazin-1-yl)((S)-3-(hydroxymethyl)pyrrolidin-1-yl)methanone

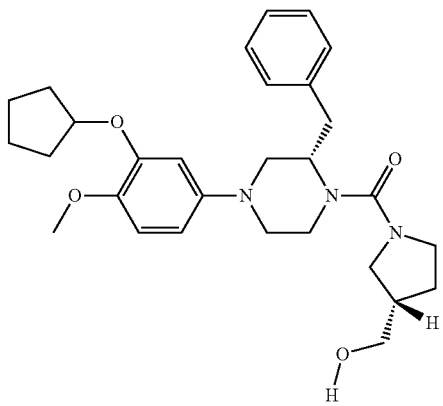 [SMILES: COc1ccc(N2CCN(C(=O)N3CC[C@H](CO)C3)[C@@H](Cc3ccccc3)C2)cc1OC1CCCC1]

Prepared by the method outlined for Example 417 with pyrrolidin-3(S)-yl-methanol to afford the title compound as an oil (20 mg, 45%). LC/MS (Method B) 2.45 min, [M+1]⁺ 494.

Example 425

Preparation of Compound 513, ((S)-2-benzyl-4-(3-(cyclopentyloxy)-4-methoxyphenyl)piperazin-1-yl)((R)-3-(hydroxymethyl)pyrrolidin-1-yl)methanone

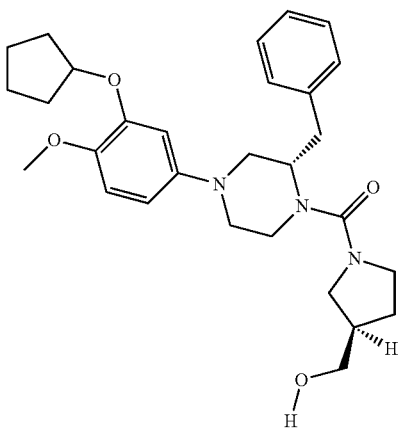 [SMILES: COc1ccc(N2CCN(C(=O)N3CC[C@@H](CO)C3)[C@@H](Cc3ccccc3)C2)cc1OC1CCCC1]

Prepared by the method outlined for Example 417 with pyrrolidin-3(R)-yl-methanol to afford the title compound as an oil (20 mg, 45%). LC/MS (Method B) 2.65 min, [M+1]$^+$ 494.

Example 426

Pharmaceutical Dosages

The following illustrate representative pharmaceutical dosage forms, containing a compound of formula I ('Compound X'), for therapeutic or prophylactic use in humans.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/ml |
| --- | --- |
| Dibasic sodium phosphate | 1 |
| Monobasic sodium phosphate | 12 |
| Sodium chloride | 0.7 |
| 1.0N Sodium hydroxide solution (pH adjustment to 7.0-7.5) | 4.5 q.s. |
| Water for injection | q.s. ad 1 mL |

| (v) Injection 2 (10 mg/ml) | mg/ml |
| --- | --- |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
| --- | --- |
| Compound X = | 20.0 |
| Oleic acid | 10.0 |
| Trichloromonofluoromethane | 5000.0 |
| Dichlorodifluoromethane | 10000.0 |
| Dichlorotetrafluoroethane | 5000.0 |

The above formulations may be obtained by conventional procedures well known in the pharmaceutical art.

All cited publications, patents, and patent documents are incorporated by reference herein, as though individually incorporated by reference. The invention has been described with reference to various specific embodiments and techniques. However, it should be understood that many variations and modifications may be made while remaining within the spirit and scope of the invention.

What is claimed is:
1. A method
of improving cognitive function in an animal comprising administering to the animal an effective amount of a compound of formula (I):

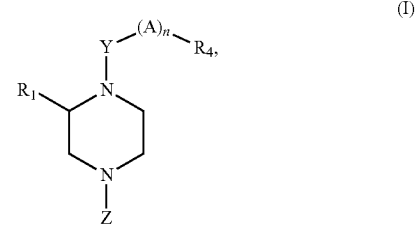

or a pharmaceutically acceptable salt thereof,
wherein:
$R_1$ is $(C_1-C_6)$alkyl or aryl$(C_1-C_6)$alkyl;
Y is —(C=O);
n is an integer from 0 to 6 inclusive;
A is —$(CR_cR_d)$—;
$R_4$ is aryl or heteroaryl;
Z is a phenyl ring substituted with one or more substituents independently selected from the group consisting of halogen, $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkoxy, $(C_3-C_8)$cycloalkoxy, $(C_3-$ $C_8$)cycloalkyl($C_1$-$C_6$)alkoxy, piperidinyloxy, piperidinyloxy($C_1$-$C_6$)alkyl, and cyano; and each $R_c$ and $R_d$ is independently H (hydrogen), OH, NH$_2$, or ($C_1$-$C_6$)alkyl, or optionally $R_c$ and $R_d$ taken together with the carbon to which they are attached is a 3 to 5 member ring consisting of C (carbon) atoms and optionally one or more O (oxygen) atoms and/or N(X) group, wherein X is absent, H (hydrogen), O (oxygen), OH, ($C_1$-$C_4$)alkyl, phenyl or benzyl, wherein any aryl, or heteroaryl of $R_1$ or $R_4$ is optionally substituted with one or more substituents independently selected from the group consisting of ($C_1$-$C_6$) alkyl, hydroxy, hydroxy($C_1$-$C_6$)alkyl, halo($C_1$-$C_6$) alkyl, phenyl, ($C_1$-$C_6$)alkoxy, ($C_1$-$C_6$)alkanoyl, ($C_1$-$C_6$) alkoxycarbonyl, ($C_1$-$C_6$)alkanoyloxy, ($C_3$-$C_8$) cycloalkyl, ($C_3$-$C_8$)cycloalkyl($C_1$-$C_6$)alkoxy, halo($C_1$-$C_6$)alkoxy, cyano, nitro, halo, ($C_1$-$C_6$)carboxy, and NR$_c$R$_d$; and wherein the piperazine core ring of formula (I) is optionally substituted at one or more carbon atoms with one or more substituents independently selected from the group consisting of oxo, halogen, ($C_1$-$C_6$)alkyl, and ($C_1$-$C_6$)alkoxy.

2. A method
of promoting neuronal plasticity in an animal comprising administering to the animal an effective amount of a compound of formula (I):

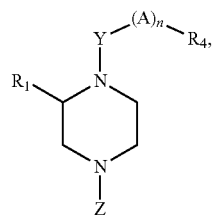

(I)

or a pharmaceutically acceptable salt thereof,
wherein:
$R_1$ is ($C_1$-$C_6$)alkyl or aryl($C_1$-$C_6$)alkyl;
Y is —(C=O);
n is an integer from 0 to 6 inclusive;
A is —(CR$_c$R$_d$)—;
$R_4$ is aryl or heteroaryl;
Z is a phenyl ring substituted with one or more substituents independently selected from the group consisting of halogen, ($C_1$-$C_6$)alkyl, halo($C_1$-$C_6$)alkyl, ($C_3$-$C_8$) cycloalkyl, ($C_3$-$C_8$)cycloalkyl($C_1$-$C_6$)alkyl, ($C_1$-$C_6$) alkoxy, halo($C_1$-$C_6$)alkoxy, ($C_3$-$C_8$)cycloalkoxy, ($C_3$-$C_8$)cycloalkyl($C_1$-$C_6$)alkoxy, piperidinyloxy, piperidinyloxy($C_1$-$C_6$)alkyl, and cyano; and each $R_c$ and $R_d$ is independently H (hydrogen), OH, NH$_2$, or ($C_1$-$C_6$)alkyl, or optionally $R_c$ and $R_d$ taken together with the carbon to which they are attached is a 3 to 5 member ring consisting of C (carbon) atoms and optionally one or more O (oxygen) atoms and/or N(X) group, wherein X is absent, H (hydrogen), O (oxygen), OH, ($C_1$-$C_4$)alkyl, phenyl or benzyl, wherein any aryl, or heteroaryl of $R_1$ or $R_4$ is optionally substituted with one or more substituents independently selected from the group consisting of ($C_1$-$C_6$) alkyl, hydroxy, hydroxy($C_1$-$C_6$)alkyl, halo($C_1$-$C_6$) alkyl, phenyl, ($C_1$-$C_6$)alkoxy, ($C_1$-$C_6$)alkanoyl, ($C_1$-$C_6$) alkoxycarbonyl, ($C_1$-$C_6$)alkanoyloxy, ($C_3$-$C_8$) cycloalkyl, ($C_3$-$C_8$)cycloalkyl($C_1$-$C_6$)alkoxy, halo($C_1$-$C_6$)alkoxy, cyano, nitro, halo, ($C_1$-$C_6$)carboxy, and NR$_c$R$_d$; and wherein the piperazine core ring of formula (I) is optionally substituted at one or more carbon atoms with one or more substituents independently selected from the group consisting of oxo, halogen, ($C_1$-$C_6$)alkyl, and ($C_1$-$C_6$)alkoxy.

3. A method
of treating an animal in need of enhancement of memory or cognition comprising administering to the animal an effective amount of a compound of formula (I):

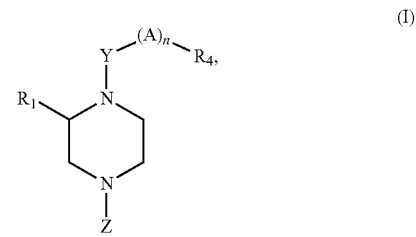

(I)

or a pharmaceutically acceptable salt thereof,
wherein:
$R_1$ is ($C_1$-$C_6$)alkyl or aryl($C_1$-$C_6$)alkyl;
Y is —(C=O);
n is an integer from 0 to 6 inclusive;
A is —(CR$_c$R$_d$)—;
$R_4$ is aryl or heteroaryl;
Z is a phenyl ring substituted with one or more substituents independently selected from the group consisting of halogen, ($C_1$-$C_6$)alkyl, halo($C_1$-$C_6$)alkyl, ($C_3$-$C_8$) cycloalkyl, ($C_3$-$C_8$)cycloalkyl($C_1$-$C_6$)alkyl, ($C_1$-$C_6$) alkoxy, halo($C_1$-$C_6$)alkoxy, ($C_3$-$C_8$)cycloalkoxy, ($C_3$-$C_8$)cycloalkyl($C_1$-$C_6$)alkoxy, piperidinyloxy, piperidinyloxy($C_1$-$C_6$)alkyl, and cyano; and each $R_c$ and $R_d$ is independently H (hydrogen), OH, NH$_2$, or ($C_1$-$C_6$)alkyl, or optionally $R_c$ and $R_d$ taken together with the carbon to which they are attached is a 3 to 5 member ring consisting of C (carbon) atoms and optionally one or more O (oxygen) atoms and/or N(X) group, wherein X is absent, H (hydrogen), O (oxygen), OH, ($C_1$-$C_4$)alkyl, phenyl or benzyl, wherein any aryl, or heteroaryl of $R_1$ or $R_4$ is optionally substituted with one or more substituents independently selected from the group consisting of ($C_1$-$C_6$) alkyl, hydroxy, hydroxy($C_1$-$C_6$)alkyl, halo($C_1$-$C_6$) alkyl, phenyl, ($C_1$-$C_6$)alkoxy, ($C_1$-$C_6$)alkanoyl, ($C_1$-$C_6$) alkoxycarbonyl, ($C_1$-$C_6$)alkanoyloxy, ($C_3$-$C_8$) cycloalkyl, ($C_3$-$C_8$)cycloalkyl($C_1$-$C_6$)alkoxy, halo($C_1$-$C_6$)alkoxy, cyano, nitro, halo, ($C_1$-$C_6$)carboxy, and NR$_c$R$_d$; and wherein the piperazine core ring of formula (I) is optionally substituted at one or more carbon atoms with one or more substituents independently selected from the group consisting of oxo, halogen, ($C_1$-$C_6$)alkyl, and ($C_1$-$C_6$)alkoxy.

4. The method of claim 3, wherein said animal has a cognitive disorder or impairment.

5. The method of claim 4, wherein said animal has age-associated memory impairment, delirium, dementia, Alzheimer's disease, Parkinson's disease, Pick's disease, multiple sclerosis, Huntington's disease, mental retardation, Wilson's disease, Creutzfeldt-Jacob disease, neurofibromatosis type I, Wernicke-Korsakoff syndrome, Rubenstein-Taybi Syndrome, autism and/or cerebrovascular disease.

6. The method of claim 3, wherein said animal has a traumatic and/or ischemic injury.

7. The method of claim 6, wherein said traumatic and/or ischemic injury comprises subdural hematoma, normal-pressure hydrocephalus, cerebrovascular disease, brain tumor and/or head or brain trauma.

8. The method of claim 3, wherein said animal has a psychiatric disorder.

9. The method of claim 8, wherein said psychiatric disorder comprises a neurological disorder, an affective disorder, a psychotic disorder, a neurotic disorder, and/or an attention deficit disorder.

10. The method of claim 3, wherein said animal has a neurological disorder.

11. The method of claim 3, wherein said animal has a disorder of the central nervous system.

12. The method of claim 3, wherein said animal has a disorder of the peripheral nervous system.

13. The method of claim 11, wherein said disorder of the central nervous system is age-associated memory impairment, mild cognitive impairment, Alzheimer's disease, Parkinson's disease or Pick's Disease.

14. The method of claim 8, wherein said psychiatric disorder is an attention deficit disorder, a schizophrenic disorder, an affective disorder, or a depressive disorder.

15. The method of claim 1, wherein said animal is a healthy animal.

16. The method of claim 1, wherein said animal is an aged animal.

17. The method of claim 1, wherein
$R_1$ is $(C_2-C_6)$alkyl, or aryl$(C_1-C_6)$alkyl; and
Z is a phenyl ring substituted with one or more substituents independently selected from the group consisting of halogen, $(C_1-C_6)$alkoxy, halo$(C_1-C_6)$alkoxy, $(C_3-C_8)$cycloalkoxy and $(C_3-C_8)$cycloalkyl$(C_1-C_6)$alkoxy.

18. The method of claim 2, wherein
$R_1$ is $(C_2-C_6)$alkyl, or aryl$(C_1-C_6)$alkyl; and
Z is a phenyl ring substituted with one or more substituents independently selected from the group consisting of halogen, $(C_1-C_6)$alkoxy, halo$(C_1-C_6)$alkoxy, $(C_3-C_8)$cycloalkoxy and $(C_3-C_8)$cycloalkyl$(C_1-C_6)$alkoxy.

19. The method of claim 3, wherein
$R_1$ is $(C_2-C_6)$alkyl, or aryl$(C_1-C_6)$alkyl; and
Z is a phenyl ring substituted with one or more substituents independently selected from the group consisting of halogen, $(C_1-C_6)$alkoxy, halo$(C_1-C_6)$alkoxy, $(C_3-C_8)$cycloalkoxy and $(C_3-C_8)$cycloalkyl$(C_1-C_6)$alkoxy.

20. The method of claim 1, wherein a compound of Formula (I), or a pharmaceutically acceptable salt thereof, is selected from the group consisting of:

(S)-1-(2-benzyl-4-(3-(cyclopentyloxy)-4-methoxyphenyl)piperazin-1-yl)-2-(thiophen-2-yl)ethanone;

(S)-1-(2-benzyl-4-(3-(cyclopentyloxy)-4-methoxyphenyl)piperazin-1-yl)-2-(furan-2-yl)ethanone;

(S)-1-(2-benzyl-4-(3-(cyclopentyloxy)-4-methoxyphenyl)piperazin-1-yl)-2-(thiophen-3-yl)ethanone;

(S)-1-(2-benzyl-4-(3-(cyclopentyloxy)-4-methoxyphenyl)piperazin-1-yl)-3-(1H-imidazol-5-yl)propan-1-one;

(S)-1-(2-benzyl-4-(3-(cyclopentyloxy)-4-methoxyphenyl)piperazin-1-yl)-2-(1H-imidazol-5-yl)ethanone;

(S)-(2-benzyl-4-(3-(cyclopentyloxy)-4-methoxyphenyl)piperazin-1-yl)(1H-imidazol-4-yl)methanone;

(S)-1-(4-(3-(cyclopentyloxy)-4-methoxyphenyl)-2-(pyrrolidin-1-ylmethyl)piperazin-1-yl)-2-(5-methyl-1H-1,2,4-triazol-3-yl)ethanone;

(S)-1-(4-(3-(cyclopentyloxy)-4-methoxyphenyl)-2-(morpholinomethyl)piperazin-1-yl)-2-(5-methyl-1H-1,2,4-triazol-3-yl)ethanone;

(R)-1-(2-((1H-pyrazol-1-yl)methyl)-4-(3-(cyclopentyloxy)-4-ethoxyphenyl)piperazin-1-yl)-2-(5-methyl-1H-1,2,4-triazol-3-yl)ethanone;

(S)-1-(2-benzyl-4-(3-(cyclopentyloxy)-4-methoxyphenyl)piperazin-1-yl)-2-(5-methyl-1H-1,2,4-triazol-3-yl)ethanone;

(S)-(2-benzyl-4-(3-(cyclopentyloxy)-4-methoxyphenyl)piperazin-1-yl)(2,4-dimethylthiazol-5-yl)methanone;

(S)-(2-benzyl-4-(3-(cyclopentyloxy)-4-methoxyphenyl)piperazin-1-yl)(3,4-dihydroxyphenyl)methanone;

(S)-(2-benzyl-4-(3-(cyclopentyloxy)-4-methoxyphenyl)piperazin-1-yl)(3-hydroxyphenyl)methanone;

(S)-1-(2-benzyl-4-(3-(cyclopentyloxy)-4-methoxyphenyl)piperazin-1-yl)-2-(2-methyl-1H-imidazol-1-yl)ethanone;

(S)-1-(2-benzyl-4-(3-(cyclopentyloxy)-4-methoxyphenyl)piperazin-1-yl)-2-(1H-imidazol-1-yl)ethanone;

(S)-1-(2-benzyl-4-(3-(cyclopentyloxy)-4-methoxyphenyl)piperazin-1-yl)-2-(thiazol-5-yl)ethanone;

(S)-1-(2-benzyl-4-(3-(cyclopentyloxy)-4-methoxyphenyl)piperazin-1-yl)-2-(2H-tetrazol-5-yl)ethanone;

(S)-1-(2-benzyl-4-(3-(cyclopentyloxy)-4-methoxyphenyl)piperazin-1-yl)-2-(2,4-dimethylthiazol-5-yl)ethanone;

(S)-1-(2-benzyl-4-(3-(cyclopentyloxy)-4-methoxyphenyl)piperazin-1-yl)-2-(furan-2-yl)ethanone;

(S)-1-(2-benzyl-4-(3-(cyclopentyloxy)-4-methoxyphenyl)piperazin-1-yl)-2-(1H-imidazol-2-yl)ethanone;

(S)-1-(2-benzyl-4-(3-cyclobutoxy-4-methoxyphenyl)piperazin-1-yl)-2-(1H-imidazol-4-yl)ethanone;

(S)-(2-benzyl-4-(3-(cyclopentyloxy)-4-methoxyphenyl)piperazin-1-yl)(1H-pyrazol-3-yl)methanone;

(S)-1-(2-benzyl-4-(3-(cyclopentyloxy)-4-methoxyphenyl)piperazin-1-yl)-2-(5-methyl-1H-pyrazol-3-yl)ethanone;

(S)-1-(2-benzyl-4-(3-(cyclopentyloxy)-4-methoxyphenyl)piperazin-1-yl)-2-(1H-pyrrol-2-yl)ethanone;

(S)-1-(2-benzyl-4-(3-(cyclopentyloxy)-4-methoxyphenyl)piperazin-1-yl)-2-(1H-pyrrol-3-yl)ethanone;

(S)-1-(2-benzyl-4-(3-(cyclopentyloxy)-4-methoxyphenyl)piperazin-1-yl)-2-(4-methylthiazol-2-yl)ethanone;

(S)-1-(2-benzyl-4-(3-cyclobutoxy-4-methoxyphenyl)piperazin-1-yl)-2-(furan-2-yl)ethanone;

(S)-1-(2-benzyl-4-(3-cyclobutoxy-4-methoxyphenyl)piperazin-1-yl)-2-(2,4-dimethylthiazol-5-yl)ethanone;

(S)-1-(2-benzyl-4-(3-(cyclopentyloxy)-4-methoxyphenyl)piperazin-1-yl)-2-(1-methyl-1H-imidazol-4-yl)ethanone;

(S)-1-(2-benzyl-4-(3-(cyclopentyloxy)-4-methoxyphenyl)piperazin-1-yl)-2-(1-methyl-1H-imidazol-5-yl)ethanone;

(S)-1-(2-benzyl-4-(3-(cyclopentyloxy)-4-methoxyphenyl)piperazin-1-yl)-2-(1-methyl-1H-imidazol-2-yl)ethanone;

(S)-1-(2-benzyl-4-(3-cyclobutoxy-4-methoxyphenyl)piperazin-1-yl)-2-(1H-pyrrol-3-yl)ethanone;

(S)-1-(2-benzyl-4-(3-(cyclopentyloxy)-4-methoxyphenyl)piperazin-1-yl)-2-(5-nitro-1H-1,2,4-triazol-3-yl)ethanone;

(S)-1-(2-benzyl-4-(3-isopropoxy-4-methoxyphenyl)piperazin-1-yl)-2-(1H-imidazol-5-yl)ethanone;

(S)-1-(2-benzyl-4-(3-isopropoxy-4-methoxyphenyl)piperazin-1-yl)-2-(1H-pyrrol-3-yl)ethanone;

(S)-1-(2-benzyl-4-(3-(cyclopentyloxy)-4-methoxyphenyl)piperazin-1-yl)-2-(5-methyl-1H-1,2,4-triazol-3-yl)ethanone;
(S)-1-(2-benzyl-4-(3-isopropoxy-4-methoxyphenyl)piperazin-1-yl)-2-(3-methyl-1H-1,2,4-triazol-5-yl)ethanone;
(S)-1-(2-benzyl-4-(3-cyclobutoxy-4-methoxyphenyl)piperazin-1-yl)-2-(3-methyl-1H-1,2,4-triazol-5-yl)ethanone;
(S)-1-(2-benzyl-4-(3,4-bis(difluoromethoxy)phenyl)piperazin-1-yl)-2-(3-methyl-1H-1,2,4-triazol-5-yl)ethanone;
(S)-1-(2-benzyl-4-(3-isopropoxy-4-methoxyphenyl)piperazin-1-yl)-2-(2H-tetrazol-5-yl)ethanone;
(S)-1-(2-benzyl-4-(3-(cyclopentyloxy)-4-methoxyphenyl)piperazin-1-yl)-2-(1H-1,2,3-triazol-1-yl)ethanone;
(S)-1-(2-benzyl-4-(3-cyclobutoxy-4-methoxyphenyl)piperazin-1-yl)-2-(2H-tetrazol-5-yl)ethanone;
(S)-1-(2-benzyl-4-(3-isopropoxy-4-methoxyphenyl)piperazin-1-yl)-2-(5-nitro-1H-1,2,4-triazol-3-yl)ethanone;
(S)-2-(3-amino-1H-1,2,4-triazol-5-yl)-1-(2-benzyl-4-(3-isopropoxy-4-methoxyphenyl)piperazin-1-yl)ethanone;
(S)-1-(2-benzyl-4-(3-cyclobutoxy-4-methoxyphenyl)piperazin-1-yl)-2-(5-nitro-1H-1,2,4-triazol-3-yl)ethanone;
(S)-2-(5-amino-1H-1,2,4-triazol-3-yl)-1-(2-benzyl-4-(3-cyclobutoxy-4-methoxyphenyl)piperazin-1-yl)ethanone;
(S)-1-(2-benzyl-4-(3-cyclobutoxy-4-methoxyphenyl)piperazin-1-yl)-2-(pyrimidin-2-yl)ethanone;
(S)-1-(2-benzyl-4-(3-isopropoxy-4-methoxyphenyl)piperazin-1-yl)-2-(pyridin-2-yl)ethanone;
(S)-1-(2-benzyl-4-(3-cyclobutoxy-4-methoxyphenyl)piperazin-1-yl)-2-(pyridin-2-yl)ethanone;
(S)-1-(2-benzyl-4-(3-isopropoxy-4-methoxyphenyl)piperazin-1-yl)-2-(pyrimidin-2-yl)ethanone;
(S)-1-(2-benzyl-4-(3-cyclobutoxy-4-(difluoromethoxy)phenyl)piperazin-1-yl)-2-(1H-imidazol-4-yl)ethanone;
(S)-1-(2-benzyl-4-(3-cyclobutoxy-4-(difluoromethoxy)phenyl)piperazin-1-yl)-2-(5-methyl-1H-1,2,4-triazol-3-yl)ethanone;
(S)-1-(2-benzyl-4-(3-(difluoromethoxy)-4-methoxyphenyl)piperazin-1-yl)-2-(5-methyl-1H-1,2,4-triazol-3-yl)ethanone;
(S)-1-(2-benzyl-4-(3-(difluoromethoxy)-4-methoxyphenyl)piperazin-1-yl)-2-(1H-imidazol-4-yl)ethanone;
(S)-1-(2-benzyl-4-(3-cyclobutoxy-4-(difluoromethoxy)phenyl)piperazin-1-yl)-2-(pyrimidin-2-yl)ethanone;
(S)-1-(2-benzyl-4-(3-(difluoromethoxy)-4-methoxyphenyl)piperazin-1-yl)-2-(pyrimidin-2-yl)ethanone;
(S)-1-(2-benzyl-4-(3-(difluoromethoxy)-4-methoxyphenyl)piperazin-1-yl)-2-(pyridin-2-yl)ethanone;
(S)-5-((2-benzyl-4-(3-(cyclopentyloxy)-4-methoxyphenyl)piperazin-1-yl)methyl)-2,4-dimethylthiazole;
(S)-(2-benzyl-4-(3-(cyclopentyloxy)-4-methoxyphenyl)piperazin-1-yl)(4-(hydroxymethyl)phenyl)methanone;
(S)-3-((2-benzyl-4-(3-(cyclopentyloxy)-4-methoxyphenyl)piperazin-1-yl)methyl)phenol;
(S)-4-((2-benzyl-4-(3-(cyclopentyloxy)-4-methoxyphenyl)piperazin-1-yl)methyl)phenol;
(S)-1-(4-(3-(cyclopentyloxy)-4-methoxyphenyl)-2-isobutylpiperazin-1-yl)-2-(1H-imidazol-4-yl)ethanone;
(S)-1-(4-(3-(cyclopropylmethoxy)-4-(difluoromethoxy)phenyl)-2-isobutylpiperazin-1-yl)-2-(1H-imidazol-4-yl)ethanone;
(S)-1-(4-(3-(cyclopentyloxy)-4-(difluoromethoxy)phenyl)-2-isobutylpiperazin-1-yl)-2-(1H-imidazol-4-yl)ethanone;
(S)-1-(4-(3-cyclobutoxy-4-methoxyphenyl)-2-isobutylpiperazin-1-yl)-2-(1H-imidazol-4-yl)ethanone;
(S)-1-(4-(3-cyclobutoxy-4-methoxyphenyl)-2-isobutylpiperazin-1-yl)-2-(1-methyl-1H-imidazol-4-yl)ethanone;
(S)-1-(4-(3-(cyclopropylmethoxy)-4-(difluoromethoxy)phenyl)-2-isobutylpiperazin-1-yl)-2-(5-methyl-1H-1,2,4-triazol-3-yl)ethanone;
(S)-1-(4-(3-(cyclopentyloxy)-4-(difluoromethoxy)phenyl)-2-isobutylpiperazin-1-yl)-2-(5-methyl-1H-1,2,4-triazol-3-yl)ethanone;
(S)-1-(2-isobutyl-4-(3-isopropoxy-4-methoxyphenyl)piperazin-1-yl)-2-(5-methyl-1H-1,2,4-triazol-3-yl)ethanone;
(S)-2-(1H-imidazol-4-yl)-1-(2-isobutyl-4-(3-isopropoxy-4-methoxyphenyl)piperazin-1-yl)ethanone;
(S)-1-(2-benzyl-4-(3-(cyclopentyloxy)-4-methoxyphenyl)piperazin-1-yl)-2-(pyridin-2-yl)ethanone;
(S)-1-(2-benzyl-4-(3-(cyclopentyloxy)-4-methoxyphenyl)piperazin-1-yl)-2-(pyridin-3-yl)ethanone;
(S)-1-(2-benzyl-4-(3-(cyclopentyloxy)-4-methoxyphenyl)piperazin-1-yl)-2-(pyridin-4-yl)ethanone;
(S)-1-(2-benzyl-4-(3-(cyclopentyloxy)-4-methoxyphenyl)piperazin-1-yl)-2-(pyrazin-2-yl)ethanone;
(S)-1-(2-benzyl-4-(3-(cyclopentyloxy)-4-methoxyphenyl)piperazin-1-yl)-2-(pyrimidin-2-yl)ethanone;
(S)-1-(4-(3-(cyclopentyloxy)-4-methoxyphenyl)-2-isobutylpiperazin-1-yl)-2-(5-methyl-1H-1,2,4-triazol-3-yl)ethanone;
(S)-1-(2-benzyl-4-(3-(cyclopentyloxy)-4-methoxyphenyl)piperazin-1-yl)-2-(pyrimidin-4-yl)ethanone;
(S)-1-(2-benzyl-4-(3-(cyclopentyloxy)-4-methoxyphenyl)piperazin-1-yl)-2-(2-fluorophenyl)ethanone;
(S)-1-(2-benzyl-4-(3-(cyclopentyloxy)-4-methoxyphenyl)piperazin-1-yl)-2-(2,6-difluorophenyl)ethanone;
(S)-1-(4-(3-cyclobutoxy-4-methoxyphenyl)-2-isobutylpiperazin-1-yl)-2-(oxazol-5-yl)ethanone;
(S)-1-(4-(3-cyclobutoxy-4-methoxyphenyl)-2-isobutylpiperazin-1-yl)-2-(3-methyl-1,2,4-oxadiazol-5-yl)ethanone;
(S)-1-(4-(3-cyclobutoxy-4-methoxyphenyl)-2-(4-fluorobenzyl)piperazin-1-(1H-pyrazol-4-yl)ethanone;
(S)-1-(4-(3-cyclobutoxy-4-methoxyphenyl)-2-(4-fluorobenzyl)piperazin-1-yl)-2-(5-methyl-1H-1,2,4-triazol-3-yl)ethanone;
(S)-1-(4-(3-cyclobutoxy-4-methoxyphenyl)-2-(4-fluorobenzyl)piperazin-1-yl)-2-(pyrimidin-2-yl)ethanone;
(S)-1-(2-benzyl-4-(3-(cyclopentyloxy)-4-methoxyphenyl)piperazin-1-yl)-2-(4H-1,2,4-triazol-3-yl)ethanone;
(S)-1-(2-benzyl-4-(3-(cyclopentyloxy)-4-methoxyphenyl)piperazin-1-yl)-2-(1H-pyrazol-4-yl)ethanone;
(S)-1-(2-benzyl-4-(3-(cyclopentyloxy)-4-methoxyphenyl)piperazin-1-yl)-2-(oxazol-5-yl)ethanone;
(S)-1-(2-benzyl-4-(3-(cyclopentyloxy)-4-methoxyphenyl)piperazin-1-yl)-2-(3-methyl-1,2,4-oxadiazol-5-yl)ethanone;
(S)-1-(2-benzyl-4-(3-cyclopropoxy-4-methoxyphenyl)piperazin-1-yl)-2-(4H-1,2,4-triazol-3-yl)ethanone;
(S)-1-(2-benzyl-4-(3-cyclobutoxy-4-methoxyphenyl)piperazin-1-yl)-2-(oxazol-5-yl)ethanone;
(S)-1-(2-benzyl-4-(3-cyclobutoxy-4-methoxyphenyl)piperazin-1-yl)-2-(3-methyl-1,2,4-oxadiazol-5-yl)ethanone;

(S)-1-(2-benzyl-4-(3-cyclobutoxy-4-methoxyphenyl)piperazin-1-yl)-2-(3-(trifluoromethyl)-1H-1,2,4-triazol-5-yl)ethanone;
(S)-1-(2-benzyl-4-(3-cyclobutoxy-4-methoxyphenyl)piperazin-1-yl)-2-(1H-pyrazol-4-yl)ethanone;
(S)-1-(2-benzyl-4-(3-cyclobutoxy-4-methoxyphenyl)piperazin-1-yl)-2-(2-methyloxazol-5-yl)ethanone;
(S)-1-(2-benzyl-4-(3-cyclobutoxy-4-methoxyphenyl)piperazin-1-yl)-2-(3-isopropyl-1H-1,2,4-triazol-5-yl)ethanone;
(S)-1-(2-benzyl-4-(3-cyclobutoxy-4-methoxyphenyl)piperazin-1-yl)-2-(3-ethyl-1H-1,2,4-triazol-5-yl)ethanone;
(S)-1-(2-benzyl-4-(3-cyclobutoxy-4-methoxyphenyl)piperazin-1-yl)-2-(1-methyl-1H-pyrazol-4-yl)ethanone;
(S)-1-(2-benzyl-4-(3-cyclobutoxy-4-methoxyphenyl)piperazin-1-yl)-2-(4H-1,2,4-triazol-3-yl)ethanone;
(S)-1-(2-benzyl-4-(3-isopropoxy-4-methoxyphenyl)piperazin-1-yl)-2-(4H-1,2,4-triazol-3-yl)ethanone;
(S)-1-(2-benzyl-4-(3-cyclobutoxy-4-(difluoromethoxy)phenyl)piperazin-1-yl)-2-(4H-1,2,4-triazol-3-yl)ethanone;
(S)-1-(2-benzyl-4-(3-(cyclopentyloxy)-4-(difluoromethoxy)phenyl)piperazin-1-yl)-2-(1H-imidazol-4-yl)ethanone;
(S)-1-(2-benzyl-4-(3-(cyclopropylmethoxy)-4-(difluoromethoxy)phenyl)piperazin-1-yl)-2-(1H-imidazol-5-yl)ethanone;
(S)-1-(2-benzyl-4-(3,4-bis(difluoromethoxy)phenyl)piperazin-1-yl)-2-(1H-imidazol-5-yl)ethanone;
1-((S)-2-benzyl-4-(4-methoxy-3-((S)-1-methylpyrrolidin-3-yloxy)phenyl)piperazin-1-yl)-2-(5-methyl-1H-1,2,4-triazol-3-yl)ethanone;
(S)-2-(5-amino-1H-1,2,4-triazol-3-yl)-1-(2-benzyl-4-(3-(cyclopentyloxy)-4-methoxyphenyl)piperazin-1-yl)ethanone;
(S)-1-(2-benzyl-4-(4-methoxy-3-(1-methylpiperidin-4-yloxy)phenyl)piperazin-1-yl)-2-(5-methyl-4H-1,2,4-triazol-3-yl)ethanone;
(S)-1-(2-benzyl-4-(3-cyclopropoxy-4-methoxyphenyl)piperazin-1-yl)-2-(3-methyl-1H-1,2,4-triazol-5-yl)ethanone;
(S)-1-(2-benzyl-4-(3-cyclobutoxy-4-methoxyphenyl)piperazin-1-yl)-2-(2-methyl-1H-imidazol-5-yl)ethanone; and
(S)-1-(2-benzyl-4-(3-(cyclopentyloxy)-4-methoxyphenyl)piperazin-1-yl)-2-(1-isopropyl-1H-imidazol-4-yl)ethanone.

21. The method of claim 3, wherein a compound of Formula (I), or a pharmaceutically acceptable salt thereof, is selected from the group consisting of:
(S)-1-(2-benzyl-4-(3-(cyclopentyloxy)-4-methoxyphenyl)piperazin-1-yl)-2-(thiophen-2-yl)ethanone;
(S)-1-(2-benzyl-4-(3-(cyclopentyloxy)-4-methoxyphenyl)piperazin-1-yl)-2-(furan-2-yl)ethanone;
(S)-1-(2-benzyl-4-(3-(cyclopentyloxy)-4-methoxyphenyl)piperazin-1-yl)-2-(thiophen-3-yl)ethanone;
(S)-1-(2-benzyl-4-(3-(cyclopentyloxy)-4-methoxyphenyl)piperazin-1-yl)-3-(1H-imidazol-5-yl)propan-1-one;
(S)-1-(2-benzyl-4-(3-(cyclopentyloxy)-4-methoxyphenyl)piperazin-1-yl)-2-(1H-imidazol-5-yl)ethanone;
(S)-(2-benzyl-4-(3-(cyclopentyloxy)-4-methoxyphenyl)piperazin-1-yl)(1H-imidazol-4-yl)methanone;
(S)-1-(4-(3-(cyclopentyloxy)-4-methoxyphenyl)-2-(pyrrolidinylmethyl)piperazin-1-yl)-2-(5-methyl-1H-1,2,4-triazol-3-yl)ethanone;
(S)-1-(4-(3-(cyclopentyloxy)-4-methoxyphenyl)-2-(morpholinomethyl)piperazin-1-yl)-2-(5-methyl-1H-1,2,4-triazol-3-yl)ethanone;
(R)-1-(2-((1H-pyrazol-1-yl)methyl)-4-(3-(cyclopentyloxy)-4-ethoxyphenyl)piperazin-1-yl)-2-(5-methyl-1H-1,2,4-triazol-3-yl)ethanone;
(S)-1-(2-benzyl-4-(3-(cyclopentyloxy)-4-methoxyphenyl)piperazin-1-yl)-2-(5-methyl-1H-1,2,4-triazol-3-yl)ethanone;
(S)-(2-benzyl-4-(3-(cyclopentyloxy)-4-methoxyphenyl)piperazin-1-yl)(2,4-dimethylthiazol-5-yl)methanone;
(S)-(2-benzyl-4-(3-(cyclopentyloxy)-4-methoxyphenyl)piperazin-1-yl)(3,4-dihydroxyphenyl)methanone;
(S)-(2-benzyl-4-(3-(cyclopentyloxy)-4-methoxyphenyl)piperazin-1-yl)(3-hydroxyphenyl)methanone;
(S)-1-(2-benzyl-4-(3-(cyclopentyloxy)-4-methoxyphenyl)piperazin-1-yl)-2-(2-methyl-1H-imidazol-1-yl)ethanone;
(S)-1-(2-benzyl-4-(3-(cyclopentyloxy)-4-methoxyphenyl)piperazin-1-yl)-2-(1H-imidazol-1-yl)ethanone;
(S)-1-(2-benzyl-4-(3-(cyclopentyloxy)-4-methoxyphenyl)piperazin-1-yl)-2-(thiazol-5-yl)ethanone;
(S)-1-(2-benzyl-4-(3-(cyclopentyloxy)-4-methoxyphenyl)piperazin-1-yl)-2-(2H-tetrazol-5-yl)ethanone;
(S)-1-(2-benzyl-4-(3-(cyclopentyloxy)-4-methoxyphenyl)piperazin-1-yl)-2-(2,4-dimethylthiazol-5-yl)ethanone;
(S)-1-(2-benzyl-4-(3-(cyclopentyloxy)-4-methoxyphenyl)piperazin-1-yl)-2-(furan-2-yl)ethanone;
(S)-1-(2-benzyl-4-(3-(cyclopentyloxy)-4-methoxyphenyl)piperazin-1-yl)-2-(1H-imidazol-2-yl)ethanone;
(S)-1-(2-benzyl-4-(3-cyclobutoxy-4-methoxyphenyl)piperazin-1-yl)-2-(1H-imidazol-4-yl)ethanone;
(S)-(2-benzyl-4-(3-(cyclopentyloxy)-4-methoxyphenyl)piperazin-1-yl)(1H-pyrazol-3-yl)methanone;
(S)-1-(2-benzyl-4-(3-(cyclopentyloxy)-4-methoxyphenyl)piperazin-1-yl)-2-(5-methyl-1H-pyrazol-3-yl)ethanone;
(S)-1-(2-benzyl-4-(3-(cyclopentyloxy)-4-methoxyphenyl)piperazin-1-yl)-2-(1H-pyrrol-2-yl)ethanone;
(S)-1-(2-benzyl-4-(3-(cyclopentyloxy)-4-methoxyphenyl)piperazin-1-yl)-2-(1H-pyrrol-3-yl)ethanone;
(S)-1-(2-benzyl-4-(3-(cyclopentyloxy)-4-methoxyphenyl)piperazin-1-yl)-2-(4-methylthiazol-2-yl)ethanone;
(S)-1-(2-benzyl-4-(3-cyclobutoxy-4-methoxyphenyl)piperazin-1-yl)-2-(furan-2-yl)ethanone;
(S)-1-(2-benzyl-4-(3-cyclobutoxy-4-methoxyphenyl)piperazin-1-yl)-2-(2,4-dimethylthi azol-5-yl)ethanone;
(S)-1-(2-benzyl-4-(3-(cyclopentyloxy)-4-methoxyphenyl)piperazin-1-yl)-2-(1-methyl-1H-imidazol-4-yl)ethanone;
(S)-1-(2-benzyl-4-(3-(cyclopentyloxy)-4-methoxyphenyl)piperazin-1-yl)-2-(1-methyl-1H-imidazol-5-yl)ethanone;
(S)-1-(2-benzyl-4-(3-(cyclopentyloxy)-4-methoxyphenyl)piperazin-1-yl)-2-(1-methyl-1H-imidazol-2-yl)ethanone;
(S)-1-(2-benzyl-4-(3-cyclobutoxy-4-methoxyphenyl)piperazin-1-yl)-2-(1H-pyrrol-3-yl)ethanone;
(S)-1-(2-benzyl-4-(3-(cyclopentyloxy)-4-methoxyphenyl)piperazin-1-yl)-2-(5-nitro-1H-1,2,4-triazol-3-yl)ethanone;
(S)-1-(2-benzyl-4-(3-isopropoxy-4-methoxyphenyl)piperazin-1-yl)-2-(1H-imidazol-5-yl)ethanone;
(S)-1-(2-benzyl-4-(3-isopropoxy-4-methoxyphenyl)piperazin-1-yl)-2-(1H-pyrrol-3-yl)ethanone;

(S)-1-(2-benzyl-4-(3-(cyclopentyloxy)-4-methoxyphenyl)piperazin-1-yl)-2-(5-methyl-1H-1,2,4-triazol-3-yl)ethanone;
(S)-1-(2-benzyl-4-(3-isopropoxy-4-methoxyphenyl)piperazin-1-yl)-2-(3-methyl-1H-1,2,4-triazol-5-yl)ethanone;
(S)-1-(2-benzyl-4-(3-cyclobutoxy-4-methoxyphenyl)piperazin-1-yl)-2-(3-methyl-1H-1,2,4-triazol-5-yl)ethanone;
(S)-1-(2-benzyl-4-(3,4-bis(difluoromethoxy)phenyl)piperazin-1-yl)-2-(3-methyl-1H-1,2,4-triazol-5-yl)ethanone;
(S)-1-(2-benzyl-4-(3-isopropoxy-4-methoxyphenyl)piperazin-1-yl)-2-(2H-tetrazol-5-yl)ethanone;
(S)-1-(2-benzyl-4-(3-(cyclopentyloxy)-4-methoxyphenyl)piperazin-1-yl)-2-(1H-1,2,3-triazol-1-yl)ethanone;
(S)-1-(2-benzyl-4-(3-cyclobutoxy-4-methoxyphenyl)piperazin-1-yl)-2-(2H-tetrazol-5-yl)ethanone;
(S)-1-(2-benzyl-4-(3-isopropoxy-4-methoxyphenyl)piperazin-1-yl)-2-(5-nitro-1H-1,2,4-triazol-3-yl)ethanone;
(S)-2-(3-amino-1H-1,2,4-triazol-5-yl)-1-(2-benzyl-4-(3-isopropoxy-4-methoxyphenyl)piperazin-1-yl)ethanone;
(S)-1-(2-benzyl-4-(3-cyclobutoxy-4-methoxyphenyl)piperazin-1-yl)-2-(5-nitro-1H-1,2,4-triazol-3-yl)ethanone;
(S)-2-(5-amino-1H-1,2,4-triazol-3-yl)-1-(2-benzyl-4-(3-cyclobutoxy-4-methoxyphenyl)piperazin-1-yl)ethanone;
(S)-1-(2-benzyl-4-(3-cyclobutoxy-4-methoxyphenyl)piperazin-1-yl)-2-(pyrimidin-2-yl)ethanone;
(S)-1-(2-benzyl-4-(3-isopropoxy-4-methoxyphenyl)piperazin-1-yl)-2-(pyridin-2-yl)ethanone;
(S)-1-(2-benzyl-4-(3-cyclobutoxy-4-methoxyphenyl)piperazin-1-yl)-2-(pyridin-2-yl)ethanone;
(S)-1-(2-benzyl-4-(3-isopropoxy-4-methoxyphenyl)piperazin-1-yl)-2-(pyrimidin-2-yl)ethanone;
(S)-1-(2-benzyl-4-(3-cyclobutoxy-4-(difluoromethoxy)phenyl)piperazin-1-yl)-2-(1H-imidazol-4-yl)ethanone;
(S)-1-(2-benzyl-4-(3-cyclobutoxy-4-(difluoromethoxy)phenyl)piperazin-1-yl)-2-(5-methyl-1H-1,2,4-triazol-3-yl)ethanone;
(S)-1-(2-benzyl-4-(3-(difluoromethoxy)-4-methoxyphenyl)piperazin-1-yl)-2-(5-methyl-1H-1,2,4-triazol-3-yl)ethanone;
(S)-1-(2-benzyl-4-(3-(difluoromethoxy)-4-methoxyphenyl)piperazin-1-yl)-2-(1H-imidazol-4-yl)ethanone;
(S)-1-(2-benzyl-4-(3-cyclobutoxy-4-(difluoromethoxy)phenyl)piperazin-1-yl)-2-(pyrimidin-2-yl)ethanone;
(S)-1-(2-benzyl-4-(3-(difluoromethoxy)-4-methoxyphenyl)piperazin-1-yl)-2-(pyrimidin-2-yl)ethanone;
(S)-1-(2-benzyl-4-(3-(difluoromethoxy)-4-methoxyphenyl)piperazin-1-yl)-2-(pyridin-2-yl)ethanone;
(S)-5-((2-benzyl-4-(3-(cyclopentyloxy)-4-methoxyphenyl)piperazin-1-yl)methyl)-2,4-dimethylthiazole;
(S)-(2-benzyl-4-(3-(cyclopentyloxy)-4-methoxyphenyl)piperazin-1-yl)(4-(hydroxymethyl)phenyl)methanone;
(S)-3-((2-benzyl-4-(3-(cyclopentyloxy)-4-methoxyphenyl)piperazin-1-yl)methyl)phenol;
(S)-4-((2-benzyl-4-(3-(cyclopentyloxy)-4-methoxyphenyl)piperazin-1-yl)methyl)phenol;
(S)-1-(4-(3-(cyclopentyloxy)-4-methoxyphenyl)-2-isobutylpiperazin-1-yl)-2-(1H-imidazol-4-yl)ethanone;
(S)-1-(4-(3-(cyclopropylmethoxy)-4-(difluoromethoxy)phenyl)-2-isobutylpiperazin-1-yl)-2-(1H-imidazol-4-yl)ethanone;
(S)-1-(4-(3-(cyclopentyloxy)-4-(difluoromethoxy)phenyl)-2-isobutylpiperazin-1-yl)-2-(1H-imidazol-4-yl)ethanone;
(S)-1-(4-(3-cyclobutoxy-4-methoxyphenyl)-2-isobutylpiperazin-1-yl)-2-(1H-imidazol-4-yl)ethanone;
(S)-1-(4-(3-cyclobutoxy-4-methoxyphenyl)-2-isobutylpiperazin-1-yl)-2-(1-methyl-1H-imidazol-4-yl)ethanone;
(S)-1-(4-(3-(cyclopropylmethoxy)-4-(difluoromethoxy)phenyl)-2-isobutylpiperazin-1-yl)-2-(5-methyl-1H-1,2,4-triazol-3-yl)ethanone;
(S)-1-(4-(3-(cyclopentyloxy)-4-(difluoromethoxy)phenyl)-2-isobutylpiperazin-1-yl)-2-(5-methyl-1H-1,2,4-triazol-3-yl)ethanone;
(S)-1-(2-isobutyl-4-(3-isopropoxy-4-methoxyphenyl)piperazin-1-yl)-2-(5-methyl-1H-1,2,4-triazol-3-yl)ethanone;
(S)-2-(1H-imidazol-4-yl)-1-(2-isobutyl-4-(3-isopropoxy-4-methoxyphenyl)piperazin-1-yl)ethanone;
(S)-1-(2-benzyl-4-(3-(cyclopentyloxy)-4-methoxyphenyl)piperazin-1-yl)-2-(pyridin-2-yl)ethanone;
(S)-1-(2-benzyl-4-(3-(cyclopentyloxy)-4-methoxyphenyl)piperazin-1-yl)-2-(pyridin-3-yl)ethanone;
(S)-1-(2-benzyl-4-(3-(cyclopentyloxy)-4-methoxyphenyl)piperazin-1-yl)-2-(pyridin-4-yl)ethanone;
(S)-1-(2-benzyl-4-(3-(cyclopentyloxy)-4-methoxyphenyl)piperazin-1-yl)-2-(pyrazin-2-yl)ethanone;
(S)-1-(2-benzyl-4-(3-(cyclopentyloxy)-4-methoxyphenyl)piperazin-1-yl)-2-(pyrimidin-2-yl)ethanone;
(S)-1-(4-(3-(cyclopentyloxy)-4-methoxyphenyl)-2-isobutylpiperazin-1-yl)-2-(5-methyl-1H-1,2,4-triazol-3-yl)ethanone;
(S)-1-(2-benzyl-4-(3-(cyclopentyloxy)-4-methoxyphenyl)piperazin-1-yl)-2-(pyrimidin-4-yl)ethanone;
(S)-1-(2-benzyl-4-(3-(cyclopentyloxy)-4-methoxyphenyl)piperazin-1-yl)-2-(2-fluorophenyl)ethanone;
(S)-1-(2-benzyl-4-(3-(cyclopentyloxy)-4-methoxyphenyl)piperazin-1-yl)-2-(2,6-difluorophenyl)ethanone;
(S)-1-(4-(3-cyclobutoxy-4-methoxyphenyl)-2-isobutylpiperazin-1-yl)-2-(oxazol-5-yl)ethanone;
(S)-1-(4-(3-cyclobutoxy-4-methoxyphenyl)-2-isobutylpiperazin-1-yl)-2-(3-methyl-1,2,4-oxadiazol-5-yl)ethanone;
(S)-1-(4-(3-cyclobutoxy-4-methoxyphenyl)-2-(4-fluorobenzyl)piperazin-1-(1H-pyrazol-4-yl)ethanone;
(S)-1-(4-(3-cyclobutoxy-4-methoxyphenyl)-2-(4-fluorobenzyl)piperazin-1-yl)-2-(5-methyl-1H-1,2,4-triazol-3-yl)ethanone;
(S)-1-(4-(3-cyclobutoxy-4-methoxyphenyl)-2-(4-fluorobenzyl)piperazin-1-yl)-2-(pyrimidin-2-yl)ethanone;
(S)-1-(2-benzyl-4-(3-(cyclopentyloxy)-4-methoxyphenyl)piperazin-1-yl)-2-(4H-1,2,4-triazol-3-yl)ethanone;
(S)-1-(2-benzyl-4-(3-(cyclopentyloxy)-4-methoxyphenyl)piperazin-1-yl)-2-(1H-pyrazol-4-yl)ethanone;
(S)-1-(2-benzyl-4-(3-(cyclopentyloxy)-4-methoxyphenyl)piperazin-1-yl)-2-(oxazol-5-yl)ethanone;
(S)-1-(2-benzyl-4-(3-(cyclopentyloxy)-4-methoxyphenyl)piperazin-1-yl)-2-(3-methyl-1,2,4-oxadiazol-5-yl)ethanone;
(S)-1-(2-benzyl-4-(3-cyclopropoxy-4-methoxyphenyl)piperazin-1-yl)-2-(4H-1,2,4-triazol-3-yl)ethanone;
(S)-1-(2-benzyl-4-(3-cyclobutoxy-4-methoxyphenyl)piperazin-1-yl)-2-(oxazol-5-yl)ethanone;
(S)-1-(2-benzyl-4-(3-cyclobutoxy-4-methoxyphenyl)piperazin-1-yl)-2-(3-methyl-1,2,4-oxadiazol-5-yl)ethanone;

(S)-1-(2-benzyl-4-(3-cyclobutoxy-4-methoxyphenyl)piperazin-1-yl)-2-(3-(trifluoromethyl)-1H-1,2,4-triazol-5-yl)ethanone;
(S)-1-(2-benzyl-4-(3-cyclobutoxy-4-methoxyphenyl)piperazin-1-yl)-2-(1H-pyrazol-4-yl)ethanone;
(S)-1-(2-benzyl-4-(3-cyclobutoxy-4-methoxyphenyl)piperazin-1-yl)-2-(2-methyloxazol-5-yl)ethanone;
(S)-1-(2-benzyl-4-(3-cyclobutoxy-4-methoxyphenyl)piperazin-1-yl)-2-(3-isopropyl-1H-1,2,4-triazol-5-yl)ethanone;
(S)-1-(2-benzyl-4-(3-cyclobutoxy-4-methoxyphenyl)piperazin-1-yl)-2-(3-ethyl-1H-1,2,4-triazol-5-yl)ethanone;
(S)-1-(2-benzyl-4-(3-cyclobutoxy-4-methoxyphenyl)piperazin-1-yl)-2-(1-methyl-1H-pyrazol-4-yl)ethanone;
(S)-1-(2-benzyl-4-(3-cyclobutoxy-4-methoxyphenyl)piperazin-1-yl)-2-(4H-1,2,4-triazol-3-yl)ethanone;
(S)-1-(2-benzyl-4-(3-isopropoxy-4-methoxyphenyl)piperazin-1-yl)-2-(4H-1,2,4-triazol-3-yl)ethanone;
(S)-1-(2-benzyl-4-(3-cyclobutoxy-4-(difluoromethoxy)phenyl)piperazin-1-yl)-2-(4H-1,2,4-triazol-3-yl)ethanone;
(S)-1-(2-benzyl-4-(3-(cyclopentyloxy)-4-(difluoromethoxy)phenyl)piperazin-1-yl)-2-(1H-imidazol-4-yl)ethanone;
(S)-1-(2-benzyl-4-(3-(cyclopropylmethoxy)-4-(difluoromethoxy)phenyl)piperazin-1-yl)-2-(1H-imidazol-5-yl)ethanone;
(S)-1-(2-benzyl-4-(3,4-bis(difluoromethoxy)phenyl)piperazin-1-yl)-2-(1H-imidazol-5-yl)ethanone;
1-((S)-2-benzyl-4-(4-methoxy-3-((S)-1-methylpyrrolidin-3-yloxy)phenyl)piperazin-1-yl)-2-(5-methyl-1H-1,2,4-triazol-3-yl)ethanone;
(S)-2-(5-amino-1H-1,2,4-triazol-3-yl)-1-(2-benzyl-4-(3-(cyclopentyloxy)-4-methoxyphenyl)piperazin-1-yl)ethanone;
(S)-1-(2-benzyl-4-(4-methoxy-3-(1-methylpiperidin-4-yloxy)phenyl)piperazin-1-yl)-2-(5-methyl-4H-1,2,4-triazol-3-yl)ethanone;
(S)-1-(2-benzyl-4-(3-cyclopropoxy-4-methoxyphenyl)piperazin-1-yl)-2-(3-methyl-1H-1,2,4-triazol-5-yl)ethanone;
(S)-1-(2-benzyl-4-(3-cyclobutoxy-4-methoxyphenyl)piperazin-1-yl)-2-(2-methyl-1H-imidazol-5-yl)ethanone; and
(S)-1-(2-benzyl-4-(3-(cyclopentyloxy)-4-methoxyphenyl)piperazin-1-yl)-2-(1-isopropyl-1H-imidazol-4-yl)ethanone.

* * * * *